United States Patent
Wagner et al.

(10) Patent No.: US 8,735,579 B2
(45) Date of Patent: May 27, 2014

(54) BENZAMIDES, PRODUCTION THEREOF, AND USE THEREOF AS MEDICAMENTS

(75) Inventors: Holger Wagner, Mettenberg (DE); Elke Langkopf, Warthausen (DE); Frank Himmelsbach, Mittelbiberach (DE); Rolf Goeggel, Ulm (DE); Birgit Jung, Laupheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 294 days.

(21) Appl. No.: 13/060,761

(22) PCT Filed: Aug. 26, 2009

(86) PCT No.: PCT/EP2009/061024
§ 371 (c)(1), (2), (4) Date: Apr. 6, 2011

(87) PCT Pub. No.: WO2010/026095
PCT Pub. Date: Mar. 11, 2010

(65) Prior Publication Data
US 2012/0108572 A1 May 3, 2012

(30) Foreign Application Priority Data
Sep. 2, 2008 (EP) .................................. 08163525

(51) Int. Cl.
| | | |
|---|---|---|
| C07D 239/24 | (2006.01) | |
| C07D 239/34 | (2006.01) | |
| C07D 239/46 | (2006.01) | |
| C07D 239/47 | (2006.01) | |
| A61K 31/505 | (2006.01) | |
| A61K 31/506 | (2006.01) | |
| A61P 11/00 | (2006.01) | |
| A61P 11/06 | (2006.01) | |

(52) U.S. Cl.
USPC ........... 544/309; 544/316; 544/317; 544/321; 514/269

(58) Field of Classification Search
USPC .................. 544/309, 316, 317, 321; 514/269
See application file for complete search history.

(56) References Cited

U.S. PATENT DOCUMENTS

| | | |
|---|---|---|
| 2011/0269737 A1 | 11/2011 | Wagner et al. |
| 2012/0108572 A1 | 5/2012 | Wagner et al. |

FOREIGN PATENT DOCUMENTS

| | | |
|---|---|---|
| CA | 2557302 A1 | 9/2005 |
| WO | 0147897 A1 | 7/2001 |
| WO | 2005085202 A1 | 9/2005 |
| WO | 2006026235 A1 | 3/2006 |
| WO | 2008057775 A2 | 5/2008 |
| WO | 2010026095 A1 | 3/2010 |
| WO | 2010026096 A1 | 3/2010 |

OTHER PUBLICATIONS

Banerjee et al., Current Opinion in Pharmacology 2012, 12:287-292.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Mass, R. D., Int. J. Radiation Oncology Bio. Phys.vol. 58(3): 932-940, 2004.*
Fabbro et al. Pharmacology & therapeutics 93, 79-98, 2002.*
International Search Report and Written Opinion for PCT/EP2009/061024 mailed Oct. 13, 2009.
U.S. Appl. No. 13/060,761, filed Feb. 25, 2011, Inventor: Holger Wagner.
U.S. Appl. No. 13/060,504, filed Feb. 24, 2011, Inventor: Holger Wagner.

* cited by examiner

*Primary Examiner* — Venkataraman Balasubramanian
(74) *Attorney, Agent, or Firm* — Michael P. Morris; Anthony P. Bottino

(57) ABSTRACT

Heteroaryloxy-substituted benzoic acid amides of general formula I

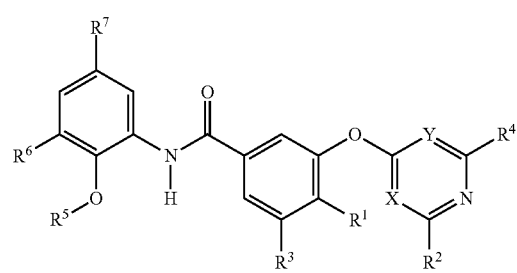

wherein the groups $R^1$ to $R^7$ as well as X and Y are defined according to claim 1, including the tautomers, the stereoisomers, the mixtures and the salts thereof. The compounds according to the invention are suitable for the treatment of respiratory complaints, particularly COPD and asthma.

29 Claims, No Drawings

BENZAMIDES, PRODUCTION THEREOF, AND USE THEREOF AS MEDICAMENTS

The present invention relates to substituted benzoic acid amides of general formula I

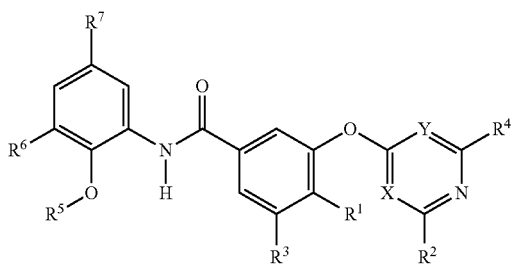

wherein the groups and radicals $R^1$, $R^2$, $R^3$, $R^4$, $R^5$, $R^6$, $R^7$, X and Y are as hereinafter defined, including the tautomers, the stereoisomers, the mixtures and the salts thereof. This invention further relates to medicaments containing a compound of formula I according to the invention and the use of a compound according to the invention for preparing a medicament for the treatment of respiratory complaints. This invention further relates to processes for preparing a medicament and a compound according to the invention.

In the literature, compounds that have an inhibitory effect on the enzyme p38 mitogen-activated protein (MAP) kinase are proposed, inter alia, for the treatment of respiratory complaints, particularly chronic obstructive bronchitis (COPD) and asthma (cf. E.g. *Journal of Allergy and Clinical Immunology* 2007, 119, 1055-1062 and Drug Discovery Today 2007, 12, 479-486 and the literature cited therein).

Published International Application WO 2005/085202 (Merck) describes compounds of general formula

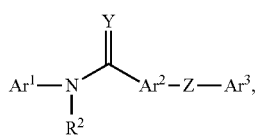

wherein $Ar^1$, $Ar^2$, $Ar^3$, Z, Y and $R^2$ are as defined therein, as inhibitors von tyrosine- and Raf-kinases that can be used inter alia for the treatment of diseases caused, mediated and/or propagated by angiogenesis.

Published International Application WO 2005/086904 (Amgen) claims compounds of general formula

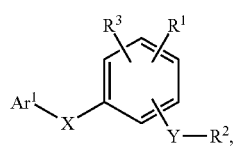

wherein $R^1$, $R^2$, $R^3$, X, Y and $Ar^1$ are as defined therein, as modulators of the PPARγ-receptor.

The inventors are not aware that benzamides of the present general structure have ever been described as inhibitors of the enzyme p38 MAP-kinase.

AIM OF THE INVENTION

The aim of the present invention is to disclose new substituted benzoic acid amides, to particularly those that have an effect on the enzyme p38 MAP-kinase. A further aim of the present invention is to indicate substituted benzoic acid amides that have an inhibitory effect on the enzyme p38 MAP-kinase, in vitro and/or in vivo, and have suitable pharmacological and/or pharmacokinetic properties, in order to be able to use them as medicaments.

A further aim of the present invention is to provide new pharmaceutical compositions which are suitable for the prevention and/or treatment of respiratory complaints, particularly COPD and asthma.

The invention also sets out to provide a process for preparing the compounds according to the invention.

Other objectives of the present invention will be apparent to the skilled man directly from the foregoing remarks and those that follow.

Gegenstand the Invention

In a first aspect the present invention relates to heteroaryloxy-substituted benzoic acid amides of general formula I

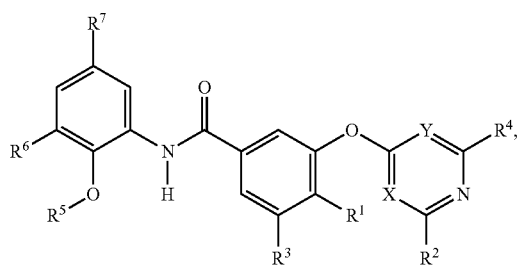

wherein
$R^1$ is $L_1$-$R_8$,
where $L_1$ is selected from a bond, O, CO, NH, CONH, NHCO, SO, $SO_2$, $SO_2NH$, $NHSO_2$ and $C_1$-$C_4$-alkylene,
where $R_8$ is selected from hydrogen, halogen, $C_{1-6}$-alkyl, $C_{2-6}$-alkynyl, $C_{2-6}$-alkenyl, $C_{3-8}$-cycloalkyl, $C_{3-8}$-heterocycloalkyl, $C_{6-10}$-aryl, $C_{5-10}$-heteroaryl, cyano, carboxy, $C_{1-4}$-alkyloxycarbonyl, nitro, amino, di-($C_{1-4}$-alkyl)-amino, hydroxy, $C_{1-6}$-alkylsulphanyl, while $R_8$ may be partly or completely fluorinated and/or may be substituted by one or more substituents L, and
wherein in heterocycloalkyl groups a methylene group may be substituted by CO, SO or $SO_2$, and
wherein $R^1$ is not hydrogen if $R^3$ denotes hydrogen, and
$R^2$ is $L_2$-$R_9$,
wherein $L_2$ is selected from a bond, O, CO, NH, CONH, NHCO, SO, $SO_2$, $SO_2NH$, $NHSO_2$ and $C_1$-$C_4$-alkylene
wherein $R_9$ is selected from hydrogen, halogen, $C_{1-6}$-alkyl, $C_{2-6}$-alkynyl, $C_{2-6}$-alkenyl, $C_{3-8}$-cycloalkyl, $C_{4-8}$-cycloalkenyl, $C_{3-8}$-heterocycloalkyl, $C_{6-10}$-aryl, $C_{5-10}$-heteroaryl, cyano, carboxy, $C_{1-4}$-alkyloxycarbonyl, nitro, amino, di-($C_{1-4}$-alkyl)-amino, hydroxy, $C_{1-6}$-alkylsulphanyl,
wherein $R_9$ may be partly or completely fluorinated and/or may be substituted by one or more substituents L, and
wherein in the alkyl groups mentioned optionally one or two $CH_2$ groups may be exchanged for O and/or $NR^N$,
wherein in the cycloalkyl groups mentioned one or two $CH_2$ groups may be replaced independently of one another by $NR^N$, O, S, CO, SO or $SO_2$ and one or two CH groups may be replaced by N, and $R^3$ is $L_3-R_{10}$ wherein $L_3$ is selected from a bond, O, CO, NH, CONH, NHCO, SO, $SO_2$, $SO_2NH$, $NHSO_2$ and $C_1-C_4$-alkylene wherein $R_{10}$ is selected from hydrogen, halogen, $C_{1-6}$-alkyl, $C_{2-6}$-alkynyl, $C_{2-6}$-alkenyl, $C_{3-8}$-cycloalkyl, $C_{4-8}$-cycloalkenyl, $C_{3-8}$-heterocycloalkyl, $C_{5-10}$-aryl, $C_{5-10}$-heteroaryl, cyano, carboxy, $C_{1-4}$-alkyloxycarbonyl, nitro, amino, di-($C_{1-4}$-alkyl)-amino, hydroxy, $C_{1-6}$-alkylsulphanyl wherein $R_{10}$ may be partly or completely fluorinated and/or may be substituted by one or more substituents L, and wherein $R^3$ is not hydrogen if $R^1$ denotes hydrogen, $R^4$ is $L_4-R_{11}$ wherein $L_4$ is selected from a bond, O, CO, NH, CONH, NHCO, wherein $R_{11}$ is selected from hydrogen, halogen, amino, $C_{1-6}$-alkyl, $C_{3-8}$-cycloalkyl, $C_{3-8}$-heterocycloalkyl, trifluoromethyl, difluoromethyl, cyano, carboxy, $C_{1-4}$-alkyloxycarbonyl, di-($C_{1-4}$-alkyl)-amino, $C_{1-4}$-alkylsulphanyl, $R^5$ is $C_{1-6}$-alkyl, $R^6$ is $L_5-R_{12}$, wherein $L_5$ is selected from a bond, NH, $C_{1-3}$-alkene-NH, NHCO, CONH, wherein $R_{12}$ is $C_{1-6}$-alkyl, NH—($C_{1-3}$-alkyl)$_2$, $C_{3-8}$-cycloalkyl, $C_{3-8}$-heterocycloalkyl, OH, $C_{1-4}$-alkylsulphanyl, $C_{1-4}$-alkylsulphinyl, $C_{1-4}$-alkylsulphonyl, $C_{3-8}$-cycloalkylsulphonylamino, $R^7$ is $C_{1-6}$-alkyl, trifluoromethyl, pentafluoroethyl, X,Y independently of one another denote N or C—$R_{13}$, wherein X and Y cannot both be N and $R_{13}$ is selected from hydrogen, fluorine, chlorine, $C_{1-4}$-alkyl, trifluoromethyl, OH, $C_{1-4}$-alkyloxy, trifluoromethoxy, difluoromethoxy and cyano, $R^N$ is selected from H, $C_{1-4}$-alkyl, 1,1,1-trifluoroethyl, cyanmethyl, acetyl, methylsulphonyl, $C_{6-10}$-arylmethyl, L is selected from among halogen, cyano, $C_{1-6}$-alkyl, $C_{1-6}$-alkyloxy, amino, $C_{1-3}$-alkylamino, di-($C_{1-3}$-alkyl)-amino, $C_{1-4}$-alkylcarbonylamino, difluoromethyl, $C_{1-4}$-alkylsulphonylamino trifluoromethyl, hydroxy, $C_{1-3}$-alkoxy, difluoromethoxy, trifluoromethoxy, acetylamino, $C_{6-10}$-aryl and $C_{5-10}$-heteroaryl.

In a preferred embodiment $R^1$ is selected from hydrogen, halogen, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{6-10}$-aryl, $C_{3-10}$-heteroaryl, $C_{6-10}$-aryl-$C_{1-3}$-alkyl, $C_{3-13}$-heteroaryl-$C_{1-3}$-alkyl, $C_{1-4}$-alkylcarbonyl, cyano, aminocarbonyl, $C_{1-4}$-alkyl-aminocarbonyl, di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)-piperazin-1-ylcarbonyl, carboxy, $C_{1-4}$-alkyloxycarbonyl, nitro, amino, $C_{1-4}$-alkylamino, di-($C_{1-3}$-alkyl)-amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-4}$-alkylsulphonylamino, hydroxy, $C_{1-6}$-alkyloxy, $C_{3-7}$-cycloalkyloxy, $C_{6-10}$-aryloxy, $C_{1-4}$-alkylsulphanyl, $C_{1-4}$-alkylsulphinyl and $C_{1-4}$-alkylsulphonyl, wherein alkyl, alkenyl, alkynyl, cycloalkyl and heterocycloalkyl groups may be partly or completely fluorinated and/or mono- or disubstituted by identical or different substituents selected from cyano, hydroxy, $C_{1-3}$-alkyloxy, acetylamino, methylsulphonylamino and $C_{1-3}$-alkyl, and wherein in cycloalkyl groups one or two methylene groups may be substituted independently of one another by O, S, CO, SO or $SO_2$, and wherein in N-heterocycloalkyl groups a methylene group may be substituted by CO or $SO_2$, wherein $R^1$ is not hydrogen if $R^3$ denotes hydrogen, and $R^2$ is selected from hydrogen, $C_{1-8}$-alkyl, $C_{2-6}$-alkenyl, $C_{2-6}$-alkynyl, $C_{3-7}$-cycloalkyl-$C_{1-4}$-alkyl, $C_{1-6}$-alkylcarbonyl-$C_{1-3}$-alkyl, $C_{6-10}$-aryl-$C_{1-4}$-alkyl, $C_{6-10}$-heteroaryl-$C_{1-4}$-alkyl, $C_{3-7}$-cycloalkyl, $C_{1-6}$-alkylcarbonyl, $C_{3-7}$-cycloalkylcarbonyl, cyano, aminocarbonyl, carboxy, amino, $C_{1-4}$-alkylcarbonylamino, $C_{1-4}$-alkylsulphonylamino, $C_{1-4}$-alkyloxy, $C_{6-10}$-aryl, $C_{5-10}$-heteroaryl, hydroxy, wherein all the above-mentioned alkyl, alkenyl, alkynyl and cycloalkyl groups may be partly or completely fluorinated and/or mono-, di- or trisubstituted by identical or different substituents selected from $C_{1-3}$-alkyl, cyano, hydroxy, $C_{1-3}$-alkyloxy, amino, $C_{1-3}$-alkylamino, di-($C_{1-3}$-alkyl)amino, acetylamino, methylsulphonylamino, $C_{6-10}$-aryl and $C_{5-10}$-heteroaryl, wherein in the alkyl groups mentioned one or two $CH_2$ groups may optionally be exchanged for O and/or $NR^N$, wherein in the cycloalkyl groups mentioned one or two $CH_2$ groups may be replaced independently of one another by $NR^N$, O, S, CO, SO or $SO_2$ and one or two CH groups may be replaced by N, and $R^3$ is selected from hydrogen, halogen, $C_{1-4}$-alkyl, $C_{2-6}$-alkynyl, $C_{2-6}$-alkenyl, $C_{3-7}$-cycloalkyl-$C_{1-3}$-alkyl, $C_{3-6}$-cycloalkyl, trifluoromethyl, difluoromethyl, hydroxy, $C_{1-4}$-alkyloxy, trifluoromethoxy, difluoromethoxy, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, $C_{1-4}$-alkylcarbonylamino, $C_{1-4}$-alkylsulphonylamino, wherein $R^3$ is not hydrogen if $R^1$ denotes hydrogen, $R^4$ is selected from hydrogen, $C_{1-4}$-alkyl, $C_{3-6}$-cycloalkyl, trifluoromethyl, difluoromethyl, cyano, carboxy, aminocarbonyl, $C_{1-3}$-alkylaminocarbonyl, di-($C_{1-3}$-alkyl)aminocarbonyl, $C_{1-4}$-alkyloxycarbonyl, amino, $C_{1-3}$-alkylamino, di-($C_{1-3}$-alkyl)amino, hydroxy, $C_{1-4}$-alkyloxy, $C_{1-4}$-alkylsulphanyl, $R^5$ is $C_{1-4}$-alkyl, $R^6$ is selected from amino-$C_{1-3}$-alkyl, $C_{1-3}$-alkylamino-$C_{1-3}$-alkyl, di-($C_{1-3}$-alkyl)amino-$C_{1-3}$-alkyl, $C_{3-6}$-cyclo-alkylamino-$C_{1-3}$-alkyl, azetidin-1-yl-$C_{1-3}$-alkyl, pyrrolidin-1-yl-$C_{1-3}$-alkyl, piperidin-1-yl-$C_{1-3}$-alkyl, hydroxy-$C_{1-3}$-alkyl, $C_{1-3}$-alkylsulphanyl-$C_{1-3}$-alkyl, $C_{1-3}$-alkylsulphinyl-$C_{1-3}$-alkyl, $C_{1-3}$-alkylsulphonyl-$C_{1-3}$-alkyl, $C_{1-6}$-alkylcarbonylamino, $C_{3-6}$-cycloalkylcarbonylamino, $C_{1-6}$-alkylsulphonylamino, $C_{3-6}$-cycloalkylsulphonylamino, $C_{1-4}$-alkylsulphinyl, $C_{1-4}$-alkylsulphonyl, $R^7$ is selected from $C_{4}$-alkyl, trifluoromethyl, pentafluoroethyl, X,Y independently of one another denote N or $CR_{13}$, wherein X and Y cannot both represent N and $R_{13}$ is selected from hydrogen, fluorine, chlorine, $C_{1-4}$-alkyl, trifluoromethyl, hydroxy, $C_{1-4}$-alkyloxy, trifluoromethoxy, difluoromethoxy, cyano, $R^N$ is selected from H, $C_{1-4}$-alkyl, 1,1,1-trifluoroethyl, cyanomethyl, acetyl, methylsulphonyl, $C_{6-10}$-arylmethyl, L selected from among fluorine, chlorine, bromine, $C_{1-3}$-alkyl, difluoromethyl, trifluoromethyl, hydroxy, $C_{1-3}$-alkoxy, difluoromethoxy, trifluoromethoxy, acetylamino, methylsulphonylamino and cyano, wherein by the $C_{5-10}$-aryl groups mentioned in the definition of the above groups are meant phenyl or naphthyl groups, which may be mono- or disubstituted independently of one another by identical or different groups L; and by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group is meant, wherein one or two methyne groups are replaced by nitrogen atoms, or an indolyl, benzofuranyl, benzothiophenyl, quinolinyl or isoquinolinyl group is meant, wherein one to three methyne groups are replaced by nitrogen atoms, wherein the above-mentioned heteroaryl groups may be mono- or disubstituted independently of one another by identical or different groups L;

wherein, unless stated otherwise, the above-mentioned alkyl groups may be straight-chain or branched, the tautomers, the stereoisomers, the mixtures and the salts thereof, particularly the physiologically acceptable salts thereof.

In another preferred embodiment
$R^1$ is selected from hydrogen, fluorine, chlorine, bromine, $C_{1-4}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, pyrrolidin-1-yl, piperidin-1-yl, morpholin-4-yl, acetylamino, methylsulphonylamino, hydroxy, $C_{1-4}$-alkyloxy, trifluoromethoxy, difluoromethoxy and $C_{1-4}$-alkylsulphonyl,
wherein the above-mentioned alkyl, cycloalkyl and N-heterocycloalkyl groups may be mono- or disubstituted by identical or different substituents selected from cyano, hydroxy, $C_{1-3}$-alkyloxy, acetylamino, methylsulphonylamino and $C_{1-3}$-alkyl, and wherein in the cycloalkyl groups mentioned one or two methylene groups may be substituted independently of one another by O, CO or $SO_2$ and in the above-mentioned N-heterocycloalkyl groups a methylene group may be substituted by CO or $SO_2$, and wherein $R^1$ is not hydrogen if $R^3$ denotes hydrogen.

In another preferred embodiment
$R^1$ is selected from hydrogen, fluorine, chlorine, bromine, $C_{1-4}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, pyrrolidin-1-yl, piperidin-1-yl, morpholin-4-yl, acetylamino, methylsulphonylamino, hydroxy, $C_{1-4}$-alkyloxy, trifluoromethoxy, difluoromethoxy and $C_{1-4}$-alkylsulphonyl, wherein $R^1$ is not hydrogen if $R^3$ denotes hydrogen.

In another preferred embodiment
$R^1$ is selected from hydrogen, fluorine, chlorine, bromine, methyl, ethyl and trifluoromethyl, wherein $R^1$ is not hydrogen if $R^3$ denotes hydrogen.

In another preferred embodiment
$R^2$ is selected from hydrogen, $C_{1-4}$-alkyl, $C_{3-6}$-cycloalkyl-$C_{1-3}$-alkyl, $C_{1-3}$-alkyl-amino-$C_{1-3}$-alkyl, $C_{3-6}$-cycloalkylamino-$C_{1-3}$-alkyl, pyrrolidinyl-$C_{1-3}$-alkyl, piperidin-$C_{1-3}$-alkyl, azepanyl-$C_{1-3}$-alkyl, piperazinyl-$C_{1-3}$-alkyl, morpholinyl-$C_{1-3}$-alkyl, homopiperazinyl-$C_{1-3}$-alkyl, pyrrolidin-3-ylamino-$C_{1-3}$-alkyl, piperidin-3-ylamino-$C_{1-3}$-alkyl, piperidin-4-ylamino-$C_{1-3}$-alkyl, $C_{3-6}$-cycloalkyl, trifluoromethyl,
cyano, aminocarbonyl, $C_{1-4}$-alkyl-aminocarbonyl, di-($C_{1-3}$-alkyl)-aminocarbonyl, piperazin-1-ylcarbonyl, morpholin-4-ylcarbonyl, carboxy, $C_{1-4}$-alkyloxycarbonyl,
amino, $C_{1-4}$-alkylamino, $C_{3-6}$-cycloalkylamino, $C_{3-6}$-cycloalkyl-$C_{1-3}$-alkylamino, pyrrolidin-1-yl, piperidin-1-yl, piperazin-1-yl, morpholin-4-yl, $C_{1-3}$-alkyl-amino-$C_{2-3}$-alkylamino, pyrrolidin-3-ylamino, piperidin-3-ylamino, piperidin-4-ylamino, pyrrolidinyl-$C_{1-3}$-alkyl-amino, piperidin-$C_{1-3}$-alkyl-amino, piperazinyl-$C_{1-3}$-alkyl-amino, morpholinyl-$C_{1-3}$-alkyl-amino, homopiperazinyl-$C_{1-3}$-alkyl-amino, acetylamino, methylsulphonylamino,
hydroxy, $C_{1-4}$-alkyloxy, trifluoromethoxy, difluoromethoxy, $C_{3-6}$-cycloalkyloxy, $C_{3-6}$-cycloalkyl-$C_{1-3}$-alkyloxy, $C_{1-3}$-alkylamino-$C_{2-3}$-alkyloxy, di-($C_{1-3}$-alkyl)-amino-$C_{2-3}$-alkyloxy, pyrrolidinyl-$C_{2-3}$-alkyloxy, piperidin-$C_{2-3}$-alkyloxy, piperazinyl-$C_{2-3}$-alkyloxy, morpholinyl-$C_{2-3}$-alkyloxy, homopiperazinyl-$C_{2-3}$-alkyloxy,
wherein the above mentioned alkyl, cycloalkyl and N-heterocycloalkyl groups may be mono- or disubstituted by identical or different substituents selected from $C_{1-3}$-alkyl, cyano, amino, $C_{1-3}$-alkylamino, di-($C_{1-3}$-alkyl)amino, acetylamino, methylsulphonylamino, hydroxy and $C_{1-3}$-alkyloxy, and
wherein in the above mentioned cycloalkyl groups one or two methylene groups may be substituted independently of one another by O and/or CO and in the above-mentioned N-heterocycloalkyl groups a methylene group may be substituted by CO or $SO_2$, and wherein optional all the NH groups contained in the above mentioned groups are replaced by N-Me, N-Et, N-iPr, N-acetyl and N—$SO_2$Me.

In another preferred embodiment
$R^2$ is selected from hydrogen, $C_{1-4}$-alkyl, $C_{1-3}$-alkylamino-$C_{1-3}$-alkyl, tetrahydrofuran-3-ylamino-$C_{1-3}$-alkyl, pyrrolidinyl-$C_{1-3}$-alkyl, piperidinyl-$C_{1-3}$-alkyl, azepanyl-$C_{1-3}$-alkyl, piperazinyl-$C_{1-3}$-alkyl.4-(1,1,1-trifluoroethyl)-piperazin-1-yl-$C_{1-3}$-alkyl, 4-cyanomethyl-piperazin-1-yl-$C_{1-3}$-alkyl, homopiperazinyl-$C_{1-3}$-alkyl, morpholinyl-$C_{1-3}$-alkyl, N-(pyrrolidin-3-yl)-N—($C_{1-3}$-alkyl)-amino-$C_{1-3}$-alkyl, pyrrolidin-3-ylamino-$C_{1-3}$-alkyl, N-[di-($C_{1-3}$-alkyl)amino-$C_{2-3}$-alkyl]-N—($C_{1-3}$-alkyl)-amino-$C_{1-3}$-alkyl,N-[di-($C_{1-3}$-alkyl) amino-$C_{2-3}$-alkyl]-amino-$C_{1-3}$-alkyl, N-(piperidinyl)-N—($C_{1-3}$-alkyl)-amino-$C_{1-3}$-alkyl, piperidinylamino-$C_{1-3}$-alkyl, $C_{1-3}$-alkyl-aminocarbonyl, piperazin-1-ylcarbonyl, morpholin-4-ylcarbonyl, amino, $C_{1-3}$-alkylamino, $C_{5-6}$-cycloalkylamino, pyrrolidin-1-yl, piperidin-1-yl, piperazin-1-yl, morpholin-4-yl, pyrrolidin-3-ylamino, N—($C_{1-3}$-alkyl)-N-(pyrrolidin-3-yl)-amino, piperidin-4-ylamino, N—($C_{1-3}$-alkyl)-N-(piperidin-4-yl)-amino, di-($C_{1-3}$-alkyl)-amino-$C_{2-3}$-alkylamino, N-[di-($C_{1-3}$-alkyl)-amino-$C_{2-3}$-alkyl]-N—($C_{1-3}$-alkyl)-amino, pyrrolidin-1-yl-$C_{2-3}$-alkyl-amino, hydroxy-$C_{2-3}$-alkyl-amino, hydroxy,
wherein in the above-mentioned N- and O-heterocycloalkyl groups a $CH_2$ group is optionally replaced by C=O and each of these cyclic groups is optionally substituted by a group selected from $C_{1-3}$-alkyl, amino, $C_{1-3}$-alkyl-amino, di-($C_{1-3}$-alkyl)-amino and hydroxy.

In another preferred embodiment
$R^2$ is selected from hydrogen, methyl, methylaminomethyl, 3-hydroxypyrrolidin-1-ylmethyl, 3-dimethylaminopyrrolidin-1-ylmethyl, N-(1-methylpyrrolidin-3-yl)-N-methyl-aminomethyl, piperidin-4-ylmethyl, N-methyl-piperidin-4-ylmethyl, azepan-4-ylmethyl, 1-methyl-azepan-4-ylmethyl, N-(2-dimethylaminoethyl)-N-methyl-aminomethyl, N-(2-dimethyl-aminoethyl)-aminomethyl, N-(1-methylpyrrolidin-3-yl)-aminomethyl, 1-methylpiperidin-4-ylaminomethyl, 1-methylpiperidin-3-yl-aminomethyl, piperazin-1-ylmethyl, 4-methyl-piperazin-1-ylmethyl, 4-(1,1,1-trifluoroethyl)-piperazin-1-ylmethyl, 4-cyanomethyl-piperazin-1-ylmethyl, piperazin-2-one-4-ylmethyl, morpholin-4-ylmethyl, tetrahydrofuran-3-ylaminomethyl, homo-piperazin-1-ylmethyl, 4-methylhomopiperazin-1-ylmethyl, methylaminocarbonyl, piperazin-1-ylcarbonyl, 4-methylpiperazin-1-ylcarbonyl, morpholin-4-ylcarbonyl, methylamino, 4-dimethylaminocyclohexyl-amino, 3-dimethylamino-pyrrolidin-1-yl, pyrrolidin-3-ylamino, N-methyl-N-pyrrolidin-3-yl-amino, N-methyl-N-(1-methylpyrrolidin-3-yl)-amino, piperidin-4-ylamino, 1-methyl-piperidin-4-ylamino, N-methyl-N-piperidin-4-yl-amino, 4-dimethylamino-piperidin-1-yl, piperazin-1-yl, piperazin-2-one-4-yl, morpholin-4-yl, 2-(dimethylamino)ethyl-amino, 2-(pyrrolidin-1-yl)ethylamino, 2-hydroxy-ethylamino, N-(2-dimethylaminoethyl)-N-methyl-amino, hydroxy.

In another preferred embodiment $R^3$ is selected from hydrogen, $C_{1-3}$-alkyl, $C_{3-6}$-cycloalkyl, fluorine, chlorine, bromine, trifluoromethyl, difluoromethyl, hydroxy, $C_{1-3}$-alkyloxy, trifluoromethoxy, difluoromethoxy and cyano, wherein $R^3$ is not hydrogen if $R^1$ denotes hydrogen.

In another preferred embodiment $R^3$ is selected from hydrogen, $C_{1-3}$-alkyl, fluorine, chlorine, trifluoromethyl, $C_{1-3}$-alkyloxy and cyano, wherein $R^3$ is not hydrogen if $R^1$ denotes hydrogen.

In another preferred embodiment $R^3$ is selected from hydrogen, methyl, fluorine and chlorine, wherein $R^3$ is not hydrogen if $R^1$ denotes hydrogen.

In another preferred embodiment $R^4$ is selected from hydrogen, $C_{1-3}$-alkyl, trifluoromethyl, carboxy, aminocarbonyl, methylaminocarbonyl, dimethylamino-carbonyl, amino, $C_{1-3}$-alkylamino, hydroxy and $C_{1-3}$-alkyloxy In another preferred embodiment $R^4$ is selected from hydrogen, methyl, dimethylamino, hydroxy and methoxy.

In another preferred embodiment $R^4$ is hydrogen.

In another preferred embodiment $R^5$ is selected from methyl, ethyl, n-propyl and isopropyl.

In another preferred embodiment $R^5$ is selected from methyl, ethyl and isopropyl.

In another preferred embodiment $R^5$ is methyl.

In another preferred embodiment $R^6$ is selected from dimethylamino-$C_{1-3}$-alkyl, cyclopropylamino-$C_{1-3}$-alkyl, pyrrolidinyl-$C_{1-3}$-alkyl, hydroxy-$C_{1-3}$-alkyl, methylsulphanyl-$C_{1-3}$-alkyl, methylsulphinyl-$C_{1-3}$-alkyl, methylsulphonyl-$C_{1-3}$-alkyl, $C_{1-4}$-alkylcarbonylamino, $C_{3-5}$-cycloalkyl-carbonylamino, $C_{1-4}$-alkylsulphonylamino, $C_{3-5}$-cycloalkylsulphonylamino, $C_{1-3}$-alkylsulphinyl and $C_{1-3}$-alkylsulphonyl.

In another preferred embodiment $R^6$ is selected from dimethylaminomethyl, cyclopropylaminomethyl, pyrrolidin-1-ylamino, hydroxymethyl, methylsulphanylmethyl, methylsulphinylmethyl, methylsulphonylmethyl, n-butylcarbonylamino, isopropylcarbonyl-amino, isobutylcarbonylamino, cyclopropylcarbonylamino, methylsulphonylamino, isopropylsulphonylamino, n-butylsulphonylamino, isobutylsulphonyl-amino, cyclopropyl-sulphonylamino, methylsulphinyl and methylsulphonyl.

In another preferred embodiment $R^6$ is methylsulphonylamino.

In another preferred embodiment $R^7$ is selected from isobutyl, tert-butyl, trifluoromethyl and pentafluoroethyl.

In another preferred embodiment $R^7$ is selected from tert-butyl, trifluoromethyl and pentafluoroethyl.

In another preferred embodiment $R^7$ is tert-butyl.

In another preferred embodiment X and Y independently of one another are selected from N, C—H, C—F, C—Cl, C—$C_{1-3}$-alkyl and $C_{1-3}$-alkyloxy, with the restriction that X and Y cannot both denote N.

In another preferred embodiment X and Y are independently of one another selected from N, C—H, C—F and C-Me, with the restriction that X and Y cannot both represent N.

In another preferred embodiment X and Y are CH and CH, N and CH or CH and N.

The compounds of general formula I according to the invention and the physiologically acceptable salts thereof have valuable pharmacological properties, particularly an inhibitory effect on the enzyme p38 MAP-kinase.

The present invention also relates to the physiologically acceptable salts of the compounds according to the invention with inorganic or organic acids. The invention relates to the respective compounds of formula I in the form of the pharmacologically acceptable salts thereof. These pharmacologically acceptable salts of the compounds of formula I may also be present in the form of their respective hydrates (e.g. monohydrates, dehydrates, etc.) as well as in the form of their respective solvates. By a hydrate of the compound according to formula I is meant, within the scope of the invention, a crystalline salt of the compound according to formula I containing water of crystallisation. By a solvate of the compound according to formula I is meant within the scope of the invention a crystalline salt of the compound according to formula I that contains molecules of solvent (e.g. ethanol, methanol, etc) in the crystal lattice. The skilled man will be familiar with standard methods of obtaining hydrates and solvates (e.g. recrystallisation from the corresponding solvent or from water).

Therefore the use of the compounds according to the invention, including the physiologically acceptable salts, as pharmaceutical compositions is also an object of this invention.

This invention further relates to medicaments containing at least one compound according to the invention or a physiologically acceptable salt according to the invention, optionally together with one or more inert carriers and/or diluents.

The invention also relates to the use of at least one compound according to the invention or a physiologically acceptable salt of such a compound for preparing a medicament that is suitable for the treatment or prevention of diseases or conditions that can be influenced by inhibiting the enzyme p38 MAP-kinase.

This invention further relates to the use of at least one compound according to the to invention for preparing a pharmaceutical composition that is suitable for treating respiratory complaints.

This invention further relates to the use of at least one compound according to the invention for preparing a pharmaceutical composition for inhibiting the enzyme p38 MAP-kinase.

This invention also relates to a process for preparing a medicament according to the invention, characterised in that a compound according to the invention is incorporated in one or more inert carriers and/or diluents by a non-chemical method.

The present invention also relates to a process for preparing the compounds of general formula I according to the invention, characterised in that a) in order to prepare compounds of general formula I, which is defined as hereinbefore and hereinafter,
a compound of general formula II,

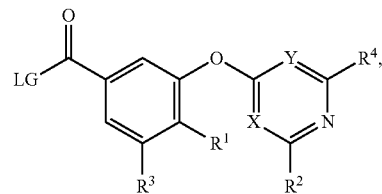

wherein $R^1$ to $R^4$, X and Y have the meanings given in claims 1 to 14 and 24 to 28 and LG denotes fluorine, chlorine, bromine, cyano, $C_{1-10}$-alkoxy, $C_{1-6}$-alkylsulphanyl, $C_{2-4}$-alkenyl-oxy, $C_{2-4}$-alkynyloxy, benzotriazol-1-yloxy, [1.2.3]triazolo[4,5-b]pyridin-3-yloxy, $C_{5-10}$-heteroaryl (linked to II via N), succinyl-N-oxy, $C_{1-4}$-alkylcarbonyloxy, di-($C_{1-4}$-alkyl)aminocarbonyloxy, pyrrol-1-ylcarbonyloxy, piperidin-1-ylcarbonyloxy, morpholin-4-ylcarbonyloxy, tri-($C_{1-4}$-alkyl)carbamimidoyloxy, N,N,N',N'-tetra-($C_{1-4}$-alkyl)-uronium- O-yl, N,N'-dicyclohexyluron-O-yl, N-(3-dimethylaminopropyl)-N'-ethyl-uronyl, di-($C_{1-4}$-alkyloxy)-phosphoryloxy, bis(di-$C_{1-4}$-alkylamino)-phosphoryloxy, dipyrrolidinyl-phosphoryloxy, $C_{6-10}$-arylsulphanyl, $C_{5-10}$-heteroarylsulphanyl, $C_{6-10}$-aryloxy or $C_{5-10}$-heteroaryloxy, wherein all the alkyl, alkenyl and alkynyl groups mentioned in the definition may be mono- or polysubstituted by fluorine, chlorine, $C_{1-3}$-alkyl and/or $C_{1-3}$-alkoxy, wherein all the aryl groups mentioned in the definition represent phenyl or naphthyl and all the heteroaryl groups represent pyridinyl, pyrimidinyl, triazinyl, imidazolyl, pyrazolyl, triazolyl or tetrazolyl, which, both aryl and heteroaryl groups, are optionally mono- or polysubstituted by identical or different groups selected from among fluorine, chlorine, bromine, $C_{1-3}$-alkyl, $C_{1-3}$-alkyloxy, nitro, cyano and di-($C_{1-3}$-alkyl)amino, is reacted with an aniline of general formula

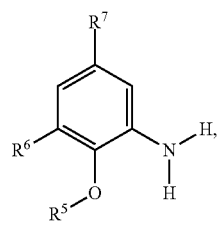

wherein $R^5$, $R^6$ and $R^7$ have the meanings given in claims 1, 2, 15 to 23, 27 and 28, optionally in the presence of a base and/or an additive such as e.g. triethylamine, pyridine, ethyldiisopropylamine, 4-dimethylaminopyridine, potassium carbonate or 1-hydroxybenzotriazole; and if necessary any protecting group used in the reactions described hereinbefore under a) and b) is cleaved again, and/or if desired a compound of general formula I thus obtained is resolved into its stereoisomers and/or if desired a compound of general formula I thus obtained is converted into the salts thereof, particularly for pharmaceutical use into the physiologically acceptable salts thereof.

In a preferred embodiment of the method a compound of general formula III

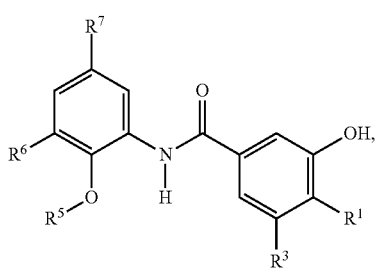

wherein $R^1$, $R^3$, $R^5$, $R^6$ and $R^7$ have the meanings given in claims 1 to 5, 9 to 11, 15 to 23, 27 and 28, is reacted with a compound of general formula IV

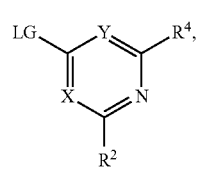

wherein $R^2$ and $R^4$ have the meanings given in claims 1, 2, 6 to 8, 12 to 14, 24 to 26, 27 and 28 and LG denotes a leaving group, in particular LG denotes F, Cl, Br, I, O—$C_{1-6}$-alkyl, O—$C_{6-10}$-aryl, S(O)$_n$—$C_{1-4}$-alkyl, S(O)$_m$—$C_{6-10}$-aryl, OSO$_2$—$C_{1-4}$-alkyl, OSO$_2$—$C_{6-10}$-aryl, NO$_2$, wherein all the above-mentioned alkyl groups are optionally mono- or polysubstituted by fluorine, $C_{1-3}$-alkyl and/or $C_{1-3}$-alkoxy, and wherein all the above-mentioned aryl groups represent phenyl or naphthyl, which may optionally be mono- or polysubstituted by identical or different groups selected from fluorine, chlorine, $C_{1-3}$-alkyl, $C_{1-3}$-alkyloxy, nitro and cyano, wherein n and m independently of one another may be 0, 1 or 2, in the presence of a base, e.g. NaH, KH, KOtBu, NaOtBu, NaOMe, NaOEt, NaOiPr, KF, $K_2CO_3$, $Cs_2CO_3$, pyridine, 4-dimethylaminopyridine, NEt$_3$ or EtNiPr$_2$, optionally in the presence of a catalyst, e.g. a Cu or Pd complex; and if necessary any protecting group used in the reactions described hereinbefore under a) and b) is cleaved again, and/or if desired a compound of general formula I thus obtained is resolved into its stereoisomers and/or if desired a compound of general formula I thus obtained is converted into the salts thereof, particularly for pharmaceutical use into the physiologically acceptable salts thereof.

DETAILED DESCRIPTION OF THE INVENTION

Unless stated otherwise, the groups, residues and substituents, particularly $R^1$ to $R^7$, $R^N$, X, Y and L, have the meanings stated hereinbefore and hereinafter.

If residues, substituents or groups occur several times in a compound, they may have the same or different meanings.

Preferred embodiments of the invention are indicated by the following definitions:

a) The definitions (a$^i$) for $R^1$ in increasing order of preference, starting with preferably (a$^1$) through particularly preferably (a$^2$) to most particularly preferably (a$^3$), are as follows:

(a$^1$): Preferably $R^1$ denotes hydrogen, fluorine, chlorine, bromine, $C_{1-4}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, pyrrolidin-1-yl, piperidin-1-yl, morpholin-4-yl, acetylamino, methylsulphonylamino, hydroxy, $C_{1-4}$-alkyloxy, trifluoromethoxy, difluoromethoxy and $C_{1-4}$-alkylsulphonyl, wherein the above-mentioned alkyl, cycloalkyl and N-heterocycloalkyl groups may be mono- or disubstituted by identical or different substituents selected from cyano, hydroxy, $C_{1-3}$-alkyloxy, acetylamino, methylsulphonylamino and $C_{1-3}$-alkyl, and wherein in the cycloalkyl groups mentioned one or two methylene groups may be substituted independently of one another by O, CO or SO$_2$ and in the above-mentioned N-heterocycloalkyl groups a methylene group may be substituted by CO or $SO_2$ and wherein $R^1$ is not hydrogen if $R^3$ denotes hydrogen.

($a^2$): Particularly preferably $R^1$ denotes hydrogen, fluorine, chlorine, bromine, $C_{1-4}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, pyrrolidin-1-yl, piperidin-1-yl, morpholin-4-yl, acetylamino, methylsulphonylamino, hydroxy, $C_{1-4}$-alkyloxy, trifluoromethoxy, difluoromethoxy and $C_{1-4}$-alkylsulphonyl, wherein $R^1$ is not hydrogen if $R^3$ denotes hydrogen.

($a^3$): Most particularly preferably $R^1$ denotes hydrogen, fluorine, chlorine, bromine, methyl, ethyl and trifluoromethyl, wherein $R^1$ is not hydrogen if $R^3$ denotes hydrogen.

b) The definitions ($b^i$) for $R^2$ in increasing order of preference, starting with preferably ($b^1$) through particularly preferably ($b^2$) to most particularly preferably ($b^3$), are as follows:

($b^1$): Preferably $R^2$ denotes hydrogen, $C_{1-4}$-alkyl, $C_{3-6}$-cycloalkyl-$C_{1-3}$-alkyl, $C_{1-3}$-alkyl-amino-$C_{1-3}$-alkyl, $C_{3-6}$-cycloalkylamino-$C_{1-3}$-alkyl, pyrrolidinyl-$C_{1-3}$-alkyl, piperidin-$C_{1-3}$-alkyl, azepanyl-$C_{1-3}$-alkyl, piperazinyl-$C_{1-3}$-alkyl, morpholinyl-$C_{1-3}$-alkyl, homopiperazinyl-$C_{1-3}$-alkyl, pyrrolidin-3-ylamino-$C_{1-3}$-alkyl, piperidin-3-ylamino-$C_{1-3}$-alkyl, piperidin-4-ylamino-$C_{1-3}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, piperazin-1-ylcarbonyl, morpholin-4-ylcarbonyl, carboxy, $C_{1-4}$-alkyloxycarbonyl, amino, $C_{1-4}$-alkylamino, $C_{3-6}$-cycloalkylamino, $C_{3-6}$-cycloalkyl-$C_{1-3}$-alkylamino, pyrrolidin-1-yl, piperidin-1-yl, piperazin-1-yl, morpholin-4-yl, $C_{1-3}$-alkyl-amino-$C_{2-3}$-alkylamino, pyrrolidin-3-ylamino, piperidin-3-ylamino, piperidin-4-ylamino, pyrrolidinyl-$C_{1-3}$-alkyl-amino, piperidin-$C_{1-3}$-alkyl-amino, piperazinyl-$C_{1-3}$-alkyl-amino, morpholinyl-$C_{1-3}$-alkyl-amino, homopiperazinyl-$C_{1-3}$-alkyl-amino, acetylamino, methylsulphonylamino, hydroxy, $C_{1-4}$-alkyloxy, trifluoromethoxy, difluoromethoxy, $C_{3-6}$-cycloalkyloxy, $C_{3-6}$-cycloalkyl-$C_{1-3}$-alkyloxy, $C_{1-3}$-alkylamino-$C_{2-3}$-alkyloxy, di-($C_{1-3}$-alkyl)-amino-$C_{2-3}$-alkyloxy, pyrrolidinyl-$C_{2-3}$-alkyloxy, piperidin-$C_{2-3}$-alkyloxy, piperazinyl-$C_{2-3}$-alkyloxy, morpholinyl-$C_{2-3}$-alkyloxy, homopiperazinyl-$C_{2-3}$-alkyloxy, wherein the above mentioned alkyl, cycloalkyl and N-heterocycloalkyl groups may be mono- or disubstituted by identical or different substituents selected from $C_{1-3}$-alkyl, cyano, amino, $C_{1-3}$-alkylamino, di-($C_{1-3}$-alkyl)amino, acetylamino, methylsulphonylamino, hydroxy and $C_{1-3}$-alkyloxy, and wherein in the above mentioned cycloalkyl groups one or two methylene groups may be substituted independently of one another by O and/or CO and in the above-mentioned N-heterocycloalkyl groups a methylene group may be substituted by CO or $SO_2$, and wherein optionally all the NH groups contained in the above mentioned groups are replaced by $NR^N$.

($b^2$): Particularly preferably $R^2$ denotes hydrogen, $C_{1-4}$-alkyl, $C_{1-3}$-alkylamino-$C_{1-3}$-alkyl, tetrahydrofuran-3-ylamino-$C_{1-3}$-alkyl, pyrrolidinyl-$C_{1-3}$-alkyl, piperidinyl-$C_{1-3}$-alkyl, azepanyl-$C_{1-3}$-alkyl, piperazinyl-$C_{1-3}$-alkyl, 4-(1,1,1-trifluoroethyl)-piperazin-1-yl-$C_{1-3}$-alkyl, 4-cyanomethyl-piperazin-1-yl-$C_{1-3}$-alkyl, homopiperazinyl-$C_{1-3}$-alkyl, morpholinyl-$C_{1-3}$-alkyl, N-(pyrrolidin-3-yl)-N—($C_{1-3}$-alkyl)-amino-$C_{1-3}$-alkyl, pyrrolidin-3-ylamino-$C_{1-3}$-alkyl, N-[di-($C_{1-3}$-alkyl)amino-$C_{2-3}$-alkyl]-N—($C_{1-3}$-alkyl)-amino-$C_{1-3}$-alkyl, N-[di-($C_{1-3}$-alkyl)amino-$C_{2-3}$-alkyl]-amino-$C_{1-3}$-alkyl, N-(piperidinyl)-N—($C_{1-3}$-alkyl)-amino-$C_{1-3}$-alkyl, piperidinylamino-$C_{1-3}$-alkyl, $C_{1-3}$-alkylaminocarbonyl, piperazin-1-ylcarbonyl, morpholin-4-ylcarbonylamino, $C_{1-3}$-alkylamino, $C_{5-6}$-cycloalkylamino, pyrrolidin-1-yl, piperidin-1-yl, piperazin-1-yl, morpholin-4-yl, pyrrolidin-3-ylamino, N—($C_{1-3}$-alkyl)-N-(pyrrolidin-3-yl)-amino, piperidin-4-ylamino, N—($C_{1-3}$-alkyl)-N-(piperidin-4-yl)-amino, di-($C_{1-3}$-alkyl)-amino-$C_{2-3}$-alkylamino, N-[di-($C_{1-3}$-alkyl)-amino-$C_{2-3}$-alkyl]-N—($C_{1-3}$-alkyl)-amino, pyrrolidin-1-yl-$C_{2-3}$-alkyl-amino, hydroxy-$C_{2-3}$-alkyl-amino, hydroxy, wherein in the above-mentioned heterocycloalkyl groups a $CH_2$ group is optionally replaced by C=O and each of these cyclic groups is optionally substituted by a group selected from $C_{1-3}$-alkyl, amino, $C_{1-3}$-alkyl-amino, di-($C_{1-3}$-alkyl)-amino and hydroxy.

($b^3$): Most particularly preferably $R^2$ denotes hydrogen, methyl, methylaminomethyl, 3-hydroxypyrrolidin-1-ylmethyl, 3-dimethylaminopyrrolidin-1-ylmethyl, N-(1-methylpyrrolidin-3-yl)-N-methyl-aminomethyl, piperidin-4-ylmethyl, N-methyl-piperidin-4-ylmethyl, azepan-4-ylmethyl, 1-methyl-azepan-4-ylmethyl, N-(2-dimethylaminoethyl)-N-methyl-aminomethyl, N-(2-dimethylaminoethyl)-aminomethyl, N-(1-methylpyrrolidin-3-yl)-aminomethyl, 1-methylpiperidin-4-ylaminomethyl, 1-methylpiperidin-3-ylaminomethyl, piperazin-1-ylmethyl, 4-methylpiperazin-1-ylmethyl, 4-(1,1,1-trifluoroethyl)-piperazin-1-ylmethyl, 4-cyanomethyl-piperazin-1-ylmethyl, piperazin-2-one-4-ylmethyl, morpholin-4-ylmethyl, tetrahydrofuran-3-ylaminomethyl, homopiperazin-1-ylmethyl, 4-methylhomopiperazin-1-ylmethyl, methylaminocarbonyl, piperazin-1-ylcarbonyl, 4-methylpiperazin-1-ylcarbonyl, morpholin-4-ylcarbonyl, methylamino, 4-dimethylaminocyclohexyl-amino, 3-dimethylamino-pyrrolidin-1-yl, pyrrolidin-3-ylamino, N-methyl-N-pyrrolidin-3-yl-amino, N-methyl-N-(1-methylpyrrolidin-3-yl)-amino, piperidin-4-ylamino, 1-methyl-piperidin-4-ylamino, N-methyl-N-piperidin-4-yl-amino, 4-dimethylamino-piperidin-1-yl, piperazin-1-yl, piperazin-2-one-4-yl, morpholin-4-yl, 2-(dimethylamino)ethyl-amino, 2-(pyrrolidin-1-yl)ethylamino, 2-hydroxyethylamino, N-(2-dimethylaminoethyl)-N-methyl-amino, hydroxy.

c) The definitions ($c^i$) for $R^3$ in increasing order of preference, starting with preferably ($c^1$) through particularly preferably ($c^2$) to most particularly preferably ($c^3$), are as follows:

($c^1$): Preferably $R^3$ denotes hydrogen, $C_{1-3}$-alkyl, $C_{3-6}$-cycloalkyl, fluorine, chlorine, bromine, trifluoromethyl, difluoromethyl, hydroxy, $C_{1-3}$-alkyloxy, trifluoromethoxy, difluoromethoxy and cyano, wherein $R^3$ is not hydrogen if $R^1$ denotes hydrogen.

($c^2$): Particularly preferably $R^3$ denotes hydrogen, $C_{1-3}$-alkyl, fluorine, chlorine, trifluoromethyl, $C_{1-3}$-alkyloxy and cyano, wherein $R^3$ is not hydrogen if $R^1$ denotes hydrogen.

($c^3$): Most particularly preferably $R^3$ denotes hydrogen, methyl, fluorine, chlorine, wherein $R^3$ is not hydrogen if $R^1$ denotes hydrogen.

d) The definitions ($d^i$) for $R^4$ in increasing order of preference, starting with preferably ($d^1$) through particularly preferably ($d^2$) to most particularly preferably ($d^3$), are as follows:

($d^1$): Preferably $R^4$ denotes hydrogen, $C_{1-3}$-alkyl, trifluoromethyl, carboxy, aminocarbonyl, methylaminocarbonyl, dimethylaminocarbonyl, amino, $C_{1-3}$-alkylamino, di-($C_{1-3}$-alkyl)-amino, hydroxy, $C_{1-3}$-alkyloxy.

($d^2$): Particularly preferably $R^4$ denotes hydrogen, methyl, dimethylamino, hydroxy, methoxy.

($d^3$): Most particularly preferably $R^4$ denotes hydrogen.

e) The definitions ($e^i$) for X and Y (X/Y) in increasing order of preference, starting with preferably ($e^1$) through particularly preferably ($e^2$) to most particularly preferably ($e^3$), are as follows:

(e¹): Preferably X/Y represents CR/CR, N/CR and CR/N, wherein R is hydrogen, fluorine, chlorine, $C_{1-3}$-alkyl and $C_{1-3}$-alkyloxy.

(e²): Particularly preferably X/Y represents CR/CR, N/CR and CR/N, wherein R is hydrogen, fluorine or methyl.

(e³): Most particularly preferably X/Y represents CH/CH, N/CH and CH/N.

f) The definitions (f$^i$) for $R^N$ in increasing order of preference, starting with preferably (f¹) through particularly preferably (f²) to most particularly preferably (f³), are as follows:

(f¹): Preferably $R^N$ denotes hydrogen, methyl, ethyl, isopropyl, acetyl, methylsulphonyl, 1,1,1-trifluoroethyl and cyanomethyl.

(f²): Particularly preferably $R^N$ denotes hydrogen, methyl, acetyl, methylsulphonyl, 1,1,1-trifluoroethyl and cyanomethyl.

(f³): Most particularly preferably $R^N$ denotes hydrogen, methyl, 1,1,1-trifluoroethyl and cyanomethyl.

g) The definitions (g$^i$) for L in increasing order of preference, starting with preferably (g¹) through particularly preferably (g²) to most particularly preferably (g³), are as follows:

(g¹): Preferably L denotes fluorine, chlorine, bromine, $C_{1-3}$-alkyl, difluoromethyl, trifluoromethyl, $C_{1-3}$-alkoxy, difluoromethoxy, trifluoromethoxy, acetylamino and cyano.

(g²): Particularly preferably L denotes fluorine, chlorine, methyl, ethyl, trifluoromethyl, methoxy, acetylamino and cyano.

(g³): Most particularly preferably L denotes fluorine, methyl, methoxy, acetylamino and cyano.

h) The definitions (h$^i$) for $R^5$ in increasing order of preference, starting with preferably (h¹) through particularly preferably (h²) to most particularly preferably (h³), are as follows:

(h¹): Preferably $R^5$ denotes methyl, ethyl, n-propyl and isopropyl.

(h²): Particularly preferably $R^5$ denotes methyl, ethyl and isopropyl.

(h³): Most particularly preferably $R^5$ denotes methyl.

j) The definitions (j$^i$) for $R^6$ in increasing order of preference, starting with preferably (j¹) through particularly preferably (j²) to most particularly preferably (j³), are as follows:

(j¹): Preferably $R^6$ denotes dimethylamino-$C_{1-3}$-alkyl, cyclopropylamino-$C_{1-3}$-alkyl, pyrrolidin-1-yl-$C_{1-3}$-alkyl, hydroxy-$C_{1-3}$-alkyl, methylsulphanyl-$C_{1-3}$-alkyl, methylsulphinyl-$C_{1-3}$-alkyl, methylsulphonyl-$C_{1-3}$-alkyl, $C_{1-4}$-alkylcarbonylamino, $C_{3-5}$-cycloalkylcarbonylamino, $C_{1-4}$-alkylsulphonylamino, $C_{3-5}$-cycloalkylsulphonylamino, $C_{1-3}$-alkylsulphinyl and $C_{1-3}$-alkylsulphonyl.

(j²): Particularly preferably $R^6$ denotes dimethylaminomethyl, cyclopropylaminomethyl, pyrrolidin-1-ylmethyl, hydroxymethyl, methylsulphanylmethyl, methylsulphinylmethyl, methyl-sulphonylmethyl, n-butylcarbonylamino, isopropylcarbonylamino, isobutylcarbonylamino, cyclopropylcarbonylamino, methylsulphonylamino, isopropylsulphonylamino, n-butylsulphonyl-amino, isobutylsulphonylamino, cyclopropylsulphonylamino, methylsulphinyl and methylsulphonyl.

(j³): Most particularly preferably $R^6$ denotes methylsulphonylamino.

k) The definitions (k$^i$) for $R^7$ in increasing order of preference, starting with preferably (k¹) through particularly preferably (k²) to most particularly preferably (k³), are as follows:

(k¹): Preferably $R^7$ denotes isobutyl, tert-butyl, trifluoromethyl and pentafluoroethyl.

(k²): Particularly preferably $R^7$ denotes tert-butyl, trifluoromethyl and pentafluoroethyl.

(k³): Most particularly preferably $R^7$ denotes tert-butyl.

Each a$^i$, b$^i$, c$^i$, d$^i$, e$^i$, g$^i$, h$^i$, j$^i$, k$^i$ represents a defined, individual embodiment of the respective group as shown above. According to the definitions shown hereinbefore each individual preferred embodiment is fully characterised by the expression (a$^i$b$^i$c$^i$d$^i$e$^i$f$^i$g$^i$h$^i$j$^i$k$^i$), while the index i in each case denotes an individual embodiment and the individual indices i are variable independently of one another. All the individual embodiments that are included by the expression in brackets, while the indices i may be varied and combined as desired according to the above definitions, should be encompassed by the present invention.

Table 1 that follows contains a list of the preferred embodiments E-1 to E-14 by way of example, in ascending order of preference from the first row to the last. Accordingly, embodiment E-14, shown in the last row of Table 1, has the highest preference.

TABLE 1

|      | $R^1$ | $R^2$ | $R^3$ | $R^4$ | X/Y | $R^N$ | L   | $R^5$ | $R^6$ | $R^7$ |
|------|-------|-------|-------|-------|-----|-------|-----|-------|-------|-------|
| E-1  | a¹    | b¹    | c¹    | d¹    | e¹  | f¹    | g¹  | h¹    | j¹    | k¹    |
| E-2  | a¹    | b²    | c²    | d²    | e²  | f²    | g²  | h²    | j²    | k²    |
| E-3  | a²    | b¹    | c²    | d²    | e²  | f²    | g²  | h²    | j²    | k²    |
| E-4  | a²    | b²    | c²    | d²    | e²  | f²    | g²  | h²    | j²    | k²    |
| E-5  | a²    | b²    | c³    | d²    | e³  | f³    | g³  | h²    | j²    | k²    |
| E-6  | a²    | b²    | c³    | d³    | e²  | f³    | g³  | h²    | j²    | k²    |
| E-7  | a²    | b²    | c²    | d³    | e³  | f³    | g³  | h²    | j²    | k²    |
| E-8  | a¹    | b¹    | c³    | d³    | e³  | f³    | g³  | h²    | j²    | k²    |
| E-9  | a²    | b¹    | c³    | d³    | e³  | f³    | g³  | h²    | j²    | k²    |
| E-10 | a¹    | b²    | c³    | d³    | e³  | f³    | g³  | h²    | j²    | k²    |
| E-11 | a²    | b²    | c³    | d³    | e³  | f³    | g³  | h²    | j²    | k²    |
| E-12 | a²    | b³    | c³    | d³    | e³  | f³    | g³  | h²    | j²    | k²    |
| E-13 | a³    | b²    | c³    | d³    | e³  | f³    | g³  | h²    | j²    | k²    |
| E-14 | a³    | b³    | c³    | d³    | e³  | f³    | g³  | h³    | j³    | k³    | including the tautomers, the stereoisomers and the mixtures thereof.

Preferred compounds of general formula I are selected from among:

N-(5-tert-butyl-3-methanesulphonylamino-2-methoxy-phenyl)-4-methyl-3-(pyridin-4-yloxy)-benzamide

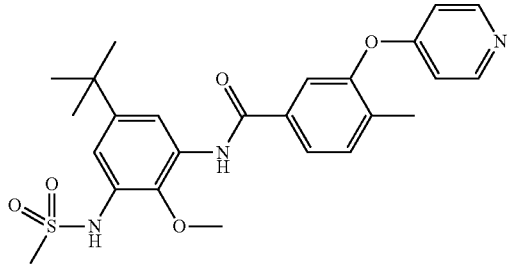 [SMILES: COc1c(NC(=O)c2ccc(C)c(Oc3ccncc3)c2)cc(C(C)(C)C)cc1NS(C)(=O)=O]

N-(5-tert-butyl-3-methanesulphonylamino-2-methoxy-phenyl)-4-methyl-3-(2-methylamino-pyrimidin-4-yloxy)-benzamide

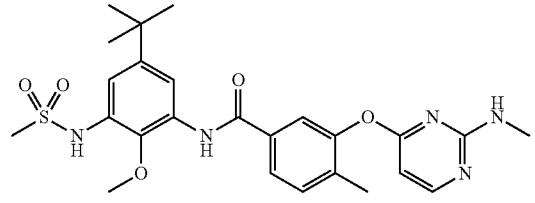

N-(5-tert-butyl-3-methanesulphonylamino-2-methoxy-phenyl)-4-methyl-3-(6-methylamino-pyrimidin-4-yloxy)-benzamide

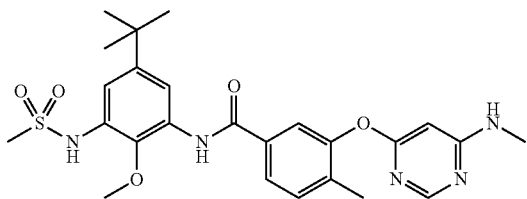

N-(5-tert-butyl-3-methanesulphonylamino-2-methoxy-phenyl)-4-methyl-3-[2-(2-pyrrolidin-1-yl-ethylamino)-pyrimidin-4-yloxy]-benzamide

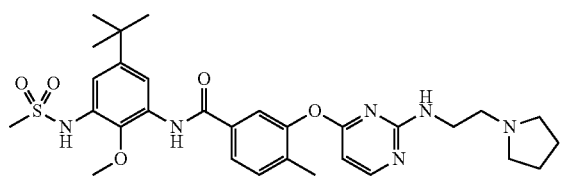 [SMILES: COc1c(NC(=O)c2ccc(C)c(Oc3ccnc(NCCN4CCCC4)n3)c2)cc(C(C)(C)C)cc1NS(C)(=O)=O]

N-(5-tert-butyl-3-methanesulphonylamino-2-methoxy-phenyl)-3-[6-(2-hydroxy-ethylamino)-pyrimidin-4-yloxy]-4-methyl-benzamide

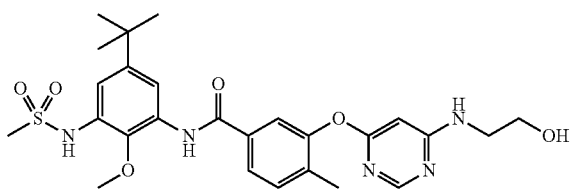 [SMILES: COc1c(NC(=O)c2ccc(C)c(Oc3cc(NCCO)ncn3)c2)cc(C(C)(C)C)cc1NS(C)(=O)=O]

N-(5-tert-butyl-3-methanesulphonylamino-2-methoxy-phenyl)-3-[6-(2-dimethylamino-ethylamino)-pyrimidin-4-yloxy]-4-methyl-benzamide

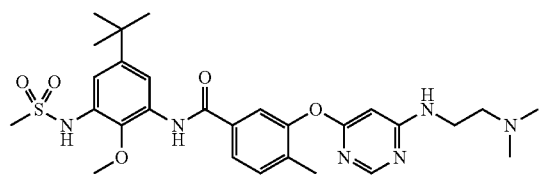

N-(5-tert-butyl-3-methanesulphonylamino-2-methoxy-phenyl)-4-methyl-3-[6-(3-oxo-piperazin-1-O-pyrimidin-4-yloxy]-benzamide

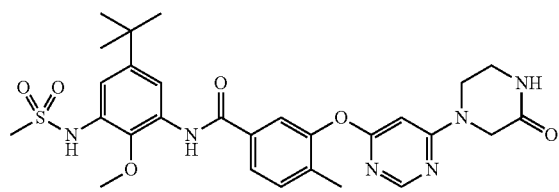 [SMILES: COc1c(NC(=O)c2ccc(C)c(Oc3cc(N4CCNC(=O)C4)ncn3)c2)cc(C(C)(C)C)cc1NS(C)(=O)=O]

N-(5-tert-butyl-3-methanesulphonylamino-2-methoxy-phenyl)-4-methyl-3-(6-pyrrolidin-1-yl-pyrimidin-4-yloxy)-benzamide

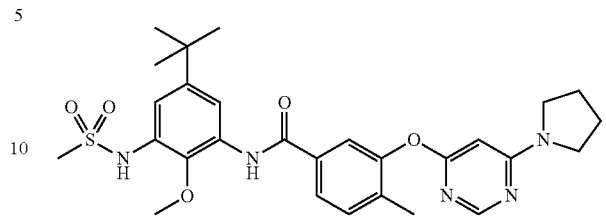

N-(5-tert-butyl-3-methanesulphonylamino-2-methoxy-phenyl)-4-methyl-3-(6-morpholin-4-yl-pyrimidin-4-yloxy)-benzamide

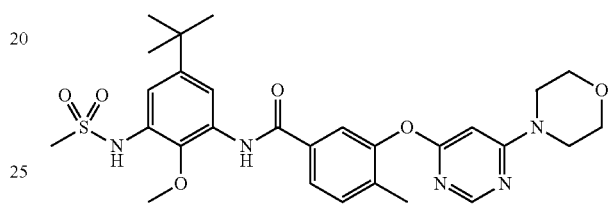

(R)—N-(5-tert-butyl-3-methanesulphonylamino-2-methoxy-phenyl)-3-[2-(3-dimethylamino-pyrrolidin-1-yl)-pyrimidin-4-yloxy]-4-methyl-benzamide

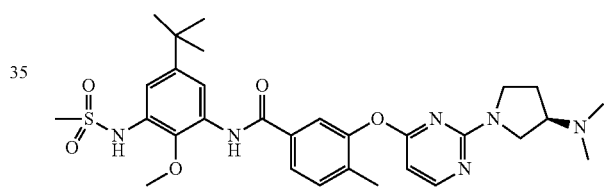

(S)—N-(5-tert-butyl-3-methanesulphonylamino-2-methoxy-phenyl)-3-[2-(3-dimethylamino-pyrrolidin-1-yl)-pyrimidin-4-yloxy]-4-methyl-benzamide

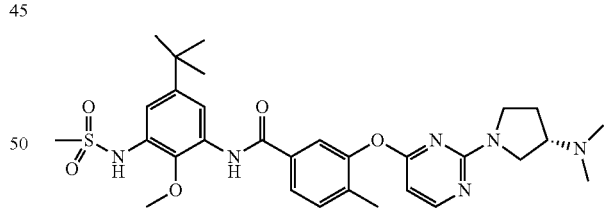

N-(5-tert-butyl-3-methanesulphonylamino-2-methoxy-phenyl)-3-[2-(4-dimethylamino-piperidin-1-yl)-pyrimidin-4-yloxy]-4-methyl-benzamide

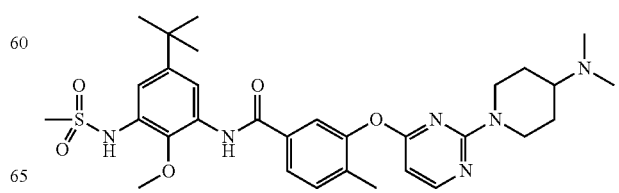

N-(5-tert-butyl-3-methanesulphonylamino-2-methoxy-phenyl)-4-methyl-3-[2-(1-methyl-piperidin-4-ylamino)-pyrimidin-4-yloxy]-benzamide

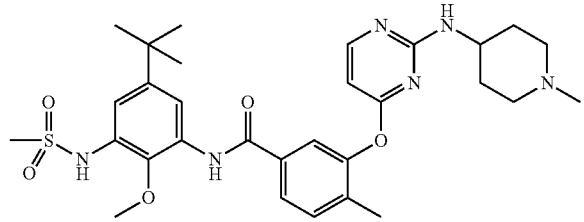

N-(5-tert-butyl-3-methanesulphonylamino-2-methoxy-phenyl)-4-methyl-3-(2-piperazin-1-yl-pyrimidin-4-yloxy)-benzamide

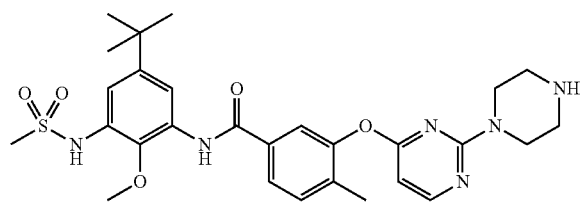 [SMILES: COc1c(NC(=O)c2ccc(C)c(Oc3ccnc(N4CCNCC4)n3)c2)cc(C(C)(C)C)cc1NS(C)(=O)=O]

N-(5-tert-butyl-3-methanesulphonylamino-2-methoxy-phenyl)-4-methyl-3-(6-piperazin-1-yl-pyrimidin-4-yloxy)-benzamide

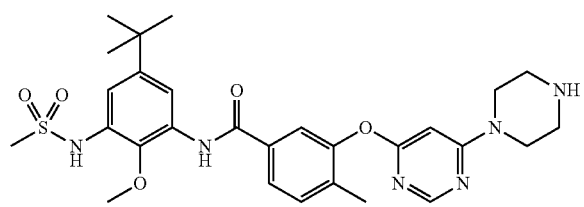 [SMILES: COc1c(NC(=O)c2ccc(C)c(Oc3cc(N4CCNCC4)ncn3)c2)cc(C(C)(C)C)cc1NS(C)(=O)=O]

N-(5-tert-butyl-3-methanesulphonylamino-2-methoxy-phenyl)-4-methyl-3-[6-(piperazine-1-carbonyl)-pyrimidin-4-yloxy]-benzamide

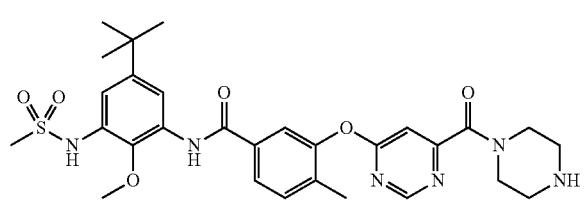 [SMILES: COc1c(NC(=O)c2ccc(C)c(Oc3cc(C(=O)N4CCNCC4)ncn3)c2)cc(C(C)(C)C)cc1NS(C)(=O)=O]

N-(5-tert-butyl-3-methanesulphonylamino-2-methoxy-phenyl)-4-chloro-3-[6-(piperazine-1-carbonyl)-pyrimidin-4-yloxy]-benzamide

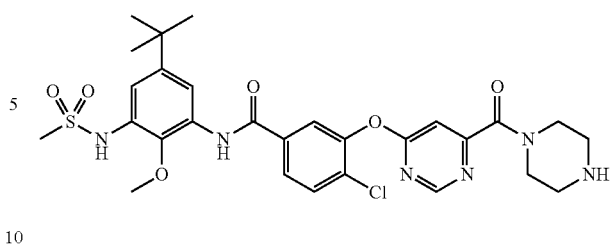

N-(5-tert-butyl-3-methanesulphonylamino-2-methoxy-phenyl)-3-(2-piperazin-1-yl-pyrimidin-4-yloxy)-4-trifluoromethyl-benzamide

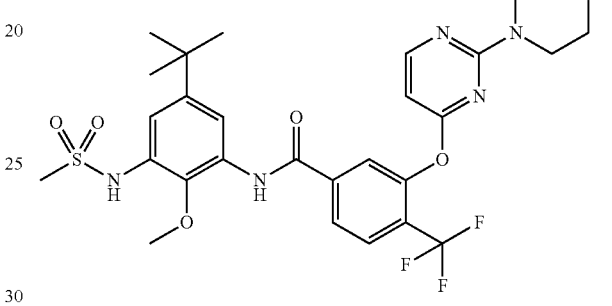

N-(5-tert-butyl-3-methanesulphonylamino-2-methoxy-phenyl)-4-chloro-3-(2-piperazin-1-yl-pyrimidin-4-yloxy)-benzamide

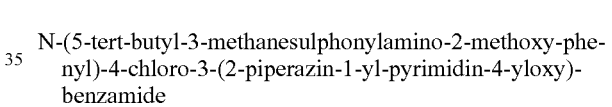

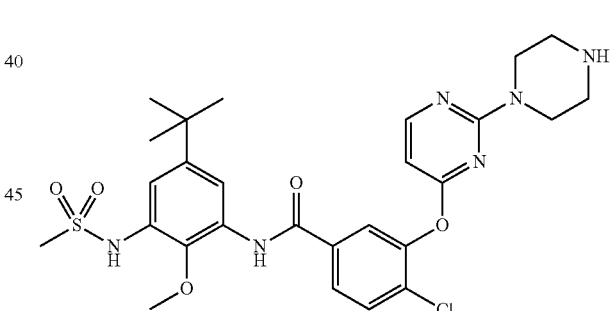

N-(5-tert-butyl-3-methanesulphonylamino-2-methoxy-phenyl)-4-methyl-3-(2-piperazin-1-ylmethyl-pyrimidin-4-yloxy)-benzamide

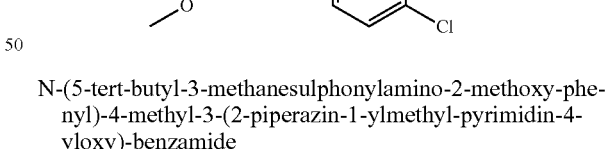

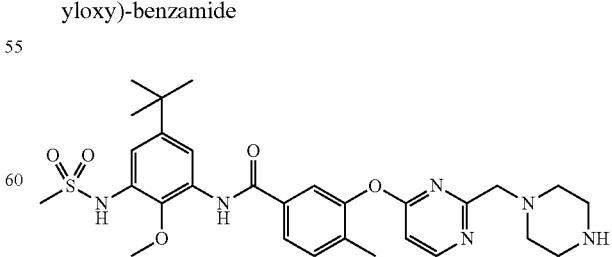

N-(5-tert-butyl-3-methanesulphonylamino-2-methoxy-phenyl)-4-methyl-3-(6-piperazin-1-ylmethyl-pyrimidin-4-yloxy)-benzamide

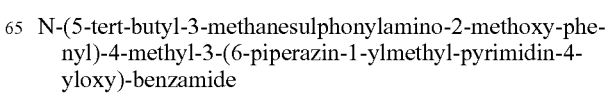

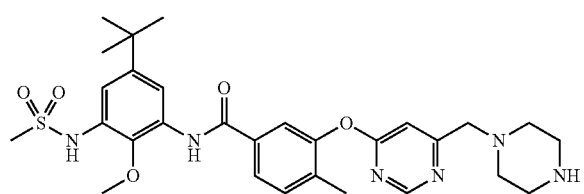

N-(5-tert-butyl-3-methanesulphonylamino-2-methoxy-phenyl)-4-methoxy-3-(2-piperazin-1-yl-pyrimidin-4-yloxy)-benzamide

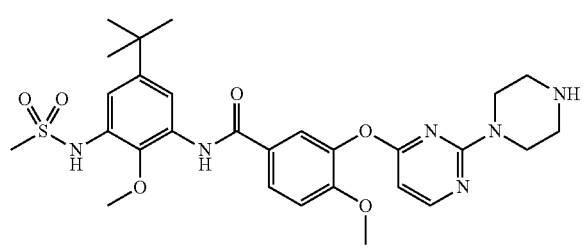 [SMILES: COc1ccc(C(=O)Nc2cc(C(C)(C)C)cc(NS(C)(=O)=O)c2OC)cc1Oc1ccnc(N2CCNCC2)n1]

N-(5-tert-butyl-3-methanesulphonylamino-2-methoxy-phenyl)-4-methyl-3-(2-piperazin-1-ylmethyl-pyridin-4-yloxy)-benzamide

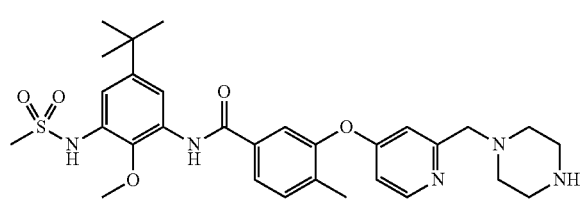

N-(5-tert-butyl-3-methanesulphonylamino-2-methoxy-phenyl)-4-fluoro-3-(2-piperazin-1-yl-pyrimidin-4-yloxy)-benzamide

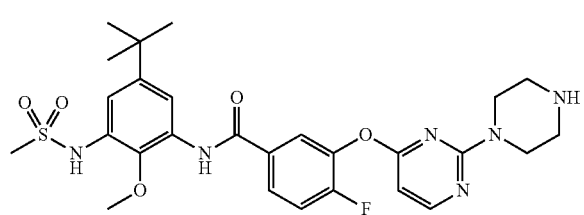 [SMILES: COc1c(NC(=O)c2ccc(F)c(Oc3ccnc(N4CCNCC4)n3)c2)cc(C(C)(C)C)cc1NS(C)(=O)=O]

N-(5-tert-butyl-3-methanesulphonylamino-2-methoxy-phenyl)-4-bromo-3-(2-piperazin-1-yl-pyrimidin-4-yloxy)-benzamide

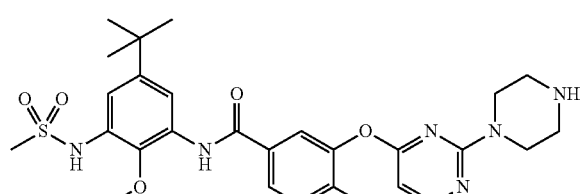

N-(5-tert-butyl-3-methanesulphonylamino-2-methoxy-phenyl)-3-chloro-4-methyl-5-(2-piperazin-1-yl-pyrimidin-4-yloxy)-benzamide

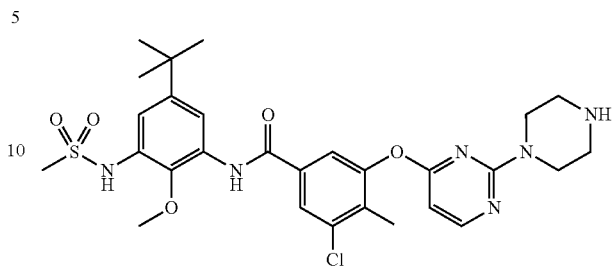

N-(5-tert-butyl-3-methanesulphonylamino-2-methoxy-phenyl)-3-fluoro-4-methyl-5-(2-piperazin-1-yl-pyrimidin-4-yloxy)-benzamide

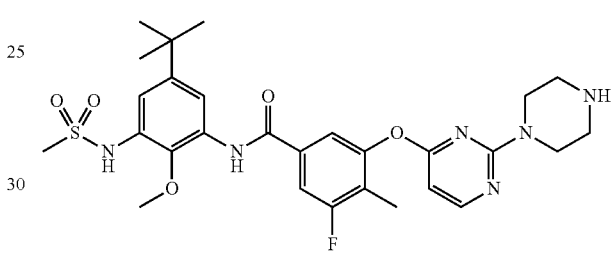

N-(5-tert-butyl-3-methanesulphonylamino-2-methoxy-phenyl)-4-methyl-3-[2-(N-methyl-N-piperidin-4-yl-amino)-pyrimidin-4-yloxy]-benzamide

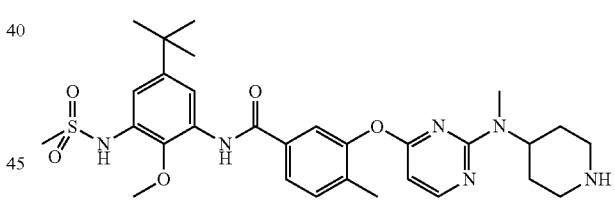

N-(5-tert-butyl-3-methanesulphonylamino-2-methoxy-phenyl)-4-ethyl-5-(2-piperazin-1-yl-pyrimidin-4-yloxy)-benzamide

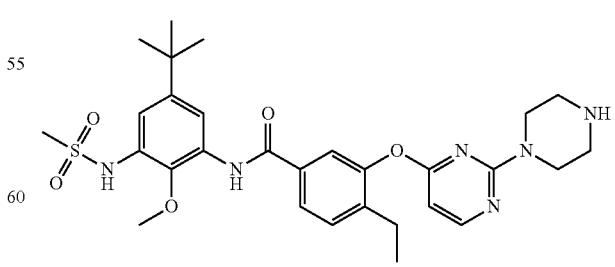

N-(5-tert-butyl-3-methanesulphonylamino-2-methoxy-phenyl)-4-methyl-3-[2-(piperidin-4-ylamino)-pyrimidin-4-yloxy]-benzamide

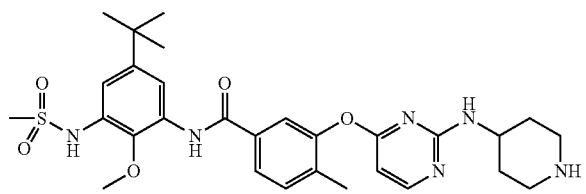 [SMILES: COc1c(NC(=O)c2ccc(C)c(Oc3ccnc(NC4CCNCC4)n3)c2)cc(C(C)(C)C)cc1NS(C)(=O)=O]

N-(5-tert-butyl-3-methanesulphonylamino-2-methoxy-phenyl)-4-methyl-3-[6-(piperidin-4-ylamino)-pyrimidin-4-yloxy]-benzamide

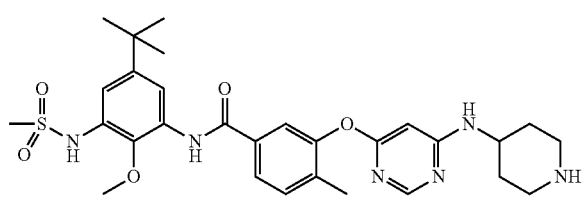 [SMILES: COc1c(NC(=O)c2ccc(C)c(Oc3cc(NC4CCNCC4)ncn3)c2)cc(C(C)(C)C)cc1NS(C)(=O)=O]

N-(5-tert-butyl-3-methanesulphonylamino-2-methoxy-phenyl)-4-methyl-3-(6-piperidin-4-ylmethyl-pyrimidin-4-yloxy)-benzamide

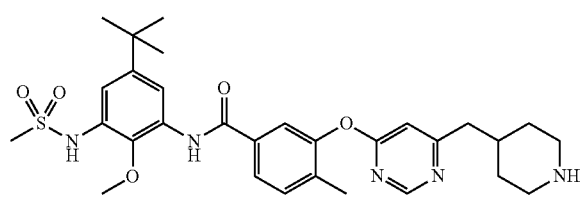

N-(5-tert-butyl-3-methanesulphonylamino-2-methoxy-phenyl)-4-methyl-3-(2-piperidin-4-ylmethyl-pyrimidin-4-yloxy)-benzamide

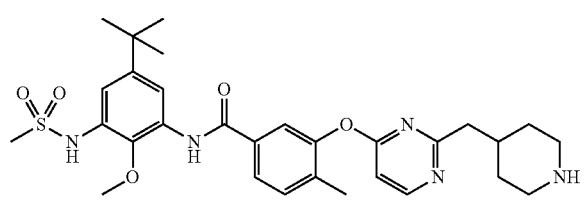

N-(5-tert-butyl-3-methanesulphonylamino-2-methoxy-phenyl)-4-methyl-3-(2-piperidin-4-ylmethyl-pyridin-4-yloxy)-benzamide

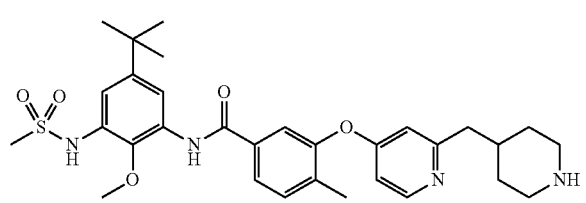

N-(5-tert-butyl-3-methanesulphonylamino-2-methoxy-phenyl)-3-methyl-5-[2-(piperazine-1-carbonyl)-pyrimidin-4-yloxy]-benzamide

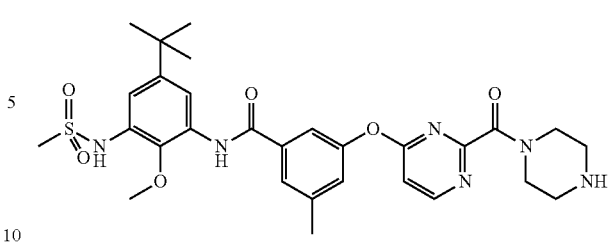

N-(5-tert-butyl-3-methanesulphonylamino-2-methoxy-phenyl)-3-methyl-5-(2-piperazin-1-ylmethyl-pyrimidin-4-yloxy)-benzamide

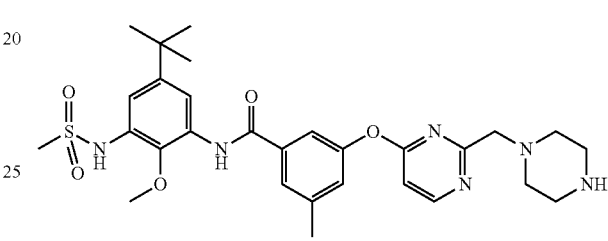

N-(5-tert-butyl-3-methanesulphonylamino-2-methoxy-phenyl)-3-methyl-5-(pyridin-4-yloxy)-benzamide

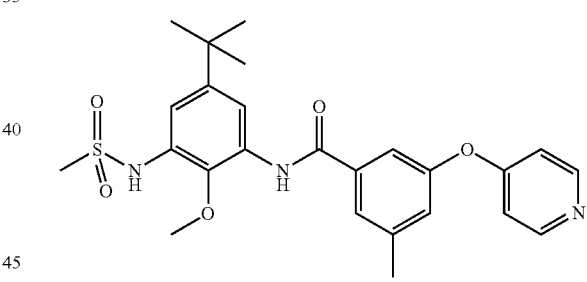

6-[5-(5-tert-butyl-3-methanesulphonylamino-2-methoxy-phenylaminocarbonyl)-2-methyl-phenoxy]-pyrimidin-4-carboxylic acid-methylamide

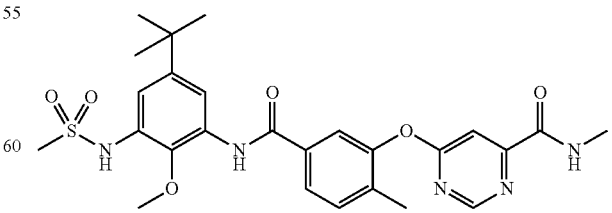

N-(5-tert-butyl-3-methanesulphonylamino-2-methoxy-phenyl)-4-methyl-3-[6-(morpholine-4-carbonyl)-pyrimidin-4-yloxy]-benzamide

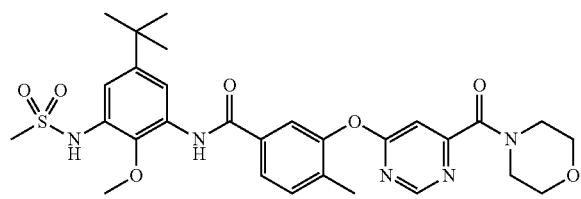 [SMILES: COc1c(NC(=O)c2ccc(C)c(Oc3cc(C(=O)N4CCOCC4)ncn3)c2)cc(C(C)(C)C)cc1NS(C)(=O)=O]

N-(5-tert-butyl-3-methanesulphonylamino-2-methoxy-phenyl)-4-methyl-3-[6-(4-methyl-piperazine-1-carbonyl)-pyrimidin-4-yloxy]-benzamide

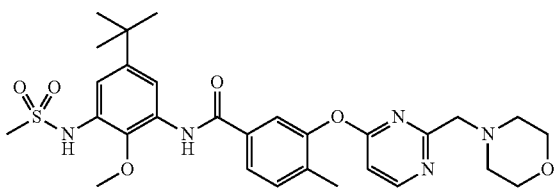

N-(5-tert-butyl-3-methanesulphonylamino-2-methoxy-phenyl)-4-methyl-3-(2-methylaminomethyl-pyrimidin-4-yloxy)-benzamide

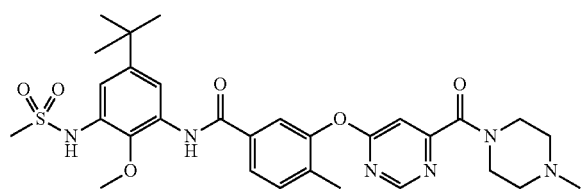

N-(5-tert-butyl-3-methanesulphonylamino-2-methoxy-phenyl)-4-methyl-3-(6-morpholin-4-ylmethyl-pyrimidin-4-yloxy)-benzamide

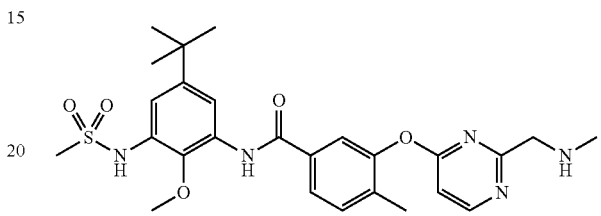

N-(5-tert-butyl-3-methanesulphonylamino-2-methoxy-phenyl)-4-methyl-3-[2-(3-oxo-piperazin-1-ylmethyl)-pyrimidin-4-yloxy]-benzamide

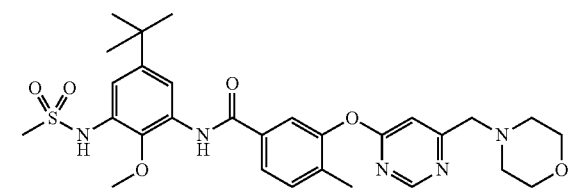 [SMILES: COc1c(NC(=O)c2ccc(C)c(Oc3cc(CN4CCOCC4)ncn3)c2)cc(C(C)(C)C)cc1NS(C)(=O)=O]

N-(5-tert-butyl-3-methanesulphonylamino-2-methoxy-phenyl)-4-methyl-3-(6-methylaminomethyl-pyrimidin-4-yloxy)-benzamide

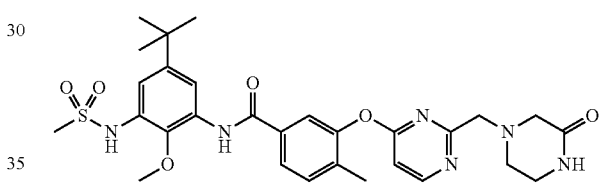

N-(5-tert-butyl-3-methanesulphonylamino-2-methoxy-phenyl)-4-methyl-3-[2-(4-methyl-piperazin-1-ylmethyl)-pyrimidin-4-yloxy]-benzamide

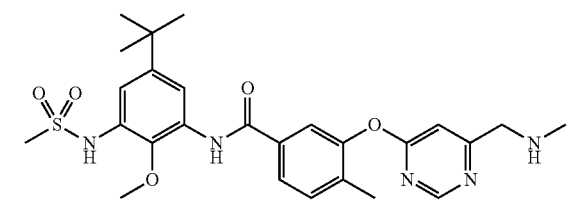

N-(5-tert-butyl-3-methanesulphonylamino-2-methoxy-phenyl)-4-methyl-3-[6-(4-methyl-piperazin-1-ylmethyl)-pyrimidin-4-yloxy]-benzamide

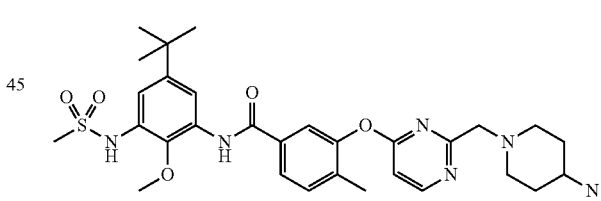

N-(5-tert-butyl-3-methanesulphonylamino-2-methoxy-phenyl)-4-methyl-3-[6-(3-oxo-piperazin-1-ylmethyl)-pyrimidin-4-yloxy]-benzamide

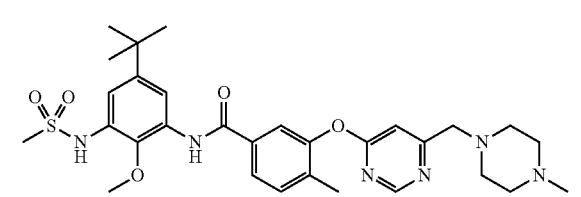

N-(5-tert-butyl-3-methanesulphonylamino-2-methoxy-phenyl)-4-methyl-3-(2-morpholin-4-ylmethyl-pyrimidin-4-yloxy)-benzamide

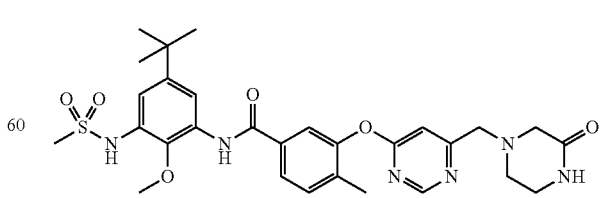

N-(5-tert-butyl-3-methanesulphonylamino-2-methoxy-phenyl)-4-methyl-3-(6-piperazin-1-ylmethyl-pyrimidin-4-yloxy)-benzamide

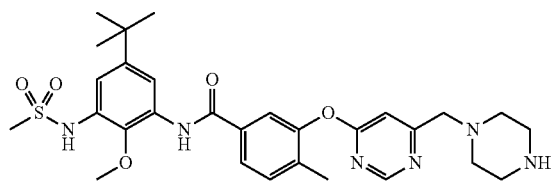 [SMILES: COc1c(NC(=O)c2ccc(C)c(Oc3cc(CN4CCNCC4)ncn3)c2)cc(C(C)(C)C)cc1NS(C)(=O)=O]

N-(5-tert-butyl-3-methanesulphonylamino-2-methoxy-phenyl)-4-methyl-3-(2-morpholin-4-ylmethyl-pyridin-4-yloxy)-benzamide

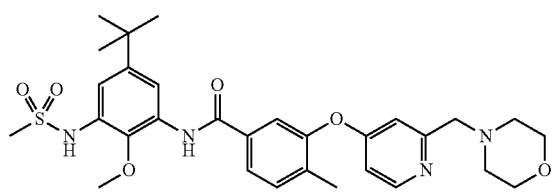 [SMILES: COc1c(NC(=O)c2ccc(C)c(Oc3ccnc(CN4CCOCC4)c3)c2)cc(C(C)(C)C)cc1NS(C)(=O)=O]

N-(5-tert-butyl-3-methanesulphonylamino-2-methoxy-phenyl)-4-methyl-3-[2-(4-methyl-piperazin-1-ylmethyl)-pyridin-4-yloxy]-benzamide

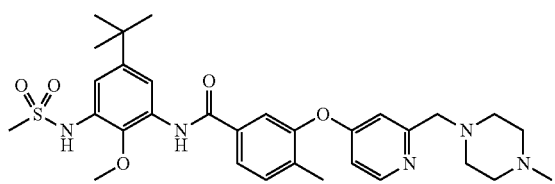

(S)—N-(5-tert-butyl-3-methanesulphonylamino-2-methoxy-phenyl)-4-methyl-3-{2-[(tetrahydro-furan-3-ylamino)-methyl]-pyridin-4-yloxy}-benzamide

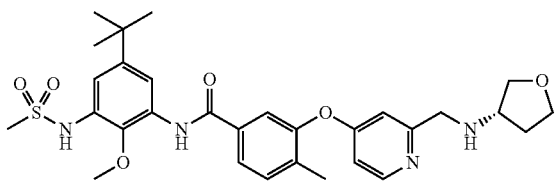 [SMILES: COc1c(NC(=O)c2ccc(C)c(Oc3ccnc(CN[C@H]4CCOC4)c3)c2)cc(C(C)(C)C)cc1NS(C)(=O)=O]

(R)—N-(5-tert-butyl-3-methanesulphonylamino-2-methoxy-phenyl)-3-[2-(3-hydroxy-pyrrolidin-1-ylmethyl)-pyridin-4-yloxy]-4-methyl-benzamide

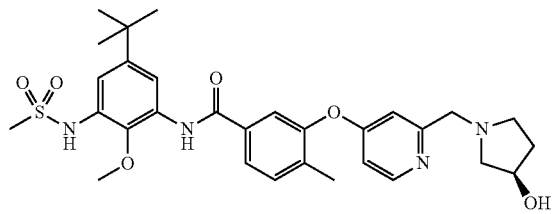 [SMILES: COc1c(NC(=O)c2ccc(C)c(Oc3ccnc(CN4CC[C@@H](O)C4)c3)c2)cc(C(C)(C)C)cc1NS(C)(=O)=O]

(S)—N-(5-tert-butyl-3-methanesulphonylamino-2-methoxy-phenyl)-3-[2-(3-hydroxy-pyrrolidin-1-ylmethyl)-pyridin-4-yloxy]-4-methyl-benzamide

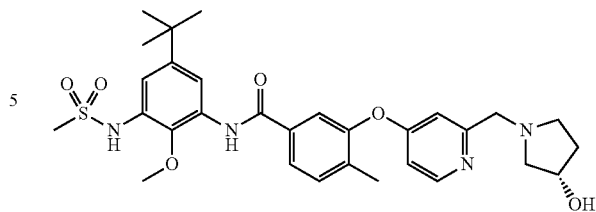

N-(5-tert-butyl-3-methanesulphonylamino-2-methoxy-phenyl)-4-methyl-3-(2-methylaminomethyl-pyridin-4-yloxy)-benzamide

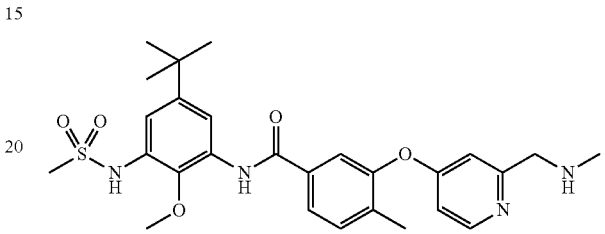

(S)—N-(5-tert-butyl-3-methanesulphonylamino-2-methoxy-phenyl)-4-methyl-3-{2-[(tetrahydro-furan-3-ylamino)-methyl]-pyridin-4-yloxy}-benzamide

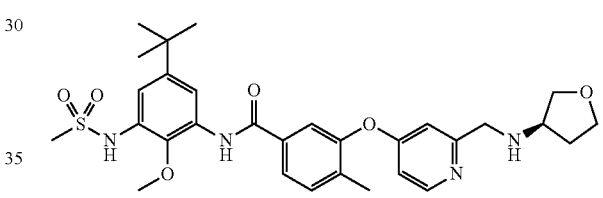

N-(5-tert-butyl-3-methanesulphonylamino-2-methoxy-phenyl)-4-methyl-3-[2-(4-methyl-homopiperazin-1-ylmethyl)-pyrimidin-4-yloxy]-benzamide

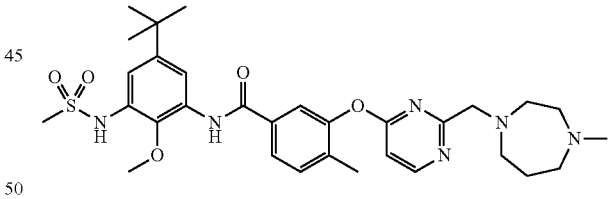

N-(5-tert-butyl-3-methanesulphonylamino-2-methoxy-phenyl)-4-methyl-3-{2-[(1-methyl-piperidin-4-ylamino)-methyl]-pyrimidin-4-yloxy}-benzamide

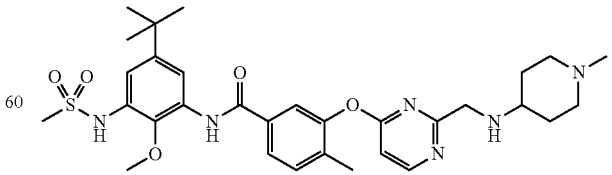

N-(5-tert-butyl-3-methanesulphonylamino-2-methoxy-phenyl)-4-methyl-3-{2-[(1-methyl-piperidin-3-ylamino)-methyl]-pyrimidin-4-yloxy}-benzamide

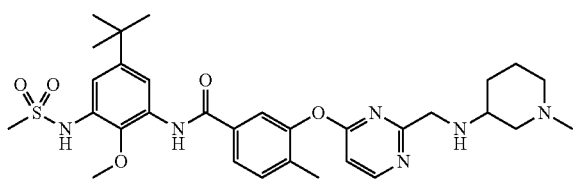

N-(5-tert-butyl-3-methanesulphonylamino-2-methoxy-phenyl)-4-methyl-3-(2-{[methyl-(1-methyl-pyrrolidin-3-yl)-amino]-methyl}-pyrimidin-4-yloxy)-benzamide

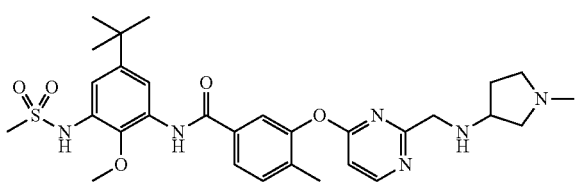

N-(5-tert-butyl-3-methanesulphonylamino-2-methoxy-phenyl)-4-methyl-3-[2-(4-methyl-homopiperazin-1-ylmethyl)-pyridin-4-yloxy]-benzamide

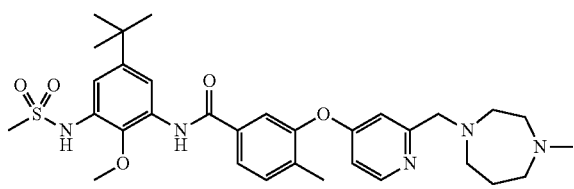

(S)—N-(5-tert-butyl-3-methanesulphonylamino-2-methoxy-phenyl)-3-[2-(3-dimethylamino-pyrrolidin-1-ylmethyl)-pyrimidin-4-yloxy]-4-methyl-benzamide

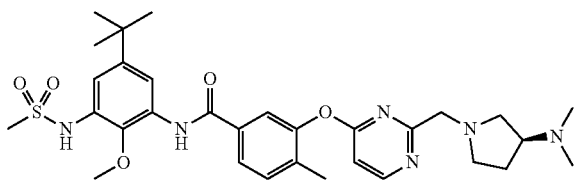

(R)—N-(5-tert-butyl-3-methanesulphonylamino-2-methoxy-phenyl)-3-[2-(3-dimethylamino-pyrrolidin-1-ylmethyl)-pyrimidin-4-yloxy]-4-methyl-benzamide

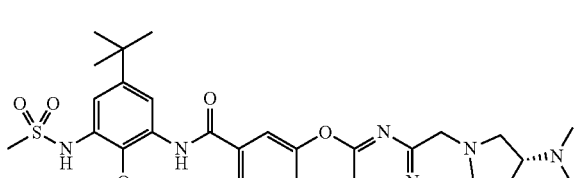

N-(5-tert-butyl-3-methanesulphonylamino-2-methoxy-phenyl)-4-methyl-3-{2-[(1-methyl-pyrrolidin-3-ylamino)-methyl]-pyrimidin-4-yloxy}-benzamide

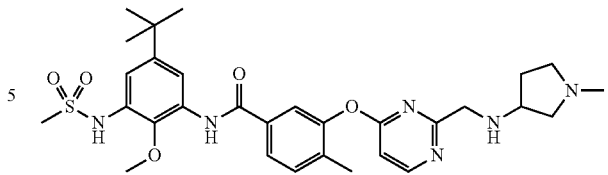

N-(5-tert-butyl-3-methanesulphonylamino-2-methoxy-phenyl)-3-(2-{[N-(2-dimethylamino-ethyl)-N-methyl-amino]-methyl}-pyrimidin-4-yloxy)-4-methyl-benzamide

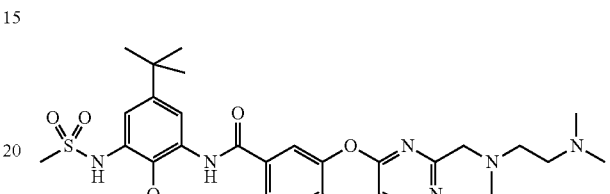

N-(5-tert-butyl-3-methanesulphonylamino-2-methoxy-phenyl)-3-{2-[(2-dimethylamino-ethylamino)-methyl]-pyrimidin-4-yloxy}-4-methyl-benzamide

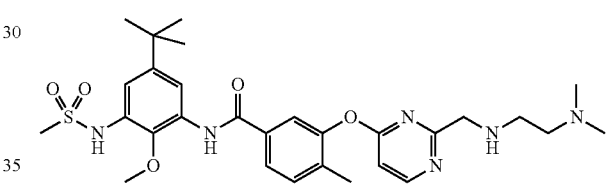

N-(5-tert-butyl-3-methanesulphonylamino-2-methoxy-phenyl)-3-(2-{[(2-dimethylamino-ethyl)-methyl-amino]-methyl}-pyridin-4-yloxy)-4-methyl-benzamide

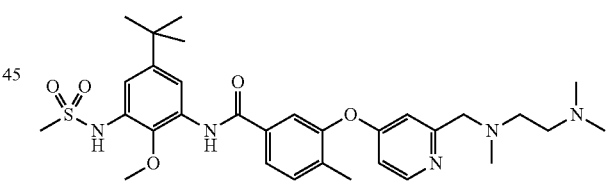

N-(5-tert-butyl-3-methanesulphonylamino-2-methoxy-phenyl)-3-{2-[(2-dimethylamino-ethylamino)-methyl]-pyridin-4-yloxy}-4-methyl-benzamide

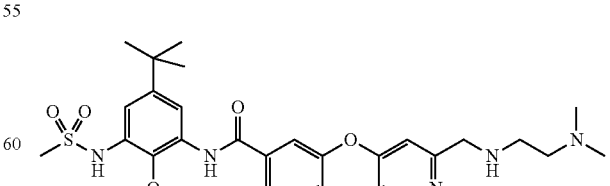

N-(5-tert-butyl-3-methanesulphonylamino-2-methoxy-phenyl)-3-methyl-5-[2-(4-methyl-piperazin-1-ylmethyl)-pyrimidin-4-yloxy]-benzamide

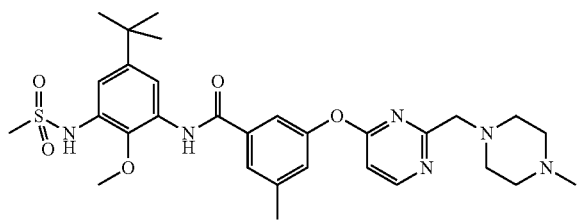

N-(5-tert-butyl-3-methanesulphonylamino-2-methoxy-phenyl)-3-{6-[(2-dimethylamino-ethylamino)-methyl]-pyrimidin-4-yloxy}-4-methyl-benzamide

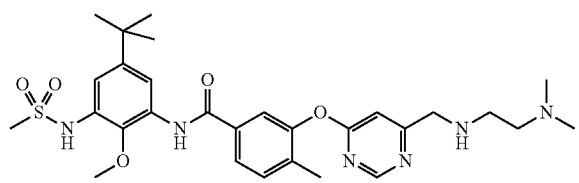

N-(5-tert-butyl-3-methanesulphonylamino-2-methoxy-phenyl)-3-(6-{[(2-dimethylamino-ethyl)-methyl-amino]-methyl}-pyrimidin-4-yloxy)-4-methyl-benzamide

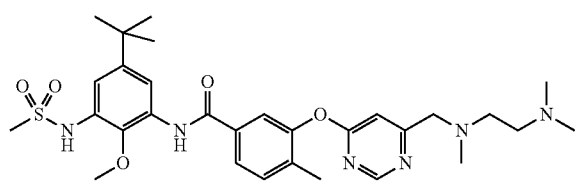

N-(5-tert-butyl-3-methanesulphonylamino-2-methoxy-phenyl)-4-methyl-3-[6-(1-methyl-piperidin-4-ylmethyl)-pyrimidin-4-yloxy]-benzamide

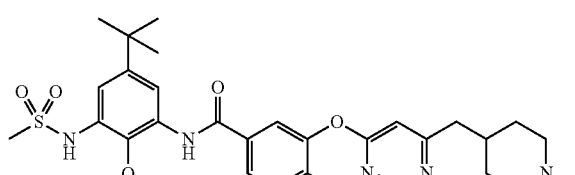

N-(5-tert-butyl-3-methanesulphonylamino-2-methoxy-phenyl)-4-methyl-3-[2-(1-methyl-piperidin-4-ylmethyl)-pyrimidin-4-yloxy]-benzamide

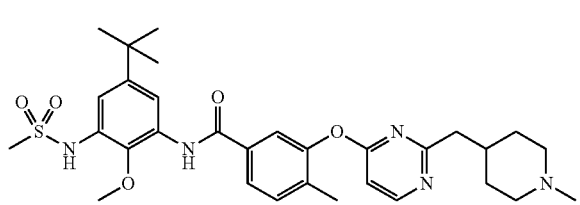

N-(5-tert-butyl-3-methanesulphonylamino-2-methoxy-phenyl)-4-methyl-3-[2-(1-methyl-piperidin-4-ylmethyl)-pyridin-4-yloxy]-benzamide

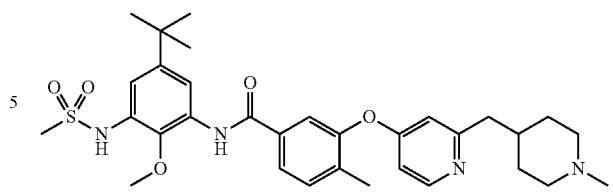

N-(5-tert-butyl-3-methanesulphonylamino-2-methoxy-phenyl)-4-methyl-3-[2-(pyrrolidin-3-ylamino)-pyrimidin-4-yloxy]-benzamide

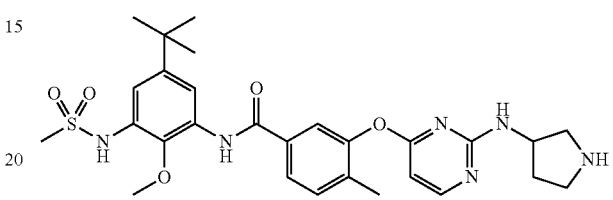

N-(5-tert-butyl-3-methanesulphonylamino-2-methoxy-phenyl)-4-chloro-3-[2-(4-methyl-piperazin-1-ylmethyl)-pyrimidin-4-yloxy]-benzamide

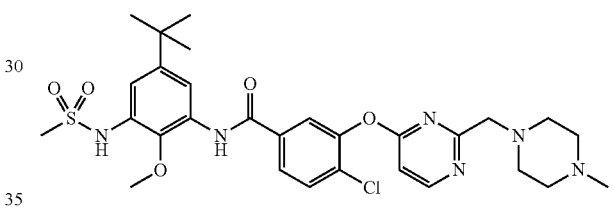

N-(5-tert-butyl-3-methanesulphonylamino-2-methoxy-phenyl)-3-chloro-4-methyl-5-[2-(4-methyl-piperazin-1-ylmethyl)-pyrimidin-4-yloxy]-benzamide

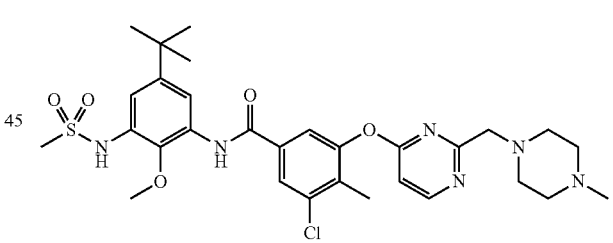

N-(5-tert-butyl-3-methanesulphonylamino-2-methoxy-phenyl)-4-chloro-3-[6-(1-methyl-piperidin-4-ylamino)-pyrimidin-4-yloxy]-benzamide

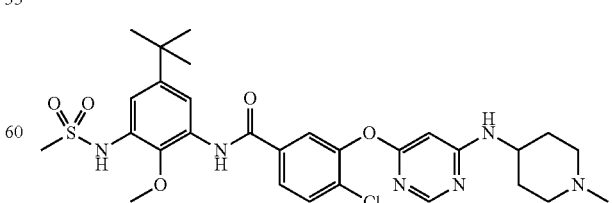

N-(5-tert-butyl-3-methanesulphonylamino-2-methoxy-phenyl)-4-chloro-3-[2-(1-methyl-piperidin-4-ylamino)-pyridin-4-yloxy]-benzamide

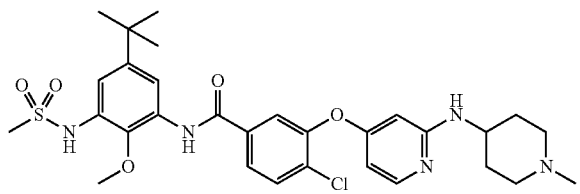

N-(5-tert-butyl-3-methanesulphonylamino-2-methoxy-phenyl)-4-chloro-3-[6-(piperidin-4-ylamino)-pyrimidin-4-yloxy]-benzamide

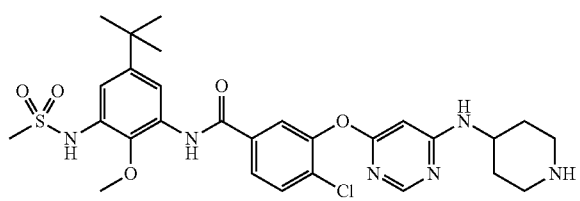 [SMILES: COc1c(NC(=O)c2ccc(Cl)c(Oc3cc(NC4CCNCC4)ncn3)c2)cc(C(C)(C)C)cc1NS(C)(=O)=O]

N-(5-tert-butyl-3-methanesulphonylamino-2-methoxy-phenyl)-4-chloro-3-[2-(1-methyl-piperidin-4-ylamino)-pyrimidin-4-yloxy]-benzamide

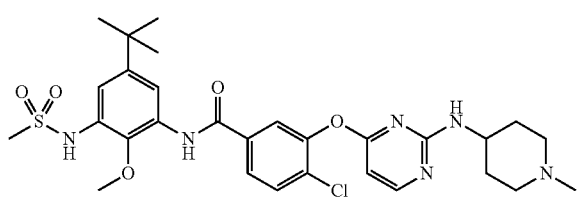

N-(5-tert-butyl-3-methanesulphonylamino-2-methoxy-phenyl)-4-methyl-3-{2-[methyl-(1-methyl-piperidin-4-yl)-amino]-pyrimidin-4-yloxy}-benzamide

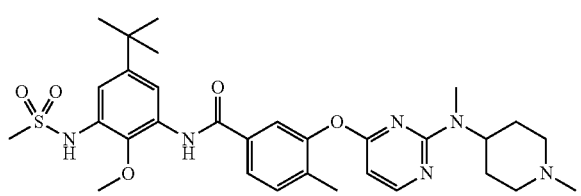

N-(5-tert-butyl-3-methanesulphonylamino-2-methoxy-phenyl)-4-methyl-3-{6-[methyl-(1-methyl-piperidin-4-yl)-amino]-pyrimidin-4-yloxy}-benzamide

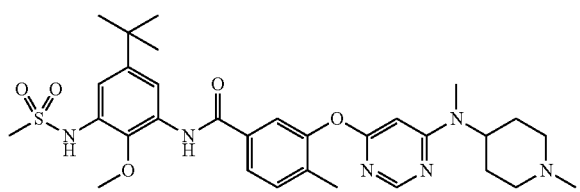

N-(5-tert-butyl-3-methanesulphonylamino-2-methoxy-phenyl)-4-chloro-3-[2-(piperidin-4-ylamino)-pyrimidin-4-yloxy]-benzamide

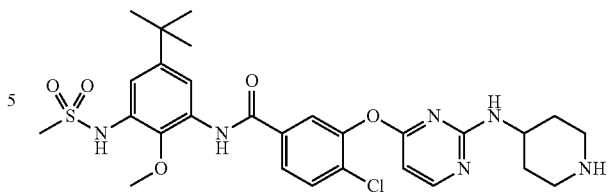

N-(5-tert-butyl-3-methanesulphonylamino-2-methoxy-phenyl)-4-chloro-3-(2-piperidin-4-ylmethyl-pyridin-4-yloxy)-benzamide

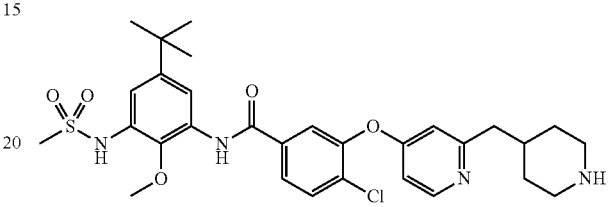

N-(5-tert-butyl-3-methanesulphonylamino-2-methoxy-phenyl)-4-chloro-3-(2-piperidin-4-ylmethyl-pyrimidin-4-yloxy)-benzamide

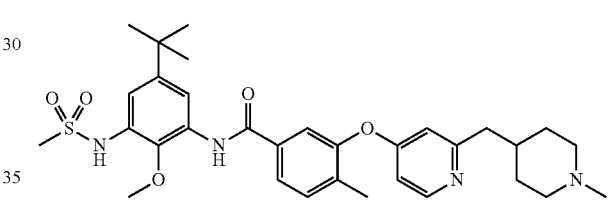

N-(5-tert-butyl-3-methanesulphonylamino-2-methoxy-phenyl)-4-chloro-3-{6-[(2-dimethylamino-ethylamino)-methyl]-pyrimidin-4-yloxy}-benzamide

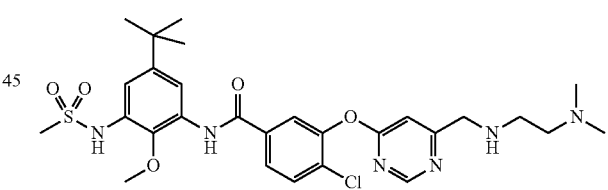

N-(5-tert-butyl-3-methanesulphonylamino-2-methoxy-phenyl)-4-chloro-3-(6-{[(2-dimethylamino-ethyl)-methyl-amino]-methyl}-pyrimidin-4-yloxy)-benzamide

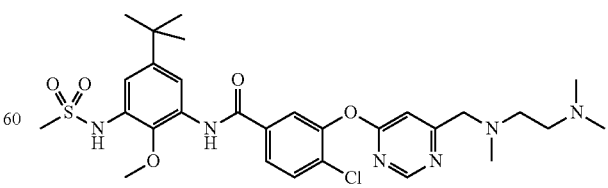

N-(5-tert-butyl-3-methanesulphonylamino-2-methoxy-phenyl)-4-chloro-3-[2-(piperidin-4-ylamino)-pyridin-4-yloxy]-benzamide

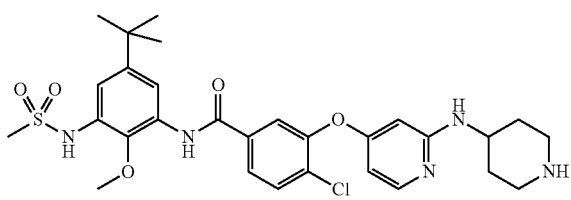 [SMILES: COc1c(NC(=O)c2ccc(Cl)c(Oc3ccnc(NC4CCNCC4)c3)c2)cc(C(C)(C)C)cc1NS(C)(=O)=O]

N-(5-tert-butyl-3-methanesulphonylamino-2-methoxy-phenyl)-4-chloro-3-(6-piperazin-1-ylmethyl-pyrimidin-4-yloxy)-benzamide

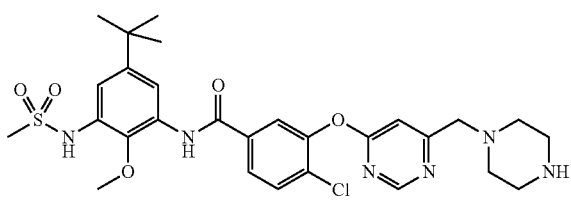 [SMILES: COc1c(NC(=O)c2ccc(Cl)c(Oc3cc(CN4CCNCC4)ncn3)c2)cc(C(C)(C)C)cc1NS(C)(=O)=O]

N-(5-tert-butyl-3-methanesulphonylamino-2-methoxy-phenyl)-4-chloro-3-(6-piperidin-4-ylmethyl-pyrimidin-4-yloxy)-benzamide

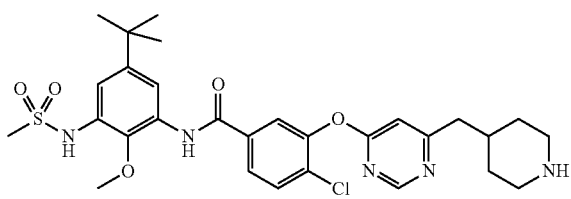 [SMILES: COc1c(NC(=O)c2ccc(Cl)c(Oc3cc(CC4CCNCC4)ncn3)c2)cc(C(C)(C)C)cc1NS(C)(=O)=O]

N-(5-tert-butyl-3-methanesulphonylamino-2-methoxy-phenyl)-4-chloro-3-[6-(4-methyl-piperazin-1-ylmethyl)-pyrimidin-4-yloxy]-benzamide

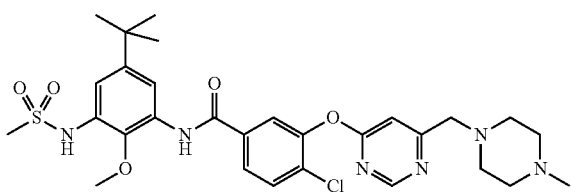

N-(5-tert-butyl-3-methanesulphonylamino-2-methoxy-phenyl)-4-chloro-3-[6-(1-methyl-piperidin-4-ylmethyl)-pyrimidin-4-yloxy]-benzamide

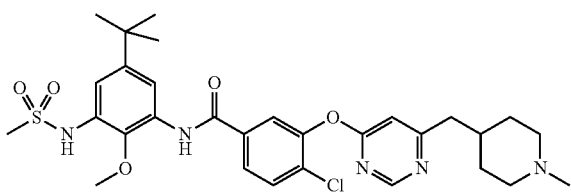

N-(5-tert-butyl-3-methanesulphonylamino-2-methoxy-phenyl)-4-chloro-3-[2-(1-methyl-piperidin-4-ylmethyl)-pyrimidin-4-yloxy]-benzamide

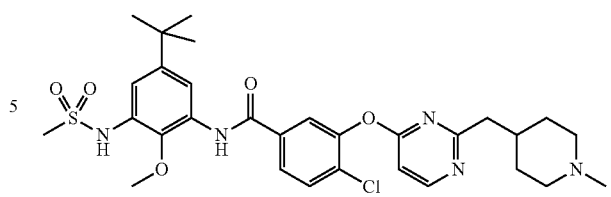

N-(5-tert-butyl-3-methanesulphonylamino-2-methoxy-phenyl)-4-chloro-3-(2-{[(2-dimethylamino-ethyl)-methyl-amino]-methyl}-pyridin-4-yloxy)-benzamide

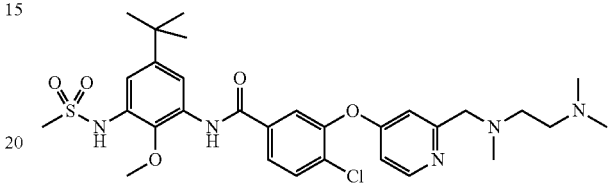

N-(5-tert-butyl-3-methanesulphonylamino-2-methoxy-phenyl)-3-[2-(trans-4-dimethylamino-cyclohexylamino)-pyrimidin-4-yloxy]-4-methyl-benzamide

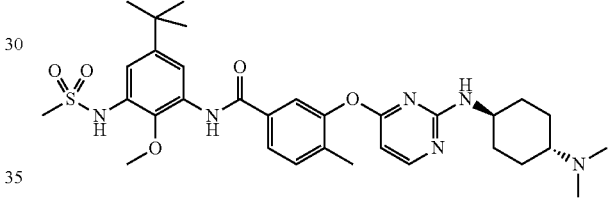

N-(5-tert-butyl-3-methanesulphonylamino-2-methoxy-phenyl)-4-chloro-3-{2-[(2-dimethylamino-ethylamino)-methyl]-pyridin-4-yloxy}-benzamide

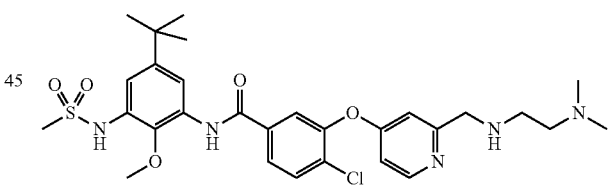

N-(5-tert-butyl-3-methanesulphonylamino-2-methoxy-phenyl)-4-chloro-3-(2-piperazin-1-ylmethyl-pyridin-4-yloxy)-benzamide

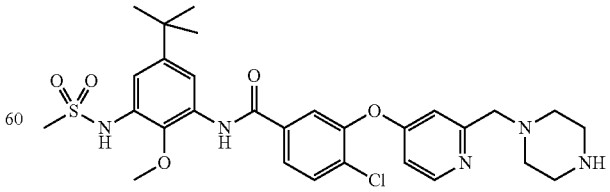

N-(5-tert-butyl-3-methanesulphonylamino-2-methoxy-phenyl)-4-methyl-3-{2-[methyl-(1-methyl-pyrrolidin-3-yl)-amino]-pyrimidin-4-yloxy}-benzamide

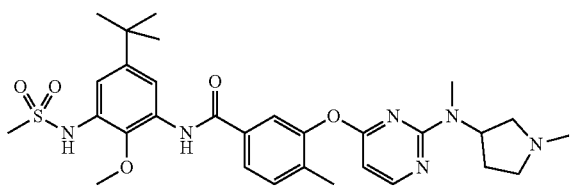

N-(5-tert-butyl-3-methanesulphonylamino-2-methoxy-phenyl)-4-chloro-3-[2-(4-methyl-piperazin-1-ylmethyl)-pyridin-4-yloxy]-benzamide

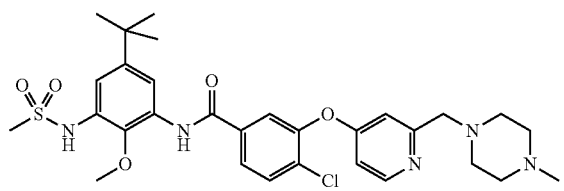

N-(5-tert-butyl-3-methanesulphonylamino-2-methoxy-phenyl)-4-methyl-3-{6-[methyl-(1-methyl-pyrrolidin-3-yl)-amino]-pyrimidin-4-yloxy}-benzamide

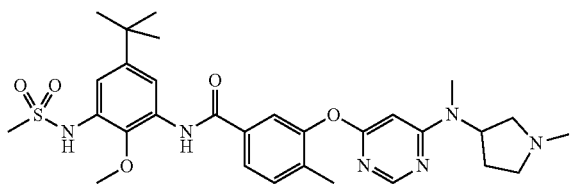

N-(5-tert-butyl-3-methanesulphonylamino-2-methoxy-phenyl)-4-chloro-3-[2-(4-methyl-[1,4]diazepan-1-ylmethyl)-pyrimidin-4-yloxy]-benzamide

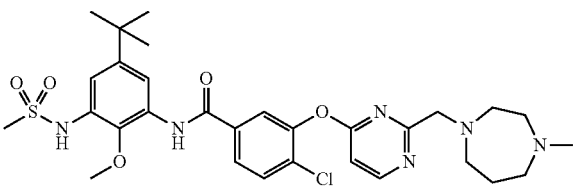

N-(5-tert-butyl-3-methanesulphonylamino-2-methoxy-phenyl)-4-chloro-3-(2-{[(2-dimethylamino-ethyl)-methyl-amino]-methyl}-pyrimidin-4-yloxy)-benzamide

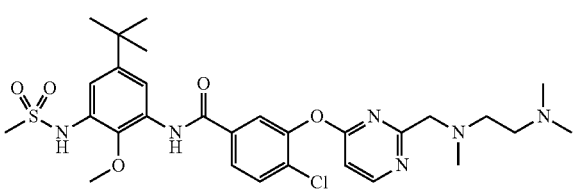

N-(5-tert-butyl-3-methanesulphonylamino-2-methoxy-phenyl)-4-chloro-3-{2-[(2-dimethylamino-ethylamino)-methyl]-pyrimidin-4-yloxy}-benzamide

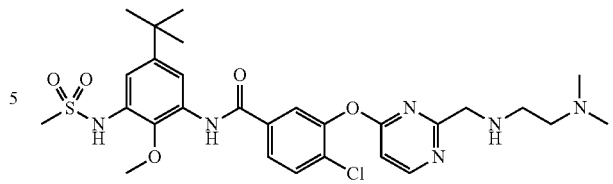

N-(5-tert-butyl-3-methanesulphonylamino-2-methoxy-phenyl)-4-chloro-3-[6-(4-methyl-[1,4]diazepan-1-ylmethyl)-pyrimidin-4-yloxy]-benzamide

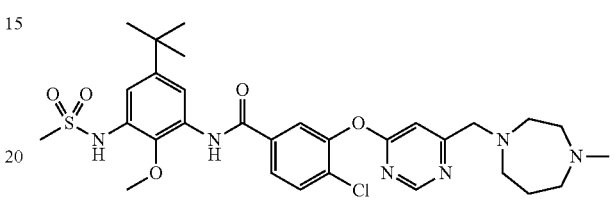

N-(5-tert-butyl-3-methanesulphonylamino-2-methoxy-phenyl)-4-chloro-3-(2-piperazin-1-ylmethyl-pyrimidin-4-yloxy)-benzamide

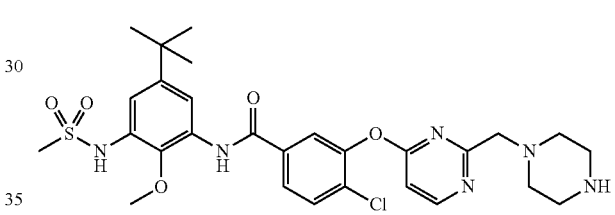

N-(5-tert-butyl-3-methanesulphonylamino-2-methoxy-phenyl)-4-chloro-3-(6-[1,4]diazepan-1-ylmethyl-pyrimidin-4-yloxy)-benzamide

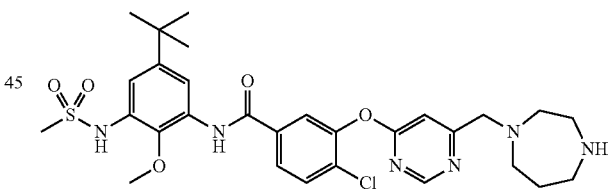

N-(5-tert-butyl-3-methanesulphonylamino-2-methoxy-phenyl)-4-chloro-3-[2-(4-methyl-[1,4]diazepan-1-ylmethyl)-pyridin-4-yloxy]-benzamide

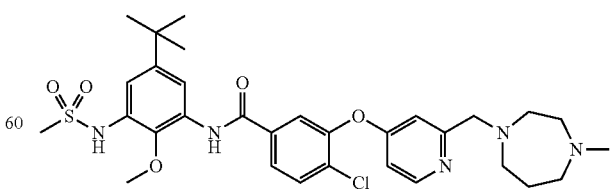

N-(5-tert-butyl-3-methanesulphonylamino-2-methoxy-phenyl)-4-chloro-3-(2-[1,4]diazepan-1-ylmethyl-pyridin-4-yloxy)-benzamide

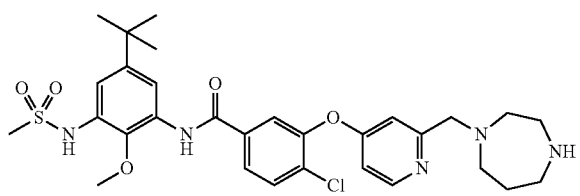 [SMILES: COc1c(NC(=O)c2ccc(Cl)c(Oc3ccnc(CN4CCCNCC4)c3)c2)cc(C(C)(C)C)cc1NS(C)(=O)=O]

N-(5-tert-butyl-3-methanesulphonylamino-2-methoxy-phenyl)-4-chloro-3-[2-(1-methyl-piperidin-4-ylmethyl)-pyridin-4-yloxy]-benzamide

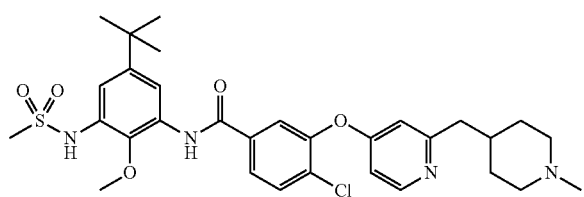

N-(5-tert-butyl-3-methanesulphonyl-2-methoxy-phenyl)-4-methyl-3-(2-piperidin-4-ylmethyl-pyrimidin-4-yloxy)-benzamide

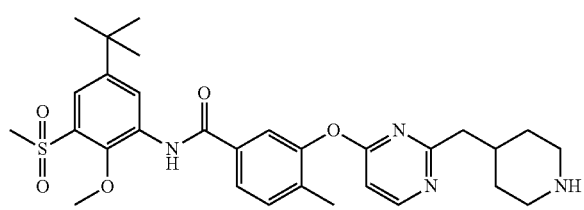 [SMILES: COc1c(NC(=O)c2ccc(C)c(Oc3ccnc(CC4CCNCC4)n3)c2)cc(C(C)(C)C)cc1S(C)(=O)=O]

N-(5-tert-butyl-3-methanesulphonylamino-2-methoxy-phenyl)-3-(2-[1,4]diazepan-1-ylmethyl-pyridin-4-yloxy)-4-methyl-benzamide

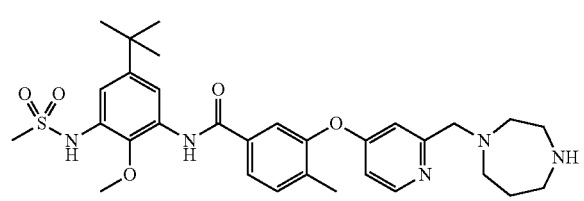 [SMILES: COc1c(NC(=O)c2ccc(C)c(Oc3ccnc(CN4CCCNCC4)c3)c2)cc(C(C)(C)C)cc1NS(C)(=O)=O]

N-(5-tert-butyl-2-methoxy-3-methylsulphanylmethyl-phenyl)-4-methyl-3-(2-piperidin-4-ylmethyl-pyridin-4-yloxy)-benzamide

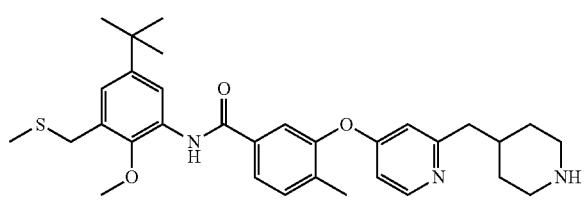 [SMILES: COc1c(CSC)cc(C(C)(C)C)cc1NC(=O)c1ccc(C)c(Oc2ccnc(CC3CCNCC3)c2)c1]

N-(5-tert-butyl-3-methanesulphonylmethyl-2-methoxy-phenyl)-4-methyl-3-(2-piperidin-4-ylmethyl-pyridin-4-yloxy)-benzamide

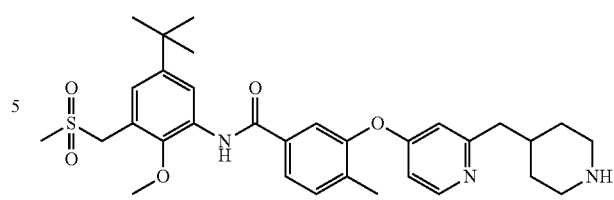

N-(5-tert-butyl-3-methanesulphinylmethyl-2-methoxy-phenyl)-4-methyl-3-(2-piperidin-4-ylmethyl-pyridin-4-yloxy)-benzamide

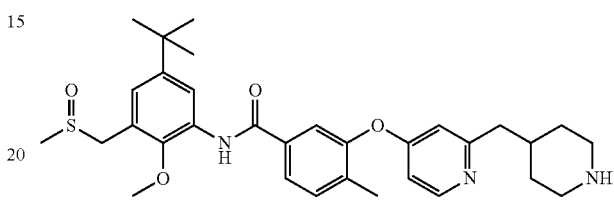

N-[5-tert-butyl-3-(cyclopropanecarbonyl-amino)-2-methoxy-phenyl]-4-methyl-3-(2-piperidin-4-ylmethyl-pyridin-4-yloxy)-benzamide

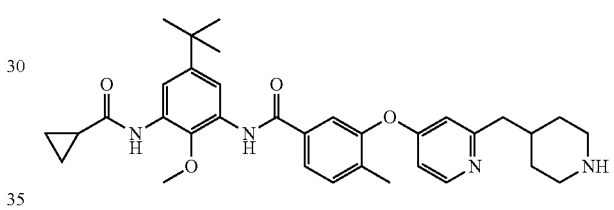

N-(5-tert-butyl-2-isopropoxy-3-methanesulphonylamino-phenyl)-4-methyl-3-(2-piperidin-4-ylmethyl-pyridin-4-yloxy)-benzamide

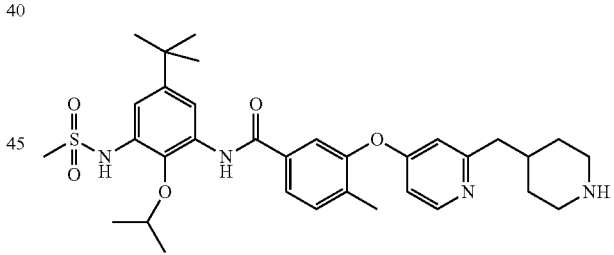

N-(5-tert-butyl-2-ethoxy-3-methanesulphonylamino-phenyl)-4-methyl-3-(2-piperidin-4-ylmethyl-pyridin-4-yloxy)-benzamide

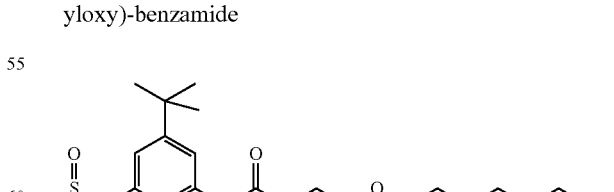

N-[5-tert-butyl-2-methoxy-3-(2-methyl-propane-1-sulphinylamino)-phenyl]-4-methyl-3-(2-piperidin-4-ylmethyl-pyridin-4-yloxy)-benzamide

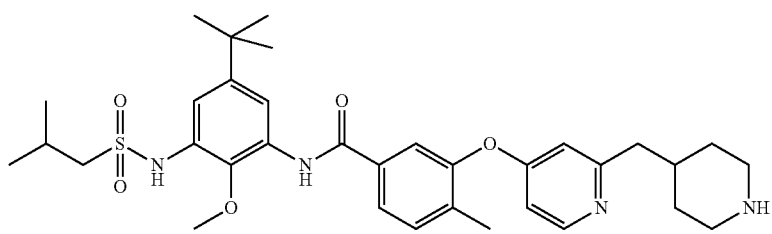 [SMILES: COc1c(NC(=O)c2ccc(C)c(Oc3ccnc(CC4CCNCC4)c3)c2)cc(C(C)(C)C)cc1NS(=O)(=O)CC(C)C]

N-[3-(butan-1-sulphonylamino)-5-tert-butyl-2-methoxy-phenyl]-4-methyl-3-(2-piperidin-4-ylmethyl-pyridin-4-yloxy)-benzamide

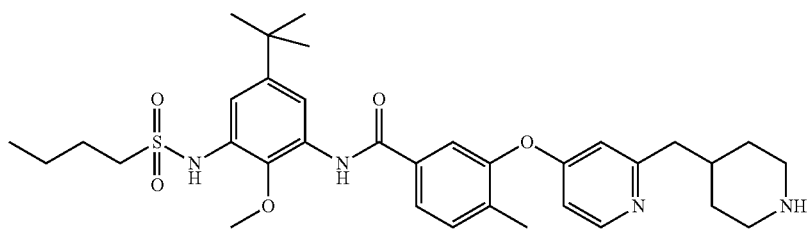 [SMILES: CCCCS(=O)(=O)Nc1cc(C(C)(C)C)cc(NC(=O)c2ccc(C)c(Oc3ccnc(CC4CCNCC4)c3)c2)c1OC]

N-(5-tert-butyl-2-methoxy-3-pentanoylamino-phenyl)-4-methyl-3-(2-piperidin-4-ylmethyl-pyridin-4-yloxy)-benzamide

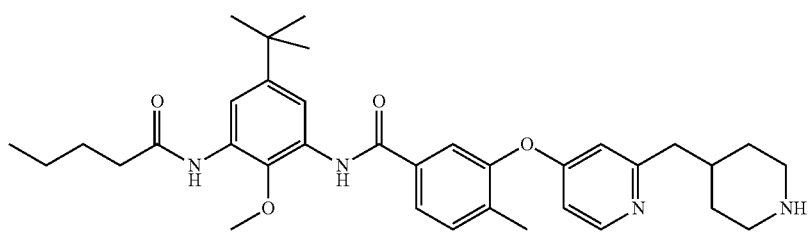 [SMILES: CCCCC(=O)Nc1cc(C(C)(C)C)cc(NC(=O)c2ccc(C)c(Oc3ccnc(CC4CCNCC4)c3)c2)c1OC]

N-(5-tert-butyl-3-methanesulphonyl-2-methoxy-phenyl)-4-methyl-3-(2-piperidin-4-ylmethyl-pyridin-4-yloxy)-benzamide

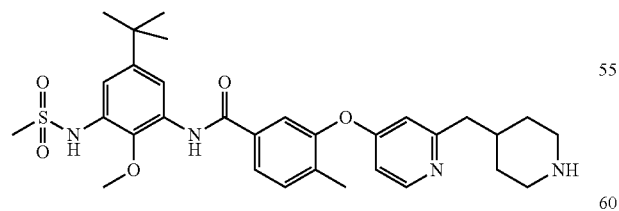

N-[5-tert-butyl-2-methoxy-3-(3-methyl-butyrylamino)-phenyl]-4-methyl-3-(2-piperidin-4-ylmethyl-pyridin-4-yloxy)-benzamide

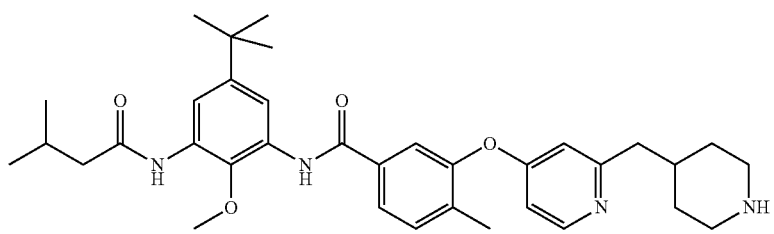 [SMILES: COc1c(NC(=O)CC(C)C)cc(C(C)(C)C)cc1NC(=O)c1ccc(C)c(Oc2ccnc(CC3CCNCC3)c2)c1]

N-(5-tert-butyl-3-isobutyrylamino-2-methoxy-phenyl)-4-methyl-3-(2-piperidin-4-ylmethyl-pyridin-4-yloxy)-benzamide

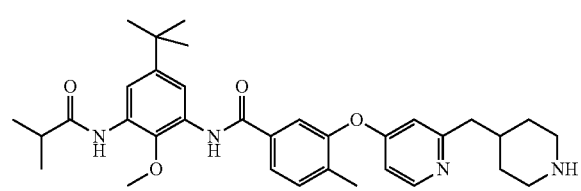 [SMILES: COc1c(NC(=O)c2ccc(C)c(Oc3ccnc(CC4CCNCC4)c3)c2)cc(C(C)(C)C)cc1NC(=O)C(C)C]

N-(5-tert-butyl-3-methanesulphinyl-2-methoxy-phenyl)-4-methyl-3-(2-piperidin-4-ylmethyl-pyridin-4-yloxy)-benzamide

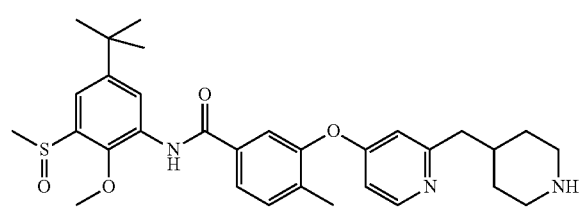 [SMILES: COc1c(NC(=O)c2ccc(C)c(Oc3ccnc(CC4CCNCC4)c3)c2)cc(C(C)(C)C)cc1S(C)=O]

N-(5-tert-butyl-3-methanesulphinylmethyl-2-methoxy-phenyl)-4-methyl-3-(2-piperidin-4-ylmethyl-pyridin-4-yloxy)-benzamide

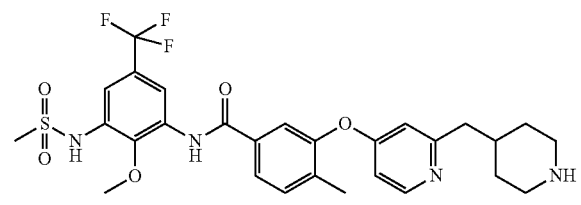 [SMILES: COc1c(NC(=O)c2ccc(C)c(Oc3ccnc(CC4CCNCC4)c3)c2)cc(C(F)(F)F)cc1NS(C)(=O)=O]

N-(5-tert-butyl-3-methanesulphinylmethyl-2-methoxy-phenyl)-4-methyl-3-(2-piperidin-4-ylmethyl-pyridin-4-yloxy)-benzamide

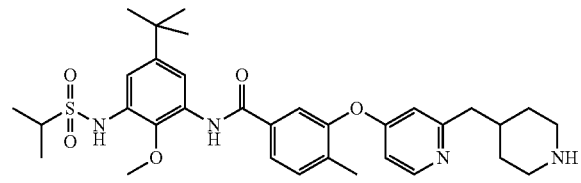

N-(5-tert-butyl-3-cyclopropanesulphonylamino-2-methoxy-phenyl)-4-methyl-3-(2-piperidin-4-ylmethyl-pyridin-4-yloxy)-benzamide

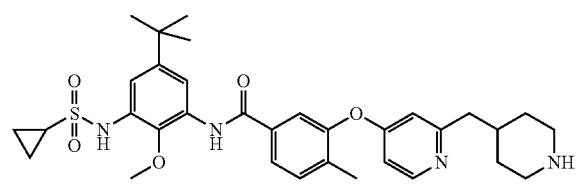 [SMILES: COc1c(NC(=O)c2ccc(C)c(Oc3ccnc(CC4CCNCC4)c3)c2)cc(C(C)(C)C)cc1NS(=O)(=O)C1CC1]

3-(2-azepan-4-ylmethyl-pyridin-4-yloxy)-N-(5-tert-butyl-3-methanesulphonylamino-2-methoxy-phenyl)-4-methyl-benzamide

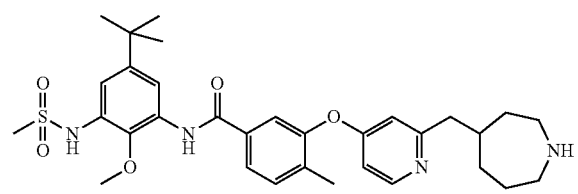 [SMILES: COc1c(NC(=O)c2ccc(C)c(Oc3ccnc(CC4CCCNCC4)c3)c2)cc(C(C)(C)C)cc1NS(C)(=O)=O]

3-(2-azepan-4-ylmethyl-pyrimidin-4-yloxy)-N-(5-tert-butyl-3-methanesulphonylamino-2-methoxy-phenyl)-4-methyl-benzamide

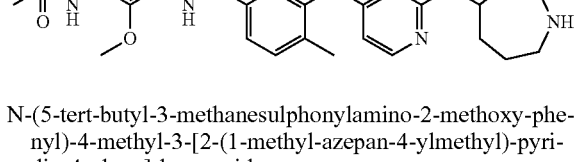

N-(5-tert-butyl-3-methanesulphonylamino-2-methoxy-phenyl)-4-methyl-3-[2-(1-methyl-azepan-4-ylmethyl)-pyridin-4-yloxy]-benzamide N-(5-tert-butyl-3-methanesulphonylamino-2-methoxy-phenyl)-4-methyl-3-[2-(1-methyl-azepan-4-ylmethyl)-pyrimidin-4-yloxy]-benzamide

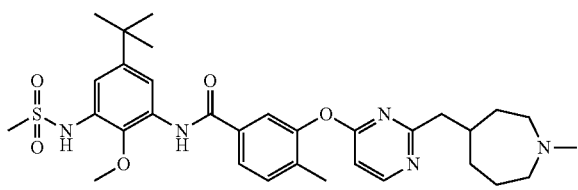

3-(6-azepan-4-ylmethyl-pyrimidin-4-yloxy)-N-(5-tert-butyl-3-methanesulphonylamino-2-methoxy-phenyl)-4-methyl-benzamide

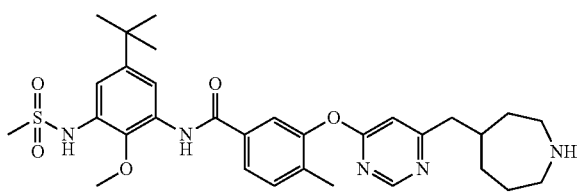 [SMILES: COc1c(NC(=O)c2ccc(C)c(Oc3cc(CC4CCCNCC4)ncn3)c2)cc(C(C)(C)C)cc1NS(C)(=O)=O]

N-(5-tert-butyl-3-methanesulphonylamino-2-methoxy-phenyl)-4-methyl-3-[6-(1-methyl-azepan-4-ylmethyl)-pyrimidin-4-yloxy]-benzamide

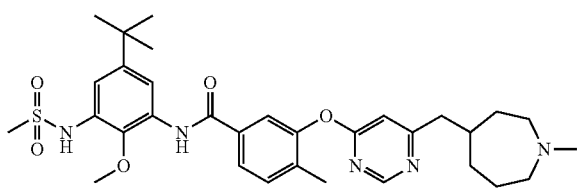

N-(3-methanesulphonylamino-2-methoxy-5-pentafluoroethyl-phenyl)-4-methyl-3-(2-piperidin-4-ylmethyl-pyridin-4-yloxy)-benzamide

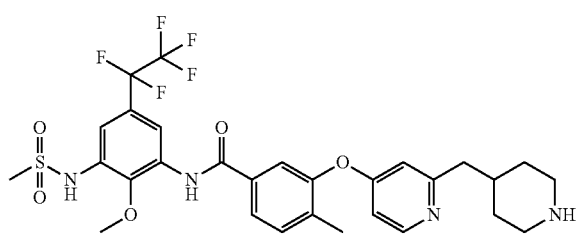 [SMILES: COc1c(NC(=O)c2ccc(C)c(Oc3ccnc(CC4CCNCC4)c3)c2)cc(C(F)(F)C(F)(F)F)cc1NS(C)(=O)=O]

N-(5-tert-butyl-3-hydroxymethyl-2-methoxy-phenyl)-4-methyl-3-[2-(4-methyl-piperazin-1-ylmethyl)-pyrimidin-4-yloxy]-benzamide

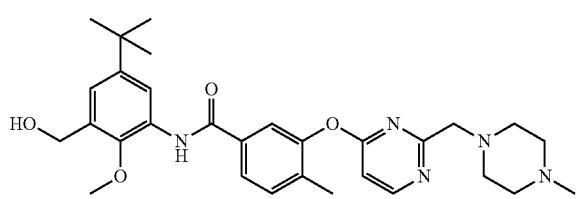 [SMILES: COc1c(CO)cc(C(C)(C)C)cc1NC(=O)c1ccc(C)c(Oc2ccnc(CN3CCN(C)CC3)n2)c1]

N-(5-tert-butyl-3-methanesulphinyl-2-methoxy-phenyl)-4-methyl-3-[2-(4-methyl-piperazin-1-ylmethyl)-pyrimidin-4-yloxy]-benzamide

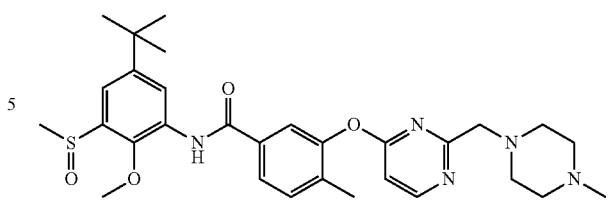

N-(5-tert-butyl-3-dimethylaminomethyl-2-methoxy-phenyl)-4-methyl-3-(2-piperidin-4-ylmethyl-pyridin-4-yloxy)-benzamide

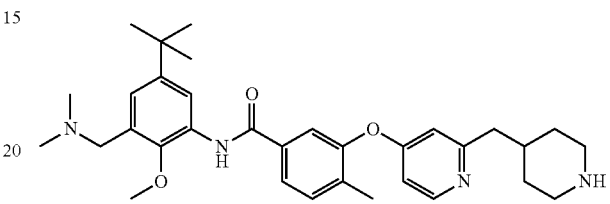

N-(5-tert-butyl-3-methanesulphonylamino-2-methoxy-phenyl)-4-methyl-3-{2-[4-(2,2,2-trifluoro-ethyl)-piperazin-1-ylmethyl]-pyridin-4-yloxy}-benzamide

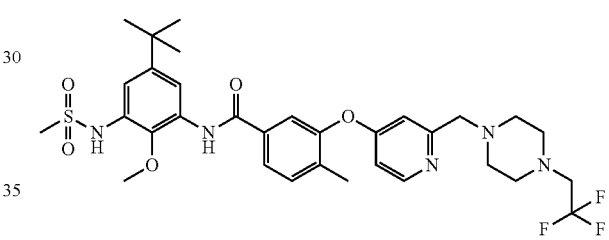

N-(5-tert-butyl-3-methanesulphonylamino-2-methoxy-phenyl)-3-[2-(4-cyanomethyl-piperazin-1-ylmethyl)-pyridin-4-yloxy]-4-methyl-benzamide

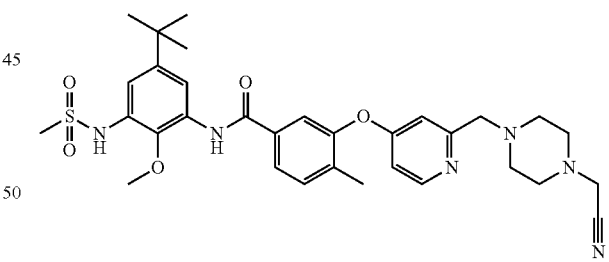

N-(5-tert-butyl-2-methoxy-3-pyrrolidin-1-ylmethyl-phenyl)-4-methyl-3-(2-piperidin-4-ylmethyl-pyridin-4-yloxy)-benzamide

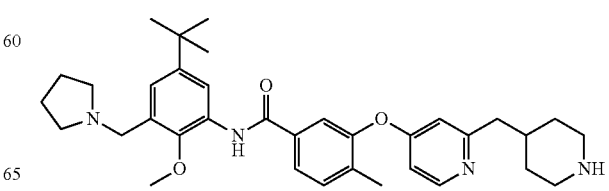

N-(5-tert-butyl-3-hydroxymethyl-2-methoxy-phenyl)-4-methyl-3-(2-piperazin-1-ylmethyl-pyridin-4-yloxy)-benzamide

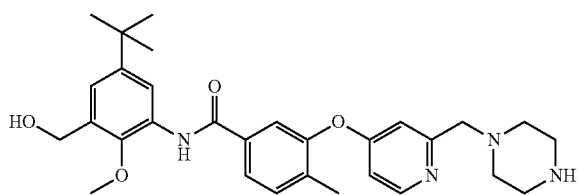 [SMILES: COc1c(CO)cc(C(C)(C)C)cc1NC(=O)c1ccc(C)c(Oc2ccnc(CN3CCNCC3)c2)c1]

N-(5-tert-butyl-3-hydroxymethyl-2-methoxy-phenyl)-4-methyl-3-[2-(4-methyl-piperazin-1-ylmethyl)-pyridin-4-yloxy]-benzamide

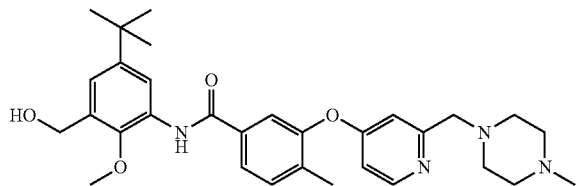 [SMILES: COc1c(CO)cc(C(C)(C)C)cc1NC(=O)c1ccc(C)c(Oc2ccnc(CN3CCN(C)CC3)c2)c1]

N-(5-tert-butyl-3-hydroxymethyl-2-methoxy-phenyl)-3-(2-[1,4]diazepan-1-ylmethyl-pyridin-4-yloxy)-4-methyl-benzamide

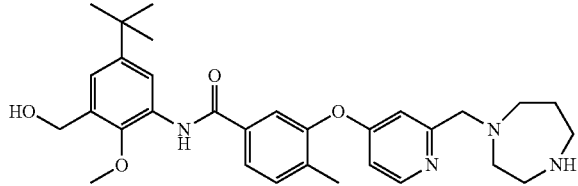 [SMILES: COc1c(CO)cc(C(C)(C)C)cc1NC(=O)c1ccc(C)c(Oc2ccnc(CN3CCCNCC3)c2)c1]

N-(5-tert-butyl-3-hydroxymethyl-2-methoxy-phenyl)-4-methyl-3-[2-(4-methyl-[1,4]diazepan-1-ylmethyl)-pyridin-4-yloxy]-benzamide

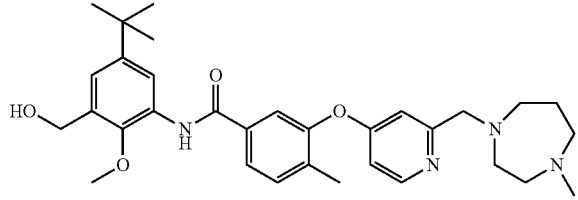 [SMILES: COc1c(CO)cc(C(C)(C)C)cc1NC(=O)c1ccc(C)c(Oc2ccnc(CN3CCCN(C)CC3)c2)c1]

N-(5-tert-butyl-3-cyclopropylaminomethyl-2-methoxy-phenyl)-4-methyl-3-(2-piperidin-4-ylmethyl-pyridin-4-yloxy)-benzamide

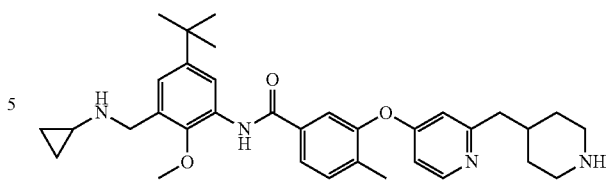

including the tautomers, the stereoisomers and the mixtures thereof.

Terms that are used hereinbefore and hereinafter to describe the compounds according to the invention are defined in more detail below.

The term "substituted", as used herein, denotes that one or more hydrogen atom(s) is or are replaced at a particular atom (of a group/of a residue) by an atom (a group/a residue) selected from a specific group, provided that the possible valency number of the corresponding atom is not exceeded and the substitution leads to a stable compound.

The term halogen denotes an atom selected from among F, Cl, Br and I.

The term $C_{1-n}$-alkyl, wherein n may have a value of 2 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n may have a value of 2 to 18, denotes a saturated, branched or unbranched hydrocarbon group with 1 to n C atoms. Examples of such groups include ethenyl, propenyl, butenyl, pentenyl, etc The term $C_{2-n}$-alkynyl, wherein n has a value of 3 to 6, denotes a branched or unbranched hydrocarbon group with 2 to n C atoms and a C≡C-triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 3-methyl-1-butynyl, 1-hexynyl, 2-hexynyl, 3-hexynyl, 4-hexynyl, 5-hexynyl etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms, wherein n denotes 4 to 15, preferably 8. Examples of such groups include cyclopropyl, cyclobutyl, cyclopentyl, cyclohexyl, cycloheptyl, cyclooctyl, cyclononyl, cyclododecyl, bicyclo[3,2,1]octyl, spiro[4,5]decyl, norpinyl, norbonyl, norcaryl, adamantyl, etc. Preferably the term $C_{3-7}$-cycloalkyl includes saturated monocyclic groups. Accordingly, $C_{3-n}$-heterocycloalkyl denotes saturated mono-, bi or spirocarbocyclic groups with 3-15, preferably 3-8, C atoms and at least one heteroatom selected from N, O or S in the ring.

The term $C_{3-n}$-cycloalkyloxy denotes a $C_{3-n}$-cycloalkyl-O group, wherein $C_{3-n}$-cycloalkyl is as hereinbefore defined.

Examples of such groups include cyclopropyloxy, cyclobutyloxy, cyclopentyloxy, cyclohexyloxy, cycloheptyloxy, etc.

The term $C_{5-n}$-cycloalkenyl denotes a $C_{5-n}$-cycloalkyl group which is as hereinbefore defined and additionally has at least one unsaturated C═C— double bond.

The term $C_{3-n}$-cycloalkylcarbonyl denotes a $C_{3-n}$-cycloalkyl-C(═O) group, wherein cycloalkyl is as hereinbefore defined. n is preferably 7.

The term $C_{3-n}$-heterocycloalkylcarbonyl denotes a $C_{3-n}$-heteroccyloalkyl-C(═O) group, wherein $C_{3-n}$-heterocycloalkyl is as hereinbefore defined. n is preferably 7.

The term $C_{3-n}$-cycloheteroalkyl denotes a saturated mono-, bi-, tri- or spirocarbocyclic group with 3-m to n-m C atoms, wherein n denotes 4 to 12 C atoms and m denotes 1 to 3 heteroatoms, selected independently of one another from $NR^N$, O, S, SO and $SO_2$, which may additionally contain a carbonyl group. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydro-pyranonyl, pyrrolidinonyl, piperidinonyl, piperazinonyl, morpholinonyl. Preferably the term $C_{3-7}$-cycloheteroalkyl includes saturated monocyclic groups with one or two heteroatoms.

The term aryl denotes aromatic carbon rings. $C_{5-10}$ aryl is preferred within the scope of the invention. Preferred examples are phenyl and naphthyl.

The term heteroaryl denotes aromatic carbon rings with at least one heteroatom in the ring selected from N, O and S. $C_{5-10}$ heteroaryl is preferred within the scope of the invention. Preferred examples are pyridine, pyrimidine.

The term tri-($C_{1-4}$-alkyl)silyl includes silyl groups which have the same or two or three different alkyl groups.

The term di-($C_{1-4}$-alkyl)amino includes amino groups which have the same or two different alkyl groups.

The term N-heterocycloalkyl denotes a saturated carbocyclic ring which comprises at least one nitrogen atom in the ring and may additionally comprise further nitrogen groups, O- and/or S-atoms in the ring. Examples of such N-heterocycloalkyl groups are pyrrolidine, piperidine, piperazine, homopiperazine and morpholine.

If alkyl groups occurring in groups, for example in $R^1$, $R^2$, $R^3$ or $R^4$, may be substituted, for example fluorinated, this includes not only alkyl groups in the groups that directly represent alkyl groups/fragments, but also in other definitions including alkyl groups/fragments, such as for example alkyloxy, alkylcarbonyl, alkoxyalkyl, etc. Thus, for example, $R^1$, $R^2$, $R^3$ or $R^4$ in the definition of alkyloxy, in which alkyl groups may be partly or completely fluorinated, also include difluoromethoxy and trifluoromethoxy. The same applies to alkyl groups/fragments in which a $CH_2$ group may be replaced by an atom, e.g. O or S, or a group, e.g. $NR^N$, CO or $SO_2$, which also includes carboxy, carboxymethyl, hydroxymethylcarbonyl, carboxyethyl, hydroxymethylcarbonyl-methyl and hydroxyethylcarbonyl, for example, in the definition of hydroxy-$C_{1-3}$-alkyl, while in alkyl groups a $CH_2$ group may be replaced by CO.

The style used above and hereinafter, in which a bond of a substituent in a phenyl group is shown towards the centre of the phenyl ring, denotes, unless otherwise stated, that this substituent may be bound to any free position of the phenyl ring bearing an H atom.

All the elements/atoms mentioned in the present specification, including those that are part of a group, include all the stable isotopic forms of the element in question. Thus, for example, the naming of the atom/element hydrogen includes, in addition to hydrogen itself, the stable isotope deuterium.

As already mentioned hereinbefore, the compounds of general formula I according to the invention and the physiologically acceptable salts thereof have valuable pharmacological properties, particularly an inhibitory effect on the enzyme p38 MAP-kinase.

The biological properties of the new compounds may be tested as follows:

The inhibition of the p38 MAP-kinase mediated signal transmission may be demonstrated for example by an enzymatic assay. In this, the amount of a substrate phosphorylated by the kinase is quantified. The test is carried out as follows:
Enzymatic Assay:

The kinase reaction is carried out in the presence of HEPES (20 mM, pH 7), MgCl2 (10 mM), DTT (1 mM) and TWEEN20 (0.01%). First, dimethylsulphoxide or inhibitor (final concentration: 1 μM) dissolved in dimethylsulphoxide are placed in a reaction vessel. Then the activated p38 MAP-kinase (final concentration 1 nM) is added and the mixture is incubated for 4 h at ambient temperature. Then a mixture of substrate (GST-tagged ATF2) and ATP is added and everything is incubated together for a further hour (final concentration ATP: 100 μM; final concentration ATF2: 10 nM).

The concentration of phosphorylated ATF2 is quantified by chemoluminescence-induced light emission. For this, a gluthathione donor bead (final concentration: 5 μg/ml) which binds to the gluthathione on the ATF2 and phospho-ATF2 antibodies are added to the reaction mixture (final concentration: 3 nM; this binds the phosphate group added by the kinase reaction) to which a Protein A Acceptor Bead (final concentration: 5 μg/ml) binds. These components are dissolved in a buffer which contains 20 mM HEPES pH 7.0, 200 mM NaCL, 80 mM EDTA as well as 0.3% BSA. This reaction mixture is incubated in the dark for 1 hour at ambient temperature. When these beads come physically close, visible light is emitted which is measured in a photometer at 520-620 nm.

Evaluation:

To determine the inhibitory activity of the compounds according to the invention a calculation is made to determine the percentage by which the kinase activity is inhibited at a fixed inhibitor concentration of 1 μM. The maximum activity is determined by non-inhibited kinase. The minimum activity or nonspecific background activity is determined using a reaction mixture without kinase. The compounds of general formula I according to the invention exhibit inhibitory values of >50%, preferably >90%, for example. Table 2 summarises the degree of inhibition of the enzyme p38 MAP-kinase—as described hereinbefore—of the compounds according to the invention detailed in the section "Preparation of the final compounds".

TABLE 2

Inhibitory effect of compounds of general formula I according to the invention on the enzyme p38 MAP-kinase at a 1 μM inhibitor concentration

| Example | % inhibitory effect at 1 μM |
|---|---|
| 1 | 90.8 |
| 2 | 97.7 |
| 3 | 98.1 |
| 3(1) | 97.0 |
| 4 | 97.7 |
| 4(1) | 96.8 |
| 4(2) | 94.8 |
| 4(3) | 96.3 |
| 4(4) | 97.5 |
| 4(5) | 97.4 |
| 4(6) | 98.0 |

TABLE 2-continued

Inhibitory effect of compounds of general formula I according to the invention on the enzyme p38 MAP-kinase at a 1 μM inhibitor concentration

| Example | % inhibitory effect at 1 μM |
|---|---|
| 4(7) | 98.6 |
| 4(8) | 98.6 |
| 4(9) | 98.6 |
| 4(10) | 100 |
| 4(11) | 99.1 |
| 4(12) | 95.8 |
| 4(13) | 96.3 |
| 4(14) | 99.4 |
| 4(15) | 99.6 |
| 4(16) | 99.4 |
| 4(17) | 98.7 |
| 4(18) | 99.0 |
| 4(19) | 98.6 |
| 4(20) | 95.6 |
| 5 | 99.0 |
| 5(1) | 96.8 |
| 5(2) | 93.2 |
| 5(3) | 95.0 |
| 5(4) | 45.3 |
| 5(5) | 98.3 |
| 5(6) | 98.3 |
| 5(7) | 97.8 |
| 5(8) | 98.9 |
| 5(9) | 98.5 |
| 5(10) | 94.6 |
| 5(11) | 98.4 |
| 5(12) | 98.6 |
| 5(13) | 98.2 |
| 5(14) | 98.5 |
| 5(15) | 96.0 |
| 5(16) | 98.9 |
| 5(17) | 98.2 |
| 5(18) | 98.7 |
| 5(19) | 99.7 |
| 5(20) | 99.5 |
| 5(21) | 88.9 |
| 5(22) | 85.7 |
| 5(23) | 98.3 |
| 5(24) | 97.9 |
| 5(25) | 97.6 |
| 5(26) | 97.6 |
| 5(27) | 99.2 |
| 5(28) | 99.0 |
| 5(29) | 99.0 |
| 5(30) | 99.0 |
| 5(31) | 99.4 |
| 5(32) | 97.9 |
| 5(33) | 99.2 |
| 5(34) | 99.1 |
| 5(35) | 98.3 |
| 5(36) | 99.3 |
| 5(37) | 99.3 |
| 5(38) | 98.8 |
| 5(39) | 99.4 |
| 5(40) | 99.5 |
| 5(41) | 99.6 |
| 5(42) | 99.5 |
| 5(43) | 98.6 |
| 5(44) | 93.2 |
| 5(45) | 99.6 |
| 5(46) | 99.6 |
| 5(47) | 97.3 |
| 5(48) | 99.4 |
| 5(49) | 99.2 |
| 5(50) | 99.6 |
| 5(52) | 99.5 |
| 5(53) | 97.0 |
| 5(54) | 99.7 |
| 5(55) | 99.6 |
| 6 | 94.4 |
| 7 | 95.6 |
| 7(2) | 96.3 |
| 7(3) | 98.8 |
| 7(4) | 98.1 |
| 7(5) | 98.5 |
| 8 | 95.0 |
| 8(1) | 55.9 |
| 8(2) | 98.7 |
| 8(3) | 95.2 |
| 8(4) | 66.0 |
| 8(5) | 95.8 |
| 8(6) | 98.7 |
| 8(7) | 94.1 |
| 8(9) | 98.4 |
| 8(10) | 98.9 |
| 8(11) | 96.7 |
| 8(12) | 97.0 |
| 8(13) | 96.8 |
| 8(14) | 91.1 |
| 8(15) | 95.9 |
| 8(16) | 98.7 |
| 8(17) | 96.7 |
| 8(18) | 98.6 |
| 8(19) | 97.0 |
| 8(20) | 99.4 |
| 8(21) | 98.5 |
| 8(22) | 98.3 |
| 8(23) | 97.8 |
| 8(24) | 92.4 |
| 8(25) | 98.6 |
| 8(26) | 97.7 |
| 8(27) | 98.4 |
| 8(28) | 81.8 |
| 8(29) | 89.0 |
| 8(30) | 91.3 |
| 8(31) | 86.5 |
| 8(32) | 92.6 |
| 8(33) | 97.1 |
| 8(34) | 99.3 |
| 8(35) | 98.6 |
| 8(36) | 82.6 |
| 8(37) | 91.3 |
| 8(38) | 98.8 |
| 8(39) | 98.9 |
| 9 | 98.4 |
| 9(1) | 99.9 |
| 9(2) | 98.5 |
| 10 | 99.6 |
| 11 | 99.2 |
| 11(1) | 99.4 |
| 11(2) | 95.4 |
| 11(3) | 99.5 |
| 11(4) | 95.1 |
| 12 | 97.5 |
| 12(1) | 99.4 |
| 12(2) | 98.7 |
| 12(3) | 99.6 |
| 12(4) | 99.3 |
| 12(5) | 99.5 |
| 12(6) | 99.6 |
| 12(7) | 99.8 |
| 13 | 98.2 |
| 13(1) | 97.0 |

Indications

In respect of their ability to inhibit the p38 MAP-kinase activity, the compounds of general formula I according to the invention and the corresponding pharmaceutically acceptable salts thereof are theoretically suitable for treating and/or preventatively treating all those conditions or ailments that are affected by an inhibition of the p38 MAP-kinase activity. The compounds according to the invention are suitable e.g. for improving an abnormal cytokine level mediated by p38 MAP-kinase, particularly for regulating the overproduction of the cytokines IL-1, IL-4, IL-8 and TNF-α. Therefore, the compounds according to the invention may be used for the prevention or treatment of diseases, particularly respiratory complaints, gastrointestinal diseases or complaints, inflammatory diseases (particularly of the airways, joints, skin or eyes), autoimmune diseases, destructive disorders of the bones, proliferation disorders, disorders of angiogenesis, neurodegenerative diseases, infectious diseases and viral diseases as well as diseases of the peripheral or central nervous system.

Preferential mention should be made of the prevention and treatment of diseases of the airways and of the lung which are accompanied by increased mucus production, inflammations and/or obstructive diseases of the airways, such as e.g. acute, allergic or chronic bronchitis, chronic obstructive bronchitis (COPD), cough, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, to pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, and alpha1-antitrypsin deficiency.

Also deserving special mention is the treatment of inflammatory diseases of the gastrointestinal tract, such as e.g. acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, inflammatory diseases of the joints such as rheumatoid arthritis or inflammatory diseases of the skin (e.g. psoriasis) and eyes.

Preferential mention should also be made of the prevention and treatment of diseases of the peripheral or central nervous system, such as e.g. Alzheimer's disease, Parkinson's disease, acute and chronic multiple sclerosis, acute and chronic pain as well as injuries to the brain caused by stroke, hypoxia or craniocerebral trauma.

The compounds according to the invention, including the physiologically acceptable salts thereof, are most particularly suitable for the prophylaxis or treatment of respiratory complaints, particularly COPD and asthma.

Combinations

By reason of their biological properties the compounds of general formula I according to the invention may be used on their own or in conjunction with other active substances of formula I according to the invention. Optionally the compounds of formula I may also be used in combination with one or more other pharmacologically active substances. For the treatment of respiratory complaints the compounds of general formula I according to the invention may be used on their own or in conjunction with other respiratory therapeutic agents, such as e.g. secretolytics (e.g. ambroxol, N-acetylcysteine, EGFR-inhibitors), broncholytics (e.g. tiotropium or ipratropium or fenoterol, salmeterol, salbutamol) and/or anti-inflammatories [e.g. theophylline or glucocorticoids (such as e.g., prednisolone, prednisone, butixocortpropionate, beclomethasone budesonide, fluticasone, mometasone, ciclesonide, dexamethasone, betamethasone), leukotrien receptor inhibitors or leukotriene biosynthesis inhibitors, antihistamines, PDE4 inhibitors (such as e.g. enprofyllin, theophyllin, roflumilast, ariflo (cilomilast), tofimilast, pumafentrin, lirimilast, arofyllin, atizoram)]. Moreover, these compounds may also be combined with non-steroidal antiinflammatory substances ("NSAID"; such as e.g. ibuprofen, celecoxib and rofecoxib), dopamine agonists, statins, antiviral active substances such as abacavir, PI3-kinase inhibitors, MRP4-inhibitors, PAF-antagonists and antiproliferative agents (e.g. methotrexate, leflunomide, FK506 (tacrolimus, prograf)). The combinations that contain one or more of the above mentioned compounds may be used together or successively, for simultaneous, sequential or separate administration. These compounds may be administered, either on their own or in combination with other active substances, by intravenous, subcutaneous, intramuscular, intraperitoneal, intranasal, inhalative, transdermal or oral route, while aerosol formulations are particularly suitable for inhalation.

For treating diseases in the region of the gastrointestinal tract, the compounds of general formula I according to the invention may also be administered on their own or in conjunction with substances having an effect on motility or secretion. These combinations may be administered either simultaneously or sequentially.

Morever, the compounds according to the invention may be used in tumour therapy in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. These combinations may be administered either simultaneously or sequentially.

Formulations

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 0.01 to 100 mg/kg, preferably 0.01 to 10 mg/kg, by inhalation, and from 0.01 to 100 mg/kg, preferably 0.01 to 10 mg/kg by oral route, in each case administered 1 to 4 times a day. For this purpose, the compounds of formula (I) prepared according to the invention, optionally in conjunction with other active substances, may be formulated together with one or more inert conventional carriers, preservatives and/or diluents, e.g. with glucose, arabinose, lactose, saccharose, maltose, dextrane, maize starch, lactose, sucrose, microcrystalline cellulose, sorbitol, mannitol, xylitol, magnesium stearate, polyvinylpyrrolidone, citric acid, tartaric acid, malic acid, ascorbic acid, maleic acid, succinic acid, fumaric acid, acetic acid, sodium chlodie, calcium carbonate, water, water/ethanol, water/glycerol, water/sorbitol, water/polyethylene glycol, propylene glycol, cetylstearyl alcohol, carboxymethylcellulose or fatty substances such as hard fat or suitable mixtures thereof, cetylpyridinium chloride, benzalkonium chloride, benzoic acid, sodium benzoate, surfactants such as soya lecithin, oleic acid, polysorbate or polyvinylpyrrolidone, to produce conventional galenic preparations such as plain or coated tablets, capsules, powders, solutions, suspensions, suppositories, emulsions, inhalable powders or aerosols. To produce propellant-containing inhalation aerosols, propellent gases or mixtures of propellent gases such as e.g. n-propane, n-butane, isobutane, halogenated hydrocarbons such as fluorinated derivatives of methane, ethane [e.g. 1,1,1,2-tetrafluoroethane (TG134a)], propane [e.g. 1,1,1,2,3,3,3-heptafluoropropane(TG227)], butane, cyclopropane or cyclobutane are used.

The dosage for the above-mentioned combination partners is expediently 1/5 of the normally recommended minimum dose to 1/1 of the normally recommended dose.

Therefore, in another aspect this invention relates to the use of a compound according to the invention or a physiologically acceptable salt of such a compound in combination with at least one of the active substances described as a combination partner for preparing a medicament that is suitable for the treatment or prevention of diseases or conditions that can be influenced by inhibition of the enzyme p38 MAP-kinase.

Preferably, this means a respiratory tract disease, particularly one of the above-mentioned diseases or conditions, most particularly COPD or asthma.

The use of the compound according to the invention, or a physiologically acceptable salt thereof, in combination with another active substance may take place simultaneously or at staggered times, but especially close together in time. When they are used simultaneously, the two active substances are given to the patient together; while if they are administered at staggered times the two active substances are given to the patient successively within a time span of less than or equal to 12 hours, but particularly less than or equal to 6 hours.

Consequently, the invention further relates to a medicament that comprises a compound according to the invention or a physiologically acceptable salt of such a compound as well as at least one of the active substances described hereinbefore as combination partners, optionally together with one or more inert carriers, preservatives and/or diluents.

The compound according to the invention, or a physiologically acceptable salt, and the additional active substance to be combined therewith may be present together in one formulation, e.g. a tablet, capsule, inhalable powder or aerosol, or separately in two identical or different formulations, e.g. as a so-called kit-of-parts.

Experimental Section

General synthesis

The compounds according to the invention may be obtained using methods of synthesis that are known in principle. Preferably the compounds may be obtained using the methods of preparation according to the invention explained in more detail hereinafter.

Compounds of general formula I may be prepared according to the methods illustrated in Schemes 1 and 2; $R^1$ to $R^4$, X and Y have the meaning as defined hereinbefore and hereinafter, Ar denotes the phenyl ring substituted by $R^5$, $R^6$ and $R^7$, $PG^1$ is a carboxylic acid protecting group (see the description of protective groups provided below), $PG^2$ is a phenol protecting group and LG denotes either a leaving group such as halogen, $C_{1-4}$-alkyloxy, 2,2,2-trifluoroethoxy, aryloxy, $C_{1-4}$-alkylsulphonyloxy, trifluoromethylsulphonyloxy, arylsulphonyloxy, nitro, cyano, $C_{1-4}$-alkylsulphanyl, $C_{1-4}$-alkylsulphinyl, $C_{1-4}$-alkylsulphonyl, arylsulphanyl, arylsulphinyl or arylsulphonyl or a $B(OH)_2$, $BF_3K$, $B(OC_{1-4}$-alkyl$)_2$ or $B(OCMe_2CMe_2O)$ group. The two strategies include the same transformations at the respective functional groups, but in a different order; therefore only the individual transformations for the sequence shown in Scheme 1 will be described.

Synthesis strategy 1 starts from 3-hydroxy-benzoic acid derivatives which are either described in the literature or may be prepared analogously to related structures in a manner that is readily apparent to the skilled man. The first reaction step in synthesis strategy 1 is the conversion of the phenolic OH group into a protected derivative, $OPG^2$. Suitable protective groups for the OH group of phenols, the preparation and deprotection thereof are dsc hereinafter and may be used analogously here; thus for example methyl, benzyl, allyl, 4-methoxybenzyl and methylsulphonyl may be used as protective groups. Then the protective group $PG^1$ of the carboxylic acid functionality is removed, in order to react the free acid with the amine component, Ar—$NH_2$, in an amide linking reaction. The liberation of carboxylic acids is described hereinafter and may be carried out accordingly. The amide linking is carried out after the conversion of the carboxylic acid group into an activated form thereof such as e.g. an acyl fluoride, chloride, bromide, cyanide, imidazolide (N-acylated), an ester, e.g. 2,2,2-trifluoroethyl ester, vinyl ester, phenyl ester, pentafluorophenyl ester, 4-nitrophenyl ester, succinyl-N-oxy-ester, triazinyl ester or arylotriazol-1-oxy ester, or a thioester such as e.g. methylsulphanylcarbonyl and phenylsulphanylcarbonyl. Mixed anhydrides of carboxylic acid with carbonic acid esters, e.g. derived from isobutyl carbonate, or other leaving groups, such as e.g. dimethylaminocarbonyloxy, pyrrol-1-ylcarbonyloxy, piperidin-1-yl-carbonyloxy, morpho-lin-4-ylcarbonyloxy, trimethylcarbamimidoyloxy, N,N,N',N'-tetramethyl-uronyl, N,N'-dicyclohexyl-uronyl, diisopropoxy-phosphoryloxy, di-(dimethylamino)phos-phoryloxy and dipyrrolidin-1-yl-phosphoryloxy, are also activated forms of carboxylic acid suitable for coupling with an amine. The above-mentioned activated acyl compounds are preferably prepared in a separate reaction step or in situ, depending on their stability. Thus, for example, the acid chloride may be obtained by treating the carboxylic acid with thionyl chloride, phosphorus oxychloride or oxalyl chloride optionally in the presence of catalytic amounts of N,N-dimethylformamide in dichloromethane, 1,2-dichloroethane, acetonitrile, toluene, benzene, tetrahydrofuran, ether or without a solvent in an excess of chlorinating reagent at temperatures between −20 and 120° C. or the imidazolide may be obtained by reacting the carboxylic acid with carbonyldiimidazole in dichloromethane, tetrahydrofuran, acetonitril or 1,4-dioxane at temperatures between 20 and 120° C. Reagents that are suitable for the in situ activation of carboxylic acids include e.g. N,N'-diisopropyl-carbodiimide, N,N'-dicyclohexylcarbodiimide, N-(3-dimethylamino-propyl)-N'-ethyl-carbodiimide, O-(benzotriazol-1-yl)-N,N,N',N'-tetramethyluroniumtetrafluoroborate (TBTU), O-(benzotriazol-1-yl)-N,N,N',N'-tetramethyluronium hexafluorophosphate (HBTU), n-propylphosphonic anhydride, O-(7-azabenzotriazol-1-yl)-N,N,N',N'-tetramethyluronium hexafluorophosphate (HATU), (benzo-triazol-1-yloxy)-tris-(dimethylamino)phosphoniumhexafluorophosphate (BOP) or (benzotriazol-1-yloxy)-tripyrrolidin-1-yl-phosphoniumhexafluorophosphate (PyBOP). The amide linking reaction is preferably carried out in a solvent such as for example dichloromethane, 1,2-dichloroethane, toluene, benzene, N,N-dimethylformamide, N,N-dimethylacetamide, N-methyl-pyrrolidinone, tetrahydrofuran, acetonitrile, dimethylsulphoxide or mixtures thereof. Alcohols, e.g. methanol, ethanol or isopropanol, or water may in some cases also be used as the solvent or co-solvent. The reactions are preferably carried out in the presence of a base such as e.g. triethylamine, pyridine, imidazole, diisopropylethylamine or potassium carbonate and optionally an additive, e.g. 4-dimethylaminopyridine or 1-hydroxybenzotriazole, at temperatures between −20 and 120° C., but preferably between 0 and 80° C.

Scheme 1: Synthtesis strategy 1 for preparing the compounds I

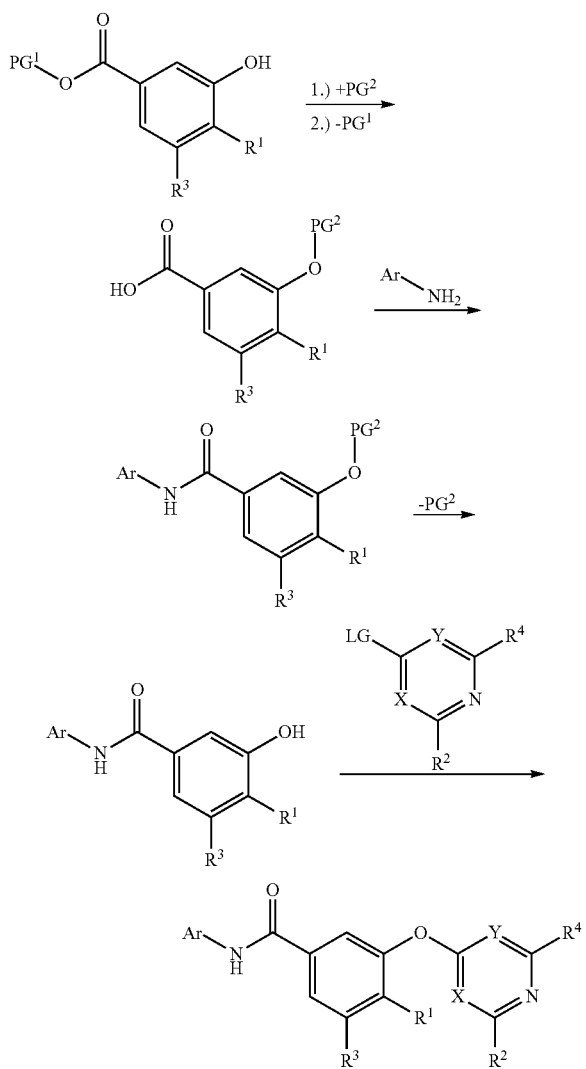

Scheme 2: Synthesis strategy 2 for preparing the compounds I

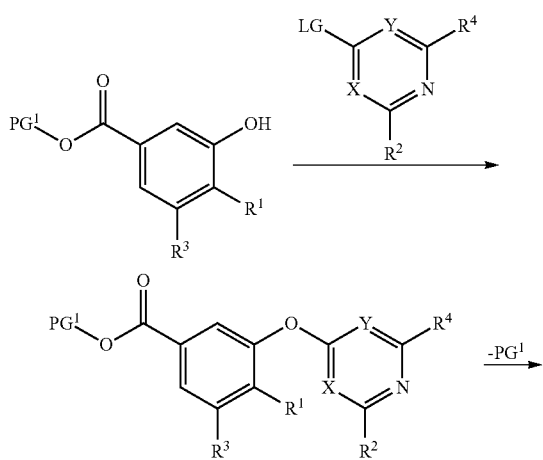

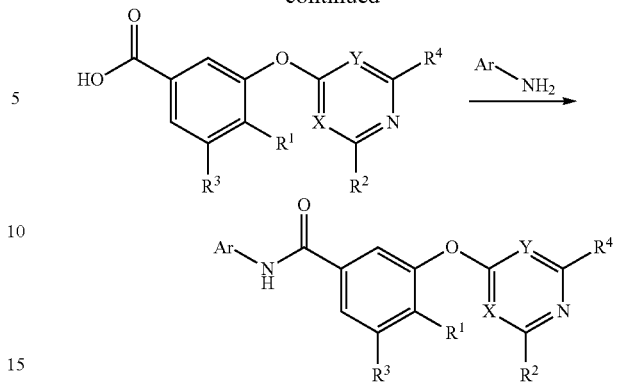

After removal of the phenolic O-protecting group (for method see below) the phenol oxygen is converted by reaction with an electrophil or nucleophil of the N-heteroaromatic group into the corresponding diarylether. In reactions with an electrophilic N-heteroaromatic group (LG=anionic leaving group) the reaction may be carried out in the presence of a transition metal catalyst or with no catalyst. Uncatalysed reactions can be carried out particularly well with N-heteroaromatic compounds which carry fluorine, chlorine, nitro, 2,2,2-trifluoroethoxy, $C_{1-4}$-alkylsulphonyloxy, trifluoromethylsulphonyloxy, arylsulphonyloxy, $C_{1-4}$-alkylsulphinyl, $C_{1-4}$-alkylsulphonyl, arylsulphinyl or arylsulphonyl as LG. For this, the phenol is deprotonated with a base such as e.g. sodium hydride, potassium hydride, KOtBu, NaOtBu, NaOMe, NaOEt, NaOiPr, KF, potassium carbonate, caesium carbonate, pyridine, 4-dimethylaminopyridine, $NEt_3$ or $EtNiPr_2$, in a solvent, such as for example tetrahydrofuran, 1,4-dioxane, 1,2-dimethoxyethane, acetone, acetonitrile, N,N-dimethylformamide, N,N-dimethylacetamide, N-methylpyrrolidinone, water, methanol, ethanol, isopropanol, dimethylsulphoxide or mixtures thereof and reacted with the electrophil at temperatures between −20 and 180° C., preferably between 0 and 120° C. The reactions may also be carried out under microwave irradiation in a microwave device. If the electrophilicity of the N-heteroaromatic group is not sufficient for substitution by the phenol component, it may be increased by forming the corresponding N-oxide (→pyridine-N-oxide, pyrimidine-N-oxide) by oxidation of a nitrogen atom which is part of the aromatic ring, in toluene, dichloromethane or 1,2-dichloroethane, for example, with e.g. 3-chloroperoxybenzoic acid (mCPBA), hydrogen peroxide or tert-butylhydroperoxide, optionally in the presence of a transition metal catalyst, e.g. methylrhenium trioxide. After the introduction of the phenol group, the N-oxides can then be converted into the N-deoxygenated heteroaromatic groups by reduction, e.g. with Zn or Fe in acetic acid or with hydrogen in the presence of a transition metal such as Pd/C or Rh/C.

Catalysed reactions are preferably carried out with azaheteroaromatic compounds which carry iodine, bromine, chlorine, trifluoromethylsulphonyloxy, mesyloxy or tosyloxy as LG. Suitable catalysts are complexes, salts or elemental forms of Cu, Ni, Pd or Fe. Phosphines, e.g. triphenylphosphine, tritolylphosphine, tri-cyclohexylphosphine, tri-tert-butylphosphine, 1,1'-bis(diphenylphosphino)ferrocene, substituted (2-phenylphen-1-yl)-di-tert-butylphosphines or (2-phenylphen-1-yl)-dicyclohexylphosphines, 2.2'-bis(diphenylphosphinyl)-1,1'-binaphthyl, 1,3-diaryl-imidazole or imidazolidinecarbene, 2,2,6,6-tetramethylheptan-3,5-dione, thienyl-2-carboxylate, phosphites, nitriles, e.g. acetonitrile or benzonitrile, or alkenes, e.g. dibenzylideneacetone or allyl, may be used in the complexes. Suitable salt forms are for example fluorides, chlorides, bromides, trifluoromethane-sulphonates, trifluoroacetates or acetates. Elemental forms of the transition metals are e.g. palladium on charcoal or nanoparticles of palladium or iron. The reactions are preferably carried out in the presence of a base such as e.g. one of those already mentioned for the uncatalysed variant, preferably with NaOtBu, $Cs_2CO_3$ or $K_3PO_4$, in a solvent, such as for example tetrahydrofuran, toluene, benzene, 1,4-dioxane, 1,2-dimethoxyethane, acetonitrile, N,N-dim ethylformamide, N,N-dimethylacetamide or N-methylpyrrolidinone, between 0 and 180° C., preferably between 20 and 120° C.

Coupling of the phenol with boron derivatives of the N-heteroaromatic group is preferably carried out under oxidative conditions with Cu(II) salts, e.g. $Cu(OCOCH_3)_2$, in the presence of molecular sieve and triethylamine, pyridine or 4-dimethylaminopyridine in dichloromethane, 1,2-dichloroethane, toluene, tetrahydrofuran or benzene at 0 to 120° C. or in the microwave at up to 160° C. The reactions may be carried out by using a co-oxidant, e.g. oxygen or pyridine-N-oxide, also with catalytic amounts of Cu(II). The precursor of the N-heteroaromatic group, $R^2$—$Ar^{het}$ (see Scheme 3), is prepared differently depending on the atom that links the groups $Ar^{het}$ and $R^2$. If $R^2$ is linked to $Ar^{het}$ via an amino group, the process preferably starts from an $Ar^{het}$ that carries a leaving group $LG^2$ in the position that is to be linked, which is nucleophilically substituted by the group $R^2$ via the amino group. This reaction may be catalysed by a transition metal, preferably a palladium or copper complex, but is preferably carried out, especially where $LG^2$=F, Cl, $NO_2$, $SOC_{1-4}$-alkyl or $SO_2C_{1-4}$-alkyl, without a catalyst in the presence of a base, e.g. KOtBu, $K_2CO_3$, $Na_2CO_3$, $Cs_2CO_3$, pyridine, 4-dimethylaminopyridine, $NEt_3$ or $EtNiPr_2$, in for example tetrahydrofuran, 1,4-dioxane, 1,2-dimethoxyethan, acetonitrile, N,N-dimethylformamide, N,N-dimethylacetamide, N-methyl-pyrrolidinone, water, methanol, ethanol, isopropanol, dimethylsulphoxide or mixtures thereof at temperatures between 0 and 180° C., preferably between 20 and 120° C. Alternatively the group $R^2$ may be attached to the $Ar^{het}$ group by a transition metal, a salt or complex thereof; $LG^2$ in this case is Cl, Br, I, $OSO_2CF_3$, $OSO_2Me$, $OSO_2ToI$, for example. Catalysts derived from palladium and copper, e.g. $Pd_2(dibenzylideneacetone)_3$ combined with (2-dimethylaminophenylphen-1-yl)-di-tert-butyl-phosphine, [2-(2,4,6-triisopropylphenyl)phen-1-yl]dicyclohexyl-phosphine, 2-chloro-1,3-bis(2,6-diisopropylphenyl)-1.3.2-diazaphospholidine or [2-(2,4,6-triisopropylphenyl)phen-1-yl]-di-tert-butyl-phosphine or CuI combined with 2-(isopropylcarbonyl)-cyclohexanone or trans-1,2-di-(methylamino)-cyclohexane, which are preferably used in solvents such as tetrahydrofuran, toluene, benzene, 1,4-dioxane, 1,2-dimethoxyethane, N,N-dimethylformamide, N,N-dimethylacetamide, N-methylpyrrolidinone or acetonitrile between 0 and 180° C., preferably between 20 and 120° C., are particularly suitable for this purpose.

Scheme 3: Method for linking the group $R^2$ to $Ar^{het}$

General:

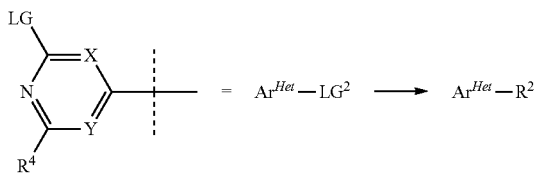

-continued linking via N:

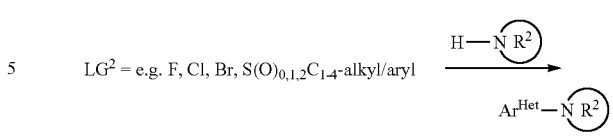

$LG^2$ = e.g. F, Cl, Br, $S(O)_{0,1,2}C_{1-4}$-alkyl/aryl linking via O:

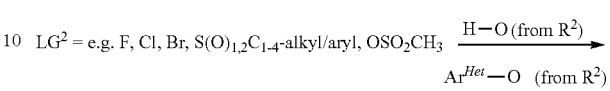

$LG^2$ = e.g. F, Cl, Br, $S(O)_{1,2}C_{1-4}$-alkyl/aryl, $OSO_2CH_3$ linking via C:

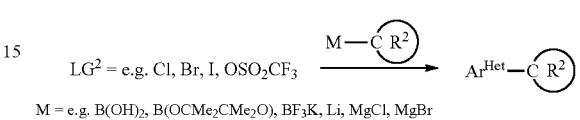

$LG^2$ = e.g. Cl, Br, I, $OSO_2CF_3$

M = e.g. $B(OH)_2$, $B(OCMe_2CMe_2O)$, $BF_3K$, Li, MgCl, MgBr

In cases where $R^2$ is attached to $Ar^{het}$ through O, the procedure as described above (see Schemes 1 and 2) may be used for preparing the diarylethers. The hydroxy group may also be introduced in a manner catalysed by transition metals or uncatalysed. The reaction conditions referred to as being suitable may be used analogously here (cf. Also on the subject of O- and N-linking: *Angew. Chem.* 2003, 115, 5558-5607 and literature cited therein).

In order to prepare an $Ar^{het}$—$R^2$ linked via a C, transition metal-catalysed coupling of a $Ar^{het}$-$LG^2$ to a C-nucleophil of $R^2$ is preferably used, wherein $LG^2$ denotes Cl, Br, I, $OSO_2CF_3$, $OSO_2Me$ or $OSO_2ToI$. Suitable catalysts may be complexes of the transition metal, preferably Pd, Ni, Fe and Cu, with phosphines [e.g. tri-tert-butylphosphine, tricyclohexylphosphine, 2.2'-bis(diphenylphosphinyl)-1,1'-binaphthyl, substituted (2-phenyl-phen-1-yl)-dicyclohexylphosphine (e.g. Xphos), substituted (2-phenyl-phen-1-yl)-di-tert-butylphosphine, triphenylphosphine, tritolylphosphine, trifurylphosphine, 1,1'-bis(diphenylphosphinyl)ferrocene], phosphites, 1,3-disubstituted imidazolecarbenes or imidazolidinecarbenes, dibenzylideneacetone, allyl or nitriles, and elemental forms of the transition metal such as e.g. palladium on charcoal or nanoparticles of Pd or Fe may also be suitable. The active complexes are frequently only prepared in situ from salt forms of the transition metal, using inter alia fluorides, chlorides, bromides, acetates, triflates or trifluoroacetates. The reaction is preferably carried out with a trifluoroborate, a boric acid or a boric acid ester (Suzuki or Suzuki-like coupling), a zinc halide (Negishi or Negishi-like coupling), a stannane (Stille or Stille-like coupling), a silane (Hiyama or Hiyama-like coupling), or a magnesium halide (Kumada or Kumada-like coupling) of the C to be coupled by $R^2$. Depending on the nature of the electrophilic and nucleophilic reactant additives such as halides, e.g. LiCl, KF, $nBu_4NF$, hydroxides, e.g. KOH, $K_2CO_3$, $Cs_2CO_3$, silver salts, e.g. $Ag_2O$ or AgOTf, and copper salts, e.g. CuCl, CuI or copper(I)thiophene carboxylate, may be advantageous or even essential. The coupling is optionally carried out in dichloromethane, N,N-dimethylformamide, N-methylpyrrolidinone, benzene, toluene, tetrahydrofuran, water, ethyl acetate, alcohol, ether, dimethylsulphoxide, 1,2-dimethoxyethane, 1,4-dioxane or mixtures thereof, while depending on the nucleophil one or other solvent may be less suitable or even totally unsuitable. The reactions are preferably carried out between −10 and 180° C.

If the group $Ar^{het}$ carries a carboxy or acyl group in the desired position the group $R^2$ may also be synthesised through this. Possible links are inter alia through a carboxylic acid amide function, wherein $R^2$ is bound to $Ar^{het}$ via an aminocarbonyl group, and an $R^2$ linked via an aminomethyl unit. The synthesis of carboxylic acid amides is described hereinbefore and may be used analogously here. The attachment via an aminomethyl unit is preferably produced by reductive amination of the acylated $Ar^{het}$ with a primary or secondary amine. For this, the reactants are reacted in the presence of a reducing agent, e.g. $NaBH(OCOCH_3)_3$, $NaH_3B(CN)$ or $NaBH_4$, and optionally a Lewis acid, e.g. Acetic acid or $ZnCl_2$, in tetrahydrofuran, 1,4-dioxane, methanol, ethanol, isopropanol, water, N,N-dimethylformamide, N-methyl-pyrrolidinone, acetonitrile, toluene, dichloromethane or 1,2-dichloroethane at −10 to 100° C. Alternatively this aminomethyl link may also be obtained by reduction of the above-mentioned carboxylic acid amide function. Suitable reducing agents for this purpose include inter alia lithium aluminium hydride, diisobutylaluminium hydride or borans, which are preferably used in tetrahydrofuran, 1,4-dioxane, ether, toluene or dichloromethane at −50 to 100° C.

Some transformations starting from compounds of general formula I or closely related compounds will now be described by means of which further structures of general formula I may be obtained.

If a compound of general structure I is obtained which carries an amino or alkylamino group, this may be converted by acylation or sulphonylation into the corresponding acylamino or sulphonylamino compound.

If a compound of general structure I is obtained which carries a hydroxy group, this may be converted by acylation or sulphonylation into the corresponding acyloxy or sulphonyloxy compound.

If a compound of general structure I is obtained which carries a hydroxy group, this may be converted by alkylation into the corresponding alkylether.

If a compound of general structure I is obtained which carries an amino group, this may be converted by reaction with an isocyanate or carbamoyl chloride into the corresponding urea derivative.

If a compound of general structure I is obtained which carries a nitro group, this may be converted by reduction into the corresponding amino compound.

If a compound of general structure I is obtained which carries a $C_{1-4}$-alkyloxycarbonyl group, this may be cleaved to form the corresponding carboxylic acid.

If a compound of general structure I is obtained which carries a carboxy group, this may be transformed by esterification to form the corresponding carboxylic acid ester.

If a compound of general structure I is obtained which carries a carboxy or ester group, this may be transformed to form the corresponding carboxylic acid amide.

If a compound of general structure I is obtained which carries a carboxy group or activated form (e.g. anhydride, carboxylic acid chloride) thereof, this may be converted by a C breakdown reaction into the corresponding amino, urea or urethane derivative.

If a compound of general structure I is obtained which contains an aromatic/heteroaromatic amino group, this may be transformed into the corresponding aromatic/heteroaromatic chloride, fluoride, bromide, cyanide, hydroxide, azide, sulphide or thiol by converting the amino group into a diazo group and subsequently reacting the latter with a chloride, fluoride, bromide, cyanide, hydroxide, azide, sulphide or thiol source.

If a compound of general structure I is obtained which contains an amino, alkylamino or dialkylamino fragment, this may be converted into the corresponding alkylamino, dialkylamino or trialkylamino derivative by alkylation with an alkyl elektrophil or by reductive alkylation with an aldehyde or ketone.

If a compound of general structure I is obtained which carries an aromatic/heteroaromatic Cl, Br, I, $F_3CO_2SO$, $MeO_2SO$ or $ToIO_2SO$ group, this may be converted into the corresponding derivatives by a transition metal-mediated substitution of the above-mentioned groups by aryl, alkenyl, alkynyl or alkyl groups.

If a compound of general structure I is obtained which carries an aromatic/heteroaromatic Cl, Br, I, $F_3CO_2SO$, $MeO_2SO$ or $ToIO_2SO$ group, this may be converted into the corresponding carboxylic acid esters by a transition metal-mediated substitution of the above-mentioned groups by alkyloxycarbonyl.

If a compound of general structure I is obtained which carries an alkenyl group, this may be converted by dihydroxylation into a compound of general formula I carrying a 1,2-dihydroxyethyl unit.

If a compound of general structure I is obtained which contains a 1,2-dihydroxyethyl fragment, this may be converted by glycol cleaving into the corresponding shortened aldehyde.

If a compound of general structure I is obtained which carries a carboxylic acid ester functionality, this may be transformed by reduction into the corresponding aldehyde.

The subsequent acylation or sulphonylation is optionally carried out in a solvent or mixture of solvents selected from $CH_2Cl_2$, benzene, chlorobenzene, toluene, tetrahydrofuran or 1,4-dioxane with a corresponding acyl or sulphonylelectrophile, optionally in the presence of a tertiary amine, an inorganic base and/or a dehydrating reagent. Commonly used reagents are for example thionyl chloride, isobutyl chloroformate, trimethylchlorosilane, sulphuric acid, methanesulphonic acid, p-toluenesulphonic acid, $PCl_3$, $P_2O_5$, N,N'-dicyclohexylcarbodiimide, N,N'-carbonyldiimidazole, triphenylphosphine with $CCl_4$ or combinations thereof, which are optionally used in the presence of 4-dimethylaminopyridine and/or 1-hydroxybenzotriazole between 0 and 150° C., preferably between 0 and 80° C.

The subsequent esterification is carried out with the corresponding alcohol, optionally in a solvent or mixture of solvents selected from $CH_2Cl_2$, N,N-dimethylformamide, benzene, chlorobenzene, toluene, tetrahydrofuran or 1,4-dioxane or particularly preferably in the alcohol itself, with an acid, e.g. hydrochloric acid or sulphuric acid, or a dehydrating reagent. Isobutyl chloroformate, trimethylchlorosilane, sulphuric acid, methanesulphonic acid, thionyl chloride, p-toluenesulphonic acid, N,N'-dicyclohexylcarbodiimide, N,N'-carbonyldiimidazole, $PCl_3$, $P_2O_5$, triphenylphosphine/$CCl_4$ or combinations thereof, optionally in the presence of 4-dimethylaminopyridine and/or 1-hydroxybenzotriazole, are among the reagents frequently used. The reactions are carried out at −20-100° C., preferably at 0-80° C.

The esterification may also be carried out with an alkyl electrophile such as e.g. MeI, $Me_2SO_4$, BnBr or allylbromide in the presence of a base, e.g. CsOH, $Cs_2CO_3$, $K_2CO_3$, NaOH, $NEt_3$.

The subsequent alkylation/etherification is optionally carried out in e.g. dichloromethane, benzene, toluene, N,N-dimethylformamide, tetrahydrofuran or 1,4-dioxane with an alkylating agent of the corresponding halide or sulphonic acid ester, e.g. MeI, MeBr, EtBr, $Me_2SO_4$, BnCl, optionally in the presence of a tertiary organic base or an inorganic base at temperatures between 0 and 150° C., preferably between 0 and 100° C.

The subsequent formation of a urea from an amine may be carried out e.g. in a solvent or mixture of solvents selected from dimethylformamide, N-methylpyrrolidinone, toluene, acetonitrile, dichloromethane 1,2-dichloroethane, tetrahydrofuran, ether, 1,2-dimethoxyethane or dioxane with an isocyanate or carbamoyl chloride, optionally in the presence of a tertiary organic base, e.g. $NEt_3$ or $EtNiPr_2$, or an inorganic base, e.g. $K_2CO_3$ or CaO, at 0 to 180° C., preferably at 5 to 120° C. The use of additives such as pyridine or 4-dimethylaminopyridine may be advantageous.

The subsequent reduction of a nitro group is carried out for example with hydrogen in the presence of a transition metal catalyst, e.g. palladium on charcoal, $PtO_2$ or Raney nickel, or with iron or zinc in the presence of an acid such as acetic acid.

The subsequent cleaving of a $C_{1-4}$-alkyloxycarbonyl group in order to form the free carboxylic acid is effected for example by acid or basic hydrolysis with HCl, sulphuric acid, LiOH, NaOH or KOH in an aqueous or alcoholic solvent or mixture of solvents.

The subsequent exchange of a carboxy group, e.g. Carboxylic acid or activated carboxylic acid group, for a nitrogen group is carried out e.g. by a breakdown reaction via the corresponding acylazide (e.g. Curtius degradation, Hofmann degradation). The acylazide is obtained e.g. by reacting the carboxylic acid with $(PhO)_2P(O)N_3$ in the presence of a base, e.g. $NEt_3$, $iPr_2NEt$, pyridine, 4-dimethylaminopyridine, $K_2CO_3$ or $Cs_2CO_3$, in e.g. cyclohexane, tert-butanol, toluene, benzene, dichloromethane, 1,2-dichloroethane, 1,4-dioxane, tetrahydrofuran, N,N-dimethylformamide or mixtures thereof. Starting from an activated carboxylic acid function, e.g. acyl chloride, mixed anhydrides with e.g. urethanes, carbonic acid esters or phosphoric acid esters, aryl esters such as pentafluorophenyl or 4-nitrophenylesters, alkyl- or arylthioesters, the acylazide may be obtained after reaction with an azide nucleophil, e.g. $NaN_3$ or $Me_3SiN_3$, optionally in the presence of an additive, e.g. $Bu_4NBr$, preferably in toluene, benzene, tetrahydrofuran, ether, 1,4-dioxane, dichloromethane, N,N-dimethylformamide, N-methylpyrrolidinone, acetonitrile, acetone, water or mixtures thereof; depending on the azide source some of the combinations mentioned are unsuitable. The acylazide is rearranged—possibly only as a result of the increase in temperature to preferably 60 to 140° C.—to form the isocyanate, which may be isolated in the case of an inert solvent. The free amine may be obtained therefrom by the addition of water, the corresponding urethane by the addition of alcohol and the corresponding urea after the addition of an amine.

The subsequent conversion of a reactive carboxylic acid functionality into the corresponding carboxylic acid amide is achieved by reaction with the corresponding amine, preferably in a solvent such as dichloromethane, N,N-dimethylformamide, N-methylpyrrolidinone, benzene, toluene, chlorobenzene, tetrahydrofuran, 1,4-dioxane, mixtures thereof or in the amine itself, optionally in the presence of a tertiary organic amine base or an inorganic base and optionally with 4-dimethylaminopyridine as additive, at temperatures of 0 to 180° C., preferably between 0 and 80° C.

The subsequent conversion of an aromatic/heteroaromatic amino group is achieved by diazotisation of the amino group with for example nitric acid, a nitrosonium source or equivalents thereof such as e.g. $NaNO_2$/HCl, $NOBF_4$, tert-butylnitrite or isoamylnitrite. The diazotisation is carried out for example in dichloromethane, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane or mixtures thereof at −10 to 100° C. (diazotisations of amino groups are described for example in Angew. Chem. Int. Ed. 1976, 15, 251 and the literature cited therein). The subsequent exchange of the diazo group for a cyano group, a chlorine or bromine atom by means of CuCN, CuCl or CuBr is known in the literature as the Sandmeyer reaction (see March's Advanced Organic Chemistry, Michael B. Smith and Jerry March, John Wiley & Sons Inc., 6. Ed., New Jersey, 2007 and literature cited therein). The reaction is preferably carried out between −10 and 120° C. in one of the above mentioned solvents or mixtures. The exchange of a diazo group for fluorine may be carried out by reacting the diazo compound with an alkali metal tetrafluoroborate or tetrafluoroboric acid at 20 to 160° C.; this reaction is known as the Schiemann reaction. Iodine may be introduced by treating the diazo compound with an iodide, e.g. NaI, preferably in water or an aqueous mixture of solvents, at 0 to 120° C. The diazo-hydroxy exchange may be achieved by reaction in the presence of water at 0 to 180° C. This reaction normally takes place without any further additives, but the addition of copper oxide or strong acid may be advantageous. Mercapto or alkylsulphanyl groups may be introduced by reacting the diazo compound with alkali metal disulphides or dialkylsulphides at temperatures of 0 to 120° C.; depending on the species of sulphur to be introduced, inert or aqueous solvent systems will be more suitable (see e.g. Synth. Commun. 2001, 31, 1857 and references cited therein).

The subsequent reductive alkylation of an amine is carried out with the corresponding carbonyl compound, such as e.g. formaldehyde, acetaldehyde, propionaldehyde, acetone or butyraldehyde, and a complex metal hydride, e.g. $NaBH_4$, $LiBH_4$, $NaHB(OCOCH_3)_3$, $NaH_3B(CN)$, preferably at a pH of 6-7 or with hydrogen, at 1 to 5 bar, in the presence of a transition metal, e.g. Pd/C. The methylation may also be carried out with formic acid or formates as reducing agent at 60 to 120° C.

The subsequent exchange of an aromatic/heteroaromatic chlorine, bromine, iodine atom or an aromatic/heteroaromatic trifluoromethylsulphonyloxy, mesyloxy or tosyloxy group for an aryl, heteroaryl, alkenyl, alkynyl or alkyl group is preferably mediated by a transition metal catalyst, e.g. those derived from Pd, Ni, Rh, Cu and Fe. Suitable catalysts or precursors thereof may be complexes of the transition metals with e.g. phosphines [e.g. tri-tert-butylphosphine, tritolylphosphine, tricyclohexylphosphine, triphenylphosphine, substituted (2-phenyl-phen-1-yl)-dicyclohexylphosphine, trifurylphosphine, substituted (2-phenyl-phen-1-yl)-di-tert-butylphosphine, 1,1'-bis(diphenylphosphino)ferrocene], 1,3-disubstituted imidazolecarbenes, 1,3-disubstituted imidazolidinecarbenes, phosphites, dibenzylideneacetone, allyl or nitriles, elemental forms of the transition metals, e.g. Pd/C or nanoparticles of Pd or Fe, salts of the transition metals, such as e.g. fluoride, chloride, bromide, acetate, trifluoromethanesulphonate or trifluoroacetate, or combinations thereof. The exchange is preferably carried out with the corresponding alkali metal trifluoroborate, boric acid or ester (Suzuki or Suzuki-like reaction), zinc halide (Negishi or Negishi-like reaction), stannan (Stille or Stille-like reaction), silane (Hiyama or Hiyama-like reaction), magnesium halide (Kumada or Kumada-like reaction) of the aryl, alkenyl or alkyl group that is to be introduced. The exchange for a terminal alkyne is preferably carried out with the same or the corresponding zinc acetylide. Depending on the course of the reaction and the nature of the reactants, additives such as e.g. halides, e.g. LiCl, KF, $nBu_4NF$, hydroxides, e.g. KOH, $K_2CO_3$, $Cs_2CO_3$, $K_3PO_4$, silver salts, e.g. $Ag_2O$ or $AgOSO_2CF_3$, copper salts, e.g. CuCl or copper(I) thiophenecarboxylate may be advantageous or even essential. CuI is a preferred additive for coupling with terminal alkynes (Sonogashira reaction). The reactions are preferably carried out in dichloromethane, N,N-dimethylformamide, N-methylpyrrolidinone, benzene, toluene, tetrahydrofuran, water, ethyl acetate, alcohol, ether, dimethylsulphoxide, 1,2-dimethoxyethane, 1,4-dioxane or mixtures thereof, the correct choice of solvent being dependent on the nucleophil and some cannot be reacted in all of them. The reactions are preferably carried out at −10 to 180° C.

The subsequent exchange of an aromatic/heteroaromatic chlorine, bromine, iodine atom or an aromatic/heteroaromatic trifluoromethylsulphonyloxy, mesyloxy or tosyloxy group for an alkyloxycarbonyl group is achieved by reacting the compound in question under a CO atmosphere in the presence of the corresponding alcohol and a transition metal catalyst. Suitable catalyst systems are e.g. $Pd(OCOCH_3)_2$ combined with $PPh_3$, $Pd(OCOCH_3)_2$ combined with $Ph_2P(CH_2)_3PPh_2$, $PdCl_2[1,1'$-bis(diphenylphosphino)ferrocene], $(BINAP)PdCl_2$, $Pd(PtBu_3)_2$, $PdCl_2(PhCN)_2/Ph_2P(CH_2)_3PPh_2$, $Pd(OCOCH_3)_2/Ph_2P(CH_2)_4PPh_2$, which are preferably used in the presence of bases, such as e.g. $KOCOCH_3$, $NaOCOCH_3$, $NEt_3$, $K_2CO_3$, $NaHCO_3$, in solvents, such as e.g. N,N-dimethylformamide, N-methylpyrrolidinone, toluene, 1,4-dioxane or the alcohol itself. The CO pressure is preferably 1 to 5 bar at temperatures between 20 and 160° C.

The subsequent dihydroxylation of an alkenyl group may be carried out with $OsO_4$ or $KMnO_4$ as oxidising agent. Preferably $OsO_4$ and $K_2OsO_4$ are used in combination with a co-oxidant, e.g. $K_3Fe(CN)_6$, N-methylmorpholine-N-oxide, NaOCl or $NaClO_2$, in catalytic amounts. Suitable solvents or ingredients of the solvent include for example water, chloroform, dichloromethane, ether, tetrahydrofuran, acetone, pyridine, acetonitrile, toluene and tert-butanol. Additives such as $MeSO_2NH_2$, KCl, bases, e.g. $K_2CO_3$, diazabicyclooctane (DABCO), or ligands, e.g. 1,4-bis(dihydroquinidyl)-phthalazine, which also allow enantioselective dihydroxylation in a uniformly chiral form (see Sharpless dihydroxylation and AD-mix-α, AD-mix-β), are advantageous or even essential. The dihydroxylation may be carried out between −50 and 60° C., but is preferably carried out between −10 and 40° C.

Alternatively this transformation may also be carried out by epoxidation of the double bond, e.g. with 3-chloroperoxybenzoic acid, dimethyldioxiran or $H_2O_2$ or $tBuO_2H$ combined with a transition metal catalyst, and subsequent opening of the oxiran with a hydroxyl nucleophil, e.g. water, LiOH, NaOH, KOH or NaOOH with subsequent reduction of the O—O— bond.

The subsequent glycol cleaving of a 1,2-dihydroxyethyl fragment is carried out either with $Pb(OCOCH_3)_4$ or $NaIO_4$ or $HIO_4$ as oxidising agent. $Pb(OCOCH_3)_4$ is used predominantly in aprotic solvents, preferably benzene or dichloromethane, at temperatures between −10 and 80° C. $NaIO_4$ on the other hand is preferably used in aqueous solvents or mixtures of organic solvents, e.g. dichloromethane, tetrahydrofuran, 1,4-dioxane, methanol, acetonitrile, with water at −10 to 80° C.; $NaIO_4$ in combination with silica gel or applied to silica gel also enables the reaction to be carried out anhydrously in one of the above-mentioned organic solvents.

The subsequent one-step reduction of a carboxylic acid ester to form the corresponding aldehyde is preferably carried out with diisobutylaluminium hydride (DIBAl-H) in dichloromethane, toluene, hexane, tetrahydrofuran or mixtures thereof at −80 to 20° C. Alternatively a two-step variant is possible comprising reducing the ester to the alcohol, e.g. with DIBAl-H, $LiAlH_4$ or $LiBH_4$, and subsequently oxidising the alcohol to form the aldehyde, e.g. with Dess-Martin-Periodinane, pyridine-$SO_3$ or pyridinium chlorochromate (PCC), in order to achieve this conversion.

In the reactions described hereinbefore, any reactive groups present such as carboxy, carbonyl, hydroxy, amino or alkylamino groups or terminal alkynes may be protected during the reaction by conventional protecting groups which are cleaved again after the reaction (cf. e.g.: *Protecting Groups*, Philip J. Kocienski, $3^{rd}$ edition, Georg Thieme Verlag, Stuttgart, 2004 and references cited therein).

For example, a protecting group for a carboxy group may be a trimethylsilyl, methyl, ethyl, tert.butyl, allyl or benzyl group.

For example, a protecting group for a carbonyl group of a ketone or aldehyde may be a ketal or acetal, e.g. derived from methanol, glycol or propane-1,3-diol.

For example, a protecting group for an aliphatic hydroxy group may be the trimethylsilyl, tert-butyldimethylsilyl, triisopropylsilyl, acetyl, pivaloyl, benzoyl, methyl, allyl, benzyl, 4-methoxybenzyl, trityl, methoxymethyl, ethoxymethyl, 2-trimethylsilylethoxymethyl or tetrahydropyranyl group.

Suitable protecting groups for a phenolic OH group, besides those already mentioned for the aliphatic hydroxy group, are methylsulphonyl, tosyl and trifluoromethylsulphonyl.

Suitable protecting groups for an amino or alkylamino group include for example the formyl, acetyl, trifluoroacetyl, ethoxycarbonyl, tert.-butoxycarbonyl, benzyloxycarbonyl, benzyl, 4-methoxybenzyl or 2,4-dimethoxybenzyl group, while additionally phthalyl or tetrachlorophthalyl are also suitable for the $NH_2$ group.

For example suitable protecting groups for a terminal alkynyl group include the trimethylsilyl, triisopropylsilyl or 2-hydroxyprop-2-yl group.

Any acyl protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 140° C., preferably 10 and 100° C. Another suitable method of cleaving an alkyl ester trifluoroacetyl group is by reaction with iodotrimethylsilane, put in as such or prepared in situ, in an inert solvent such as dichloromethane, 1,2-dichloroethane, toluene or acetonitrile.

Any acetal or ketal protecting group used is preferably cleaved in an aqueous solvent, e.g. in water, isopropanol/water, tetrahydrofuran/water or 1,4-dioxane/water, in the presence of an acid such as acetic acid, trifluoroacetic acid, hydrochloric acid or sulphuric acid, at temperatures between 0 and 120° C., preferably at temperatures between 10 and 100° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids such as e.g. hydrochloric acid, trifluoroacetic acid or acetic acid are also suitable. For cleaving in organic solvents, such as for example diethyl ether, tetrahydrofuran or dichloromethane, it is also suitable to use fluoride reagents, such as e.g. tetrabutylammonium fluoride or HF. Besides the use of strong acids, the latter is another suitable method for cleaving larger silyl groups, such as e.g. tert-butyldimethylsilyl and triisopropylsilyl.

A benzyl, methoxybenzyl or benzyloxycarbonyl group is advantageously cleaved hydrogenolytically, e.g. with hydrogen in the presence of a catalyst such as palladium on charcoal, palladium hydroxide or platinum oxide, in a suitable solvent such as methanol, ethanol, ethyl acetate or glacial acetic acid, optionally with the addition of an acid such as hydrochloric acid, at temperatures between 0 and 100° C., but preferably between 20 and 60° C., and under a hydrogen pressure of 1 to 7 bar, preferably 3 to 5 bar. Trimethylsilyl iodide, boron trichloride or boron trifluoride in the presence of a moppin-up reagent, e.g. anisole, thioanisole or pentamethylbenzene, may also be used for cleaving benzylethers including the substituted derivatives thereof. The cleaving of electron-rich benzyl groups, such as e.g. 4-methoxybenzyl, may also be carried out oxidatively with e.g. 2,3-dichloro-5, 6-dicyano-1,4-benzoquinone (DDQ) or cerium ammonium nitrate (CAN), preferably in alcoholic or aqueous solutions, between 10 and 120° C. The 2,4-dimethoxybenzyl group is preferably cleaved in trifluoroacetic acid in the presence of a mopping-up reagent, e.g. anisole.

A tert.butyl or tert.butyloxycarbonyl group is preferably cleaved by treating with an acid such as trifluoroacetic acid or hydrochloric acid, optionally using a solvent such as dichloromethane, 1,4-dioxane, methanol, isopropanol or diethyl ether.

A methyl group on a tertiary amine may be cleaved by treating with 1-chloroethylchloroformate. HBr or $BBr_3$ are particularly suitable for cleaving methylethers.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae II and III used as starting materials are known from the literature in some cases or may be prepared using methods known from the literature and analogously to the methods described in the Examples, optionally with the additional introduction of protecting groups.

EXAMPLES

The following Examples are intended to illustrate the present invention in more detail without restricting it.

The compounds described below were characterised using a characteristic mass after ionisation in a mass spectrometer, an Rf value on a TLC plate and/or their retention time during analytical HPLC.

HPLC methods used:

Method 1: Column: Merck Cromolith Speed ROD, RP18e, 50×4.6 mm; 1.5 ml/min; UV detection: 230 nm/254 nm; eluant A: water (0.1% formic acid), eluant B: acetonitrile (0.1% formic acid)

gradient:

| time (min.) | % eluant B |
|---|---|
| 0.00 | 10 |
| 4.50 | 90 |
| 5.00 | 90 |
| 5.50 | 10 |

Method 2: Column: Agilent Zorbax Bonus RP, 50×2.1 mm, 3.5 µm; 1.2 ml/min; UV detection: 230 nm/254 nm; eluant A: water (0.1% formic acid), eluant B: acetonitrile (0.1% formic acid)

gradient:

| time (min.) | % eluant B |
|---|---|
| 0.00 | 10 |
| 4.50 | 99 |
| 5.00 | 99 |
| 5.50 | 10 |

Method 3: Column: Waters Xbridge C18, 30×4.6 mm, 2.5 µm; 1.6 ml/min; UV detection: 230 nm/254 nm; eluant A: water (0.1% ammonia), eluant B: methanol gradient:

| time (min.) | % eluant B |
|---|---|
| 0.00 | 10 |
| 0.15 | 10 |
| 4.00 | 100 |
| 4.40 | 100 |
| 4.55 | 10 |
| 5.00 | 10 |

Preparation of the Starting Compounds

Example I

N-(5-tert-butyl-3-methanesulphonylamino-2-methoxy-phenyl)-3-hydroxy-4-methyl-benzamide

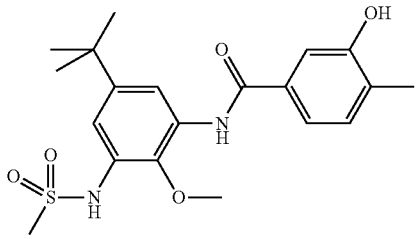 [SMILES: COc1c(NC(=O)c2ccc(C)c(O)c2)cc(C(C)(C)C)cc1NS(C)(=O)=O]

7.10 g 3-benzyloxy-N-(5-tert-butyl-3-methanesulphonylamino-2-methoxy-phenyl)-4-methyl-benzamide are hydrogenated in a mixture of 70 ml of methanol and 40 ml of tetrahydrofuran in the presence of 800 mg palladium on activated charcoal (10% Pd) at ambient temperature and 50 psi partial hydrogen pressure. Then the catalyst is suction filtered and the filtrate is evaporated down using the rotary evaporator. A white solid remains, which is reacted further without any further purification.

Yield: 5.90 g (100% of theory)
Mass spectrum (ESI$^+$): m/z=407 [M+H]$^+$

The following compounds are obtained analogously to Example I:

(1) N-(5-tert-butyl-3-methanesulphonylamino-2-methoxy-phenyl)-3-hydroxy-4-chloro-benzamide

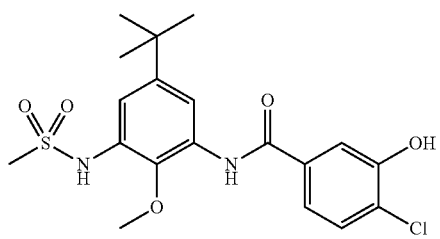 [SMILES: COc1c(NC(=O)c2ccc(Cl)c(O)c2)cc(C(C)(C)C)cc1NS(C)(=O)=O]

$R_f$ value: 0.40 (silica gel, petroleum ether/ethyl acetate=1:1)
Mass spectrum (ESI$^+$): m/z=427/429 (Cl) [M+H]$^+$ (2) N-(5-tert-butyl-3-methanesulphonylamino-2-methoxy-phenyl)-3-hydroxy-4-trifluoromethyl-benzamide

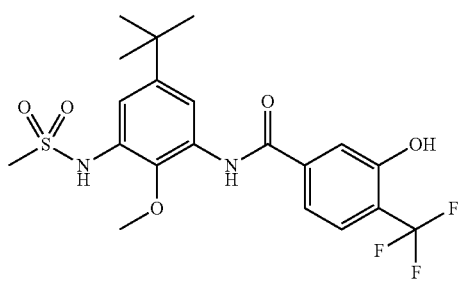 [SMILES: COc1c(NC(=O)c2ccc(C(F)(F)F)c(O)c2)cc(C(C)(C)C)cc1NS(C)(=O)=O]

$R_f$ value: 0.51 (silica gel, petroleum ether/ethyl acetate=1:1)
Mass spectrum (ESI$^+$): m/z=461 [M+H]$^+$ (3) N-(5-tert-butyl-3-methanesulphonylamino-2-methoxy-phenyl)-3-hydroxy-4-methoxy-benzamide

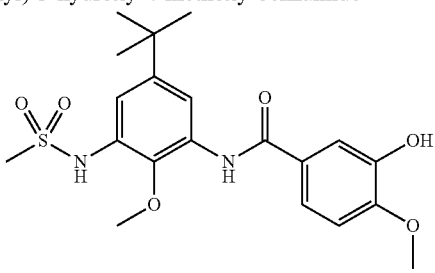

$R_f$ value: 0.20 (silica gel, cyclohexane/ethyl acetate=1:1)
Mass spectrum (ESI$^+$): m/z=423 [M+H]$^+$ (4) N-(5-tert-butyl-3-methanesulphonylamino-2-methoxy-phenyl)-3-hydroxy-4-fluoro-benzamide

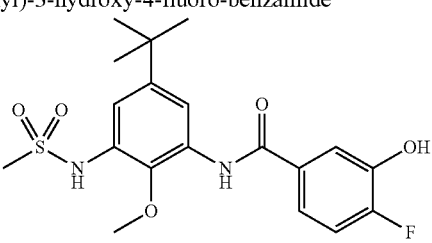

$R_f$ value: 0.45 (silica gel, petroleum ether/ethyl acetate=1:1)
Mass spectrum (ESI$^+$): m/z=411 [M+H]$^+$ (5) N-(5-tert-butyl-3-methanesulphonylamino-2-methoxy-phenyl)-3-chloro-5-hydroxy-4-methyl-benzamide

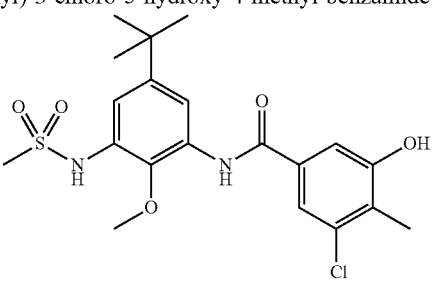

$R_f$ value: 0.42 (silica gel, cyclohexane/ethyl acetate=1:1)
Mass spectrum (ESI$^+$): m/z=441/443 (Cl) [M+H]$^+$ (6) N-(5-tert-butyl-3-methanesulphonylamino-2-methoxy-phenyl)-3-fluoro-5-hydroxy-4-methyl-benzamide

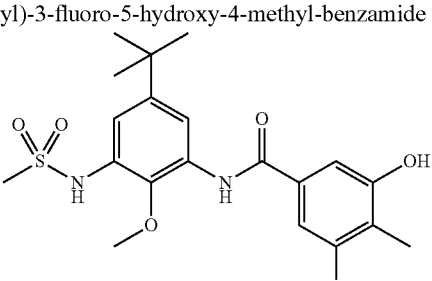

$R_f$ value: 0.40 (silica gel, cyclohexane/ethyl acetate=1:1)
Mass spectrum (ESI$^+$): m/z=425 [M+H]+

(7) N-(5-tert-butyl-3-methanesulphonylamino-2-methoxy-phenyl)-3-hydroxy-5-methyl-benzamide

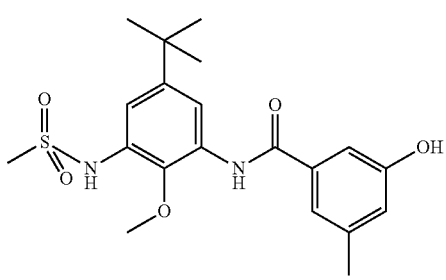 [SMILES: COc1c(NC(=O)c2cc(C)cc(O)c2)cc(C(C)(C)C)cc1NS(C)(=O)=O]

$R_f$ value: 0.35 (silica gel, cyclohexane/ethyl acetate=1:1)
Mass spectrum (ESI$^+$): m/z=407 [M+H]$^+$ (8) N-(5-tert-butyl-3-methanesulphonyl-2-methoxy-phenyl)-3-hydroxy-4-methyl-benzamide

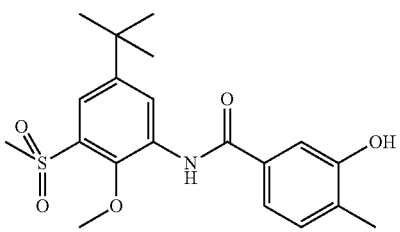

$R_f$ value: 0.55 (silica gel, cyclohexane/ethyl acetate=1:1)

Example II 3-benzyloxy-N-(5-tert-butyl-3-methanesulphonylamino-2-methoxy-phenyl)-4-methyl-benzamide

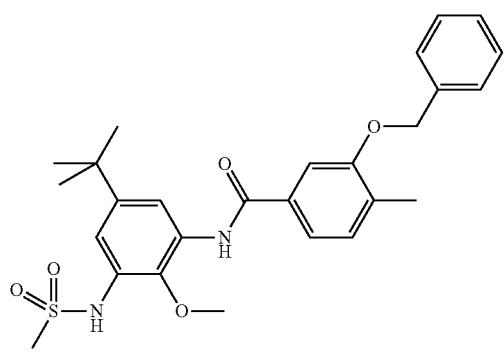 [SMILES: COc1c(NC(=O)c2ccc(C)c(OCc3ccccc3)c2)cc(C(C)(C)C)cc1NS(C)(=O)=O]

10.59 g of O-(7-azabenzotriazol-1-yl)-N,N,N',N'-tetramethyl-uronium hexafluorophosphate, 9.54 ml diisopropyl-ethylamine and 1.26 g 1-hydroxy-7-azabenzotriazole are added to 4.50 g 3-benzyloxy-4-methyl-benzoic acid in 25 ml N,N-dimethylformamide under an argon atmosphere. The mixture is stirred for 15 minutes at ambient temperature, before 5.74 g N-(3-amino-5-tert-butyl-2-methoxyphenyl-methanesulphonamide-hydrochloride are added. The reaction mixture is stirred overnight at 50° C. After cooling to ambient temperature the reaction mixture is diluted with ethyl acetate, washed with water, 1 N hydrochloric acid and saturated aqueous sodium chloride solution, dried on magnesium sulphate and evaporated down. The flask residue is stirred with methanol, and the resulting white precipitate is suction filtered and dried.

Yield: 7.10 g (77% of theory)
Mass spectrum (ESI$^+$): m/z=497 [M+H]$^+$

The following compounds are obtained analogously to Example II:

(1) 3-benzyloxy-N-(5-tert-butyl-3-methanesulphonylamino-2-methoxy-phenyl)-4-chloro-benzamide

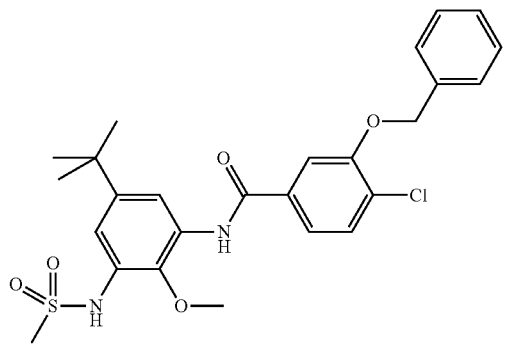 [SMILES: COc1c(NC(=O)c2ccc(Cl)c(OCc3ccccc3)c2)cc(C(C)(C)C)cc1NS(C)(=O)=O]

$R_f$ value: 0.68 (silica gel, petroleum ether/ethyl acetate=1:1)
Mass spectrum (ESI$^+$): m/z=517/519 (Cl) [M+H]$^+$ (2) 3-benzyloxy-N-(5-tert-butyl-3-methanesulphonylamino-2-methoxy-phenyl)-4-trifluoromethyl-benzamide

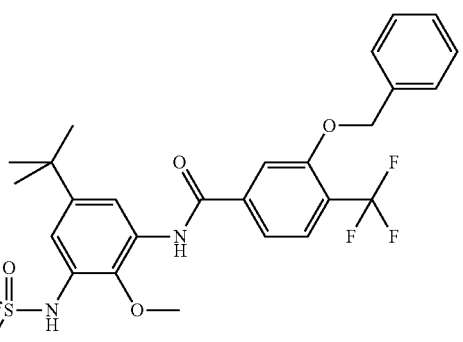

$R_f$ value: 0.70 (silica gel, petroleum ether/ethyl acetate=1:1)
Mass spectrum (ESI$^+$): m/z=551 [M+H]$^+$ (3) 3-benzyloxy-N-(5-tert-butyl-3-methanesulphonylamino-2-methoxy-phenyl)-4-fluoro-benzamide

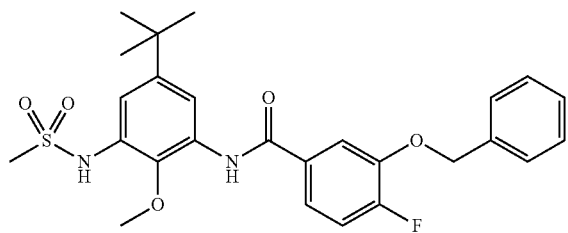 [SMILES: COc1c(NC(=O)c2ccc(F)c(OCc3ccccc3)c2)cc(C(C)(C)C)cc1NS(C)(=O)=O]

R$_f$ value: 0.60 (silica gel, petroleum ether/ethyl acetate=1:1)
Mass spectrum (ESI$^+$): m/z=501 [M+H]$^+$ (4) tert-butyl 4-{4-[2-bromo-5-(5-tert-butyl-3-methanesulphonylamino-2-methoxy-phenyl-aminocarbonyl)-phenoxy]-pyrimidin-2-yl}-piperazine-1-carboxylate R$_f$ value: 0.40 (silica gel, cyclohexane/ethyl acetate=1:1)
Mass spectrum (ESI$^+$): m/z=733/735 (Br) [M+H]$^+$ (5) tert-butyl 4-{4-[5-(5-tert-butyl-3-methanesulphonylamino-2-methoxy-phenylaminocarbonyl)-2-ethyl-phenoxy]-pyrimidin-2-yl}-piperazine-1-carboxylate R$_f$ value: 0.40 (silica gel, cyclohexane/ethyl acetate=1:1)
Mass spectrum (ESI$^+$): m/z=683 [M+H]$^+$ (6) 3-benzyloxy-N-(5-tert-butyl-3-methanesulphonylamino-2-methoxy-phenyl)-5-methyl-benzamide

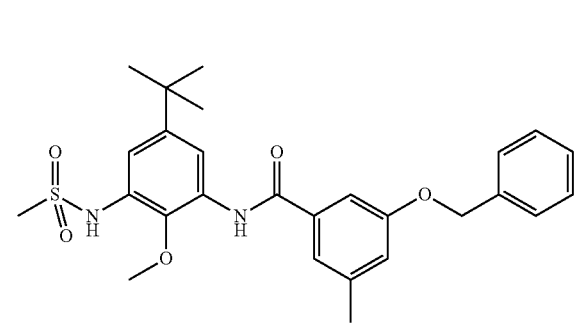 [SMILES: COc1c(NC(=O)c2cc(C)cc(OCc3ccccc3)c2)cc(C(C)(C)C)cc1NS(C)(=O)=O]

R$_f$ value: 0.35 (silica gel, cyclohexane/ethyl acetate=2:1)
Mass spectrum (ESI$^+$): m/z=497 [M+H]$^+$ (7) 3-benzyloxy-N-(5-tert-butyl-3-methanesulphonyl-2-methoxy-phenyl)-4-methyl-benzamide

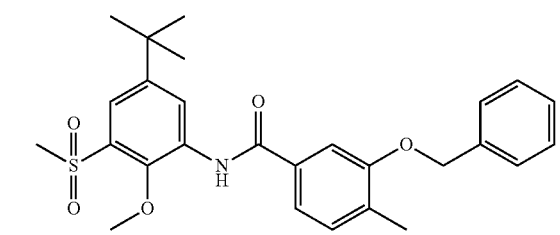 [SMILES: COc1c(NC(=O)c2ccc(C)c(OCc3ccccc3)c2)cc(C(C)(C)C)cc1S(C)(=O)=O]

R$_f$ value: 0.77 (silica gel, cyclohexane/ethyl acetate=2:1)
Mass spectrum (ESI$^+$): m/z=482 [M+H]$^+$ (8) tert-butyl 4-{4-[5-(5-tert-butyl-2-methoxy-3-methylsulphanylmethyl-phenylcarbamoyl)-2-methyl-phenoxy]-pyridin-2-ylmethyl}-piperidine-1-carboxylate

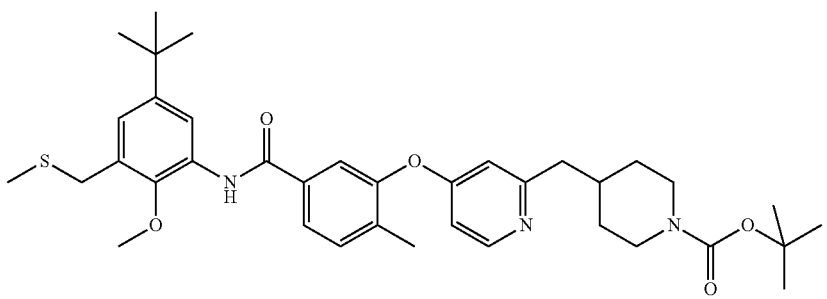 [SMILES: COc1c(CSC)cc(C(C)(C)C)cc1NC(=O)c1ccc(C)c(Oc2ccnc(CC3CCN(C(=O)OC(C)(C)C)CC3)c2)c1]

(The reaction is carried out with 2-(benzotriazol-1-yl)-N,N,N',N'-tetramethyl-uronium-tetrafluoroborate as coupling reagent)

HPLC (method 1): retention time=4.00 min
Mass spectrum (ESI⁺): m/z=648 [M+H]⁺

(9) tert-butyl 4-{4-[5-(5-tert-butyl-2-methoxy-3-methylsulphonylmethyl-phenylcarbamoyl)-2-methyl-phenoxy]-pyridin-2-ylmethyl}-piperidine-1-carboxylate

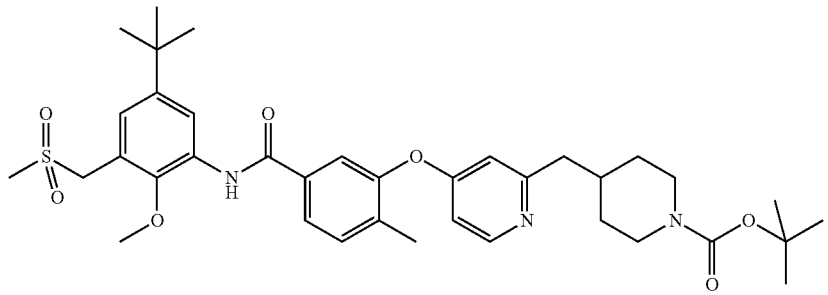 [SMILES: COc1c(CS(C)(=O)=O)cc(C(C)(C)C)cc1NC(=O)c1ccc(C)c(Oc2ccnc(CC3CCN(C(=O)OC(C)(C)C)CC3)c2)c1]

(The reaction is carried out with 2-(benzotriazol-1-yl)-N,N,N',N'-tetramethyl-uronium-tetrafluoroborate as coupling reagent)

HPLC (method 1): retention time=3.37 min
Mass spectrum (ESI⁺): m/z=680 [M+H]⁺

(10) tert-butyl 4-{4-[5-(5-tert-butyl-2-methoxy-3-methylsulphinylmethyl-phenylcarbamoyl)-2-methyl-phenoxy]-pyridin-2-ylmethyl}-piperidine-1-carboxylate

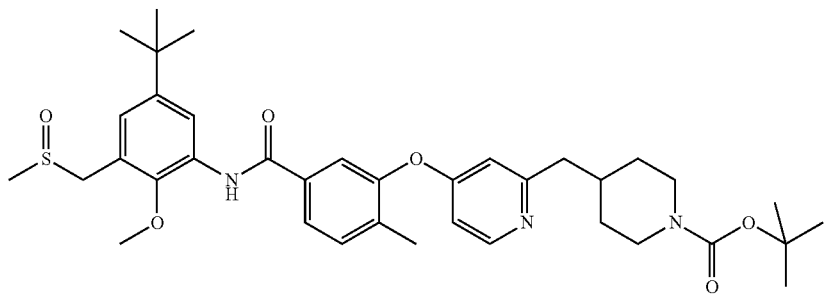

(The reaction is carried out with 2-(benzotriazol-1-yl)-N,N,N',N'-tetramethyl-uronium-tetrafluoroborate as coupling reagent)

HPLC (method 1): retention time=3.18 min
Mass spectrum (ESI⁺): m/z=664 [M+H]⁺

(11) tert-butyl 4-{4-[5-(3-amino-5-tert-butyl-2-methoxyphenylcarbamoyl)-2-methyl-phenoxy]-pyridin-2-ylmethyl}-piperidine-1-carboxylate

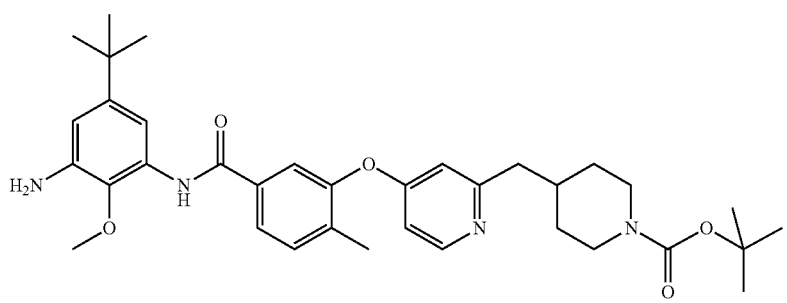 [SMILES: COc1c(N)cc(C(C)(C)C)cc1NC(=O)c1ccc(C)c(Oc2ccnc(CC3CCN(C(=O)OC(C)(C)C)CC3)c2)c1]

(The reaction is carried out with 2-(benzotriazol-1-yl)-N,N,N',N'-tetramethyl-uronium-tetrafluoroborate as coupling reagent)

Mass spectrum (ESI$^+$): m/z=603 [M+H]$^+$

(12) tert-butyl 4-{4-[5-(5-tert-butyl-2-isopropoxy-3-methanesulphonylamino-phenylcarbamoyl)-2-methyl-phenoxy]-pyridin-2-ylmethyl}-piperidine-1-carboxylate

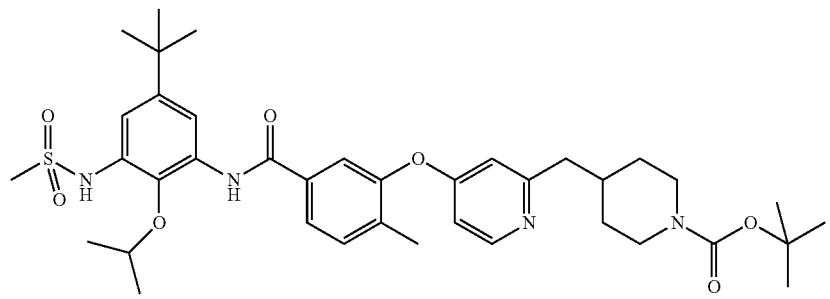 [SMILES: Cc1ccc(C(=O)Nc2cc(C(C)(C)C)cc(NS(C)(=O)=O)c2OC(C)C)cc1Oc1ccnc(CC2CCN(C(=O)OC(C)(C)C)CC2)c1]

(The reaction is carried out with 2-(benzotriazol-1-yl)-N,N,N',N'-tetramethyl-uronium-tetrafluoroborate as coupling reagent)

HPLC (method 1): retention time=3.60 min
Mass spectrum (ESI$^+$): m/z=709 [M+H]$^+$

(13) tert-butyl 4-{4-[5-(5-tert-butyl-2-ethoxy-3-methanesulphonylamino-phenylcarbamoyl)-2-methyl-phenoxy]-pyridin-2-ylmethyl}-piperidine-1-carboxylate

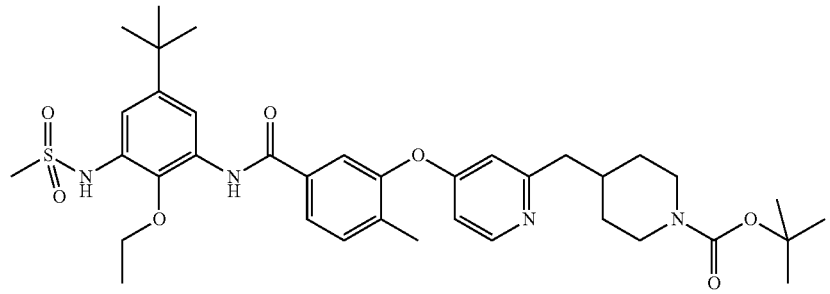 [SMILES: CCOc1c(NC(=O)c2ccc(C)c(Oc3ccnc(CC4CCN(C(=O)OC(C)(C)C)CC4)c3)c2)cc(C(C)(C)C)cc1NS(C)(=O)=O]

(The reaction is carried out with 2-(benzotriazol-1-yl)-N,N,N',N'-tetramethyl-uronium-tetrafluoroborate as coupling reagent)

HPLC (method 1): retention time=3.54 min
Mass spectrum (ESI$^+$): m/z=695 [M+H]$^+$ Example III N-(5-tert-butyl-3-methanesulphonylamino-2-methoxy-phenyl)-3-(2-chloro-pyrimidin-4-yloxy)-4-methyl-benzamide

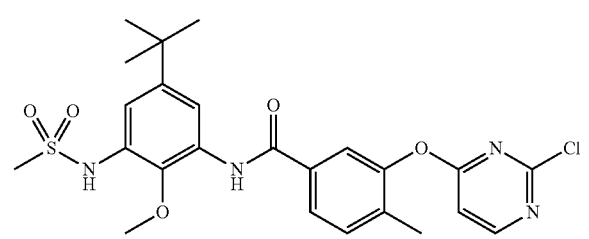 [SMILES: COc1c(NC(=O)c2ccc(C)c(Oc3ccnc(Cl)n3)c2)cc(C(C)(C)C)cc1NS(C)(=O)=O]

567 mg 2,4-dichloropyrimidine and 663 mg potassium carbonate are added to 1.50 g N-(5-tert-butyl-3-methanesulphonylamino-2-methoxy-phenyl)-3-hydroxy-4-methyl-benzamide in 15 ml acetonitrile and 3 ml N,N-dimethylformamide, and the reaction mixture is stirred overnight at ambient temperature. Then another 57 mg 2,4-dichloropyrimidine are added, and the mixture is stirred for a further hour at ambient temperature. For working up the reaction mixture is diluted with water and the white precipitate formed is filtered off, washed with water and dried in the desiccator.

Yield: 1.69 g (88% of theory)

$R_f$ value: 0.30 (silica gel, petroleum ether/ethyl acetate=1:1)

Mass spectrum (ESI$^+$): m/z=519/521 (Cl) [M+H]$^+$

The following compounds are obtained analogously to Example III:

(1) N-(5-tert-butyl-3-methanesulphonylamino-2-methoxy-phenyl)-3-(6-chloro-pyrimidin-4-yloxy)-4-methyl-benzamide

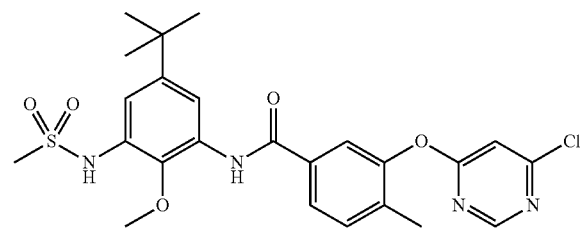

(reaction takes place in the presence of potassium-tert-butoxide at 50° C.)

$R_f$ value: 0.66 (silica gel, petroleum ether/ethyl acetate=1:2)

Mass spectrum (ESI$^+$): m/z=519/521 (Cl) [M+H]$^+$ 5

(2) N-(5-tert-butyl-3-methanesulphonylamino-2-methoxy-phenyl)-3-(2-chloro-pyrimidin-4-yloxy)-4-trifluoromethyl-benzamide

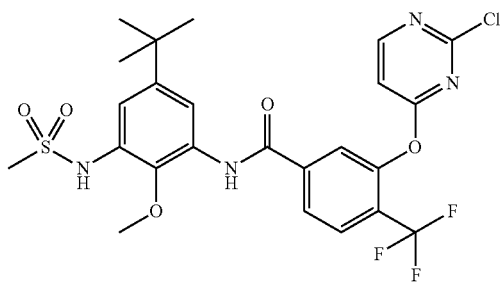 [SMILES: COc1c(NC(=O)c2ccc(C(F)(F)F)c(Oc3ccnc(Cl)n3)c2)cc(C(C)(C)C)cc1NS(C)(=O)=O]

(reaction takes place in dimethylsulphoxide in the presence of potassium-tert-butoxide)

$R_f$ value: 0.44 (silica gel, petroleum ether/ethyl acetate=1:1)

Mass spectrum (ESI$^+$): m/z=573/575 (Cl) [M+H]$^+$ (3) N-(5-tert-butyl-3-methanesulphonylamino-2-methoxy-phenyl)-3-(2-chloro-pyrimidin-4-yloxy)-4-chloro-benzamide

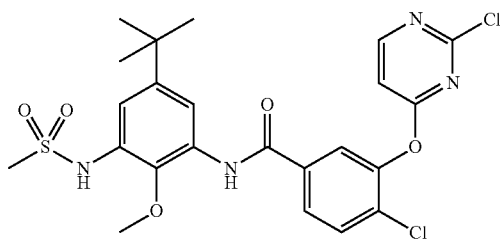 [SMILES: COc1c(NC(=O)c2ccc(Cl)c(Oc3ccnc(Cl)n3)c2)cc(C(C)(C)C)cc1NS(C)(=O)=O]

(reaction takes place in dimethylsulphoxide in the presence of potassium-tert-butoxide)

$R_f$ value: 0.34 (silica gel, petroleum ether/ethyl acetate=1:1)

Mass spectrum (ESI$^+$): m/z=539/541/541 (2 Cl) [M+H]$^+$ (4) methyl 3-(2-chloro-pyrimidin-4-yloxy)-4-methyl-benzoate

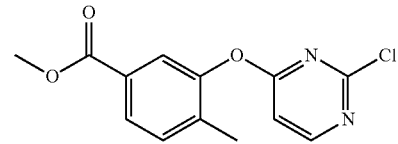 [SMILES: COC(=O)c1ccc(C)c(Oc2ccnc(Cl)n2)c1]

(reaction takes place in dimethylsulphoxide in the presence of potassium-tert-butoxide)

$R_f$ value: 0.87 (silica gel, dichloromethane/methanol=95:5)

Mass spectrum (ESI$^+$): m/z=279/281 (Cl) [M+H]$^+$ (5) N-(5-tert-butyl-3-methanesulphonylamino-2-methoxy-phenyl)-3-(2-chloro-pyrimidin-4-yloxy)-4-methoxy-benzamide

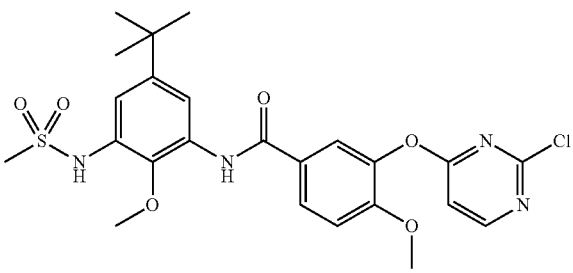 [SMILES: COc1ccc(C(=O)Nc2cc(C(C)(C)C)cc(NS(C)(=O)=O)c2OC)cc1Oc1ccnc(Cl)n1]

(reaction takes place in dimethylsulphoxide in the presence of potassium-tert-butoxide)

$R_f$ value: 0.15 (silica gel, cyclohexane/ethyl acetate=1:1)
Mass spectrum (ESI$^+$): m/z=535/537 (Cl) [M+H]$^+$ (6) N-(5-tert-butyl-3-methanesulphonylamino-2-methoxy-phenyl)-3-(2-fluoro-pyrimidin-4-yloxy)-4-chloro-benzamide

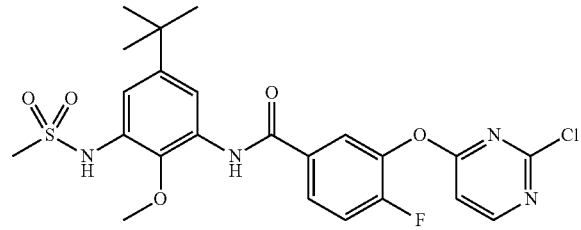 [SMILES: COc1c(NC(=O)c2ccc(F)c(Oc3ccnc(Cl)n3)c2)cc(C(C)(C)C)cc1NS(C)(=O)=O]

(reaction takes place in dimethylsulphoxide in the presence of potassium-tert-butoxide)

$R_f$ value: 0.41 (silica gel, petroleum ether/ethyl acetate=1:1)

Mass spectrum (ESI$^+$): m/z=523/525 (Cl) [M+H]$^+$ (7) methyl 4-bromo-3-(2-chloro-pyrimidin-4-yloxy)-benzoate

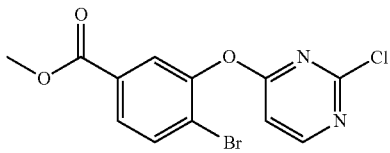 [SMILES: COC(=O)c1ccc(Br)c(Oc2ccnc(Cl)n2)c1]

(reaction takes place in dimethylsulphoxide in the presence of potassium-tert-butoxide)

$R_f$ value: 0.45 (silica gel, petroleum ether/ethyl acetate=7:3)

Mass spectrum (ESI$^+$): m/z=343/345/347 (Cl+Br) [M+H]$^+$ (8) N-(5-tert-butyl-3-methanesulphonylamino-2-methoxyphenyl)-3-chloro-5-(2-chloro-pyrimidin-4-yloxy)-4-methyl-benzamide

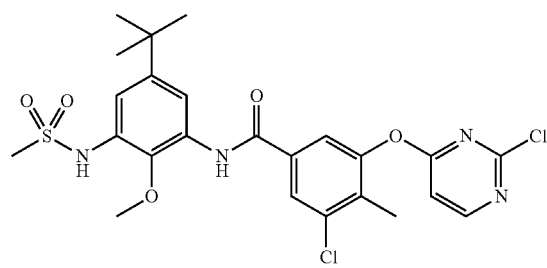 [SMILES: COc1c(NC(=O)c2cc(Cl)c(C)c(Oc3ccnc(Cl)n3)c2)cc(C(C)(C)C)cc1NS(C)(=O)=O]

(reaction takes place in dimethylsulphoxide in the presence of potassium-tert-butoxide)

$R_f$ value: 0.30 (silica gel, cyclohexane/ethyl acetate=1:1)

Mass spectrum (ESI$^+$): m/z=553/555/557 (2 Cl) [M+H]$^+$ (9) N-(5-tert-butyl-3-methanesulphonylamino-2-methoxyphenyl)-3-chloro-5-(2-fluoro-pyrimidin-4-yloxy)-4-methyl-benzamide

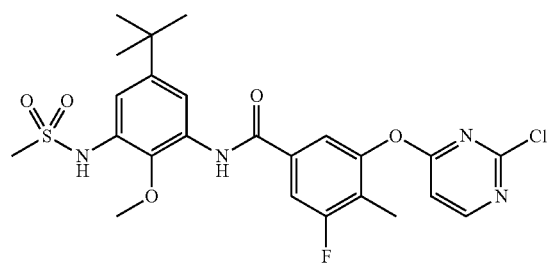 [SMILES: COc1c(NC(=O)c2cc(F)c(C)c(Oc3ccnc(Cl)n3)c2)cc(C(C)(C)C)cc1NS(C)(=O)=O]

(reaction takes place in dimethylsulphoxide in the presence of potassium-tert-butoxide)

$R_f$ value: 0.28 (silica gel, cyclohexane/ethyl acetate=1:1)

Mass spectrum (ESI$^+$): m/z=537/539 (Cl) [M+H]$^+$

(10) N-(5-tert-butyl-3-methanesulphonylamino-2-methoxyphenyl)-3-(2-chloro-pyrimidin-4-yloxy)-5-methyl-benzamide

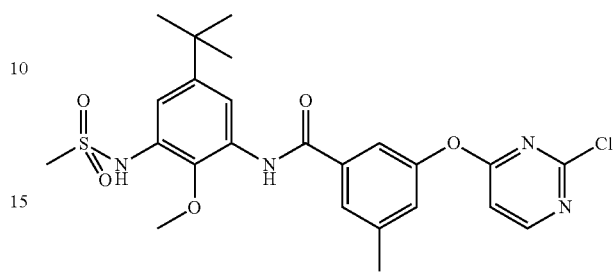

(reaction takes place in dimethylsulphoxide in the presence of potassium-tert-butoxide)

$R_f$ value: 0.30 (silica gel, cyclohexane/ethyl acetate=1:1)

Mass spectrum (ESI$^+$): m/z=519/521 (Cl) [M+H]$^+$

(11) N-(5-tert-butyl-3-methanesulphonylamino-2-methoxyphenyl)-4-chloro-3-(2-chloro-pyridin-4-yloxy)-benzamide

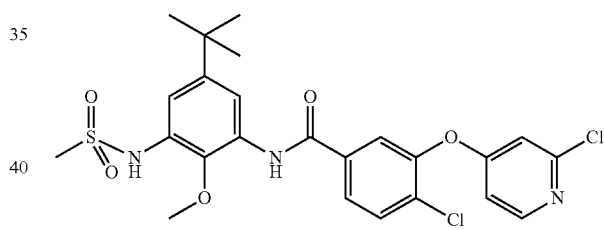

(reaction takes place in dimethylsulphoxide in the presence of potassium carbonate with 2-chloro-4-fluoropyridine at 60° C.)

$R_f$ value: 0.30 (silica gel, dichloromethane/methanol=98:2)

Mass spectrum (ESI$^+$): m/z=538/540/540 (2 Cl) [M+H]$^+$

(12) methyl 6-[5-(5-tert-butyl-3-methanesulphonylamino-2-methoxy-phenylcarbamoyl)-2-chloro-phenoxy]-pyrimidin-4-carboxylate

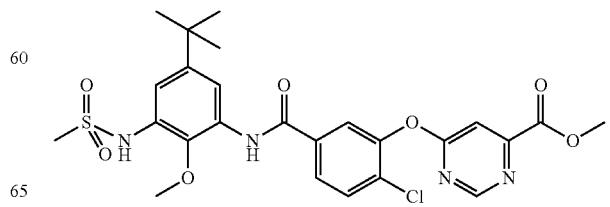

(reaction takes place in dimethylsulphoxide in the presence of caesium carbonate with methyl 6-chloro-pyrimidine-4-carboxylate at 45° C.)

$R_f$ value: 0.43 (silica gel, cyclohexane/ethyl acetate=1:1)
Mass spectrum (ESI⁺): m/z=563/565 (Cl) [M+H]⁺

(13) N-(5-tert-butyl-3-methanesulphonylamino-2-methoxy-phenyl)-4-chloro-3-(6-chloro-pyrimidin-4-yloxy)-benzamide

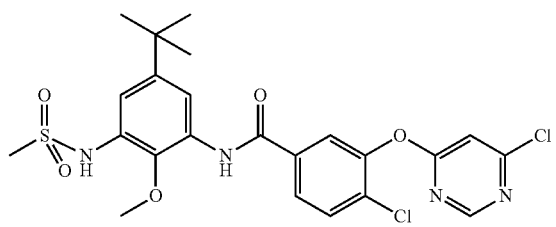 [SMILES: COc1c(NC(=O)c2ccc(Cl)c(Oc3cc(Cl)ncn3)c2)cc(C(C)(C)C)cc1NS(C)(=O)=O]

(reaction takes place in dimethylsulphoxide in the presence of potassium-tert-butoxide at ambient temperature)

$R_f$ value: 0.35 (silica gel, cyclohexane/ethyl acetate=1:1)

Mass spectrum (ESI⁺): m/z=539/541/543 (2 Cl) [M+H]⁺

(14) N-(5-tert-butyl-3-methanesulphonyl-2-methoxy-phenyl)-3-(2-chloro-pyrimidin-4-yloxy)-4-methyl-benzamide

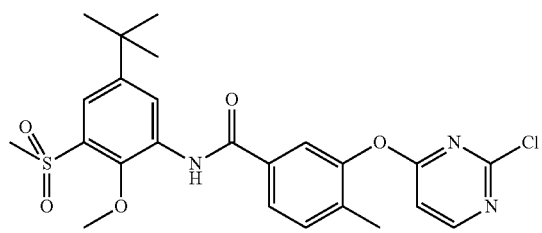 [SMILES: COc1c(NC(=O)c2ccc(C)c(Oc3ccnc(Cl)n3)c2)cc(C(C)(C)C)cc1S(C)(=O)=O]

(reaction takes place in dimethylsulphoxide in the presence of potassium-tert-butoxide at ambient temperature)

$R_f$ value: 0.47 (silica gel, cyclohexane/ethyl acetate=1:1)
Mass spectrum (ESI⁺): m/z=504/506 (Cl) [M+H]⁺

(15) methyl 3-(2-chloro-pyridin-4-yloxy)-4-methyl-benzoate

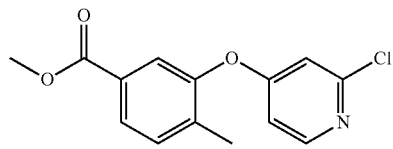 [SMILES: COC(=O)c1ccc(C)c(Oc2ccnc(Cl)c2)c1]

(reaction takes place in dimethylsulphoxide in the presence of potassium-tert-butoxide at ambient temperature)

HPLC (method 1): retention time=4.05 min
Mass spectrum (ESI⁺): m/z=278/280 (Cl) [M+H]⁺

Example IV tert-butyl 4-{4-[5-(5-tert-butyl-3-methanesulphonylamino-2-methoxy-phenylaminocarbonyl)-2-methyl-phenoxy]-pyrimidin-2-yl}-piperazine-1-carboxylate

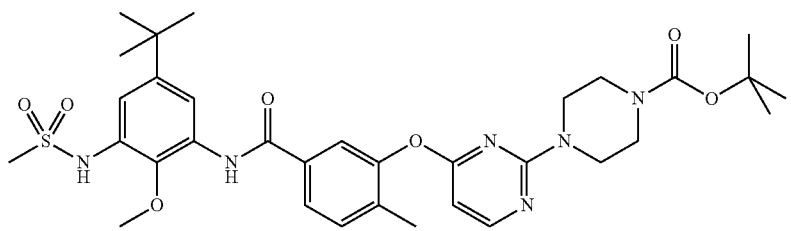 [SMILES: COc1c(NC(=O)c2ccc(C)c(Oc3ccnc(N4CCN(C(=O)OC(C)(C)C)CC4)n3)c2)cc(C(C)(C)C)cc1NS(C)(=O)=O]

188 mg tert-butyl piperazine-1-carboxylate and 247 µl N,N-diisopropylethylamine are added to a solution of 350 mg N-(5-tert-butyl-3-methanesulphonylamino-2-methoxy-phenyl)-3-(2-chloro-pyrimidin-4-yloxy)-4-methyl-benzamide in 1,4-dioxane. The reaction mixture is stirred for 4 h at 70° C. and then left overnight to cool to ambient temperature. The reaction mixture is then diluted with ethyl acetate, washed with 3M aqueous potassium carbonate solution, dried on magnesium sulphate and evaporated down. The crude product is purified by chromatography through a silica gel column with ethyl acetate/cyclohexane (40:60→100:0) as eluant.

Yield: 433 mg (96% of theory)

$R_f$ value: 0.80 (silica gel, dichloromethane/methanol/conc. ammonia=90:10:1)

Mass spectrum (ESI⁺): m/z=669 [M+H]⁺

The following compounds are obtained analogously to Example IV:

(1) tert-butyl 4-{6-[5-(5-tert-butyl-3-methanesulphonylamino-2-methoxy-phenylcarbamoyl)-2-methyl-phenoxy]-pyrimidin-4-yl}-piperazine-1-carboxylate

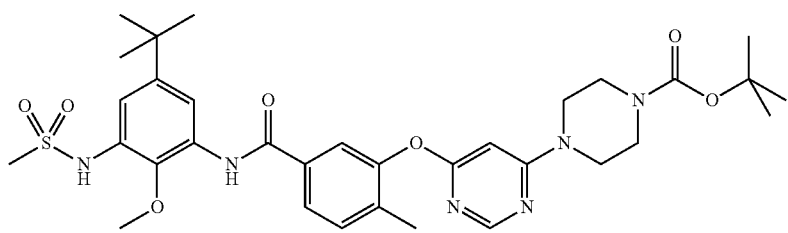 [SMILES: COc1c(NC(=O)c2ccc(C)c(Oc3cc(N4CCN(C(=O)OC(C)(C)C)CC4)ncn3)c2)cc(C(C)(C)C)cc1NS(C)(=O)=O]

R*f* value: 0.41 (silica gel, petroleum ether/ethyl acetate=1:2)

Mass spectrum (ESI+): m/z=669 [M+H]+

(2) tert-butyl 4-{4-[5-(5-tert-butyl-3-methanesulphonylamino-2-methoxy-phenylaminocarbonyl)-2-trifluoromethyl-phenoxy]-pyrimidin-2-yl}-piperazine-1-carboxylate

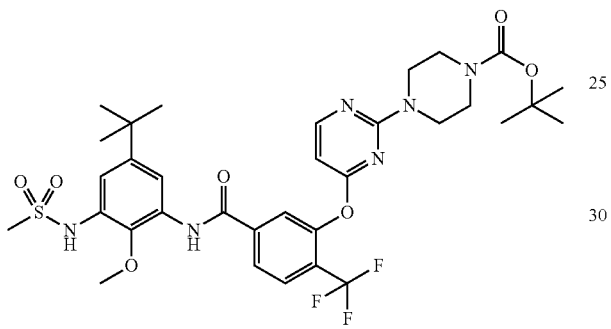

R*f* value: 0.40 (silica gel, petroleum ether/ethyl acetate=1:1)

Mass spectrum (ESI+): m/z=723 [M+H]+

(3) tert-butyl 4-{4-[5-(5-tert-butyl-3-methanesulphonylamino-2-methoxy-phenylaminocarbonyl)-2-chloro-phenoxy]-pyrimidin-2-yl}-piperazine-1-carboxylate

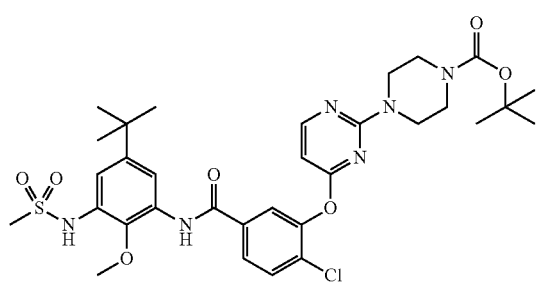 [SMILES: COc1c(NC(=O)c2ccc(Cl)c(Oc3ccnc(N4CCN(C(=O)OC(C)(C)C)CC4)n3)c2)cc(C(C)(C)C)cc1NS(C)(=O)=O]

R*f* value: 0.38 (silica gel, petroleum ether/ethyl acetate=1:1)

Mass spectrum (ESI+): m/z=689/691 (Cl) [M+H]+

(4) tert-butyl 4-[4-(5-methoxycarbonyl-2-methyl-phenoxy)-pyrimidin-2-yl]-piperazine-1-carboxylate

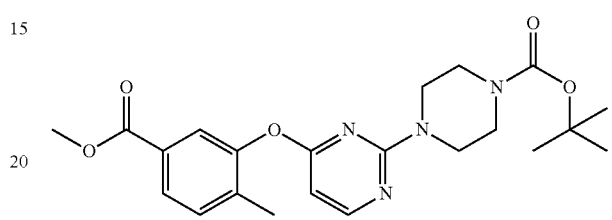

(reaction takes place in tetrahydrofuran in the presence of triethylamine at ambient temperature)

R*f* value: 0.81 (silica gel, dichloromethane/methanol=95:5)

Mass spectrum (ESI+): m/z=429 [M+H]+

(5) tert-butyl 4-{4-[5-(5-tert-butyl-3-methaneulfonylamino-2-methoxy-phenylaminocarbonyl)-2-methoxy-phenoxy]-pyrimidin-2-yl}-piperazine-1-carboxylate

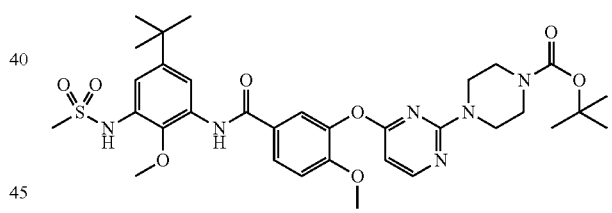

(reaction takes place in acetonitrile in the presence of triethylamine at reflux temperature)

R*f* value: 0.58 (silica gel, dichloromethane/methanol=95:5)

Mass spectrum (ESI+): m/z=685 [M+H]+

(6) tert-butyl 4-{4-[5-(5-tert-butyl-3-methanesulphonylamino-2-methoxy-phenylaminocarbonyl)-2-fluoro-phenoxy]-pyrimidin-2-yl}-piperazine-1-carboxylate

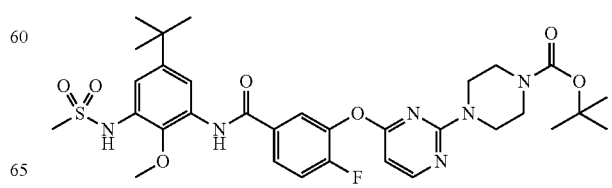

(reaction takes place in tetrahydrofuran in the presence of triethylamine at 50° C.)
R$_f$ value: 0.48 (silica gel, petroleum ether/ethyl acetate=1:1)
Mass spectrum (ESI$^+$): m/z=673 [M+H]$^+$
(7) tert-butyl 4-[4-(2-bromo-5-methoxycarbonyl-phenoxy)-pyrimidin-2-yl]-piperazine-1-carboxylate

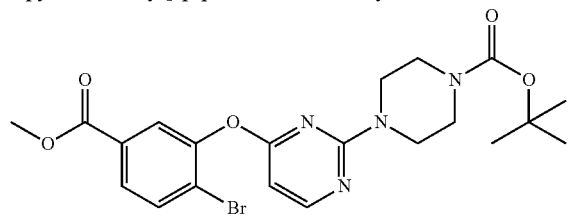

(reaction takes place in acetonitrile in the presence of triethylamine at 80° C.)
R$_f$ value: 0.40 (silica gel, dichloromethane/methanol=98:2)
Mass spectrum (ESI$^+$): m/z=493/495 (Br) [M+H]$^+$
(8) tert-butyl 4-{4-[5-(5-tert-butyl-3-methanesulphonylamino-2-methoxy-phenylaminocarbonyl)-3-chloro-2-methyl-phenoxy]-pyrimidin-2-yl}-piperazin-carboxylate

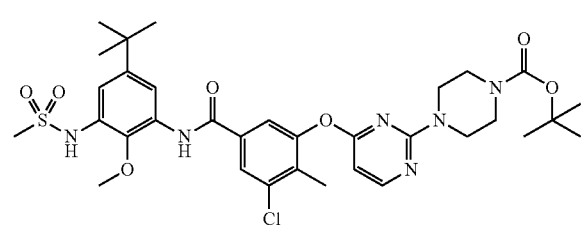 [SMILES: COc1c(NC(=O)c2cc(Cl)c(C)c(Oc3ccnc(N4CCN(C(=O)OC(C)(C)C)CC4)n3)c2)cc(C(C)(C)C)cc1NS(C)(=O)=O]

(reaction takes place in acetonitrile in the presence of triethylamine at 80° C.)
R$_f$ value: 0.48 (silica gel, cyclohexane/ethyl acetate=1:1)
Mass spectrum (ESI$^+$): m/z=703/705 (Cl) [M+H]$^+$
(9) tert-butyl 4-{4-[5-(5-tert-butyl-3-methanesulphonylamino-2-methoxy-phenylaminocarbonyl)-3-fluoro-2-methyl-phenoxy]-pyrimidin-2-yl}-piperazin-carboxylate

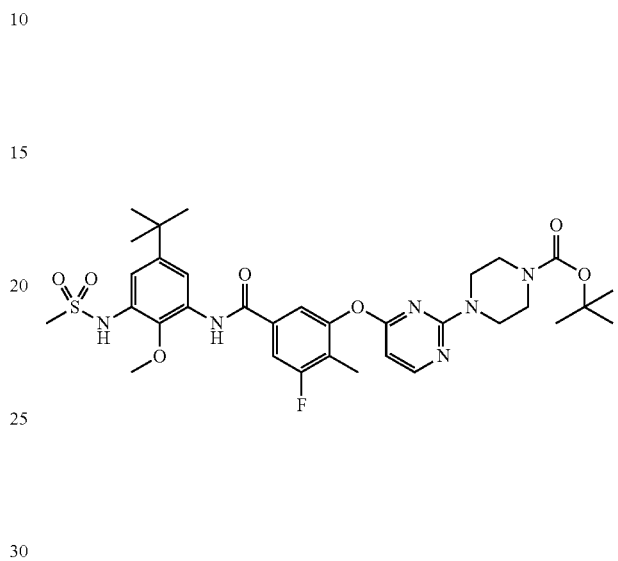

(reaction takes place in acetonitrile in the presence of triethylamine at 80° C.)
R$_f$ value: 0.40 (silica gel, cyclohexane/ethyl acetate=1:1)
Mass spectrum (ESI$^+$): m/z=687 [M+H]$^+$
(10) tert-butyl 4-({4-[5-(5-tert-butyl-3-methanesulphonylamino-2-methoxy-phenylaminocarbonyl)-2-methyl-phenoxy]-pyrimidin-2-yl}-N-methyl-amino)-piperidine-1-carboxylate

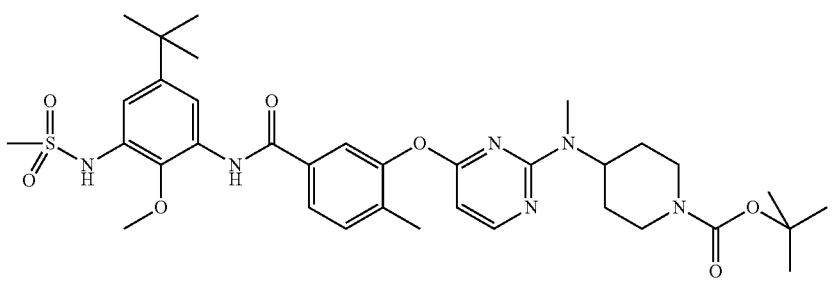 [SMILES: COc1c(NC(=O)c2ccc(C)c(Oc3ccnc(N(C)C4CCN(C(=O)OC(C)(C)C)CC4)n3)c2)cc(C(C)(C)C)cc1NS(C)(=O)=O]

(reaction takes place in N,N-dimethylformamide at 50° C.)
Mass spectrum (ESI$^+$): m/z=697 [M+H]$^+$
(11) tert-butyl 4-({4-[5-(5-tert-butyl-3-methanesulphonylamino-2-methoxy-phenylaminocarbonyl)-2-methyl-phenoxy]-pyrimidin-2-yl}-amino)-piperidine-1-carboxylate

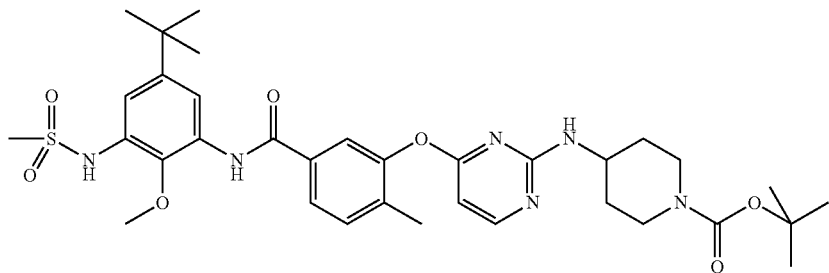 [SMILES: COc1c(NC(=O)c2ccc(C)c(Oc3ccnc(NC4CCN(C(=O)OC(C)(C)C)CC4)n3)c2)cc(C(C)(C)C)cc1NS(C)(=O)=O]

(reaction takes place in N,N-dimethylformamide in the presence of triethylamine at 50° C.)

$R_f$ value: 0.38 (silica gel, petroleum ether/ethyl acetate/acetic acid=50:50:0.1)

Mass spectrum (ESI⁺): m/z=683 [M+H]⁺

(12) tert-butyl 4-{6-[5-(5-tert-butyl-3-methanesulphonylamino-2-methoxy-phenylaminocarbonyl)-2-methyl-phenoxy]-pyrimidin-4-ylamino}-piperidine-1-carboxylate

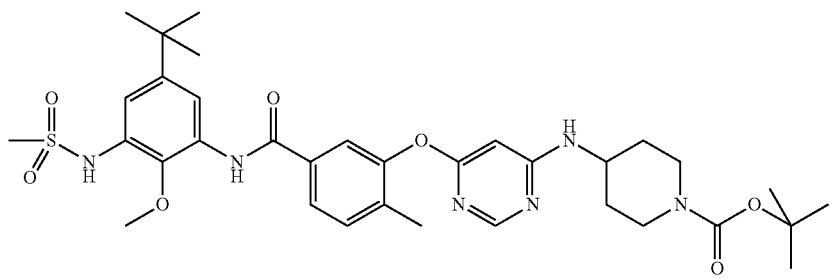

(reaction takes place in N,N-dimethylformamide at 50° C.)

Mass spectrum (ESI⁺): m/z=683 [M+H]⁺

(13) tert-butyl 3-{4-[5-(5-tert-butyl-3-methanesulphonylamino-2-methoxy-phenylcarbamoyl)-2-methyl-phenoxy]-pyrimidin-2-ylamino}-pyrrolidine-1-carboxylate

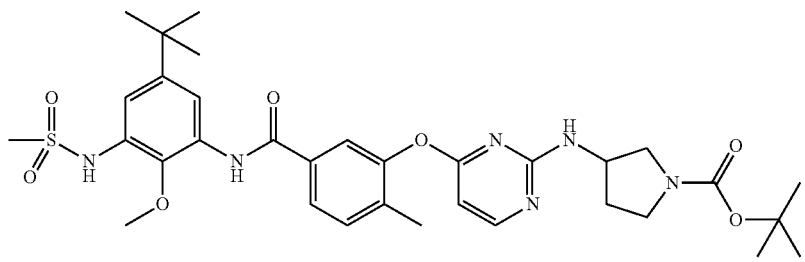 [SMILES: COc1c(NC(=O)c2ccc(C)c(Oc3ccnc(NC4CCN(C(=O)OC(C)(C)C)C4)n3)c2)cc(C(C)(C)C)cc1NS(C)(=O)=O]

(reaction takes place in N,N-dimethylformamide in the presence of ethyldiisopropylamine at 50° C.)

$R_f$ value: 0.58 (silica gel, dichloromethan/methanol/NH₄OH=90:10:0.1)

Mass spectrum (ESI⁺): m/z=669 [M+H]⁺

(14) tert-butyl 3-({4-[5-(5-tert-butyl-3-methanesulphonylamino-2-methoxy-phenylcarbamoyl)-2-methyl-phenoxy]-pyrimidin-2-yl}-methyl-amino)-pyrrolidine-1-carboxylate

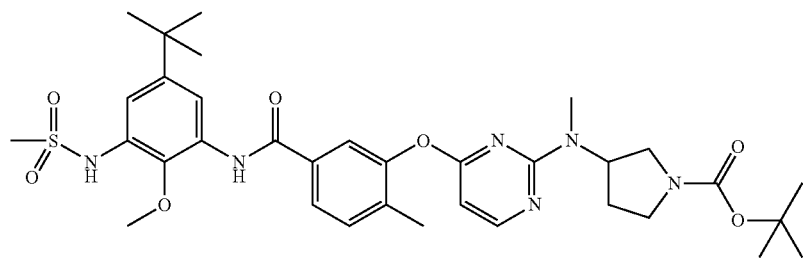 [SMILES: COc1c(NC(=O)c2ccc(C)c(Oc3ccnc(N(C)C4CCN(C(=O)OC(C)(C)C)C4)n3)c2)cc(C(C)(C)C)cc1NS(C)(=O)=O]

(reaction takes place in N,N-dimethylformamide in the presence of ethyldiisopropylamine at 50° C.)

$R_f$ value: 0.75 (silica gel, dichloromethan/methanol/ $NH_4OH$=90:10:0.1)

Mass spectrum (ESI⁺): m/z=683 [M+H]⁺

(15) tert-butyl 4-({6-[5-(5-tert-butyl-3-methanesulphonylamino-2-methoxy-phenylcarbamoyl)-2-methyl-phenoxy]-pyrimidin-4-yl}-methyl-amino)-piperidine-1-carboxylate

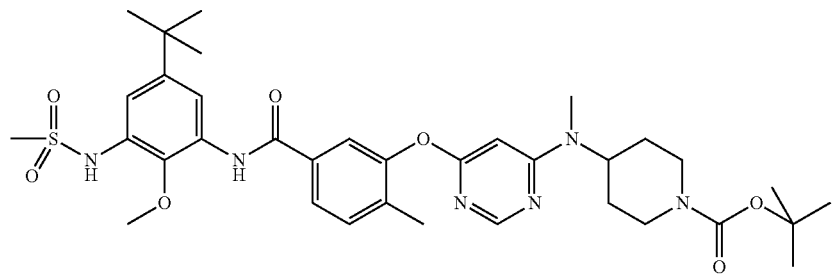 [SMILES: COc1c(NC(=O)c2ccc(C)c(Oc3cc(N(C)C4CCN(C(=O)OC(C)(C)C)CC4)ncn3)c2)cc(C(C)(C)C)cc1NS(C)(=O)=O]

(reaction takes place in N,N-dimethylformamide in the presence of ethyldiisopropylamine at 40° C.)

Mass spectrum (ESI⁺): m/z=697 [M+H]⁺

(16) tert-butyl 3-{6-[5-(5-tert-butyl-3-methanesulphonylamino-2-methoxy-phenylcarbamoyl)-2-methyl-phenoxy]-pyrimidin-4-ylamino}-pyrrolidine-1-carboxylate

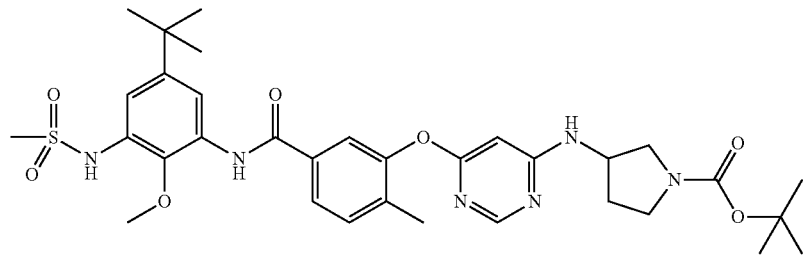 [SMILES: COc1c(NC(=O)c2ccc(C)c(Oc3cc(NC4CCN(C(=O)OC(C)(C)C)C4)ncn3)c2)cc(C(C)(C)C)cc1NS(C)(=O)=O]

(reaction takes place in dimethylsulphoxide in the presence of ethyldiisopropylamine at 40° C.)

HPLC (method 1): retention time=4.16 min

Mass spectrum (ESI⁺): m/z=669 [M+H]⁺

(17) tert-butyl 4-{6-[5-(5-tert-butyl-3-methanesulphonylamino-2-methoxy-phenylcarbamoyl)-2-chloro-phenoxy]-pyrimidin-4-ylamino}-piperidine-1-carboxylate

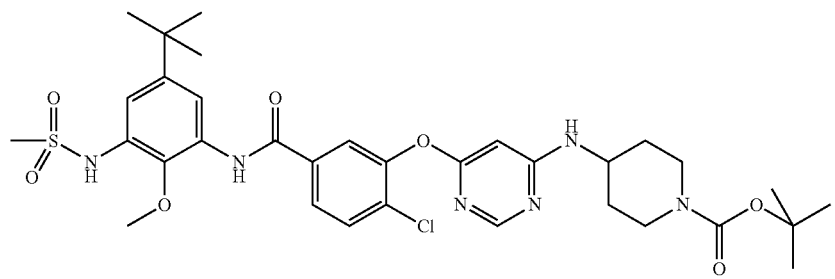

(reaction takes place in acetonitrile in the presence of triethylamine at 70° C.)
R$_f$ value: 0.45 (silica gel, dichloromethan/methanol=95:5)
Mass spectrum (ESI$^+$): m/z=703/705 (Cl) [M+H]$^+$
(18) tert-butyl 4-{4-[5-(5-tert-butyl-3-methanesulphonylamino-2-methoxy-phenylcarbamoyl)-2-chloro-phenoxy]-pyrimidin-2-ylamino}-piperidine-1-carboxylate

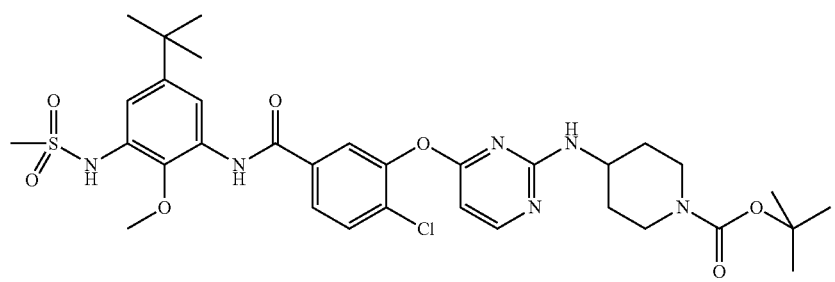 [SMILES: COc1c(NC(=O)c2ccc(Cl)c(Oc3ccnc(NC4CCN(C(=O)OC(C)(C)C)CC4)n3)c2)cc(C(C)(C)C)cc1NS(C)(=O)=O]

(reaction takes place in acetonitrile in the presence of triethylamine at 90° C.)
R$_f$ value: 0.40 (silica gel, dichloromethan/methanol=95:5)
Mass spectrum (ESI$^+$): m/z=703/705 (Cl) [M+H]$^+$

Example V

6-Chloro-pyrimidine-4-carboxylic acid-methylamide

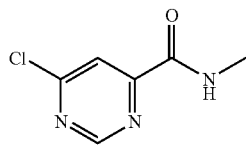

0.5 ml of a 2 M methylamide solution in tetrahydrofuran and 1 ml 1 N sodium hydroxide solution are added to 177 mg 6-chloro-pyrimidin-4-carboxylic acid chloride in 5 ml dichloromethane under an argon atmosphere and while cooling with a bath of ice/acetone. The reaction mixture is heated overnight with stirring to ambient temperature and then combined with some saturated aqueous sodium hydrogen carbonate solution and extracted with dichloromethane. The combined organic phases are washed with 0.1 N hydrochloric acid and saturated sodium chloride solution, dried on magnesium sulphate and evaporated down.
Yield: 110 mg (64% of theory)
R$_f$ value: 0.52 (silica gel, petroleum ether/ethyl acetate=1:1)
The following compound is obtained analogously to Example V:
(1) tert-butyl 4-(6-chloro-pyrimidin-4-carbonyl)-piperazine-1-carboxylate

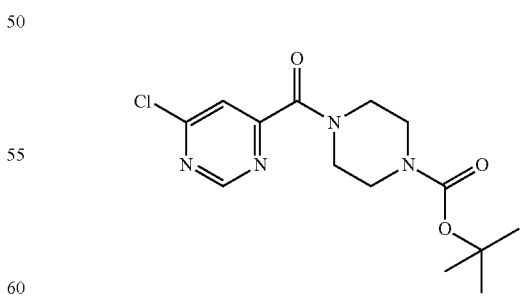

R$_f$ value: 0.68 (silica gel, petroleum ether/ethyl acetate=1:2)

Example VI tert-butyl 4-{6-[5-(5-tert-butyl-3-methanesulphonylamino-2-methoxy-phenylaminocarbonyl)-2-methyl-phenoxy]-pyrimidin-4-carbonyl}-piperazine-1-carboxylate

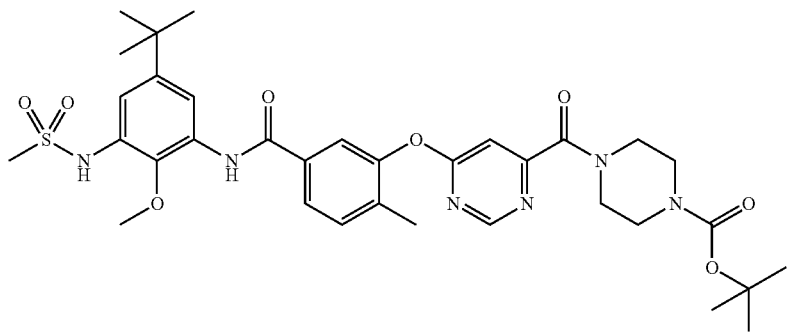 [SMILES: COc1c(NC(=O)c2ccc(C)c(Oc3cc(C(=O)N4CCN(C(=O)OC(C)(C)C)CC4)ncn3)c2)cc(C(C)(C)C)cc1NS(C)(=O)=O]

75 mg potassium-tert-butoxide are added at ambient temperature under an argon atmosphere to 225 mg N-(5-tert-butyl-3-methanesulphonylamino-2-methoxy-phenyl)-3-hydroxy-4-methyl-benzamide in 3 ml N,N-dimethylformamide. After ten minutes 210 mg tert-butyl 4-(6-chloro-pyrimidin-4-carbonyl)-piperazine-1-carboxylate are added, and the reaction mixture is stirred for six days at ambient temperature. For working up the reaction mixture is mixed with water and extracted with ethyl acetate. The combined ethyl acetate extracts are washed with saturated sodium chloride solution, dried on magnesium sulphate and evaporated down. The flask residue is chromatographed through a silica gel column with cyclohexane/ethyl acetate (50:50→20:80).

Yield: 292 mg (76% of theory)

$R_f$ value: 0.20 (silica gel, petroleum ether/ethyl acetate=1:2)

Mass spectrum (ESI$^-$): m/z=695 [M−H]$^-$

The following compounds are obtained analogously to Example VI:

(1) tert-butyl 4-{6-[5-(5-tert-butyl-3-methanesulphonylamino-2-methoxy-phenylaminocarbonyl)-2-chloro-phenoxy]-pyrimidin-4-carbonyl}-piperazine-1-carboxylate

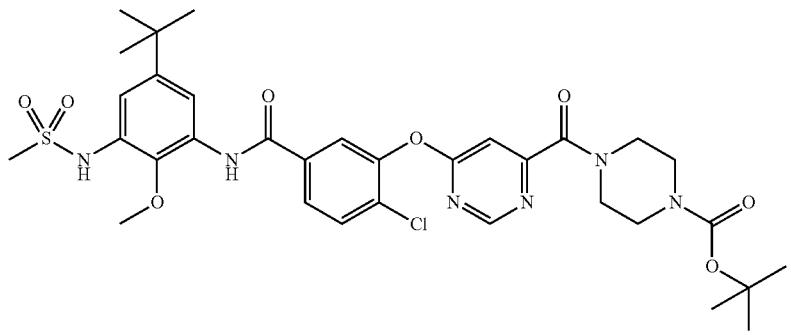 [SMILES: COc1c(NC(=O)c2ccc(Cl)c(Oc3cc(C(=O)N4CCN(C(=O)OC(C)(C)C)CC4)ncn3)c2)cc(C(C)(C)C)cc1NS(C)(=O)=O]

$R_f$ value: 0.45 (silica gel, petroleum ether/ethyl acetate=1:2)

Mass spectrum (ESI$^-$): m/z=715/717 (Cl) [M−H]$^-$ (2) tert-butyl 4-[4-(2-ethyl-5-methoxycarbonyl-phenoxy)-pyrimidin-2-yl]-piperazine-1-carboxylate

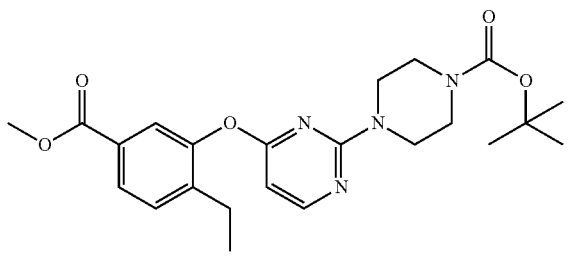 [SMILES: CCc1ccc(C(=O)OC)cc1Oc1ccnc(N2CCN(C(=O)OC(C)(C)C)CC2)n1]

(reaction takes place in dimethylsulphoxide)

R$_f$ value: 0.45 (silica gel, petroleum ether/ethyl acetate=7:3)

Mass spectrum (ESI$^+$): m/z=443 [M+H]$^+$

Example VII

N-(5-tert-butyl-3-methanesulphonylamino-2-methoxy-phenyl)-3-(6-formyl-pyrimidin-4-yloxy)-4-methyl-benzamide

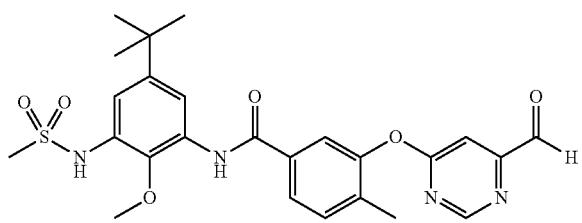 [SMILES: COc1c(NC(=O)c2ccc(C)c(Oc3cc(C=O)ncn3)c2)cc(C(C)(C)C)cc1NS(C)(=O)=O]

At –65° C. under an argon atmosphere 7.40 ml diisobutyl-aluminium hydride (1 M in tetrahydrofuran) are added dropwise to 1.00 g methyl 6-[5-(5-tert-butyl-3-methanesulphonyl-amino-2-methoxy-phenylaminocarbonyl)-2-methyl-phenoxy]-pyrimidine-4-carboxylate in 15 ml of tetrahydrofuran, whereupon the temperature rises to –50° C. After 2 h stirring another 7.40 ml diisobutyl-aluminium hydride (1 M in tetrahydrofuran) are added at –50° C. The reaction mixture is heated to ambient temperature overnight with stirring in the cooling bath and then neutralised with 8 ml 1 M aqueous potassium-sodium tartrate solution and extracted several times with ethyl acetate and dichloromethane. The combined organic phases are washed with saturated aqueous sodium chloride solution, dried on magnesium sulphate and evaporated down. The crude product is further reacted without any further purification.

Yield: 640 mg (68% of theory)

Mass spectrum (ESI$^-$): m/z=511 [M–H]$^-$

The following compounds are obtained analogously to Example VII:

(1) N-(5-tert-butyl-3-methanesulphonylamino-2-methoxy-phenyl)-3-(2-formyl-pyrimidin-4-yloxy)-4-methyl-benzamide

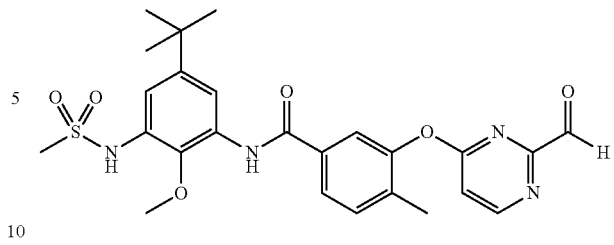

R$_f$ value: 0.40 (silica gel, dichloromethane/methanol=95:5)

Mass spectrum (ESI$^-$): m/z=511 [M–H]$^-$ (2) N-(5-tert-butyl-3-methanesulphonylamino-2-methoxy-phenyl)-3-(2-formyl-pyridin-4-yloxy)-4-methyl-benzamide

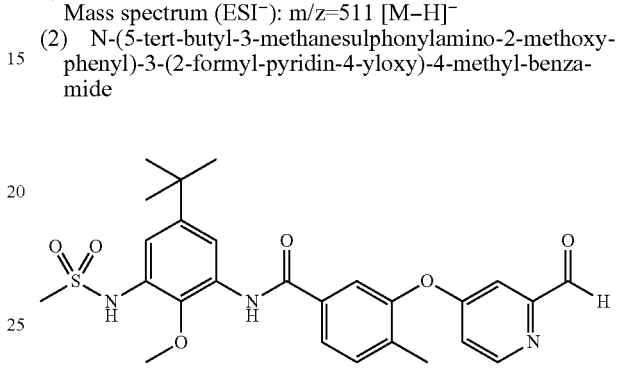

R$_f$ value: 0.63 (silica gel, dichloromethane/methanol/conc. ammonia=90:10:1)

Mass spectrum (ESI$^+$): m/z=512 [M+H]$^+$ (3) 4-[3-(5-tert-butyl-3-methanesulphonylamino-2-methoxy-phenylaminocarbonyl)-5-methyl-phenoxy]-pyrimidine-2-carboxylic acid

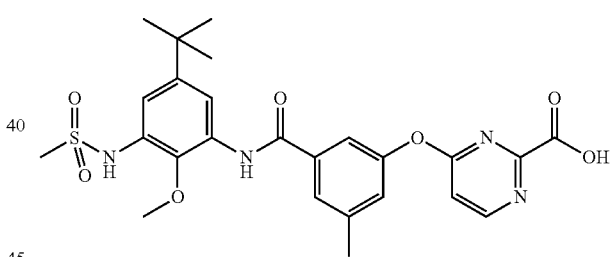

(is obtained instead of the desired N-(5-tert-butyl-3-methanesulphonylamino-2-methoxy-phenyl)-3-(2-formyl-pyrimidin-4-yloxy)-5-methyl-benzamide)

Mass spectrum (ESI$^+$): m/z=529 [M+H]$^+$ (4) N-(5-tert-butyl-3-methanesulphonylamino-2-methoxy-phenyl)-4-chloro-3-(6-formyl-pyrimidin-4-yloxy)-benzamide

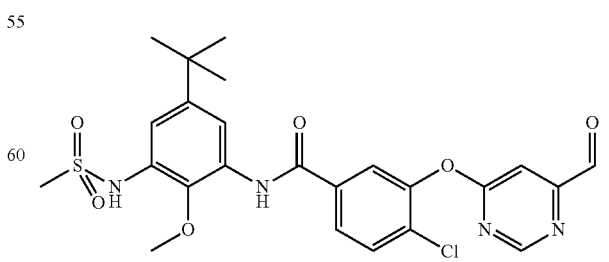

R$_f$ value: 0.33 (silica gel, dichloromethane/methanol=95:5)

(5) N-(5-tert-butyl-3-methanesulphonylamino-2-methoxy-phenyl)-4-chloro-3-(2-formyl-pyridin-4-yloxy)-benzamide

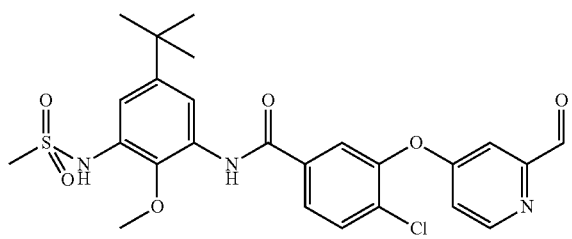 [SMILES: COc1c(NC(=O)c2ccc(Cl)c(Oc3ccnc(C=O)c3)c2)cc(C(C)(C)C)cc1NS(C)(=O)=O]

$R_f$ value: 0.35 (silica gel, dichloromethane/methanol=95:5)

Mass spectrum (ESI⁺): m/z=532/534 (Cl) [M+H]+

(6) N-(5-tert-butyl-3-methanesulphonylamino-2-methoxy-phenyl)-4-chloro-3-(2-formyl-pyrimidin-4-yloxy)-benzamide

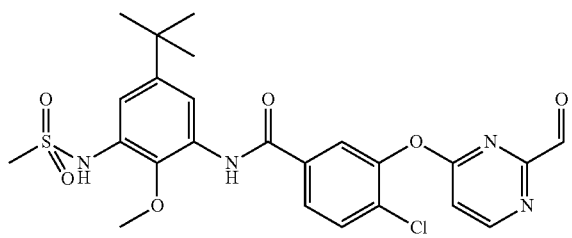 [SMILES: COc1c(NC(=O)c2ccc(Cl)c(Oc3ccnc(C=O)n3)c2)cc(C(C)(C)C)cc1NS(C)(=O)=O]

$R_f$ value: 0.43 (silica gel, dichloromethane/methanol=95:5)

Example VIII

Methyl 6-[5-(5-tert-butyl-3-methanesulphonylamino-2-methoxy-phenylaminocarbonyl)-2-methyl-phenoxy]-pyrimidin-4-carboxylate

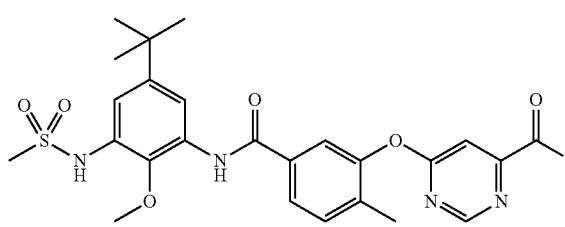

30 ml N,N-dimethylformamide are added to 2.05 g N-(5-tert-butyl-3-methanesulphonylamino-2-methoxy-phenyl)-3-(2-chloro-pyrimidin-4-yloxy)-4-methyl-benzamide in a mixture of 5 ml acetonitrile and 50 ml of methanol under an argon atmosphere. Then 0.81 ml triethylamine and 242 mg dichloro-[1,1-bis(diphenyl-phosphino)ferrocene]-palladium (II)-dichloromethane complex are added. The mixture is combined with carbon monoxide in a pressurised container (5 bar) heated for approx. 15 h to 70° C. After cooling to ambient temperature the catalyst is filtered off and the filtrate is evaporated down. The flask residue is stirred with diethyl ether, suction filtered and dried.

Yield: 2.15 g (100% of theory)

$R_f$ value: 0.61 (silica gel, dichloromethane/methanol=95:5)

Mass spectrum (ESI⁺): m/z=543 [M+H]⁺

The following compounds are obtained analogously to Example VIII:

(1) methyl 4-[5-(5-tert-butyl-3-methanesulphonylamino-2-methoxy-phenylaminocarbonyl)-2-methyl-phenoxy]-pyrimidine-2-carboxylate

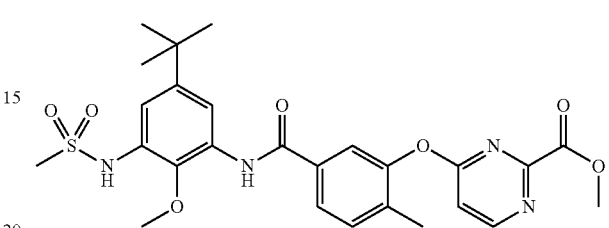

$R_f$ value: 0.18 (silica gel, petroleum ether/ethyl acetate=3:7)

Mass spectrum (ESI⁺): m/z=543 [M+H]⁺

(2) methyl 4-[5-(5-tert-butyl-3-methanesulphonylamino-2-methoxy-phenylaminocarbonyl)-2-methyl-phenoxy]-pyridine-2-carboxylate

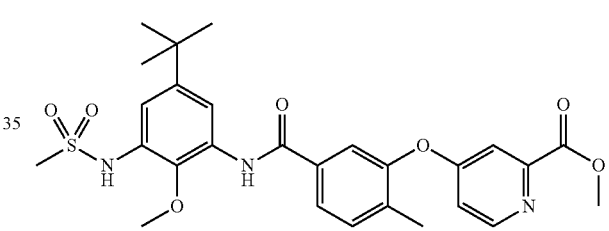

$R_f$ value: 0.75 (silica gel, dichloromethane/methanol/conc. ammonia=90:10:1)

Mass spectrum (ESI⁺): m/z=542 [M+H]⁺

(3) methyl 4-[3-(5-tert-butyl-3-methanesulphonylamino-2-methoxy-phenylaminocarbonyl)-5-methyl-phenoxy]-pyrimidine-2-carboxylate

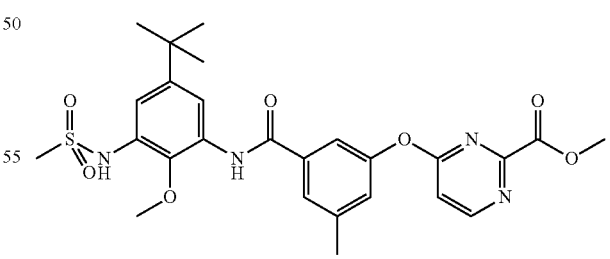

$R_f$ value: 0.40 (Reversed phase ready-made TLC plate (E. Merck), acetonitrile/water/trifluoroacetic acid=50:50:1)

Mass spectrum (ESI⁺): m/z=543 [M+H]⁺

(4) methyl 4-[5-(5-tert-butyl-3-methanesulphonylamino-2-methoxy-phenylcarbamoyl)-2-chloro-phenoxy]-pyridine-2-carboxylate

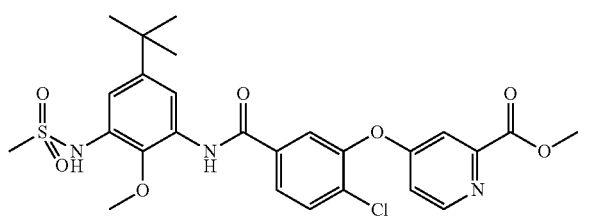

R$_f$ value: 0.50 (silica gel, dichloromethane/methanol=95:5)

Mass spectrum (ESI$^+$): m/z=562/564 (Cl) [M+H]$^+$ (5) methyl 4-[5-(5-tert-butyl-3-methanesulphonylamino-2-methoxy-phenylcarbamoyl)-2-chloro-phenoxy]-pyrimidine-2-carboxylate

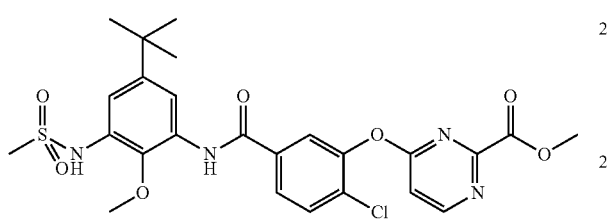

R$_f$ value: 0.50 (silica gel, dichloromethane/methanol=95:5)

Mass spectrum (ESI$^+$): m/z=563/565 (Cl) [M+H]$^+$

Example IX 3-benzyloxy-4-chloro-benzoic acid

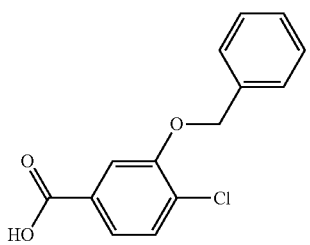 [SMILES: O=C(O)c1ccc(Cl)c(OCc2ccccc2)c1]

2.67 ml benzylbromide are added dropwise to 1.73 g 3-hydroxy-4-chloro-benzoic acid and 3.04 g potassium carbonate in 10 ml N,N-dimethylformamide, and the reaction mixture is stirred overnight at ambient temperature. Then the reaction mixture is mixed with water and extracted with ethyl acetate. The combined organic phases are dried on magnesium sulphate and evaporated down. The flask residue is taken up in 5 ml of methanol, combined with 3 ml of 10 M aqueous potassium hydroxide solution and stirred for 4 h at 50° C. gerührt. The reddish solution is diluted with water and acidified with 3 N aqueous hydrochloric acid. The precipitate formed is suction filtered, washed with water and dried.

Yield: 2.50 g (95% of theory)

Mass spectrum (ESI$^-$): m/z=261/263 (Cl) [M−H]$^-$

R$_f$ value: 0.60 (silica gel, petroleum ether/ethyl acetate=1:1)

The following compounds are obtained analogously to Example IX:

(1) 3-benzyloxy-4-trifluoromethyl-benzoic acid

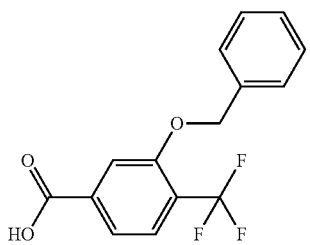 [SMILES: O=C(O)c1ccc(C(F)(F)F)c(OCc2ccccc2)c1]

R$_f$ value: 0.60 (silica gel, petroleum ether/ethyl acetate=1:1)

Mass spectrum (ESI$^-$): m/z=295 [M−H]$^-$ (2) 3-benzyloxy-5-chloro-4-methyl-benzoic acid

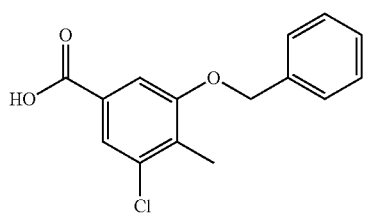 [SMILES: Cc1c(Cl)cc(C(=O)O)cc1OCc1ccccc1]

R$_f$ value: 0.75 (silica gel, cyclohexane/ethyl acetate/acetic acid=50:50:0.1)

Mass spectrum (ESI$^-$): m/z=275/277 (Cl) [M−H]$^-$ (3) 3-benzyloxy-5-fluoro-4-methyl-benzoic acid

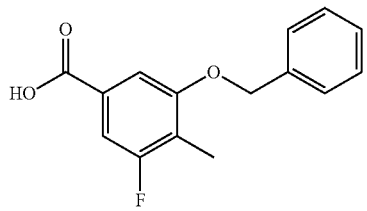 [SMILES: Cc1c(F)cc(C(=O)O)cc1OCc1ccccc1]

R$_f$ value: 0.75 (silica gel, cyclohexane/ethyl acetate/acetic acid=50:50:0.1)

Mass spectrum (ESI$^-$): m/z=259 [M−H]$^-$ (4) 3-benzyloxy-4-methyl-benzoic acid

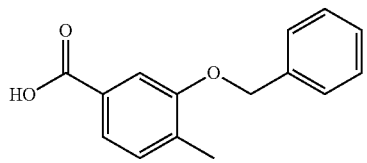 [SMILES: Cc1ccc(C(=O)O)cc1OCc1ccccc1]

HPLC (method 2): retention time=3.41 min

Mass spectrum (ESI$^-$): m/z=241 [M−H]$^-$

Example X

Tert-butyl 4-[4-(5-carboxy-2-methyl-phenoxy)-pyrimidin-2-yl]-piperazine-1-carboxylate

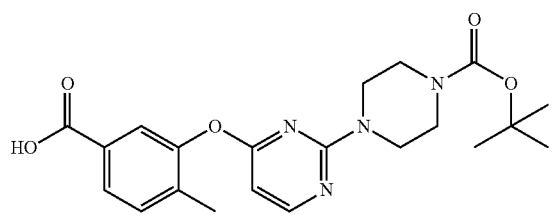 [SMILES: Cc1ccc(C(=O)O)cc1Oc1ccnc(N2CCN(C(=O)OC(C)(C)C)CC2)n1]

6.77 ml 1 N sodium hydroxide solution are added to 1.45 g tert-butyl 4-[4-(5-methoxycarbonyl-2-methyl-phenoxy)-pyrimidin-2-yl]-piperazine-1-carboxylate in 15 ml of tetrahydrofuran, and the reaction mixture is stirred overnight at ambient temperature. Then it is heated for another 3 h to 50° C. until the reaction is complete. The reaction mixture is evaporated down, mixed with some water and acidified with 1 N hydrochloric acid. The precipitate formed is suction filtered and dried.

Yield: 1.26 g (90% of theory)

$R_f$ value: 0.35 (silica gel, dichloromethane/methanol=95:5)

Mass spectrum (ESI$^+$): m/z=415 [M+H]$^+$

The following compounds are obtained analogously to Example X:

(1) tert-butyl 4-[4-(2-bromo-5-carboxy-phenoxy)-pyrimidin-2-yl]-piperazine-1-carboxylate

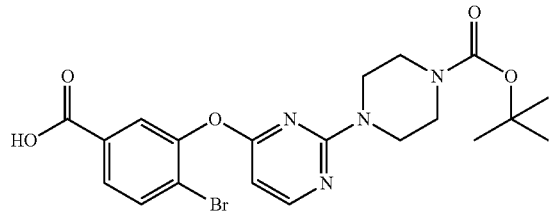 [SMILES: CC(C)(C)OC(=O)N1CCN(c2nccc(Oc3cc(C(=O)O)ccc3Br)n2)CC1]

(ester cleaving is carried out with lithium hydroxide in a tetrahydrofuran/methanol mixture)

$R_f$ value: 0.13 (silica gel, dichloromethane/methanol=98:2)

Mass spectrum (ESI$^+$): m/z=479/481 (Br) [M+H]$^+$ (2) tert-butyl 4-[4-(5-carboxy-2-ethyl-phenoxy)-pyrimidin-2-yl]-piperazine-1-carboxylate

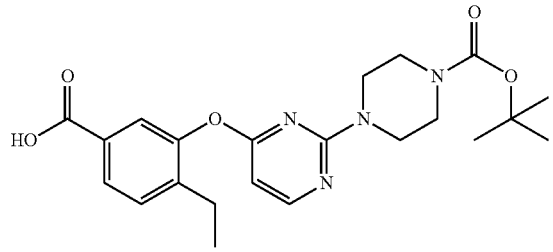 [SMILES: CCc1ccc(C(=O)O)cc1Oc1ccnc(N2CCN(C(=O)OC(C)(C)C)CC2)n1]

(ester cleaving is carried out with lithium hydroxide in a tetrahydrofuran/methanol mixture)

$R_f$ value: 0.58 (silica gel, cyclohexane/ethyl acetate/acetic acid=50:50:0.1)

Mass spectrum (ESI$^+$): m/z=429 [M+H]$^+$ (3) 4-methyl-3-[2-(4-methyl-piperazin-1-ylmethyl)-pyrimidin-4-yloxy]-benzoic acid

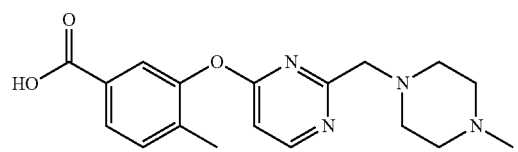 [SMILES: Cc1ccc(C(=O)O)cc1Oc1ccnc(CN2CCN(C)CC2)n1]

$R_f$ value: 0.35 (silica gel, dichloromethane/methanol/conc. ammonia=95:5:0.1)

Mass spectrum (ESI$^+$): m/z=343 [M+H]$^+$ (4) tert-butyl 4-[4-(5-carboxy-2-methyl-phenoxy)-pyridin-2-ylmethyl]-piperidine-1-carboxylate

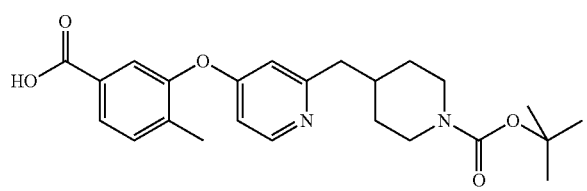 [SMILES: Cc1ccc(C(=O)O)cc1Oc1ccnc(CC2CCN(C(=O)OC(C)(C)C)CC2)c1]

(The Reaction is Carried Out Using Ethanol Instead of Tetrahydrofuran)

HPLC (method 1): retention time=2.70 min

Mass spectrum (ESI$^+$): m/z=427 [M+H]$^+$ (5) 3-(2-chloro-pyridin-4-yloxy)-4-methyl-benzoic acid

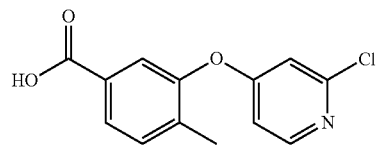 [SMILES: Cc1ccc(C(=O)O)cc1Oc1ccnc(Cl)c1]

(The reaction is carried out using ethanol instead of tetrahydrofuran)

Example XI

Tert-butyl 4-{4-[5-(5-tert-butyl-3-methanesulphonylamino-2-methoxy-phenylaminocarbonyl)-2-methyl-phenoxy]-pyrimidin-2-ylmethyl}-piperazine-1-carboxylate

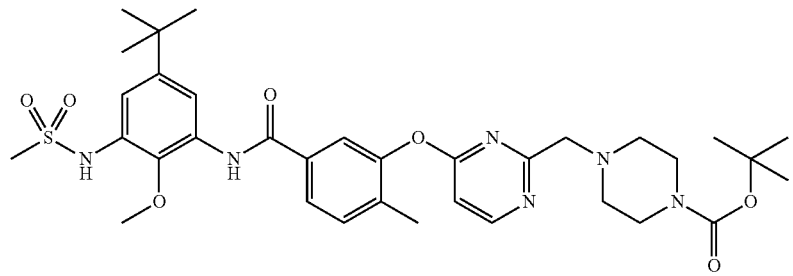 [SMILES: COc1c(NC(=O)c2ccc(C)c(Oc3ccnc(CN4CCN(C(=O)OC(C)(C)C)CC4)n3)c2)cc(C(C)(C)C)cc1NS(C)(=O)=O]

262 mg tert-butyl piperazine-1-carboxylate, 89 µl acetic acid and 89 mg sodium triacetoxy-borohydride are added to 180 mg N-(5-tert-butyl-3-methanesulphonylamino-2-methoxy-phenyl)-3-(2-formyl-pyrimidin-4-yloxy)-4-methyl-benzamide in 8 ml ClCH$_2$CH$_2$Cl, and the reaction mixture is stirred for 3.5 h at ambient temperature. For working up the reaction mixture is diluted with some dichloromethane and stirred with saturated aqueous sodium hydrogen carbonate solution. The organic phase is washed with water, dried on magnesium sulphate and evaporated down. The flask residue is chromatographed through a silica gel column with dichloromethane/methanol (98:29→6:4). The resin-like product is stirred with a little diethyl ether and left to stand until it has crystallised completely. Then the solid is suction filtered and dried.

Yield: 112 mg (58% of theory)

R$_f$ value: 0.53 (silica gel, dichloromethane/methanol=95:5)

Mass spectrum (ESI$^-$): m/z=681 [M−H]$^-$

The following compounds are obtained analogously to Example XI:

(1) tert-butyl 4-{6-[5-(5-tert-butyl-3-methanesulphonylamino-2-methoxy-phenylaminocarbonyl)-2-methyl-phenoxy]-pyrimidin-4-ylmethyl}-piperazine-1-carboxylate

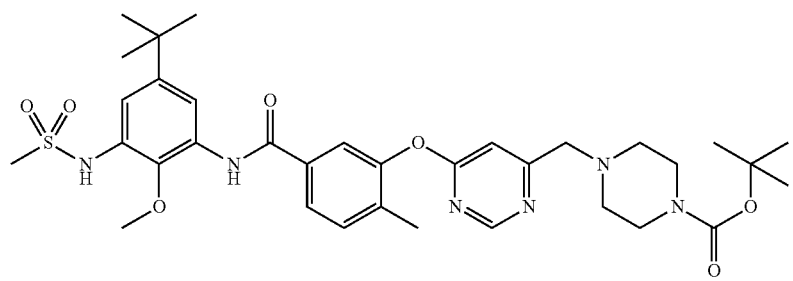 [SMILES: COc1c(NC(=O)c2ccc(C)c(Oc3cc(CN4CCN(C(=O)OC(C)(C)C)CC4)ncn3)c2)cc(C(C)(C)C)cc1NS(C)(=O)=O]

R$_f$ value: 0.84 (silica gel, dichloromethane/methanol/conc. ammonia=90:10:1)

Mass spectrum (ESI$^+$): m/z=683 [M+H]$^+$ (2) tert-butyl 4-{4-[5-(5-tert-butyl-3-methanesulphonylamino-2-methoxy-phenylaminocarbonyl)-2-methyl-phenoxy]-pyridin-2-ylmethyl}-piperazine-1-carboxylate

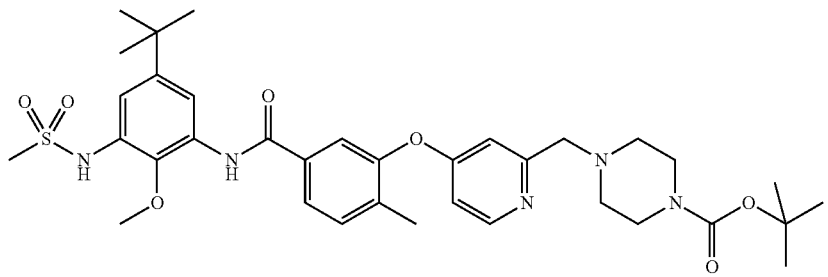 [SMILES: COc1c(NC(=O)c2ccc(C)c(Oc3ccnc(CN4CCN(C(=O)OC(C)(C)C)CC4)c3)c2)cc(C(C)(C)C)cc1NS(C)(=O)=O]

R$_f$ value: 0.72 (silica gel, dichloromethane/methanol/conc. ammonia=90:10:1)
Mass spectrum (ESI$^+$): m/z=682 [M+H]$^+$ (3) tert-butyl 4-{4-[3-(5-tert-butyl-3-methanesulphonylamino-2-methoxy-phenylaminocarbonyl)-5-methyl-phenoxy]-pyrimidin-2-ylmethyl}-piperazine-1-carboxylate

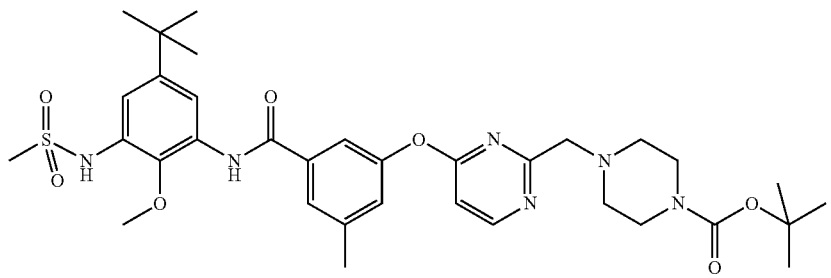 [SMILES: COc1c(NC(=O)c2cc(C)cc(Oc3ccnc(CN4CCN(C(=O)OC(C)(C)C)CC4)n3)c2)cc(C(C)(C)C)cc1NS(C)(=O)=O]

R$_f$ value: 0.65 (silica gel, dichloromethane/methanol=90:10)
Mass spectrum (ESI$^+$): m/z=683 [M+H]$^+$ (4) tert-butyl 4-{6-[5-(5-tert-butyl-3-methanesulphonylamino-2-methoxy-phenylcarbamoyl)-2-chloro-phenoxy]-pyrimidin-4-ylmethyl}-piperazine-1-carboxylate

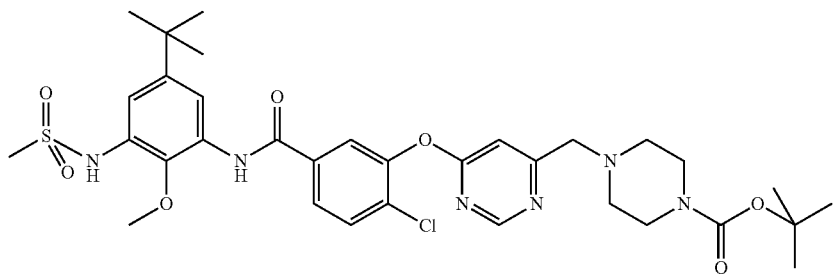 [SMILES: COc1c(NC(=O)c2ccc(Cl)c(Oc3cc(CN4CCN(C(=O)OC(C)(C)C)CC4)ncn3)c2)cc(C(C)(C)C)cc1NS(C)(=O)=O]

R$_f$ value: 0.40 (silica gel, dichloromethane/methanol=95:5)
Mass spectrum (ESI$^+$): m/z=703/705 (Cl) [M+H]$^+$ (5) tert-butyl 4-{4-[5-(5-tert-butyl-3-methanesulphonylamino-2-methoxy-phenylcarbamoyl)-2-chloro-phenoxy]-pyridin-2-ylmethyl}-piperazine-1-carboxylate

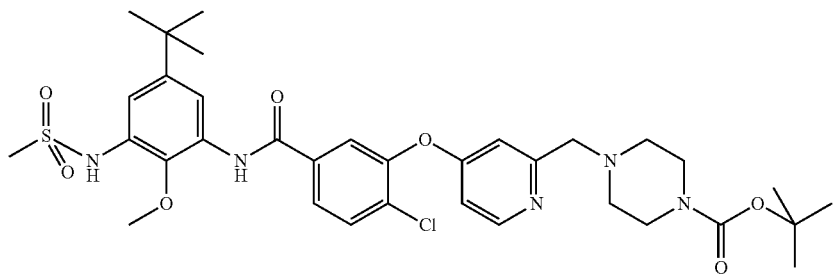 [SMILES: COc1c(NC(=O)c2ccc(Cl)c(Oc3ccnc(CN4CCN(C(=O)OC(C)(C)C)CC4)c3)c2)cc(C(C)(C)C)cc1NS(C)(=O)=O]

R$_f$ value: 0.45 (silica gel, dichloromethane/methanol=95:5)

Mass spectrum (ESI$^+$): m/z=702/704 (Cl) [M+H]$^+$ (6) tert-butyl 4-{4-[5-(5-tert-butyl-3-methanesulphonylamino-2-methoxy-phenylcarbamoyl)-2-chloro-phenoxy]-pyrimidin-2-ylmethyl}-piperazine-1-carboxylate

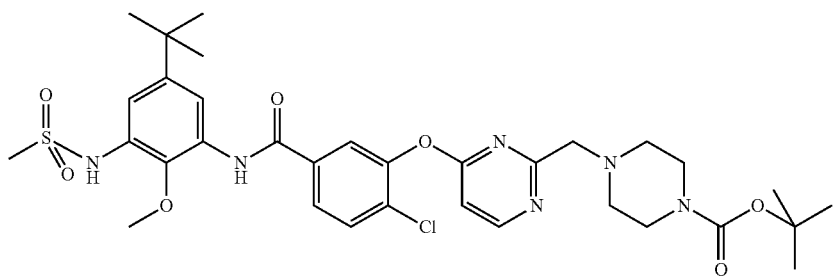 [SMILES: COc1c(NC(=O)c2ccc(Cl)c(Oc3ccnc(CN4CCN(C(=O)OC(C)(C)C)CC4)n3)c2)cc(C(C)(C)C)cc1NS(C)(=O)=O]

R$_f$ value: 0.39 (silica gel, dichloromethane/methanol=95:5)

Mass spectrum (ESI$^-$): m/z=701/703 (Cl) [M−H]$^-$ (7) tert-butyl 4-{6-[5-(5-tert-butyl-3-methanesulphonylamino-2-methoxy-phenylcarbamoyl)-2-chloro-phenoxy]-pyrimidin-4-ylmethyl}-[1,4]diazepan-1-carboxylate

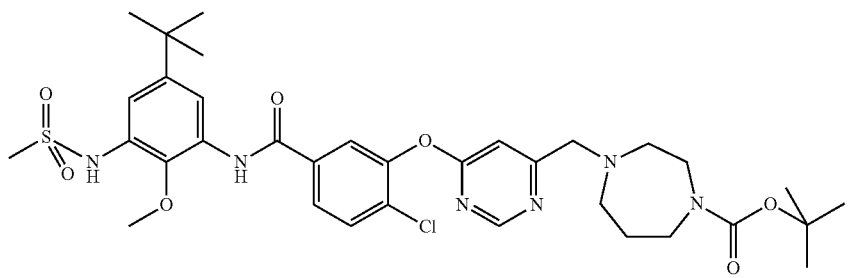 [SMILES: COc1c(NC(=O)c2ccc(Cl)c(Oc3cc(CN4CCCN(C(=O)OC(C)(C)C)CC4)ncn3)c2)cc(C(C)(C)C)cc1NS(C)(=O)=O]

R$_f$ value: 0.40 (silica gel, dichloromethane/methanol=95:5)

Mass spectrum (ESI$^+$): m/z=717/719 (Cl) [M+H]$^+$ (8) tert-butyl 4-{4-[5-(5-tert-butyl-3-methanesulphonylamino-2-methoxy-phenylcarbamoyl)-2-chloro-phenoxy]-pyridin-2-ylmethyl}-[1,4]diazepan-1-carboxylate

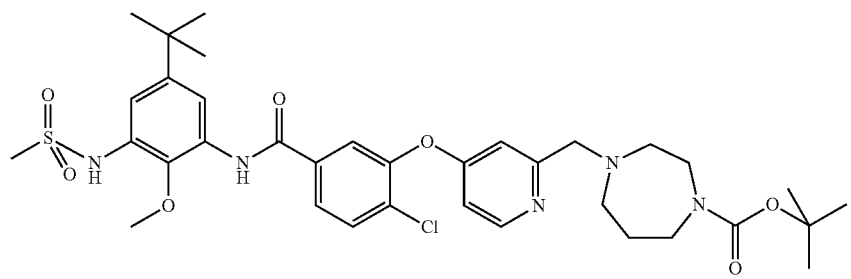 [SMILES: COc1c(NC(=O)c2ccc(Cl)c(Oc3ccnc(CN4CCCN(C(=O)OC(C)(C)C)CC4)c3)c2)cc(C(C)(C)C)cc1NS(C)(=O)=O]

Rf value: 0.30 (silica gel, dichloromethane/methanol=95:5)
Mass spectrum (ESI+): m/z=716/718 (Cl) [M+H]+
(9) tert-butyl 4-{4-[5-(5-tert-butyl-3-methanesulphonylamino-2-methoxy-phenylcarbamoyl)-2-methyl-phenoxy]-pyridin-2-ylmethyl}-[1,4]diazepan-1-carboxylate

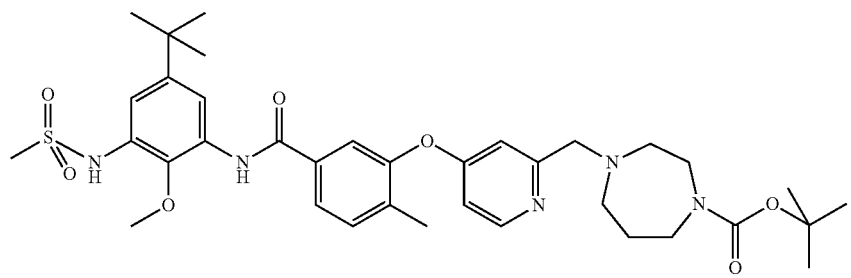 [SMILES: COc1c(NC(=O)c2ccc(C)c(Oc3ccnc(CN4CCCN(C(=O)OC(C)(C)C)CC4)c3)c2)cc(C(C)(C)C)cc1NS(C)(=O)=O]

Rf value: 0.6 (silica gel, dichloromethane/methanol=90:10)
Mass spectrum (ESI+): m/z=696 [M+H]+
(10) (5-tert-butyl-2-methoxy-3-nitro-benzyl)-dimethylamine (5-tert-butyl-2-methoxy-3-nitro-benzaldehyde and dimethylamine are reacted with one another)
Rf value: 0.69 (silica gel, dichloromethane/methanol/conc. ammonia=90:10:0.1)
Mass spectrum (ESI+): m/z=267 [M+H]+
(11) tert-butyl 4-{4-[5-(5-tert-butyl-2-methoxy-3-pyrrolidin-1-ylmethyl-phenylcarbamoyl)-2-methyl-phenoxy]-pyridin-2-ylmethyl}-piperidine-1-carboxylate

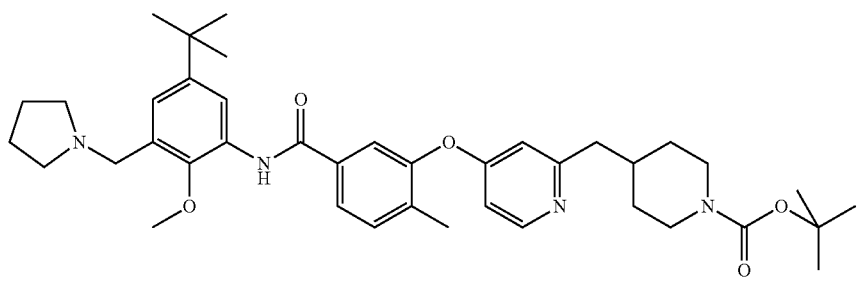 [SMILES: COc1c(CN2CCCC2)cc(C(C)(C)C)cc1NC(=O)c1ccc(C)c(Oc2ccnc(CC3CCN(C(=O)OC(C)(C)C)CC3)c2)c1]

tert-butyl (4-{4-[5-(5-tert-butyl-3-formyl-2-methoxy-phenylcarbamoyl)-2-methyl-phenoxy]-pyridin-2-ylmethyl}-piperidine-1-carboxylate and pyrrolidine are reacted with one another)

Mass spectrum (ESI⁺): m/z=671 [M+H]⁺

(12) (5-tert-butyl-2-methoxy-3-nitro-benzyl)-cyclopropylamine

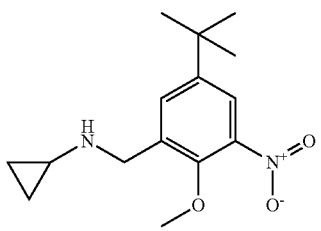 [SMILES: COc1c(CNC2CC2)cc(C(C)(C)C)cc1[N+](=O)[O-]]

(5-tert-butyl-2-methoxy-3-nitro-benzaldehyde and cyclopropylamine are used)

Mass spectrum (ESI⁺): m/z=279 [M+H]⁺

Example XII

N-(5-tert-butyl-3-methanesulphonylamino-2-methoxy-phenyl)-3-(2-chloro-pyridin-4-yloxy)-4-methyl-benzamide

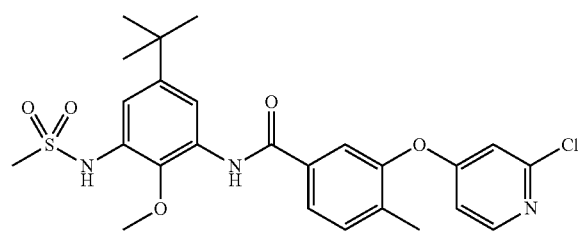 [SMILES: COc1c(NC(=O)c2ccc(C)c(Oc3ccnc(Cl)c3)c2)cc(C(C)(C)C)cc1NS(C)(=O)=O]

545 mg sodium hydride (60% in mineral oil) are added to 2.77 g N-(5-tert-butyl-3-methanesulphonylamino-2-methoxy-phenyl)-3-hydroxy-4-methyl-benzamide in 15 ml N,N-dimethylformamide under an argon atmosphere and while cooling with an ice bath, and the reaction mixture is stirred at ambient temperature until no further hydrogen development can be detected. Then 1.63 g 2-chloro-4-iodopyridine are added, and the reaction mixture is stirred overnight at 110° C. After cooling to ambient temperature the solvent is distilled off using the rotary evaporator. The flask residue is taken up in ethyl acetate, washed with saturated aqueous sodium hydrogen carbonate solution and saturated aqueous sodium chloride solution, dried on magnesium sulphate and evaporated down. The flask residue is chromatographed through a silica gel column with petroleum ether/ethyl acetate (80:20→30:70) as eluant. The product is stirred with diethyl ether, suction filtered and dried.

Yield: 1.77 g (50% of theory)

$R_f$ value: 0.30 (silica gel, petroleum ether/ethyl acetate=1:1)

Mass spectrum (ESI⁺): m/z=518/520 (Cl) [M+H]⁺

Example XIII 3-benzyloxy-N-(5-tert-butyl-3-methanesulphonylamino-2-methoxy-phenyl)-4-methoxy-benzamide

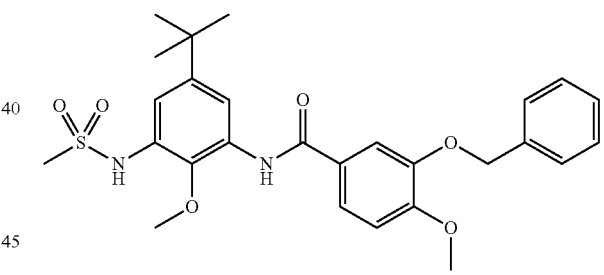

0.86 ml of triethylamine are added to 526 mg N-(3-amino-5-tert-butyl-2-methoxyphenyl)methanesulphonamide-hydrochloride in 7 ml acetonitrile. Then a solution of 3-benzyloxy-4-methoxy-benzoyl chloride in 3 ml acetonitrile is added batchwise, and the reaction mixture is stirred for 30 minutes at ambient temperature, whereupon a light-coloured precipitate is formed. The light suspension is partially evaporated down, the residue is mixed with water and acidified. The precipitate is suction filtered, washed with water and a little methanol and dried.

Yield: 679 mg (86% of theory)

$R_f$ value: 0.35 (silica gel, cyclohexane/ethyl acetate=1:1)

Mass spectrum (ESI⁺): m/z=513 [M+H]⁺

The following compounds are obtained analogously to Example XIII:

(1) 3-benzyloxy-N-(5-tert-butyl-3-methanesulphonylamino-2-methoxy-phenyl)-5-chloro-4-methyl-benzamide

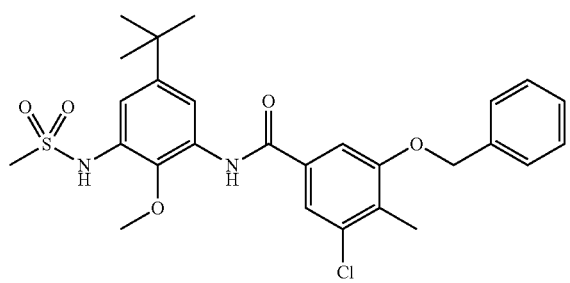 [SMILES: COc1c(NC(=O)c2cc(Cl)c(C)c(OCc3ccccc3)c2)cc(C(C)(C)C)cc1NS(C)(=O)=O]

R$_f$ value: 0.67 (silica gel, cyclohexane/ethyl acetate=1:1)
Mass spectrum (ESI$^+$): m/z=531/533 (Cl) [M+H]$^+$ (2) 3-benzyloxy-N-(5-tert-butyl-3-methanesulphonylamino-2-methoxy-phenyl)-5-fluoro-4-methyl-benzamide

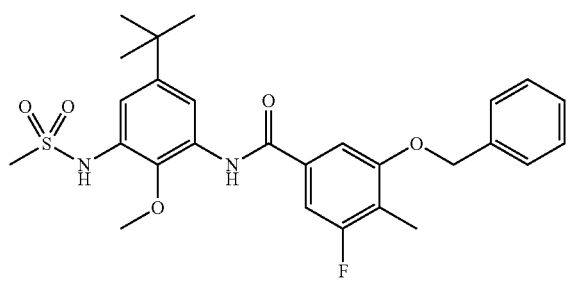 [SMILES: COc1c(NC(=O)c2cc(F)c(C)c(OCc3ccccc3)c2)cc(C(C)(C)C)cc1NS(C)(=O)=O]

R$_f$ value: 0.68 (silica gel, cyclohexane/ethyl acetate=1:1)
Mass spectrum (ESI$^+$): m/z=515 [M+H]$^+$ Example XIV 3-benzyloxy-5-chloro-4-methyl-benzoyl chloride

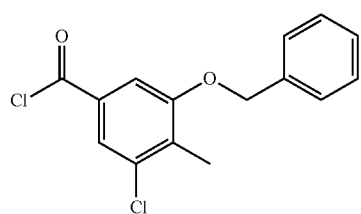

350 mg 3-benzyloxy-5-chloro-4-methyl-benzoic acid in 10 ml acetonitrile are combined with 0.60 ml thionylchloride and gently refluxed for 15 minutes. Then the reaction mixture is evaporated down and evaporated again with toluene. The acid chloride is further reacted without any further purification.

The following compound is obtained analogously to Example XIV:

(1) 3-benzyloxy-5-fluoro-4-methyl-benzoyl chloride

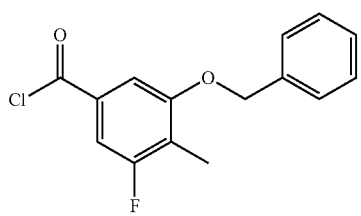 [SMILES: Cc1c(F)cc(C(=O)Cl)cc1OCc1ccccc1]

Example XV 3-chloro-5-hydroxy-4-methyl-benzoic acid

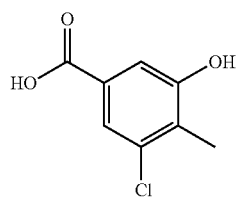

840 mg 3-amino-5-chloro-4-methyl-benzoic acid are suspended in 20 ml 30% aqueous sulphuric acid and stirred for 10 minutes at 90° C. The fine suspension is cooled with a bath of ice and common salt and at an internal temperature of 0-5° C. a solution of 325 mg sodium nitrite in 4.5 ml of water is added dropwise. The reaction mixture is stirred for another 30 minutes at an internal temperature of 0° C. and then poured into 40 ml of a 20% aqueous sulphuric acid solution stirred at 135° C. After 1.5 h the reaction mixture is cooled in the ice bath, diluted with ice water and extracted with tert-butylmethylether. The combined extracts are washed with water and saturated aqueous sodium chloride solution, dried on magnesium sulphate and evaporated down.

Yield: 790 mg (94% of theory)

R$_f$ value: 0.55 (silica gel, cyclohexane/ethyl acetate/acetic acid=50:50:0.1)

Mass spectrum (ESI$^-$): m/z=185/187 (Cl) [M−H]$^-$

The following compound is obtained analogously to Example XV:

(1) 3-fluoro-5-hydroxy-4-methyl-benzoic acid

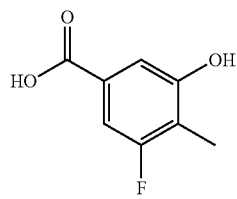

(methyl 3-fluoro-5-hydroxy-4-methyl-benzoate is used as starting material; the ester group is hydrolysed under the reaction conditions to form the acid)

$R_f$ value: 0.55 (silica gel, cyclohexane/ethyl acetate/acetic acid=50:50:0.1)
Mass spectrum (ESI⁻): m/z=169 [M–H]⁻

Example XVI 3-amino-5-chloro-4-methyl-benzoic acid

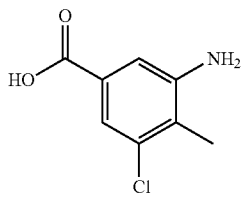

Prepared by shaking a solution of 1.00 g 3-chloro-4-methyl-5-nitro-benzoic acid in 20 ml of tetrahydrofuran with 100 mg Raney nickel in an atmosphere of 50 psi partial hydrogen pressure at ambient temperature. After 9 h reaction time the catalyst is filtered off and the filtrate is evaporated down.

Yield: 0.85 g (99% of theory)
$R_f$ value: 0.60 (silica gel, cyclohexane/ethyl acetate/acetic acid=50:50:0.1)
Mass spectrum (ESI⁻): m/z=184/186 (Cl) [M–H]⁻

The following compound is obtained analogously to Example XVI:
(1) methyl 3-amino-5-fluoro-4-methyl-benzoate

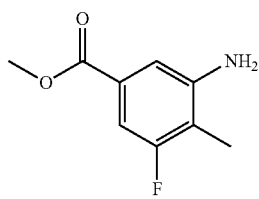

$R_f$ value: 0.35 (silica gel, petroleum ether/ethyl acetate=7:3)
Mass spectrum (ESI⁺): m/z=184 [M+H]⁺

Example XVII

Methyl 3-fluoro-4-methyl-5-nitro-benzoate

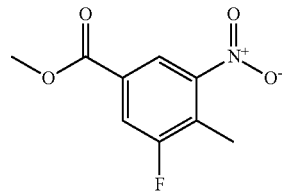

A solution of 1.00 g methyl 3-amino-4-methyl-5-nitro-benzoate in 15 ml 1,4-dioxane is rapidly added dropwise with stirring to 3.89 g nitrosyltetrafluoroborate in 15 ml 1,4-dioxane under an argon atmosphere. The reaction mixture is stirred for one hour at ambient temperature, then for a further hour at 55° C. and then a further eight hours at 90-95° C. After standing overnight at ambient temperature the reaction mixture is evaporated down and the residue is divided between tert-butylmethylether and water. The organic phase is washed with aqueous sodium hydrogen carbonate solution, water and saturated aqueous sodium chloride solution, dried on magnesium sulphate and evaporated down. The crude product is chromatographed through a silica gel column with petroleum ether/ethyl acetate (95:5).

Yield: 310 mg (31% of theory)
$R_f$ value: 0.60 (silica gel, petroleum ether/ethyl acetate=7:3)

Example XVIII

Tert-butyl 4-{6-[5-(5-tert-butyl-3-methanesulphonylamino-2-methoxy-phenylaminocarbonyl)-2-methyl-phenoxy]-pyrimidin-4-ylmethyl}-piperidine-1-carboxylate

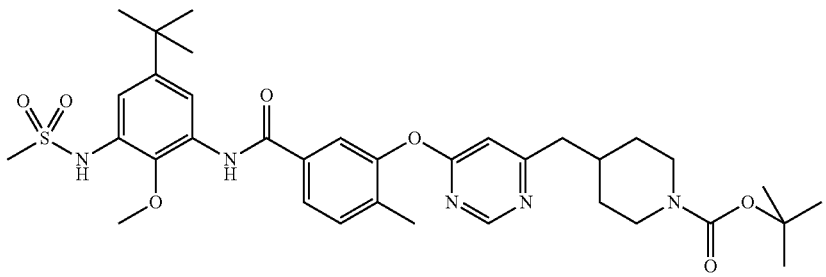 [SMILES: COc1c(NC(=O)c2ccc(C)c(Oc3cc(CC4CCN(C(=O)OC(C)(C)C)CC4)ncn3)c2)cc(C(C)(C)C)cc1NS(C)(=O)=O]

750 mg potassium carbonate and 55 mg palladium-dichloro[1,1'-bis(diphenylphosphino)ferrocene]*CH$_2$Cl$_2$ are added under an argon atmosphere to 400 mg N-(5-tert-butyl-3-methanesulphonylamino-2-methoxy-phenyl)-3-(6-chloro-pyrimidin-4-yloxy)-4-methyl-benzamide in 3.5 ml N,N-dimethylformamide and 350 µl water. Then 1.35 ml of the reaction solution of the hydroboration product of Example XIX are added, and the reaction mixture is stirred for 3 h at 60° C. For working up the reaction mixture is evaporated down, the residue is taken up in ethyl acetate and filtered. The filtrate is washed several times with water and once with saturated aqueous sodium chloride solution, dried on magnesium sulphate and evaporated down. The crude product is purified through a silica gel column with dichloromethane/ethyl acetate (40:60→30:70).

Yield: 480 mg (91% of theory)
HPLC (method 1): retention time=4.59 min
Mass spectrum (ESI$^+$): m/z=682 [M+H]$^+$ The following compounds are obtained analogously to Example XVIII:

(1) tert-butyl 4-{4-[5-(5-tert-butyl-3-methanesulphonylamino-2-methoxy-phenylaminocarbonyl)-2-methyl-phenoxy]-pyrimidin-2-ylmethyl}-piperidine-1-carboxylate

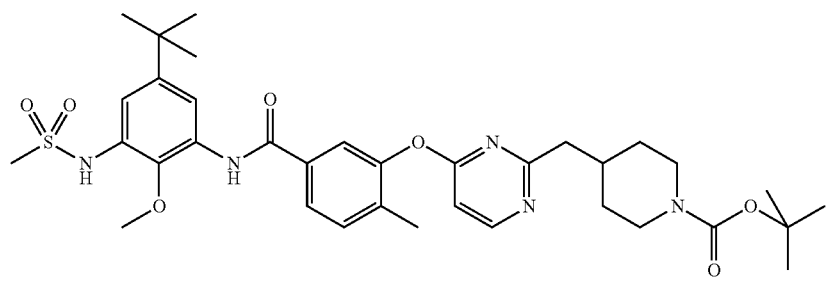 [SMILES: COc1c(NC(=O)c2ccc(C)c(Oc3ccnc(CC4CCN(C(=O)OC(C)(C)C)CC4)n3)c2)cc(C(C)(C)C)cc1NS(C)(=O)=O]

HPLC (method 1): retention time=4.59 min
Mass spectrum (ESI$^+$): m/z=682 [M+H]$^+$ (2) tert-butyl 4-{4-[5-(5-tert-butyl-3-methanesulphonylamino-2-methoxy-phenylcarbamoyl)-2-methyl-phenoxy]-pyridin-2-ylmethyl}-piperidine-1-carboxylate

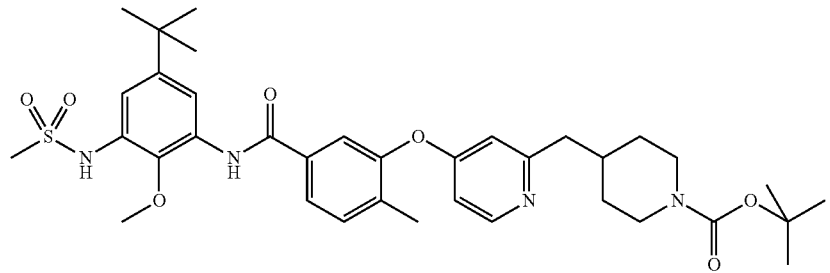 [SMILES: COc1c(NC(=O)c2ccc(C)c(Oc3ccnc(CC4CCN(C(=O)OC(C)(C)C)CC4)c3)c2)cc(C(C)(C)C)cc1NS(C)(=O)=O]

HPLC (method 1): retention time=3.39 min
Mass spectrum (ESI$^+$): m/z=681 [M+H]$^+$ (3) tert-butyl 4-{4-[5-(5-tert-butyl-3-methanesulphonylamino-2-methoxy-phenylcarbamoyl)-2-chloro-phenoxy]-pyridin-2-ylmethyl}-piperidine-1-carboxylate

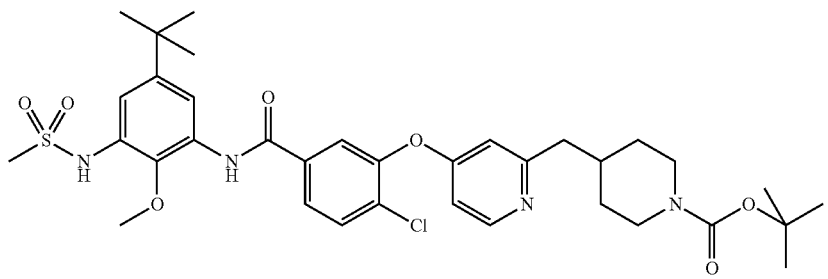 [SMILES: COc1c(NC(=O)c2ccc(Cl)c(Oc3ccnc(CC4CCN(C(=O)OC(C)(C)C)CC4)c3)c2)cc(C(C)(C)C)cc1NS(C)(=O)=O]

$R_f$ value: 0.35 (silica gel, dichloromethane/methanol=95:5)

Mass spectrum (ESI⁺): m/z=701/703 (Cl) [M+H]⁺

(4) tert-butyl 4-{4-[5-(5-tert-butyl-3-methanesulphonylamino-2-methoxy-phenylcarbamoyl)-2-chloro-phenoxy]-pyrimidin-2-ylmethyl}-piperidine-1-carboxylate

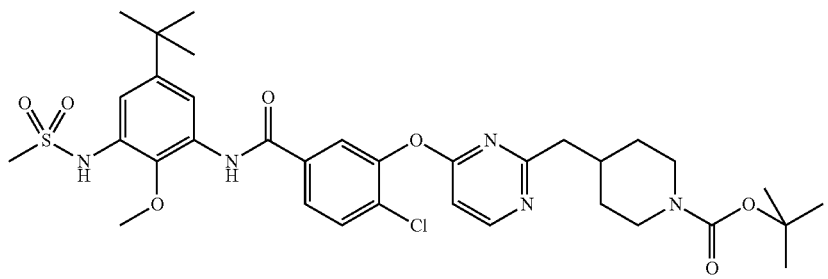 [SMILES: COc1c(NC(=O)c2ccc(Cl)c(Oc3ccnc(CC4CCN(C(=O)OC(C)(C)C)CC4)n3)c2)cc(C(C)(C)C)cc1NS(C)(=O)=O]

$R_f$ value: 0.15 (silica gel, cyclohexane/ethyl acetate=1:1)

Mass spectrum (ESI⁺): m/z=702/704 (Cl) [M+H]⁺

(5) tert-butyl 4-{4-[5-(5-tert-butyl-3-methanesulphonylamino-2-methoxy-phenylcarbamoyl)-2-chloro-phenoxy]-pyrimidin-2-ylmethyl}-piperidine-1-carboxylate

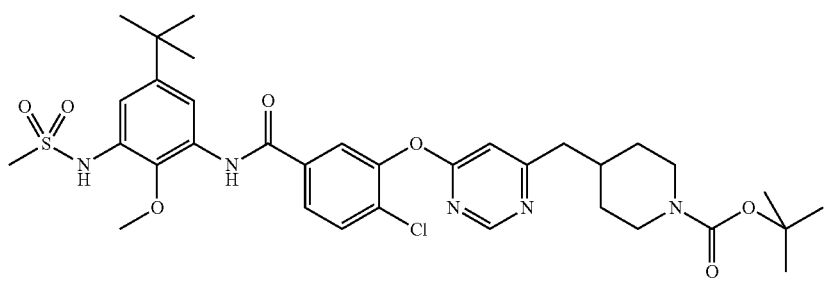 [SMILES: COc1c(NC(=O)c2ccc(Cl)c(Oc3cc(CC4CCN(C(=O)OC(C)(C)C)CC4)ncn3)c2)cc(C(C)(C)C)cc1NS(C)(=O)=O]

$R_f$ value: 0.40 (silica gel, dichloromethane/methanol=95:5)

Mass spectrum (ESI⁻): m/z=700/702 (Cl)

(6) tert-butyl 4-{4-[5-(5-tert-butyl-3-methanesulphonyl-2-methoxy-phenylcarbamoyl)-2-methyl-phenoxy]-pyrimidin-2-ylmethyl}-piperidine-1-carboxylate

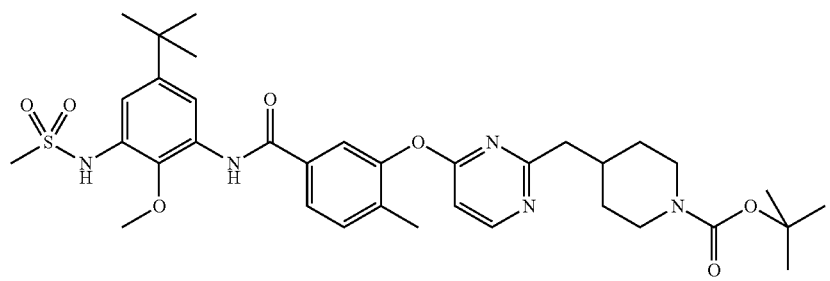 [SMILES: COc1c(NC(=O)c2ccc(C)c(Oc3ccnc(CC4CCN(C(=O)OC(C)(C)C)CC4)n3)c2)cc(C(C)(C)C)cc1NS(C)(=O)=O]

R$_f$ value: 0.15 (silica gel, cyclohexane/ethyl acetate=1:1)
Mass spectrum (ESI$^+$): m/z=667 [M+H]$^+$ (7) tert-butyl 4-[4-(5-methoxycarbonyl-2-methyl-phenoxy)-pyridin-2-ylmethyl]-piperidine-1-carboxylate

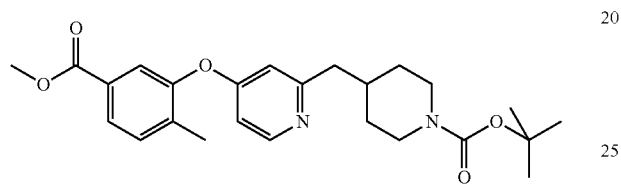

HPLC (method 1): retention time=3.05 min
Mass spectrum (ESI$^+$): m/z=441 [M+H]$^+$ (8) tert-butyl 4-{4-[5-(5-tert-butyl-3-methanesulphonylamino-2-methoxy-phenylcarbamoyl)-2-methyl-phenoxy]-pyridin-2-ylmethyl}-azepan-1-carboxylate

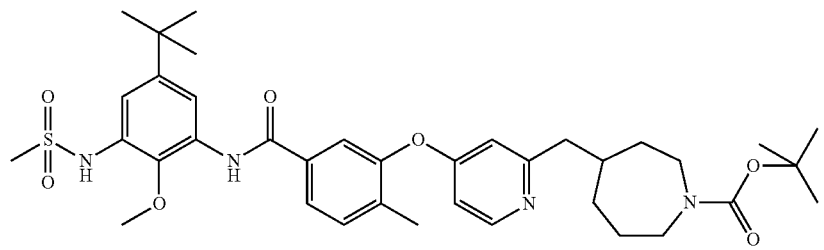 [SMILES: COc1c(NC(=O)c2ccc(C)c(Oc3ccnc(CC4CCCN(C(=O)OC(C)(C)C)CC4)c3)c2)cc(C(C)(C)C)cc1NS(C)(=O)=O]

R$_f$ value: 0.35 (silica gel, dichloromethane/methanol=95:5)
Mass spectrum (ESI$^+$): m/z=695 [M+H]$^+$ (9) tert-butyl 4-{4-[5-(5-tert-butyl-3-methanesulphonylamino-2-methoxy-phenylcarbamoyl)-2-methyl-phenoxy]-pyrimidin-2-ylmethyl}-azepan-1-carboxylate

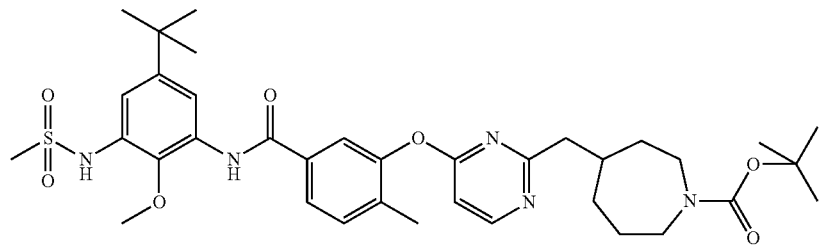 [SMILES: COc1c(NC(=O)c2ccc(C)c(Oc3ccnc(CC4CCCN(C(=O)OC(C)(C)C)CC4)n3)c2)cc(C(C)(C)C)cc1NS(C)(=O)=O]

R$_f$ value: 0.20 (silica gel, ethyl acetate/petroleum ether=7:3)

Mass spectrum (ESI⁺): m/z=696 [M+H]⁺

(10) tert-butyl 4-{6-[5-(5-tert-butyl-3-methanesulphony-lamino-2-methoxy-phenylcarbamoyl)-2-methyl-phenoxy]-pyrimidin-4-ylmethyl}-azepan-1-carboxylate

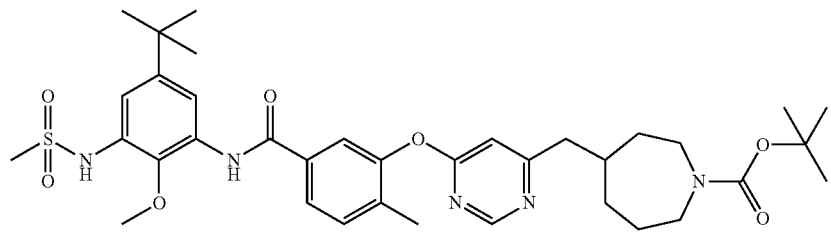 [SMILES: COc1c(NC(=O)c2ccc(C)c(Oc3cc(CC4CCCN(C(=O)OC(C)(C)C)CC4)ncn3)c2)cc(C(C)(C)C)cc1NS(C)(=O)=O]

Mass spectrum (ESI⁺): m/z=696 [M+H]⁺

Example XIX

Tert-butyl 4-(9-bora-bicyclo[3.3.1]non-9-ylmethyl)-piperidine-1-carboxylate

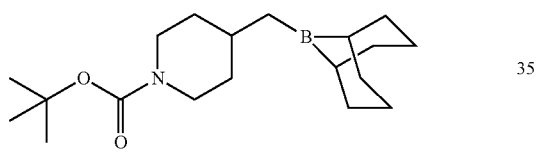

6.29 ml of a 0.5 M solution of 9-borabicyclo[3.3.1]nonane in tetrahydrofuran are added to 620 mg tert-butyl 4-methylene-piperidine-1-carboxylate under an argon atmosphere, and the reaction mixture is refluxed for 1 h. After cooling to ambient temperature the reaction solution is further reacted without any further working up.

The following compound is obtained analogously to Example XIX:

(1) tert-butyl 4-(9-bora-bicyclo[3.3.1]non-9-ylmethyl)-azepan-1-carboxylate

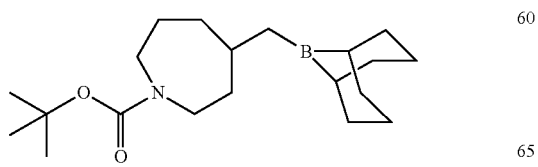

Example XX

Tert-butyl 4-{4-[3-(5-tert-butyl-3-methanesulphonylamino-2-methoxy-phenylaminocarbonyl)-5-methyl-phenoxy]-pyrimidine-2-carbonyl}-piperazine-1-carboxylate

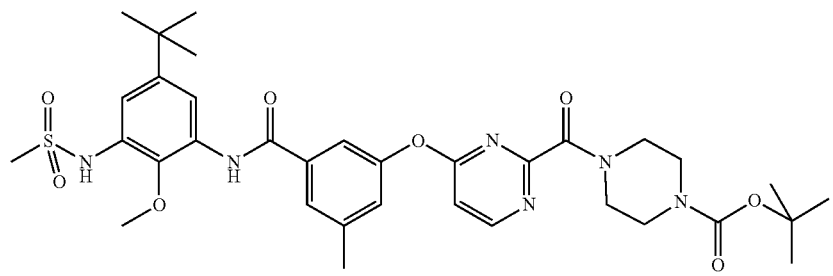 [SMILES: COc1c(NC(=O)c2cc(C)cc(Oc3ccnc(C(=O)N4CCN(C(=O)OC(C)(C)C)CC4)n3)c2)cc(C(C)(C)C)cc1NS(C)(=O)=O]

A mixture of 39 mg 4-[3-(5-tert-butyl-3-methanesulphonylamino-2-methoxy-phenyl-aminocarbonyl)-5-methyl-phenoxy]-pyrimidine-2-carboxylic acid, 25 mg O-(benzotriazol-1-yl)-1,1,3,3-tetramethyluronium-tetrafluoroborate, 25 µl diisopropylethylamine and 15 mg tert-butyl piperazine-1-carboxylate in 3 ml N,N-dimethylformamide is stirred overnight at ambient temperature. Then the reaction mixture is evaporated down and the flask residue is chromatographed through a silica gel column with dichloromethane/methanol (100:0→90:10) as eluant.

Yield: 37 mg (72% of theory)

$R_f$ value: 0.15 (Reversed phase ready-made TLC plate (E. Merck), acetonitrile/water/trifluoroacetic acid=50:50:1)

Example XXI

N-(5-tert-butyl-3-methanesulphonylamino-2-methoxy-phenyl)-3-(2-formyl-m pyrimidin-4-yloxy)-5-methyl-benzamide

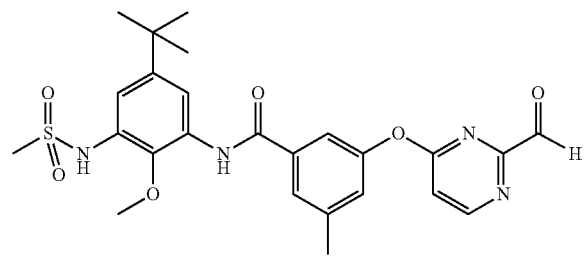 [SMILES: COc1c(NC(=O)c2cc(C)cc(Oc3ccnc(C=O)n3)c2)cc(C(C)(C)C)cc1NS(C)(=O)=O]

A solution of 400 mg sodium periodate in 3 ml of water is added dropwise to a suspension of 3.00 g silica gel in 12 ml dichloromethane. Then a solution of 247 mg N-(5-tert-butyl-3-methanesulphonylamino-2-methoxy-phenyl)-3-[2-(1,2-dihydroxy-ethyl)-pyrimidin-4-yloxy]-5-methyl-benzamide in 3 ml dichloromethane is added, and the reaction mixture is stirred for two hours at ambient temperature. Then the reaction mixture is suction filtered and the filter cake is washed with dichloromethane/ethyl acetate. The filtrate is dried on magnesium sulphate and concentrated by rotary evaporation.

Yield: 215 (93% of theory)

$R_f$ value: 0.40 (Reversed phase ready-made TLC plate (E. Merck), acetonitrile/water/trifluoroacetic acid=50:50:1)

Mass spectrum (ESI⁺): m/z=513 [M+H]⁺

The following compound is obtained analogously to Example XXI:

(1) N-(5-tert-butyl-3-methanesulphonylamino-2-methoxy-phenyl)-3-(6-formyl-pyrimidin-4-yloxy)-4-methyl-benzamide

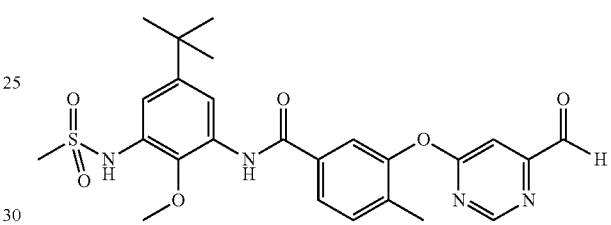

HPLC (method 1): retention time=3.46 min
Mass spectrum (ESI⁺): m/z=513 [M+H]⁺

Example XXII

N-(5-tert-butyl-3-methanesulphonylamino-2-methoxy-phenyl)-3-[2-(1,2-dihydroxy-ethyl)-pyrimidin-4-yloxy]-5-methyl-benzamide

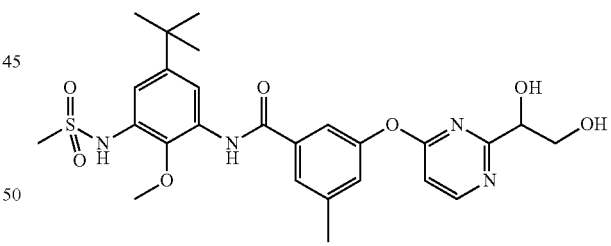

360 mg N-methyl-morpholine-N-oxide, 110 µl of a 4% aqueous osmium to tetroxide solution and 300 µl of water are added to 298 mg N-(5-tert-butyl-3-methanesulphonylamino-2-methoxy-phenyl)-3-methyl-5-(2-vinyl-pyrimidin-4-yloxy)-benzamide in 3 ml acetone, and the reaction mixture is stirred overnight at ambient temperature. Then a solution of 400 mg sodium sulphite in 10 ml of water is added. The mixture is stirred for half an hour and then evaporated down in vacuo. The residue is extracted with ethyl acetate, the aqueous phase is combined with saturated aqueous sodium chloride solution and extracted again with ethyl acetate. The combined organic phases are dried on magnesium sulphate and evaporated down.

Yield: 247 mg (78% of theory)

$R_f$ value: 0.45 (Reversed phase ready-made TLC plate (E. Merck), acetonitrile/water/trifluoroacetic acid=50:50:1)

Mass spectrum (ESI⁺): m/z=545 [M+H]⁺

The following compound is obtained analogously to Example XXII:

(1) N-(5-tert-butyl-3-methanesulphonylamino-2-methoxy-phenyl)-3-[6-(1,2-dihydroxy-ethyl)-pyrimidin-4-yloxy]-4-methyl-benzamide

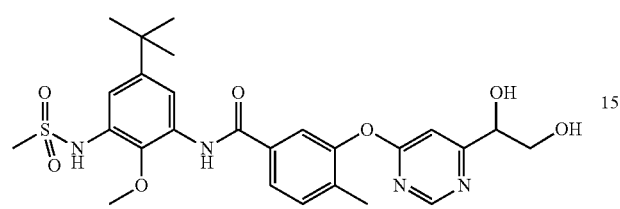

HPLC (method 1): retention time=3.15 min
Mass spectrum (ESI⁺): m/z=545 [M+H]⁺

Example XXIII

N-(5-tert-butyl-3-methanesulphonylamino-2-methoxy-phenyl)-3-methyl-5-(2-vinyl-pyrimidin-4-yloxy)-benzamide

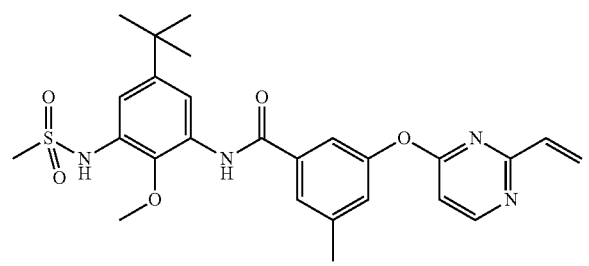 [SMILES: C=Cc1nccc(Oc2cc(C)cc(C(=O)Nc3cc(C(C)(C)C)cc(NS(C)(=O)=O)c3OC)c2)n1]

120 µl water and 240 mg tetrakistriphenylphosphine palladium(0) are added to to 529 mg N-(5-tert-butyl-3-methanesulphonylamino-2-methoxy-phenyl)-3-(2-chloro-pyrimidin-4-yloxy)-5-methyl-benzamide and 600 mg potassium-vinyltrifluoroborate in 8 ml of tetrahydrofuran and 2 ml of toluene under an argon atmosphere, and the reaction mixture is stirred overnight at 100° C. For working up the reaction mixture is diluted with ethyl acetate, washed with water, 10% aqueous ammonium chloride solution and saturated aqueous sodium chloride solution, dried on magnesium sulphate and evaporated down. The flask residue is chromatographed through a silica gel column with cylohexan/ethyl acetate (80:20→0:100) as eluant.

Yield: 298 mg (57% of theory)

$R_f$ value: 0.20 (silica gel, cyclohexane/ethyl acetate=1:1)

Mass spectrum (ESI⁺): m/z=511 [M+H]⁺

The following compound is obtained analogously to Example XXIII:

(1) N-(5-tert-butyl-3-methanesulphonylamino-2-methoxy-phenyl)-4-methyl-3-(6-vinyl-pyrimidin-4-yloxy)-benzamide

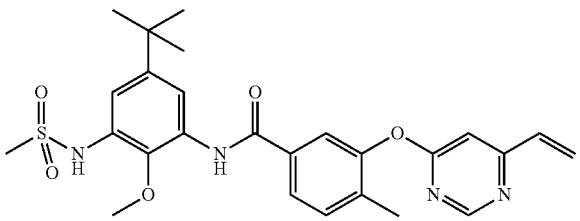 [SMILES: C=Cc1cc(Oc2cc(C(=O)Nc3cc(C(C)(C)C)cc(NS(C)(=O)=O)c3OC)ccc2C)ncn1]

HPLC (method 1): retention time=4.08 min
Mass spectrum (ESI⁺): m/z=511 [M+H]⁺

Example XXIV

Methyl 4-methyl-3-[2-(4-methyl-piperazin-1-ylmethyl)-pyrimidin-4-yloxy]-benzoate

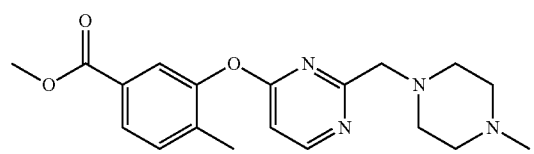

225 mg potassium-tert-butoxide are added to 264 mg methyl 3-hydroxy-4-methyl-benzoate in 4 ml dimethylsulphoxide under an argon atmosphere. After a few minutes 360 mg 4-chloro-2-(4-methyl-piperazin-1-ylmethyl)-pyrimidine dissolved in 2 ml dimethylsulphoxide are added, and the reaction mixture is stirred overnight at ambient temperature. For working up the reaction mixture is mixed with water and extracted with ethyl acetate. The combined ethyl acetate extracts are washed with saturated aqueous sodium chloride solution, dried on magnesium sulphate and evaporated down. The crude product is purified by chromatography through a silica gel column with dichloromethane/methanol/conc. ammonia (96:4:0→95:4:1).

Yield: 313 mg (55% of theory)

$R_f$ value: 0.28 (silica gel, dichloromethane/methanol/conc. ammonia=95:5:0.1)

Mass spectrum (ESI⁺): m/z=357 [M+H]⁺

Example XXV 4-chloro-2-(4-methyl-piperazin-1-ylmethyl)-pyrimidine

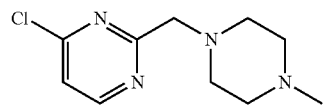

700 mg 2-(4-methyl-piperazin-1-ylmethyl)-pyrimidin-4-ol in 4 ml acetonitrile are heated to boiling and mixed with 2 ml phosphorus oxychloride. After 10 minutes the reaction mixture is evaporated down in a water jet vacuum, mixed with ice and dichloromethane and made alkaline with saturated aqueous sodium carbonate solution while cooling with an ice bath. After the hydrolysis has ended the aqueous phase is extracted with dichloromethane and the combined ethyl acetate extracts are washed with dilute sodium carbonate solution and dried on magnesium sulphate. The solution is stirred with 2 g silica gel and suction filtered. The filter cake is washed with acetone and the filtrate is evaporated down. The yellowish resin-like crude product is further reacted without any further purification.

Yield: 385 mg (51% of theory)

$R_f$ value: 0.40 (silica gel, dichloromethane/methanol/conc. ammonia=95:5:0.1)

Mass spectrum (ESI⁺): m/z=227/229 (Cl) [M+H]⁺

Example XXVI 2-(4-methyl-piperazin-1-ylmethyl)-pyrimidin-4-ol

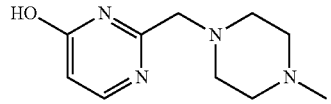

A mixture of 1.74 g 2-chloromethyl-pyrimidin-4-ol and 1.60 ml N-methylpiperazine in 65 ml n-propanol is heated for 4.5 h at reflux temperature. Then the reaction mixture is combined with 12 ml of 1 N aqueous sodium hydroxide solution and evaporated down. The flask residue is re-evaporated with toluene and evaporated to dryness. The solid evaporation residue is stirred with 150 ml acetone at ambient temperature, suction filtered and washed with 100 ml acetone. The filtrate is evaporated down and dried overnight in the desiccator.

Yield: 1.54 g (62% of theory)

$R_f$ value: 0.20 (silica gel, dichloromethane/methanol/conc. ammonia=95:5:0.1)

Mass spectrum (ESI⁺): m/z=209 [M+H]⁺

Example XXVII 2-chloromethyl-pyrimidin-4-ol

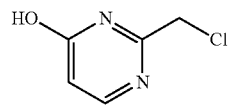

30.50 g sodium-2-ethoxycarbonyl-ethenolate and 18.06 g chloracetamidine hydrochloride are combined with 300 ml of water, and the reaction mixture is left to stand for three days at ambient temperature. Then the resulting dark precipitate is suction filtered, the filtrate is adjusted to pH 5-6 with 3 N aqueous hydrochloric acid and partially evaporated down. The residue is extracted with a total of 500 ml methylethylketone. The combined extracts are washed with saturated aqueous sodium chloride solution, dried on magnesium sulphate and evaporated down. The crude product is briefly heated to boiling with 30 ml of methanol, cooled in the ice bath, filtered off, washed with a little cold methanol and dried.

Yield: 5.98 g (30% of theory)

$R_f$ value: 0.25 (silica gel, ethyl acetate)

Mass spectrum (ESI⁺): m/z=145/147 (Cl) [M+H]⁺

Example XXXVIII 5-tert-butyl-2-methoxy-3-nitro-aniline

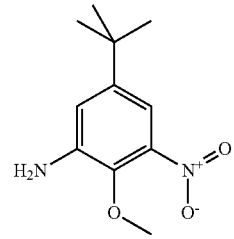 [SMILES: COc1c(N)cc(C(C)(C)C)cc1[N+](=O)[O-]]

2.0 g 5-tert-butyl-2-methoxy-1,3-dinitro-benzene are dissolved in 20 ml of ethanol, combined with 100 µl water and 100 mg of 10% palladium on activated charcoal and then refluxed. 1.9 ml of 4-methyl-cyclohexene are added and the mixture is refluxed for a further 2 hours. Then a further 950 µl of 4-methyl-cyclohexene are added dropwise and then refluxed for 16 hours. The solvents are then eliminated in vacuo, the residue is taken up in ethyl acetate and washed successively with saturated aqueous sodium hydrogen carbonate solution and saturated aqueous sodium chloride solution. After drying with sodium sulphate the solvents are eliminated in vacuo and the residue is dried in vacuo.

Yield: 1.7 g (96% of theory)

$R_f$ value: 0.20 (silica gel, petroleum ether/ethyl acetate=9:1)

Example XXXIX

N-(5-tert-butyl-3-methanesulphonylamino-2-methoxy-phenyl)-4-chloro-3-(2-chloro-pyridin-4-yloxy)-benzamide

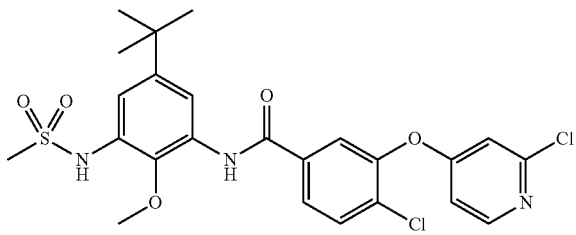 [SMILES: COc1c(NC(=O)c2ccc(Cl)c(Oc3ccnc(Cl)c3)c2)cc(C(C)(C)C)cc1NS(C)(=O)=O]

A mixture of 500 mg N-(5-tert-butyl-3-methanesulphonylamino-2-methoxy-phenyl)-4-chloro-3-hydroxy-benzamide, 170 mg 2-chloro-4-fluoro-pyridine, 240 mg K₂CO₃ and 3 ml dimethylsulphoxide is heated to 50° C. and stirred overnight at this temperature. The mixture is then cooled to ambient temperature and diluted with water. The precipitate formed is filtered off, washed with water and dried.

Yield: 485 mg (77% of theory)

$R_f$ value: 0.65 (silica gel, dichloromethane/methanol=95:5)

Mass spectrum (ESI⁺): m/z=538/540/542 (2 Cl) [M+H]⁺

Example XL

Tert-butyl 4-{4-[5-(5-tert-butyl-3-methanesulphonylamino-2-methoxy-phenylcarbamoyl)-2-chloro-phenoxy]-pyridin-2-ylamino}-piperidine-1-carboxylate

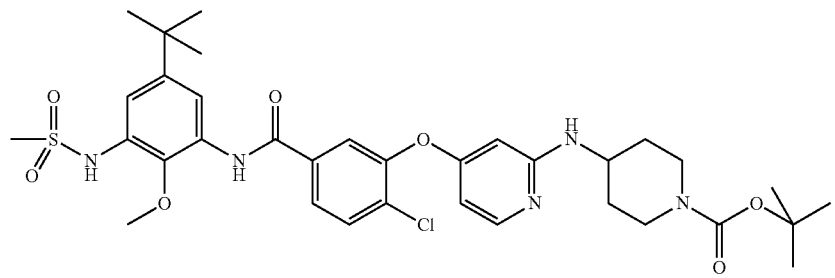 [SMILES: COc1c(NC(=O)c2ccc(Cl)c(Oc3ccnc(NC4CCN(C(=O)OC(C)(C)C)CC4)c3)c2)cc(C(C)(C)C)cc1NS(C)(=O)=O]

55 µl of 2,8,9-triisobutyl-2.5.8.9-tetraaza-1-phosphabicyclo[3.3.3]undecane and 36 mg of Pd$_2$(dibenzylideneacetone)$_3$ are added to a mixture of 350 mg N-(5-tert-butyl-3-methanesulphonylamino-2-methoxy-phenyl)-4-chloro-3-(2-chloro-pyridin-4-yloxy)-benzamide, 110 mg tert-butyl 4-amino-piperidine-1-carboxylate and 290 mg of KO$^t$Bu in 6 ml of toluene kept under an argon atmosphere. The mixture is heated to 105° C. and stirred for 40 h at this temperature. Then the mixture is cooled to ambient temperature and ethyl acetate added. The mixture is then washed once each with dilute citric acid, water and saturated saline solution. The organic phase is dried (Na$_2$SO$_4$), and then the solvent is removed. The flask residue is chromatographed on silica gel with dichloromethane/methanol (100:0→95:5) as eluant.

Yield: 35 mg (8% of theory)

R$_f$ value: 0.35 (silica gel, dichloromethane/methanol=95:5)

Mass spectrum (ESI$^+$): m/z=702/704 (Cl) [M+H]$^+$

Example XLI 5-tert-butyl-3-methanesulphonyl-2-methoxy-aniline

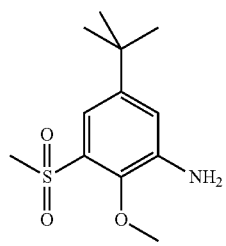 [SMILES: COc1c(N)cc(C(C)(C)C)cc1S(C)(=O)=O]

A mixture of 14.5 g 5-tert-butyl-1-methanesulphonyl-2-methoxy-3-nitro-benzene, 3.0 g 10% palladium on charcoal and 250 ml of methanol is shaken for 6 h at ambient temperature under a hydrogen atmosphere (50 psi). Then the catalyst is filtered off and the filtrate is evaporated to dryness.

Yield: 1.7 g (96% of theory)

R$_f$ value: 0.3 (silica gel, petroleum ether/ethyl acetate=4:1)

The following compounds are obtained analogously to Example XLI:

(1) 5-tert-butyl-3-methanesulphonylmethyl-2-methoxy-aniline

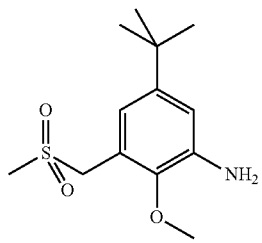 [SMILES: COc1c(N)cc(C(C)(C)C)cc1CS(C)(=O)=O]

HPLC (method 1): retention time=2.81 min
Mass spectrum (ESI$^+$): m/z=272 [M+H]$^+$ (2) 5-tert-butyl-3-methanesulphinylmethyl-2-methoxy-aniline

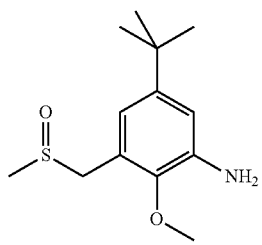 [SMILES: COc1c(N)cc(C(C)(C)C)cc1CS(C)=O]

HPLC (method 1): retention time=2.39 min
Mass spectrum (ESI$^+$): m/z=256 [M+H]$^+$ (3) 1,3-diamino-5-tert-butyl-2-isopropoxy-benzene

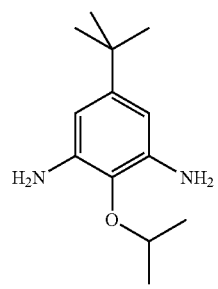 [SMILES: CC(C)Oc1c(N)cc(C(C)(C)C)cc1N]

(5-tert-butyl-2-isopropoxy-1,3-dinitro-benzene is used as starting compound)
Mass spectrum (ESI$^+$): m/z=223 [M+H]$^+$ (4) 1,3-diamino-5-tert-butyl-2-ethoxy-benzene

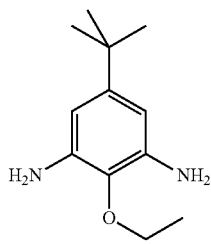

(5-tert-butyl-2-ethoxy-1,3-dinitro-benzene is used as starting compound)
HPLC (method 1): retention time=1.94 min
Mass spectrum (ESI$^+$): m/z=209 [M+H]$^+$ (5) 5-tert-butyl-3-methanesulphinyl-2-methoxy-aniline

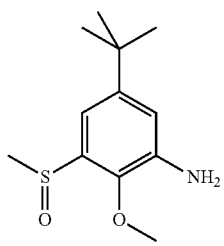 [SMILES: COc1c(N)cc(C(C)(C)C)cc1S(C)=O]

(The reaction is carried out with palladium hydroxide in ethyl acetate)
$R_f$-value: 0.3 (silica gel, petroleum ether/ethyl acetate=1:1)

(6) 1,3-diamino-2-methoxy-5-trifluoromethyl-benzene

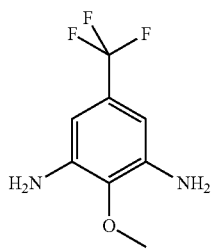

(2-methoxy-1,3-dinitro-5-trifluoromethyl-benzene is used as starting compound and Raney nickel is used as catalyst)
HPLC (method 1): retention time=1.94 min
Mass spectrum (ESI$^+$): m/z=209 [M+H]$^+$ (7) propane-2-sulphonic acid-(3-amino-5-tert-butyl-2-methoxy-phenyl)-amide

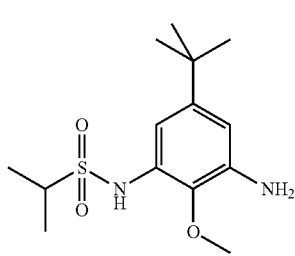 [SMILES: COc1c(N)cc(C(C)(C)C)cc1NS(=O)(=O)C(C)C]

(propane-2-sulphonic acid-(5-tert-butyl-2-methoxy-3-nitro-phenyl)-amide is used as starting compound)
HPLC (method 1): retention time=3.42 min (8) cyclopropanesulphonic acid-(3-amino-5-tert-butyl-2-methoxy-phenyl)-amide

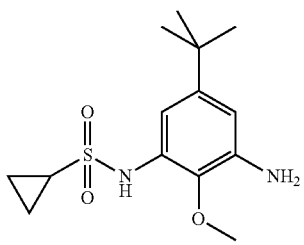 [SMILES: COc1c(N)cc(C(C)(C)C)cc1NS(=O)(=O)C1CC1]

(cyclopropanesulphonic acid-(5-tert-butyl-2-methoxy-3-nitro-phenyl)-amide is used as starting compound)
HPLC (method 1): retention time=3.24 min
Mass spectrum (ESI$^+$): m/z=299 [M+H]$^+$ (9) 1,3-diamino-2-methoxy-5-pentafluoroethyl-benzene

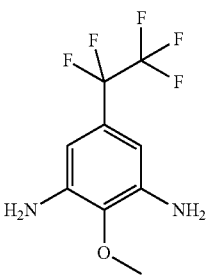 [SMILES: COc1c(N)cc(C(F)(F)C(F)(F)F)cc1N]

(2-methoxy-1,3-dinitro-5-pentafluoroethyl-benzene is used as starting compound and Raney nickel is used as catalyst)
HPLC (method 1): retention time=3.19 min
Mass spectrum (ESI$^+$): m/z=257 [M+H]$^+$

(10) (3-amino-5-tert-butyl-2-methoxy-phenyl)-methanol

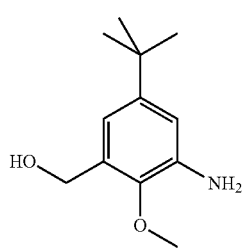

[The reaction is carried out in ethyl acetate and methanol (5:1)]
HPLC (method 1): retention time=2.08 min
Mass spectrum (ESI$^+$): m/z=210 [M+H]$^+$

(11) 5-tert-butyl-3-dimethylaminomethyl-2-methoxy-aniline

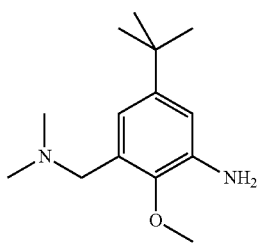 [SMILES: COc1c(N)cc(C(C)(C)C)cc1CN(C)C]

R$_f$ value: 0.28 (silica gel, dichloromethane/methanol/conc. ammonia=90:10:0.1)

Mass spectrum (ESI$^+$): m/z=237 [M+H]$^+$

(12) methyl 3-amino-5-tert-butyl-2-methoxy-benzoate

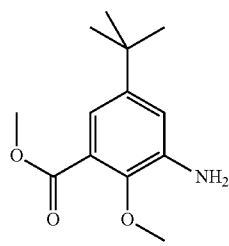 [SMILES: COC(=O)c1cc(C(C)(C)C)cc(N)c1OC]

HPLC (method 1): retention time=2.08 min
Mass spectrum (ESI$^+$): m/z=238 [M+H]$^+$

(13) tert. Butyl (3-amino-5-tert-butyl-2-methoxy-benzyl)-cyclopropyl-carbamate

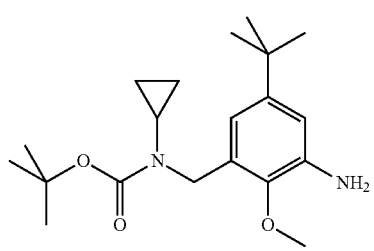 [SMILES: COc1c(N)cc(C(C)(C)C)cc1CN(C(=O)OC(C)(C)C)C1CC1]

Mass spectrum (ESI$^+$): m/z=349 [M+H]$^+$

Example XLII 5-tert-butyl-1-methanesulphonyl-2-methoxy-3-nitro-benzene

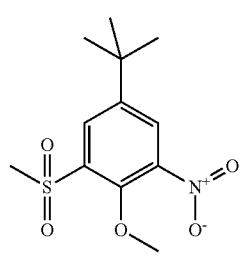 [SMILES: COc1c([N+](=O)[O-])cc(C(C)(C)C)cc1S(C)(=O)=O]

850 mg 77% m-chloroperoxybenzoic acid are added to an ice-cooled solution of 500 mg 5-tert-butyl-2-methoxy-1-methylsulphanyl-3-nitro-benzene (may be obtained starting from 5-tert-butyl-2-methoxy-3-nitro-aniline analogously to the method described in *Syn. Commun.* 1984, 14, 215-8 or in *Syn. Commun.* 2001, 31, 1857-62) in 10 ml dichloromethane. The solution is stirred for 6 h at ambient temperature and then diluted with dichloromethane. The dilute reaction solution is washed with saturated aqueous Na$_2$CO$_3$ solution and saturated aqueous saline solution and dried (Na$_2$SO$_4$). Then the solvent is removed and the residue is chromatographed on silica gel with petroleum ether/ethyl acetate (9:1) as eluant.

Yield: 350 mg (62% of theory)

R$_f$ value: 0.3 (silica gel, petroleum ether/ethyl acetate=9:1)

The following compound is obtained analogously to Example XLII:

(1) 5-tert-butyl-1-methanesulphonylmethyl-2-methoxy-3-nitro-benzene

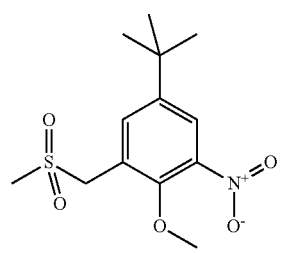 [SMILES: COc1c(CS(C)(=O)=O)cc(C(C)(C)C)cc1[N+](=O)[O-]]

HPLC (method 1): retention time=3.69 min

Example XLIII 5-tert-butyl-1-methanesulphinyl-2-methoxy-3-nitro-benzene

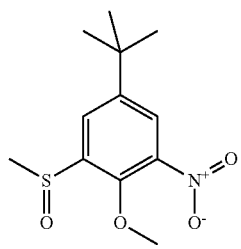 [SMILES: COc1c([N+](=O)[O-])cc(C(C)(C)C)cc1S(C)=O]

At ambient temperature 1.1 ml of a 35% aqueous hydrogen peroxide solution are added to a solution of 500 mg 5-tert-butyl-2-methoxy-1-methylsulphanyl-3-nitro-benzene (may be obtained starting from 5-tert-butyl-2-methoxy-3-nitro-aniline analogously to the method described in *Syn. Commun.* 1984, 14, 215-8 or in *Syn. Commun.* 2001, 31, 1857-62) in 15 ml of 1,1,1,3,3,3-hexafluoroisopropanol. The solution is stirred for 5 h at ambient temperature and then quenched with 10% aqueous Na$_2$S$_2$O$_3$ solution. The resulting mixture is extracted with ethyl acetate, and the combined extracts are washed with saturated aqueous NaHCO$_3$ solution and saturated aqueous saline solution. The organic phase is dried (Na$_2$SO$_4$) and the solvent is distilled off. The residue is chromatographed on silica gel with petroleum ether/ethyl acetate (20:1) as eluant.

Yield: 350 mg (66% of theory)

$R_f$ value: 0.2 (silica gel, petroleum ether/ethyl acetate=9:1)

The following compound is obtained analogously to Example XLIII:

(1) 5-tert-butyl-1-methanesulphinylmethyl-2-methoxy-3-nitro-benzene

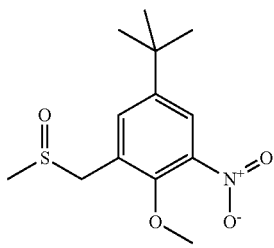 [SMILES: COc1c(CS(C)=O)cc(C(C)(C)C)cc1[N+](=O)[O-]]

HPLC (method 1): retention time=3.28 min

Mass spectrum (ESI$^+$): m/z=286 [M+H]$^+$

Example XLIV

Methyl 3-(2-chloro-pyridin-4-yloxy)-4-methyl-benzoate

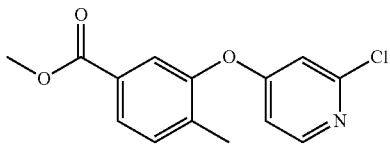 [SMILES: COC(=O)c1ccc(C)c(Oc2ccnc(Cl)c2)c1]

At ambient temperature 1.6 ml methyl iodide are added to a mixture of 6.21 g 3-(2-chloro-pyridin-4-yloxy)-4-methyl-benzoic acid, 4.88 g potassium carbonate to and 30 ml N,N-dimethylformamide. The mixture is stirred overnight at ambient temperature. Then the mixture is added to ice-cold water, and the precipitate is filtered off and dried at 45° C.

Yield: 6.26 g (96% of theory)

Mass spectrum (ESI$^+$): m/z=278/280 (Cl) [M+H]$^+$

The following compounds are obtained analogously to Example XLIV:

(1) 5-tert-butyl-2-methoxy-3-nitro-benzaldehyde

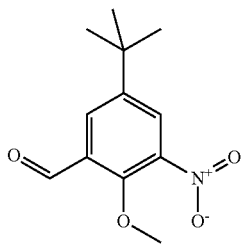 [SMILES: COc1c(C=O)cc(C(C)(C)C)cc1[N+](=O)[O-]]

HPLC (method 1): retention time=4.21 min

Mass spectrum (ESI$^+$): m/z=238 [M+H]$^+$ (2) 5-tert-butyl-2-isopropoxy-1,3-dinitro-benzene

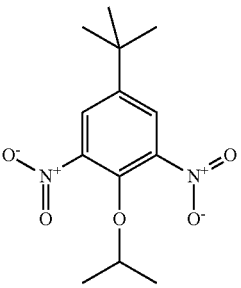 [SMILES: CC(C)Oc1c([N+](=O)[O-])cc(C(C)(C)C)cc1[N+](=O)[O-]]

(4-tert-butyl-2,6-dinitro-phenol and isopropyliodide are reacted with one another)

HPLC (method 1): retention time=4.68 min (3) 5-tert-butyl-2-ethoxy-1,3-dinitro-benzene

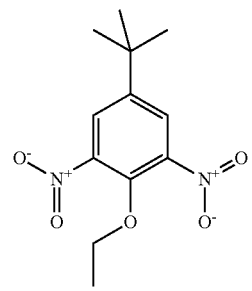 [SMILES: CCOc1c([N+](=O)[O-])cc(C(C)(C)C)cc1[N+](=O)[O-]]

(4-tert-butyl-2,6-dinitro-phenol and ethyl iodide are reacted with one another) HPLC (method 1): retention time=4.58 min Example XLV 5-tert-butyl-2-methoxy-3-methylsulphanylmethyl-aniline

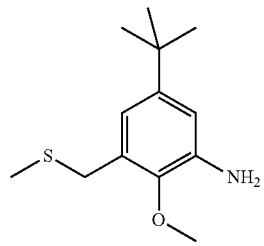 [SMILES: COc1c(N)cc(C(C)(C)C)cc1CSC]

A mixture of 1.00 g 5-tert-butyl-2-methoxy-1-methylsulphanylmethyl-3-nitro-benzene, 4.20 g tin dichloride dihydrate and 15 ml of ethanol is refluxed for 2 h. Then the solvent is removed, and water and dichloromethane are added to the residue. The mixture is filtered through Celite, and the aqueous part of the filtrate is separated off and extracted twice with dichloromethane. The combined organic phases are dried (Na$_2$SO$_4$), and the solvent is removed. The residue is chromatographed on aluminium oxide with cyclohexane/ethyl acetate (4:1→1:4) as eluant.

Yield: 0.62 g (70% of theory)

HPLC (method 1): retention time=3.85 min

Mass spectrum (ESI$^+$): m/z=240 [M+H]$^+$

Example XLVI 5-tert-butyl-2-methoxy-1-methylsulphanylmethyl-3-nitro-benzene

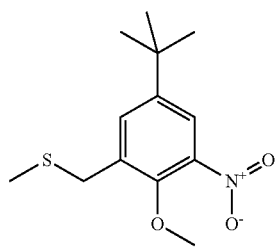 [SMILES: COc1c(CSC)cc(C(C)(C)C)cc1[N+](=O)[O-]]

At ambient temperature 1.50 g sodium thiomethoxide are added to a solution of 4.64 g 5-tert-butyl-2-methoxy-3-nitro-benzyl methanesulphonate in 50 ml of 1,4-dioxane. The solution is stirred overnight at 40° C. Then the solvent is removed and the residue is chromatographed on silica gel with cyclohexane/ethyl acetate (98:2→60:40) as eluant.

Yield: 2.91 g (87% of theory)

HPLC (method 1): retention time=4.74 min

Example XLVII 5-tert-butyl-2-methoxy-3-nitro-benzyl methanesulphonate

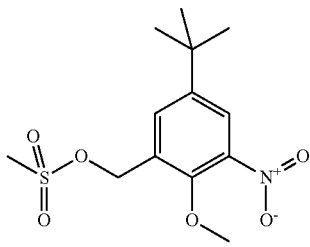 [SMILES: COc1c(COS(C)(=O)=O)cc(C(C)(C)C)cc1[N+](=O)[O-]]

1.20 ml methanesulphonic acid chloride are added to an ice-cooled solution of 3.43 g (5-tert-butyl-2-methoxy-3-nitro-phenyl)-methanol and 2.40 ml triethylamine in 30 ml dichloromethane. The solution is stirred for 2 h while cooling with ice and then diluted with dichloromethane. The dilute solution is washed three times with water and once with saturated aqueous saline solution, dried (MgSO$_4$) and evaporated to dryness.

Yield: 3.97 g (87% of theory)

Mass spectrum (ESI$^+$): m/z=335 [M+NH$_4$]$^+$

Example XLVIII (5-tert-butyl-2-methoxy-3-nitro-phenyl)-methanol

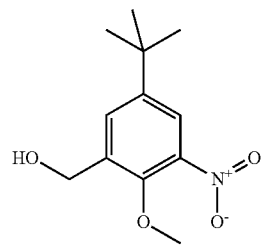 [SMILES: COc1c(CO)cc(C(C)(C)C)cc1[N+](=O)[O-]]

At approx. 10° C., 0.65 g sodium borohydride are added to a solution of 3.75 g 5-tert-butyl-2-methoxy-3-nitro-benzaldehyde in 15 ml dichloromethane and 15 ml of methanol. The solution is stirred for 2 h at ambient temperature and then evaporated down. The residue is combined with aqueous acetic acid and extracted with ethyl acetate. The combined extracts are washed with water and with saturated aqueous saline solution, dried (MgSO$_4$) and evaporated to dryness.

Yield: 3.63 g (96% of theory)

HPLC (method 1): retention time=3.64 min

Mass spectrum (ESI$^-$): m/z=238 [M−H]$^-$

Example IL 5-tert-butyl-2-hydroxy-3-nitro-benzaldehyde

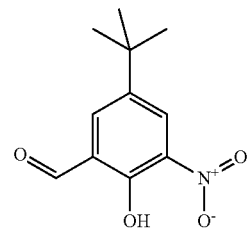 [SMILES: CC(C)(C)c1cc(C=O)c(O)c([N+](=O)[O-])c1]

At −30° C. 4.84 g nitroniumtetrafluoroborate are added to a solution of 5.00 g 5-tert-butyl-2-hydroxy-benzaldehyde in 200 ml acetonitrile. The solution is heated to −15° C. within 1 h and then combined with ethyl acetate and saturated aqueous NaHCO$_3$ solution. The resulting mixture is extracted with ethyl acetate, and the combined extracts are washed with saturated aqueous saline solution, dried (MgSO$_4$) and evaporated down. The residue is taken up in 2 ml of water and 40 ml concentrated acetic acid, and the resulting mixture is refluxed for 2 h. The cooled solution is poured into ice-cold water, and the precipitate formed is filtered off and dissolved in ethyl acetate. The organic solution is dried (MgSO$_4$) and evaporated down. The oil remaining rapidly solidifies.

Yield: 5.89 g (94% of theory)

HPLC (method 1): retention time=4.04 min

Mass spectrum (ESI$^-$): m/z=222 [M−H]$^-$

The following compounds are obtained analogously to Example IL:

(1) 4-tert-butyl-2,6-dinitro-phenol

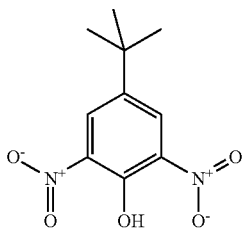

(4-tert-butyl-phenol is reacted with 2.7 equivalents of nitronium tetrafluoroborate)
HPLC (method 1): retention time=4.09 min
Mass spectrum (ESI⁻): m/z=239 [M−H]⁻
(2) 2-methoxy-1,3-dinitro-5-trifluoromethyl-benzene

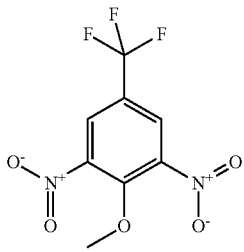

(1-methoxy-2-nitro-4-trifluoromethyl-benzene is used as starting compound) HPLC (method 1): retention time=3.93 min
(3) 2-methoxy-1,3-dinitro-5-pentafluoroethyl-benzene

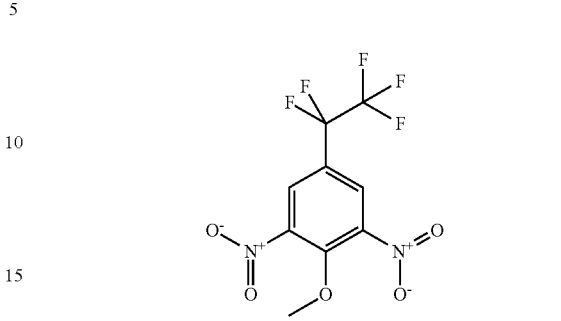

(1-methoxy-4-pentafluoroethyl-benzene is reacted with 2.7 equivalents of nitronium tetrafluoroborate)
HPLC (method 1): retention time=4.23 min Example L Tert-butyl 4-(4-{5-[5-tert-butyl-3-(cyclopropanecarbonyl-amino)-2-methoxy-phenylcarbamoyl]-2-methyl-phenoxy}-pyridin-2-ylmethyl)-piperidine-1-carboxylate

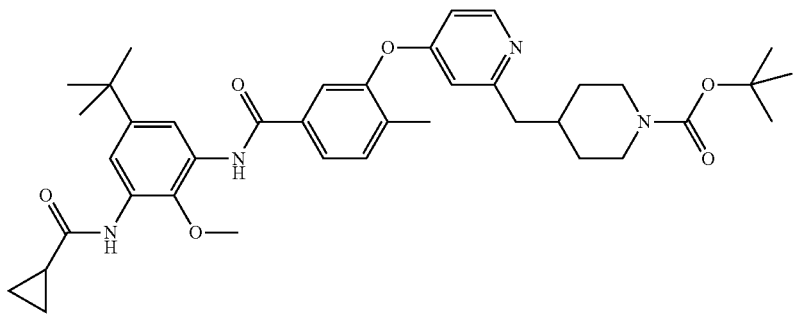 [SMILES: COc1c(NC(=O)c2ccc(C)c(Oc3ccnc(CC4CCN(C(=O)OC(C)(C)C)CC4)c3)c2)cc(C(C)(C)C)cc1NC(=O)C1CC1]

At ambient temperature 36 μl cyclopropanecarboxylic acid chloride are added to a solution of 160 mg tert-butyl 4-{4-[5-(3-amino-5-tert-butyl-2-methoxy-phenylcarbamoyl)-2-methyl-phenoxy]-pyridin-2-ylmethyl}-piperidine-1-carboxylate and 70 μl triethylamine in 2 ml dichloromethane. The solution is stirred overnight at ambient temperature and then mixed with water. The mixture is extracted with dichloromethane, and the combined extracts are washed with water and saturated aqueous saline solution, dried (MgSO₄) and evaporated down. The residue is chromatographed on silica gel with cyclohexane/ethyl acetate (50:500:100) as eluant.

Yield: 5.89 g (94% of theory)
HPLC (method 1): retention time=3.56 min
Mass spectrum (ESI⁺): m/z=671 [M+H]⁺

The following compounds are obtained analogously to Example L:
(1) tert-butyl 4-{4-[5-(5-tert-butyl-2-methoxy-3-pentanoylamino-phenylcarbamoyl)-2-methyl-phenoxy]-pyridin-2-ylmethyl}-piperidine-1-carboxylate

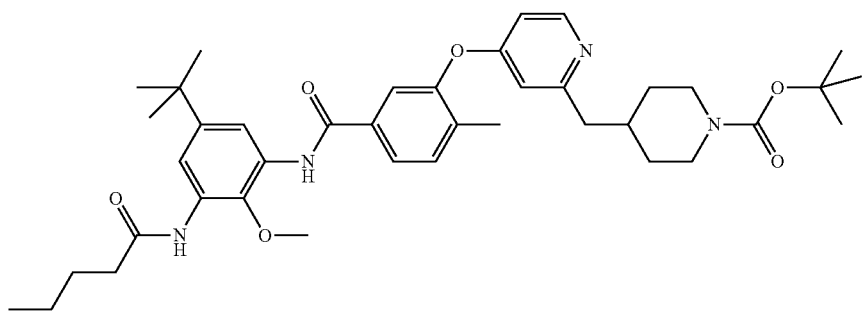

(valeric acid chloride is used as acylating reagent) HPLC (method 1): retention time=3.80 min
Mass spectrum (ESI+): m/z=687 [M+H]+

(2) tert-butyl 4-(4-{5-[5-tert-butyl-2-methoxy-3-(3-methyl-butyrylamino)-phenylcarbamoyl]-2-methyl-phenoxy}-pyridin-2-ylmethyl)-piperidine-1-carboxylate

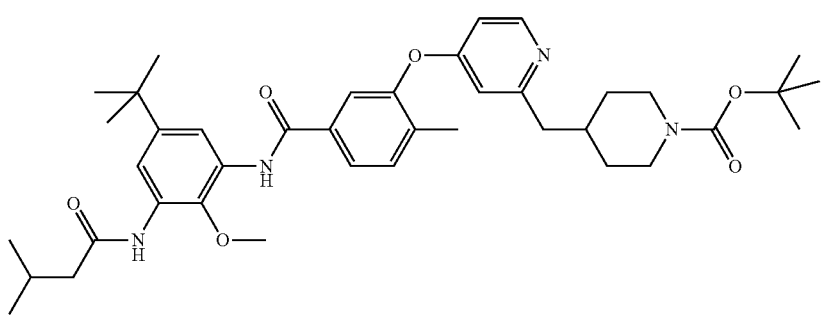

(isovaleric acid chloride is used as acylating reagent)
HPLC (method 1): retention time=3.77 min
Mass spectrum (ESI+): m/z=687 [M+H]+

(3) tert-butyl 4-{4-[5-(5-tert-butyl-3-isobutyrylamino-2-methoxy-phenylcarbamoyl)-2-methyl-phenoxy]-pyridin-2-ylmethyl}-piperidine-1-carboxylate

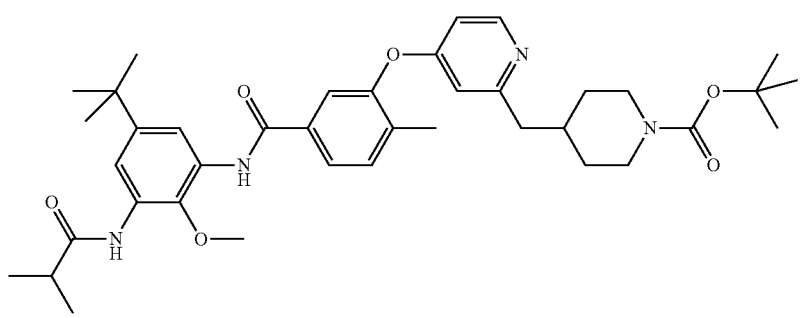 [SMILES: COc1c(NC(=O)c2ccc(C)c(Oc3ccnc(CC4CCN(C(=O)OC(C)(C)C)CC4)c3)c2)cc(C(C)(C)C)cc1NC(=O)C(C)C]

(isobutyric acid chloride is used as acylating reagent)
HPLC (method 1): retention time=3.62 min
Mass spectrum (ESI+): m/z=673 [M+H]+

Example LI

N-(3-amino-5-tert-butyl-2-isopropoxy-phenyl)-methanesulphonamide

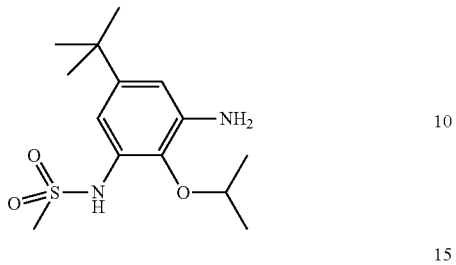

At ambient temperature 0.20 ml methanesulphonic acid chloride are added dropwise to a solution of 0.48 g 1,3-diamino-5-tert-butyl-2-isopropoxy-benzene and 0.35 ml of pyridine in 5 ml dichloromethane. The solution is stirred for 2 h at ambient temperature and then evaporated down. The residue is chromatographed on silica gel with cyclohexane/ethyl acetate (90:10-40:60) as eluant.

Yield: 0.35 g (54% of theory)
HPLC (method 1): retention time=3.42 min
Mass spectrum (ESI$^+$): m/z=301 [M+H]$^+$ The following compounds are obtained analogously to Example LI:

(1) N-(3-amino-5-tert-butyl-2-ethoxy-phenyl)-methanesulphonamide

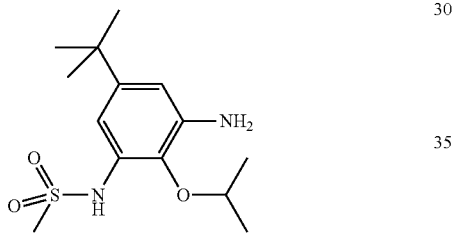

HPLC (method 1): retention time=3.16 min
Mass spectrum (ESI$^+$): m/z=287 [M+H]$^+$ (2) tert-butyl 4-(4-{5-[5-tert-butyl-2-methoxy-3-(2-methyl-propane-1-sulphonylamino)-phenylcarbamoyl]-2-methyl-phenoxy}-pyridin-2-ylmethyl)-piperidine-1-carboxylate

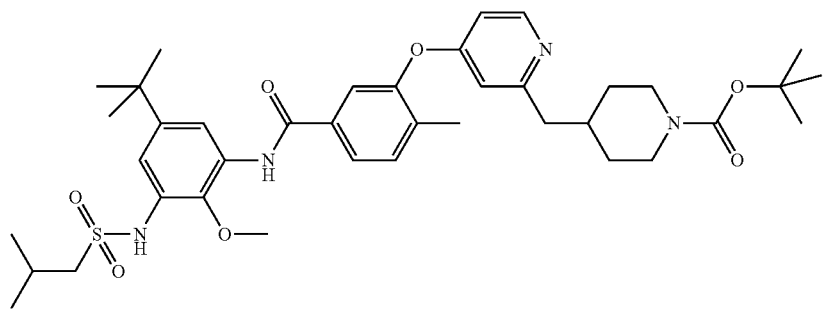 [SMILES: COc1c(NC(=O)c2ccc(C)c(Oc3ccnc(CC4CCN(C(=O)OC(C)(C)C)CC4)c3)c2)cc(C(C)(C)C)cc1NS(=O)(=O)CC(C)C]

(isobutanesulphonic acid chloride is used as sulphonylating reagent) to HPLC (method 1): retention time=3.86 min
Mass spectrum (ESI$^+$): m/z=723 [M+H]$^+$ (3) tert-butyl 4-(4-{5-[3-(butan-1-sulphonylamino)-5-tert-butyl-2-methoxy-phenylcarbamoyl]-2-methyl-phenoxy}-pyridin-2-ylmethyl)-piperidine-1-carboxylate

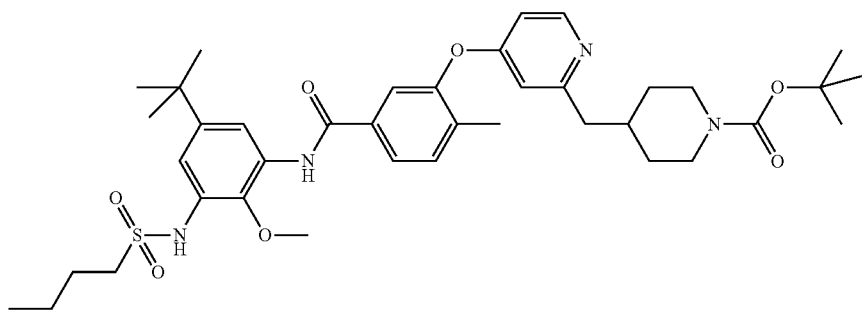 [SMILES: CCCCS(=O)(=O)Nc1cc(C(C)(C)C)cc(NC(=O)c2ccc(C)c(Oc3ccnc(CC4CCN(C(=O)OC(C)(C)C)CC4)c3)c2)c1OC]

(n-butanesulphonic acid chloride is used as sulphonylation reagent)

HPLC (method 1): retention time=3.85 min

Mass spectrum (ESI⁺): m/z=723 [M+H]⁺

(4) N-(3-amino-2-methoxy-5-trifluoromethyl-phenyl)-methanesulphonamide

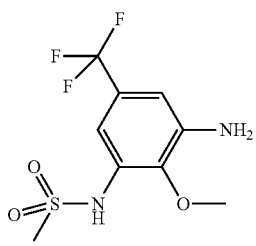 [SMILES: COc1c(N)cc(C(F)(F)F)cc1NS(C)(=O)=O]

HPLC (method 1): retention time=2.93 min

Mass spectrum (ESI⁺): m/z=285 [M+H]⁺

(5) propane-2-sulphonic acid-(5-tert-butyl-2-methoxy-3-nitro-phenyl)-amide

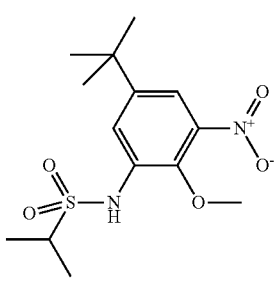 [SMILES: COc1c(NS(=O)(=O)C(C)C)cc(C(C)(C)C)cc1[N+](=O)[O-]]

(isopropylsulphonic acid chloride is used as sulphonylation reagent)

HPLC (method 1): retention time=4.18 min

Mass spectrum (ESI⁺): m/z=331 [M+H]⁺

(6) cyclopropanesulphonic acid-(5-tert-butyl-2-methoxy-3-nitro-phenyl)-amide

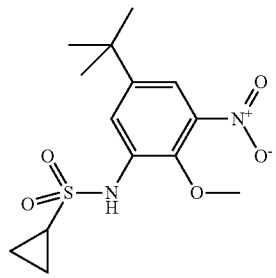 [SMILES: COc1c(NS(=O)(=O)C2CC2)cc(C(C)(C)C)cc1[N+](=O)[O-]]

(cyclopropylsulphonic acid chloride is used as sulphonylation reagent)

HPLC (method 1): retention time=4.09 min

Mass spectrum (ESI⁺): m/z=329 [M+H]⁺

(7) N-(3-amino-2-methoxy-5-pentafluoroethyl-phenyl)-methanesulphonamide

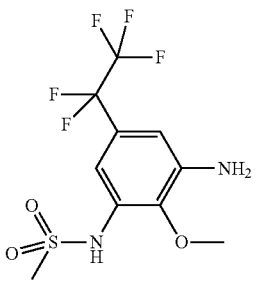 [SMILES: COc1c(N)cc(C(F)(F)C(F)(F)F)cc1NS(C)(=O)=O]

Mass spectrum (ESI⁺): m/z=335 [M+H]⁺

Example LII

Tert-butyl 4-{4-[5-(5-tert-butyl-3-methanesulphonyl-2-methoxy-phenylcarbamoyl)-2-methyl-phenoxy]-pyridin-2-ylmethyl}-piperidine-1-carboxylate

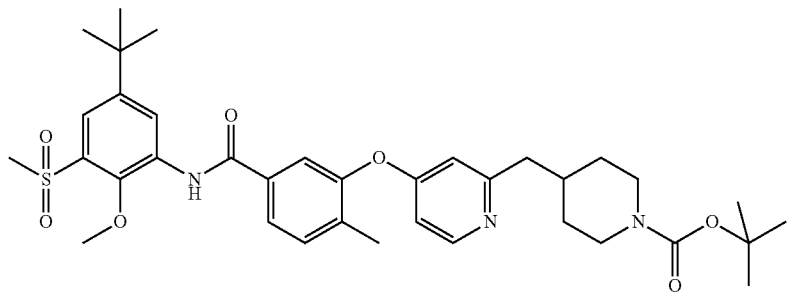 [SMILES: COc1c(NC(=O)c2ccc(C)c(Oc3ccnc(CC4CCN(C(=O)OC(C)(C)C)CC4)c3)c2)cc(C(C)(C)C)cc1S(C)(=O)=O]

At ambient temperature 10 µl N,N-dimethylformamide and 100 µl oxalyl chloride are successively added dropwise to a solution of 140 mg tert-butyl 4-[4-(5-carboxy-2-methyl-phenoxy)-pyridin-2-ylmethyl]-piperidine-1-carboxylate in 2 ml acetonitrile. The solution is stirred for 2 h at ambient temperature and then evaporated to dryness. The residue is taken up in 2 ml 1,2-dichloroethane and combined at ambient temperature with 85 mg 5-tert-butyl-3-methanesulphonyl-2-methoxy-aniline and 180 µl triethylamine. The solution is stirred overnight at ambient temperature and then washed with water and saturated aqueous saline solution and dried ($Na_2SO_4$). The solvent is evaporated off, and the residue is chromatographed on silica gel with cyclohexane/ethyl acetate (50:40→0:100) as eluant.

Yield: 0.35 g (54% of theory)

Mass spectrum (ESI$^+$): m/z=666 [M+H]$^+$

Example LII tert-butyl 4-{4-[5-(5-tert-butyl-3-methanesulphinyl-2-methoxy-phenylcarbamoyl)-2-methyl-phenoxy]-pyridin-2-ylmethyl}-piperidine-1-carboxylate

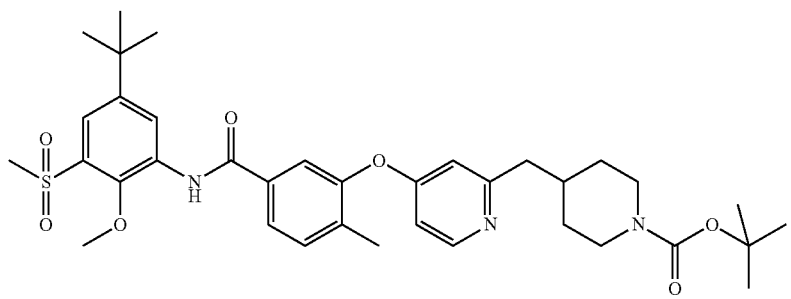 [SMILES: COc1c(NC(=O)c2ccc(C)c(Oc3ccnc(CC4CCN(C(=O)OC(C)(C)C)CC4)c3)c2)cc(C(C)(C)C)cc1S(C)(=O)=O]

At ambient temperature 560 µl of a 50% solution of propanephosphoric acid cycloanhydride in ethyl acetate are added to a solution of 120 mg tert-butyl 4-[4-(5-carboxy-2-methyl-phenoxy)-pyridin-2-ylmethyl]-piperidine-1-carboxylate, mg 5-tert-butyl-3-methanesulphinyl-2-methoxy-aniline and 145 µl triethylamine in 4 ml of tetrahydrofuran. The solution is heated to 80° C. and stirred overnight at this temperature. Then the solution is evaporated to dryness and the residue is combined with saturated aqueous $NaHCO_3$ solution and ethyl acetate. The organic phase is separated off and washed with water and saturated aqueous saline solution and dried ($Na_2SO_4$). The solvent is evaporated off, and the residue is chromatographed on silica gel with dichloromethane/10% methanolic ammonia solution (99:1→90:10) as eluant.

Yield: 105 mg (57% of theory)

HPLC (method 1): retention time=3.21 min

Mass spectrum (ESI$^+$): m/z=650 [M+H]$^+$

The following compounds are obtained analogously to Example LIII:

(1) tert-butyl 4-{4-[5-(3-methanesulphonylamino-2-methoxy-5-trifluoromethyl-phenylcarbamoyl)-2-methyl-phenoxy]-pyridin-2-ylmethyl}-piperidine-1-carboxylate

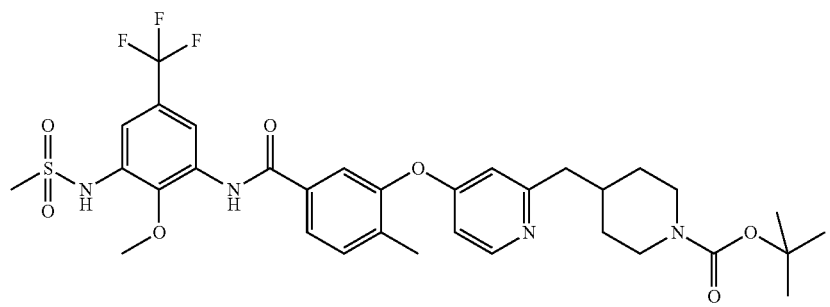 [SMILES: COc1c(NC(=O)c2ccc(C)c(Oc3ccnc(CC4CCN(C(=O)OC(C)(C)C)CC4)c3)c2)cc(C(F)(F)F)cc1NS(C)(=O)=O]

HPLC (method 1): retention time=3.35 min
Mass spectrum (ESI⁺): m/z=693 [M+H]⁺

(2) tert-butyl 4-(4-{5-[5-tert-butyl-2-methoxy-3-(propane-2-sulphonylamino)-phenylcarbamoyl]-2-methyl-phenoxy}-pyridin-2-ylmethyl)-piperidine-1-carboxylate

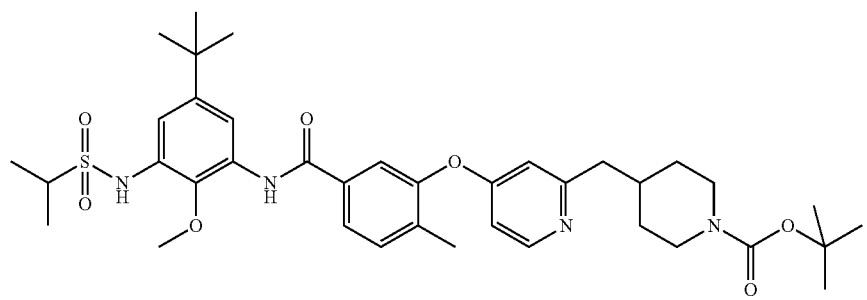 [SMILES: COc1c(NC(=O)c2ccc(C)c(Oc3ccnc(CC4CCN(C(=O)OC(C)(C)C)CC4)c3)c2)cc(C(C)(C)C)cc1NS(=O)(=O)C(C)C]

HPLC (method 1): retention time=3.67 min
Mass spectrum (ESI⁺): m/z=709 [M+H]⁺

(3) tert-butyl 4-{4-[5-(5-tert-butyl-3-cyclopropanesulphonylamino-2-methoxy-phenylcarbamoyl)-2-methyl-phenoxy]-pyridin-2-ylmethyl}-piperidine-1-carboxylate

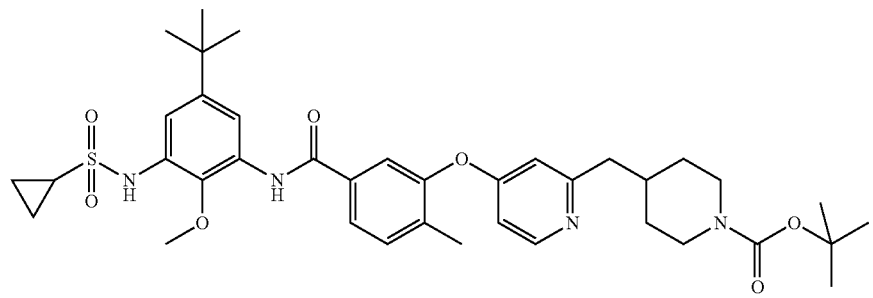 [SMILES: COc1c(NC(=O)c2ccc(C)c(Oc3ccnc(CC4CCN(C(=O)OC(C)(C)C)CC4)c3)c2)cc(C(C)(C)C)cc1NS(=O)(=O)C1CC1]

HPLC (method 1): retention time=3.63 min
Mass spectrum (ESI⁺): m/z=707 [M+H]⁺

(4) tert-butyl 4-{4-[5-(3-methanesulphonylamino-2-methoxy-5-pentafluoroethyl-phenylcarbamoyl)-2-methyl-phenoxy]-pyridin-2-ylmethyl}-piperidine-1-carboxylate

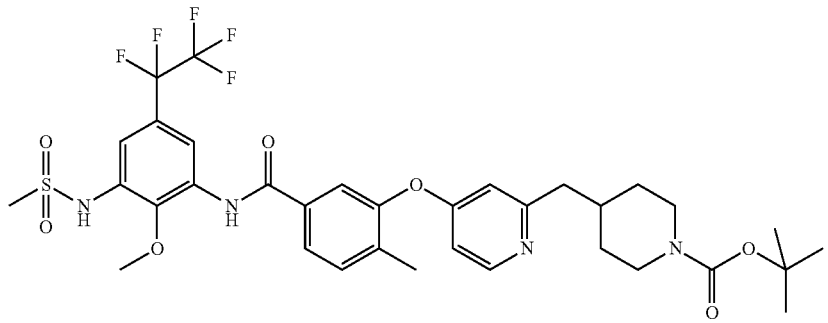 [SMILES: COc1c(NC(=O)c2ccc(C)c(Oc3ccnc(CC4CCN(C(=O)OC(C)(C)C)CC4)c3)c2)cc(C(F)(F)C(F)(F)F)cc1NS(C)(=O)=O]

HPLC (method 1): retention time=3.55 min
Mass spectrum (EI): m/z=316 [M*]+

(5) tert-butyl 4-{4-[5-(5-tert-butyl-3-dimethylaminomethyl-2-methoxy-phenylcarbamoyl)-2-methyl-phenoxy]-pyridin-2-ylmethyl}-piperidine-1-carboxylate

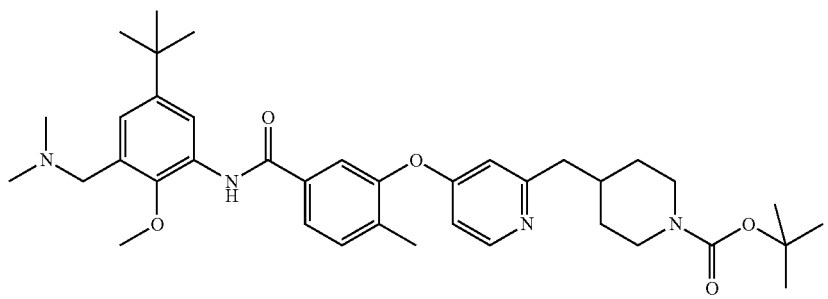 [SMILES: COc1c(CN(C)C)cc(C(C)(C)C)cc1NC(=O)c1ccc(C)c(Oc2ccnc(CC3CCN(C(=O)OC(C)(C)C)CC3)c2)c1]

HPLC (method 1): retention time=2.71 min
Mass spectrum (ESI+): m/z=645 [M+H]+

(6) tert-butyl 4-{4-[5-(5-tert-butyl-2-methoxy-3-trimethylsilyloxymethyl-phenylcarbamoyl)-2-methyl-phenoxy]-pyridin-2-ylmethyl}-piperidine-1-carboxylate

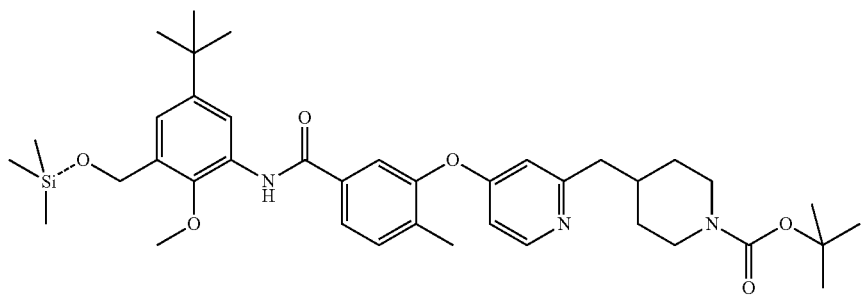

HPLC (method 1): retention time=3.33 min (7) methyl 5-tert-butyl-3-[3-(2-chloro-pyridin-4-yloxy)-4-methyl-benzoylamino]-2-methoxy-benzoate

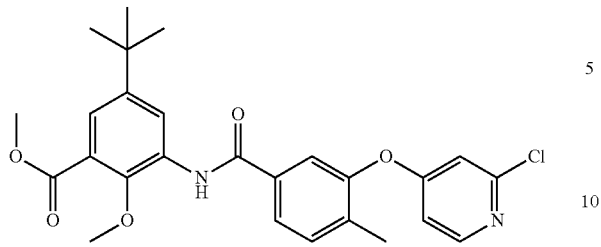

HPLC (method 3): retention time=4.21 min
Mass spectrum (ESI$^+$): m/z=483/485 (Cl) [M+H]$^+$ (8) tert-butyl 4-[4-(5-{3-[(tert-butoxycarbonyl-cyclopropyl-amino)-methyl]-5-tert-butyl-2-methoxy-phenylcarbamoyl}-2-methyl-phenoxy)-pyridin-2-ylmethyl]-piperidine-1-carboxylate

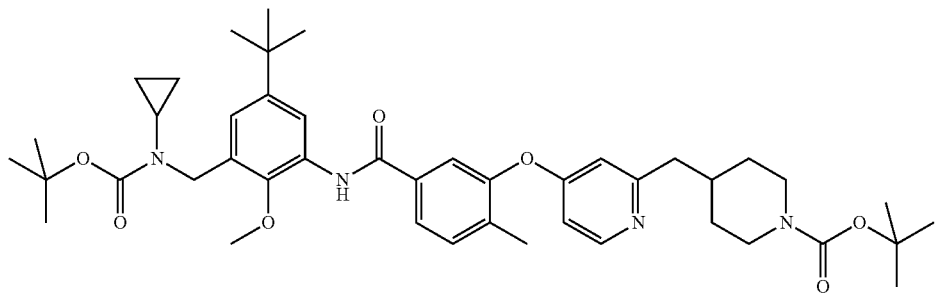 [SMILES: COc1c(CN(C(=O)OC(C)(C)C)C2CC2)cc(C(C)(C)C)cc1NC(=O)c1ccc(C)c(Oc2ccnc(CC3CCN(C(=O)OC(C)(C)C)CC3)c2)c1]

Example LIV 1-methoxy-4-pentafluoroethyl-benzene

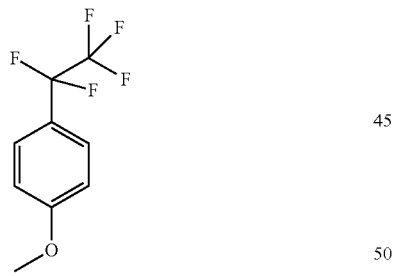

A mixture of 2.00 g 4-iodo-anisol, 2.00 g pentafluoroethyl-trimethylsilane, 0.60 g potassium fluoride, 2.43 g copper iodide and 15 ml N,N-dimethylformamide is stirred overnight at 80° C. Then the mixture is stirred for a further 36 h at 80° C., while a further 2.00 g pentafluoroethyl-trimethylsilane are added after 4 h, 12 h and 24 h. After cooling to ambient temperature 2 M aqueous ammonia solution is added and the mixture is filtered. The filtrate is extracted with ethyl acetate, and the combined organic extracts are dried (Na$_2$SO$_4$) and evaporated down. The residue is chromatographed on silica gel with petroleum ether/ethyl acetate (9:1) as eluant.

Yield: 1.14 g (59% of theory)
HPLC (method 1): retention time=4.40 min
Mass spectrum (EI): m/z=226 [M*]$^+$

Example LV

Tert-butyl 4-{4-[5-(5-tert-butyl-3-formyl-2-methoxy-phenylcarbamoyl)-2-methyl-phenoxy]-pyridin-2-ylmethyl}-piperidine-1-carboxylate

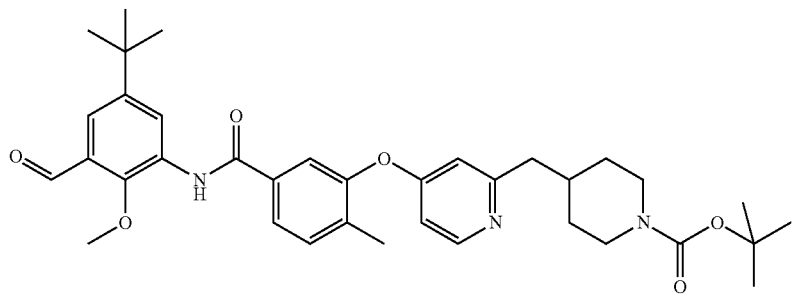 [SMILES: COc1c(C=O)cc(C(C)(C)C)cc1NC(=O)c1ccc(C)c(Oc2ccnc(CC3CCN(C(=O)OC(C)(C)C)CC3)c2)c1]

120 mg of 1,1,1-triacetoxy-1,1-dihydro-1,2-benziodoxol-3(1H)-one ("Dess-Martin-Periodinane") are added to an ice-cooled solution of 200 mg of tert-butyl 4-{4-[5-(5-tert-butyl-3-hydroxymethyl-2-methoxy-phenylcarbamoyl)-2-methyl-phenoxy]-pyridin-2-ylmethyl}-piperidine-1-carboxylate in 6 ml dichloromethane. The cooling bath is removed, and the solution is stirred overnight at ambient temperature. Then the solution is diluted with dichloromethane and washed with aqueous $K_2CO_3$ solution and aqueous $Na_2S_2O_3$ solution. The organic phase is dried ($Na_2SO_4$) and the solvent is removed. The residue is chromatographed on silica gel with dichloromethane/methanol (99:1→90:10) as eluant.

Yield: 55 mg (46% of theory)
HPLC (method 3): retention time=4.34 min
Mass spectrum (ESI$^+$): m/z=616 [M+H]$^+$

Example LVI 5-tert-butyl-2-methoxy-3-trimethylsilyloxymethyl-phenylamine

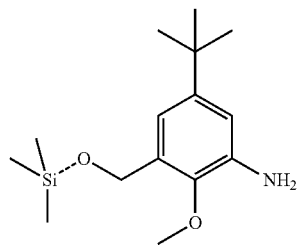

At ambient temperature 0.45 ml trimethylsilyl chloride are added dropwise to a solution of 0.50 g (3-amino-5-tert-butyl-2-methoxy-phenyl)-methanol and 0.39 g imidazole in 6 ml of tetrahydrofuran. The solution is stirred for 2 h at ambient temperature and then evaporated to dryness. The residue is taken up in ethyl acetate and washed with aqueous 10% $K_2CO_3$ solution and saturated aqueous saline solution. Then the organic phase is dried ($Na_2SO_4$) and evaporated down. The residue is chromatographed on silica gel with cyclohexane/ethyl acetate (95:5→50:50) as eluant.

Yield: 0.51 g (76% of theory)
$R_f$ value: 0.5 (silica gel, cyclohexane/ethyl acetate=3:2)

Example LVII

Methyl 5-tert-butyl-2-methoxy-3-[4-methyl-3-(2-piperazin-1-ylmethyl-pyridin-4-yloxy)-benzoylamino]-benzoate

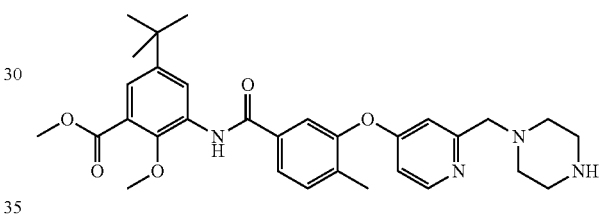

At ambient temperature 1.4 mL of a 5-6 M isopropanolic hydrochloric acid solution are added to a solution of 270 mg tert-butyl 4-{4-[5-(5-tert-butyl-2-methoxy-3-methoxycarbonyl-phenylcarbamoyl)-2-methyl-phenoxy]-pyridin-2-ylmethyl}-piperazine-1-carboxylate in 6 ml dichloromethane. The solution is stirred overnight at ambient temperature and then diluted with dichloromethane. The solution is washed with saturated aqueous $NaHCO_3$ solution and the aqueous phase is extracted once with dichloromethane. The combined organic phases are dried ($Na_2SO_4$), and the solvent is removed completely.

Yield: 215 mg (94% of theory)
HPLC (method 1): retention time=2.61 min
Mass spectrum (ESI$^+$): m/z=547 [M+H]$^+$ The following compound is obtained analogously to Example LVII:

(1) methyl 5-tert-butyl-3-[3-(2-[1,4]diazepan-1-ylmethyl-pyridin-4-yloxy)-4-methyl-benzoylamino]-2-methoxy-benzoate

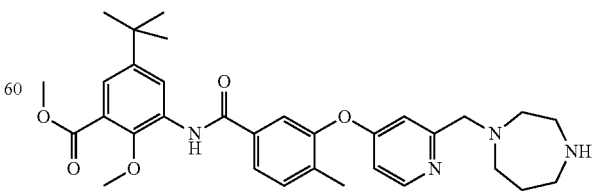

HPLC (method 1): retention time=2.73 min
Mass spectrum (ESI$^+$): m/z=561 [M+H]$^+$

Example LVIII

Tert-butyl 4-{4-[5-(5-tert-butyl-2-methoxy-3-methoxycarbonyl-phenylcarbamoyl)-2-methyl-phenoxy]-pyridin-2-ylmethyl}-piperazine-1-carboxylate

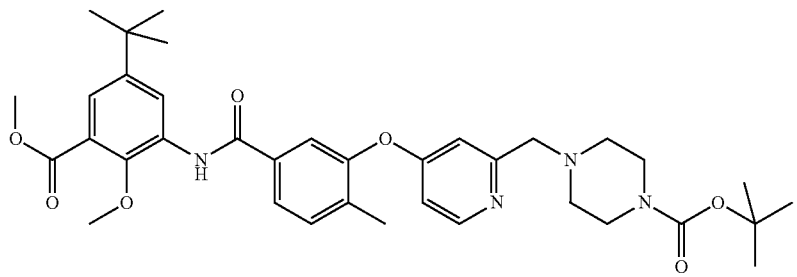 [SMILES: COC(=O)c1cc(C(C)(C)C)cc(NC(=O)c2ccc(C)c(Oc3ccnc(CN4CCN(C(=O)OC(C)(C)C)CC4)c3)c2)c1OC]

A mixture of 414 mg methyl 5-tert-butyl-3-[3-(2-chloro-pyridin-4-yloxy)-4-methyl-benzoylamino]-2-methoxy-benzoate, 370 mg potassium-(4-tert-butyloxycarbonyl-piperazin-1-ylmethyl)-trifluoroborate, 0.84 g Cs$_2$CO$_3$, 0.80 ml of water and 8 ml of tetrahydrofuran is flushed for 10 min with argon. Then 200 mg of 2-dicyclohexylphosphinyl-2',4',6'-triisopropyl-1,1'-biphenyl (XPhos) and 20 mg palladium(II) acetate are added, and the mixture is heated to 80° C. The reaction mixture is stirred overnight at 80° C. in an argon atmosphere. After cooling to ambient temperature the mixture is evaporated down and the residue is taken up in ethyl acetate and water. The organic phase is separated off, washed with water and aqueous saturated saline solution and dried (MgSO$_4$). The solvent is removed, and the residue is chromatographed on silica gel with dichloromethane/methanol (99:1→90:10) and then chromatographed by reversed phase (HPLC, Xbridge C18) with methanol/water/ammonia.

Yield: 270 mg (49% of theory)
HPLC (method 1): retention time=3.54 min
Mass spectrum (ESI$^+$): m/z=647 [M+H]$^+$ The following compound is obtained analogously to Example LVIII:

(1) tert-butyl 4-{4-[5-(5-tert-butyl-2-methoxy-3-methoxycarbonyl-phenylcarbamoyl)-2-methyl-phenoxy]-pyridin-2-ylmethyl}-[1,4]diazepan-1-carboxylate

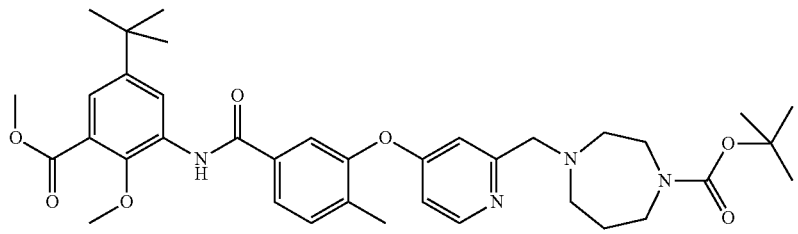 [SMILES: COC(=O)c1cc(C(C)(C)C)cc(NC(=O)c2ccc(C)c(Oc3ccnc(CN4CCCN(C(=O)OC(C)(C)C)CC4)c3)c2)c1OC]

HPLC (method 3): retention time=4.39 min
Mass spectrum (ESI$^+$): m/z=661 [M+H]$^+$

Example LIX

Potassium-(4-tert-butyloxycarbonyl-piperazin-1-ylmethyl)-trifluoroborate

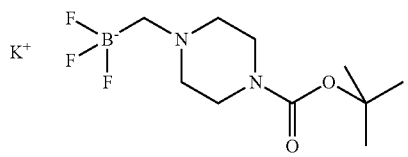 [SMILES: [K+] ; CC(C)(C)OC(=O)N1CCN(C[B-](F)(F)F)CC1]

5.00 g potassium-bromomethyl-trifluoroborate are added to a solution of 4.87 g tert-butyl piperazine-1-carboxylate in 25 ml of tetrahydrofuran. The mixture is stirred for 3 h at 80° C. and then cooled to ambient temperature. The solvent is removed, and the residue is suspended in 50 ml acetone and combined with 3.44 g potassium carbonate. The mixture is stirred overnight at ambient temperature. Then the mixture is filtered and the filtrate is evaporated down.

The oil remaining is combined with diisopropylether and the colourless precipitate formed after a while is separated off and dried.

Yield: 4.20 g (55% of theory)
Mass spectrum (ESI$^-$): m/z=267 [M]$^-$ [4-tert-butyloxycarbonyl-piperazin-1-ylmethyl)-trifluoroborate]

The following compound is obtained analogously to Example LIX:

(1) potassium-(4-tert-butyloxycarbonyl-homopiperazin-1-ylmethyl)-trifluoroborate

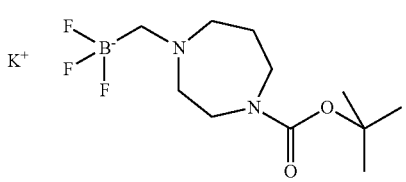 [SMILES: [K+] ; CC(C)(C)OC(=O)N1CCCN(C[B-](F)(F)F)CC1]

Mass spectrum (ESI⁻): m/z=281 [M]⁻ [4-tert-butyloxycarbonyl-homopiperazin-1-ylmethyl)-trifluoroborate]

Example LX 5-tert-butyl-2-methoxy-3-nitro-benzoic acid

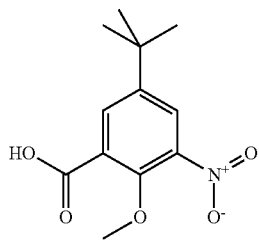 [SMILES: COc1c(C(=O)O)cc(C(C)(C)C)cc1[N+](=O)[O-]]

A mixture of 2.3 ml 65% nitric acid and 2.6 ml 96% sulphuric acid is added dropwise to an ice-cooled solution of 5.00 g 5-tert-butyl-2-methoxy-benzoic acid in 15 ml 96% sulphuric acid. The solution is stirred for 1.5 h in the cooling bath and then for 1 h at ambient temperature. Then the solution is added to ice water, and the precipitate formed is filtered off and taken up in dichloromethane. The dichloromethane phase is dried (Na₂SO₄), and the solvent is eliminated completely.

Yield: 5.40 g (89% of theory)

Example LXI

Methyl 5-tert-butyl-2-methoxy-3-nitro-benzoate

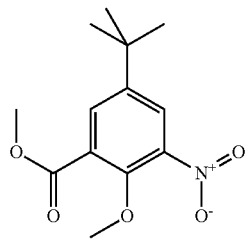 [SMILES: COC(=O)c1cc(C(C)(C)C)cc([N+](=O)[O-])c1OC]

2.3 ml of thionyl chloride are added dropwise to an ice-cooled solution of 5.40 g 5-tert-butyl-2-methoxy-3-nitro-benzoic acid in 50 ml of methanol. The cooling bath is removed and the solution is heated to 60° C. The solution is stirred overnight at 60° C. and then cooled to ambient temperature. The solution is evaporated down completely and the residue is mixed with water. The aqueous mixture is extracted with ethyl acetate, and the combined extracts are dried (MgSO₄). The solvent is removed, and the residue is chromatographed on silica gel with cyclohexane/ethyl acetate (98:260:40).

Yield: 2.69 g (47% of theory)
HPLC (method 1): retention time=4.30 min
Mass spectrum (ESI⁺): m/z=268 [M+H]⁺

Example LXII

Tert.Butyl (5-tert-butyl-2-methoxy-3-nitro-benzyl)-cyclopropyl-carbamate

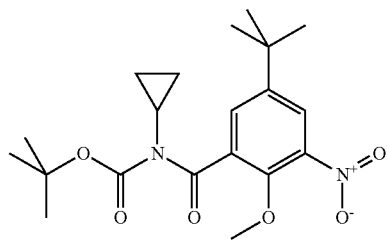 [SMILES: COc1c(C(=O)N(C(=O)OC(C)(C)C)C2CC2)cc(C(C)(C)C)cc1[N+](=O)[O-]]

At ambient temperature 0.44 g (tBuOCO)₂O are added to a solution of 0.53 g (5-tert-butyl-2-methoxy-3-nitro-benzyl)-cyclopropylamine, 0.3 ml triethylamine and a spatula tip of 4-dimethylaminopyridine in 6 ml of tetrahydrofuran. The solution is stirred overnight at ambient temperature and then evaporated down. The residue is taken up in ethyl acetate and washed with water and saturated aqueous saline solution and then dried (MgSO₄). The solvent is removed, and the residue is used without further purification to reduce the nitro group.

Preparation of the End Compounds

Example 1

N-(5-tert-butyl-3-methanesulphonylamino-2-methoxy-phenyl)-4-methyl-3-(1-oxy-pyridin-4-yloxy)-benzamide

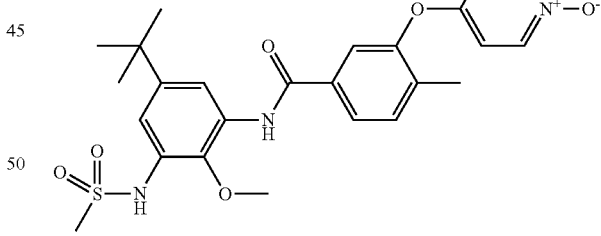

962 mg caesium carbonate are added under an argon atmosphere to 800 mg N-(5-tert-butyl-3-methanesulphonylamino-2-methoxy-phenyl)-3-hydroxy-4-methyl-benzamide in 5 ml N-methylpyrrolidinone. After 30 minutes 306 mg 4-chloro-pyridin-N-oxide are added, and the reaction mixture is stirred for 1 h at 80° C. Then the reaction mixture is heated to 100° C. and stirred overnight at this temperature. Then another 255 mg 4-chloropyridine-N-oxide and 641 mg caesium carbonate are added, and the reaction mixture is stirred for a further 24 h at 100° C. For working up the cooled reaction mixture is diluted with ethyl acetate, washed with water and saturated aqueous sodium chloride solution, dried on magnesium sulphate and evaporated down. The flask residue is purified by

Example 2

N-(5-tert-butyl-3-methanesulphonylamino-2-methoxy-phenyl)-4-methyl-3-(pyridin-4-yloxy)-benzamide

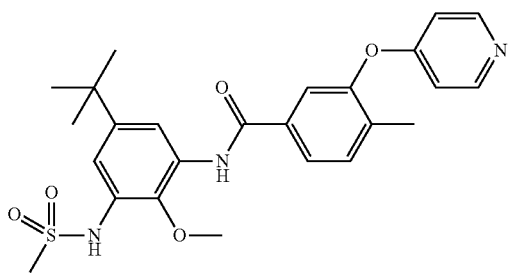 [SMILES: COc1c(NC(=O)c2ccc(C)c(Oc3ccncc3)c2)cc(C(C)(C)C)cc1NS(C)(=O)=O]

150 mg N-(5-tert-butyl-3-methanesulphonylamino-2-methoxy-phenyl)-4-methyl-3-(1-oxy-pyridin-4-yloxy)-benzamide in 10 ml of tetrahydrofuran are hydrogenated in the presence of 20 mg rhodium on activated charcoal (5% Rh) at ambient temperature and 50 psi partial hydrogen pressure. After 2 h a further 20 mg catalyst are added. As the reaction is not yet complete, another 50 mg and then a further 40 mg catalyst are added. As no further reaction can be observed, the reaction is stopped. The catalyst is suction filtered and the filtrate is evaporated down. The flask residue is purified by chromatography through a reversed-phase column with acetonitrile/water/conc. ammonia as eluant.

Yield: 65 mg (45% of theory)
Mass spectrum (ESI⁺): m/z=484 [M+H]⁺

Example 3

N-(5-tert-butyl-3-methanesulphonylamino-2-methoxy-phenyl)-4-methyl-3-(2-methylamino-pyrimidin-4-yloxy)-benzamide

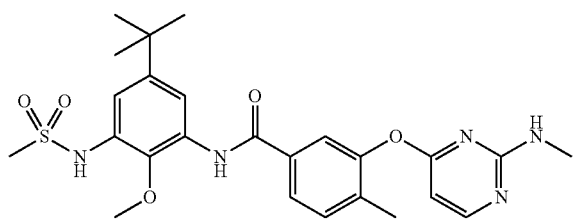

A mixture of 200 mg N-(5-tert-butyl-3-methanesulphonylamino-2-methoxy-phenyl)-3-(2-chloro-pyrimidin-4-yloxy)-4-methyl-benzamide and 2 ml of a 2 M methylamine solution in tetrahydrofuran is stirred overnight at ambient temperature in a closed microwave glass container. For working up the reaction mixture is diluted with ethyl acetate, washed with water and saturated aqueous sodium chloride solution, dried on magnesium sulphate and evaporated down. The crude product is chromatographed on a silica gel column with ethyl acetate/cyclohexane (50:50→100:0) as eluant.

Yield: 146 mg (74% of theory)
R$_f$ value: 0.09 (silica gel, petroleum ether/ethyl acetate=1:1)
Mass spectrum (ESI⁺): m/z=514 [M+H]⁺

The following compound is obtained analogously to Example 3:

(1) N-(5-tert-butyl-3-methanesulphonylamino-2-methoxy-phenyl)-4-methyl-3-(6-methylamino-pyrimidin-4-yloxy)-benzamide

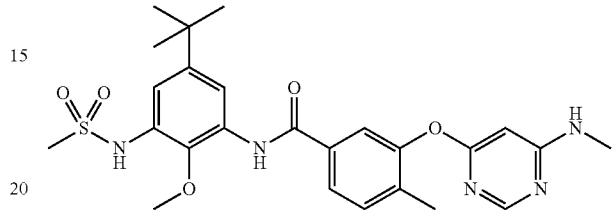

R$_f$ value: 0.11 (silica gel, petroleum ether/ethyl acetate=1:2)
Mass spectrum (ESI⁺): m/z=514 [M+H]⁺

Example 4

N-(5-tert-butyl-3-methanesulphonylamino-2-methoxy-phenyl)-4-methyl-3-[2-(2-pyrrolidin-1-yl-ethylamino)-pyrimidin-4-yloxy]-benzamide

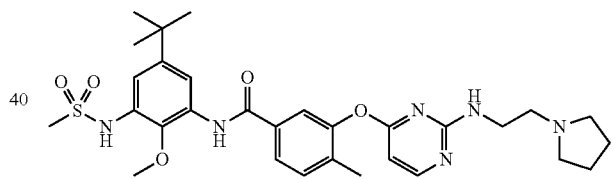

147 μl 1-(2-aminoethyl)pyrrolidin and 161 μl triethylamine are added to 300 mg N-(5-tert-butyl-3-methanesulphonylamino-2-methoxy-phenyl)-3-(2-chloro-pyrimidin-4-yloxy)-4-methyl-benzamide in 3 ml of 1,4-dioxane, and the reaction mixture is heated to 70° C. for 5 h. Then the heating is switched off, and the mixture is stirred overnight at ambient temperature. For working up the reaction mixture is diluted with ethyl acetate, washed with 3 M aqueous potassium carbonate solution, dried on magnesium sulphate and evaporated down. The crude product is chromatographed through a silica gel column with dichloromethane/methanol (75:25→0:100) as eluant.

Yield: 183 mg (53% of theory)
R$_f$ value: 0.2 (silica gel, dichloromethane/methanol/conc. ammonia=90:10:1)
Mass spectrum (ESI⁺): m/z=597 [M+H]⁺

The following compounds are obtained analogously to Example 4:

(1) N-(5-tert-butyl-3-methanesulphonylamino-2-methoxy-phenyl)-3-[6-(2-hydroxy-ethylamino)-pyrimidin-4-yloxy]-4-methyl-benzamide

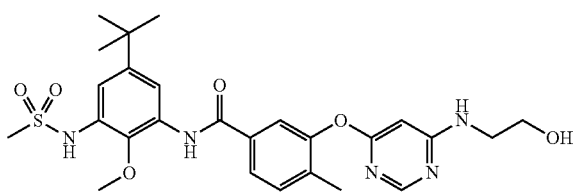 [SMILES: COc1c(NC(=O)c2ccc(C)c(Oc3cc(NCCO)ncn3)c2)cc(C(C)(C)C)cc1NS(C)(=O)=O]

(reaction takes place in tetrahydrofuran at 50° C.)
$R_f$ value: 0.4 (silica gel, dichloromethane/methanol/conc. ammonia=90:10:1)
Mass spectrum (ESI$^+$): m/z=544 [M+H]$^+$ 5

(2)  N-(5-tert-butyl-3-methanesulphonylamino-2-methoxy-phenyl)-3-[6-(2-dimethylamino-ethylamino)-pyrimidin-4-yloxy]-4-methyl-benzamide

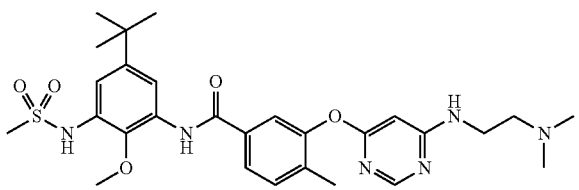

(reaction takes place in tetrahydrofuran at 50° C.)
$R_f$ value: 0.3 (silica gel, dichloromethane/methanol/conc. ammonia=90:10:1)
Mass spectrum (ESI$^+$): m/z=571 [M+H]$^+$ (3)  N-(5-tert-butyl-3-methanesulphonylamino-2-methoxy-phenyl)-4-methyl-3-[6-(3-oxo-piperazin-1-yl)-pyrimidin-4-yloxy]-benzamide

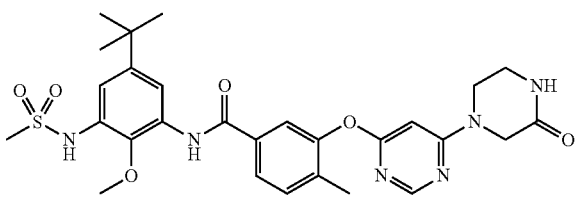 [SMILES: COc1c(NC(=O)c2ccc(C)c(Oc3cc(N4CCNC(=O)C4)ncn3)c2)cc(C(C)(C)C)cc1NS(C)(=O)=O]

(reaction takes place in tetrahydrofuran at 50° C.)
$R_f$ value: 0.5 (silica gel, dichloromethane/methanol/conc. ammonia=90:10:1)
Mass spectrum (ESI$^+$): m/z=583 [M+H]$^+$ (4)  N-(5-tert-butyl-3-methanesulphonylamino-2-methoxy-phenyl)-4-methyl-3-(6-pyrrolidin-1-yl-pyrimidin-4-yloxy)-benzamide

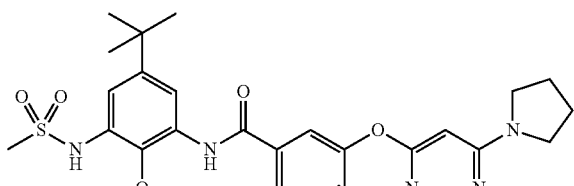

(reaction takes place in tetrahydrofuran at ambient temperature)
$R_f$ value: 0.3 (silica gel, dichloromethane/methanol/conc. ammonia=90:10:1)
Mass spectrum (ESI$^+$): m/z=554 [M+H]$^+$ 5

(5)  N-(5-tert-butyl-3-methanesulphonylamino-2-methoxy-phenyl)-4-methyl-3-(6-morpholin-4-yl-pyrimidin-4-yloxy)-benzamide

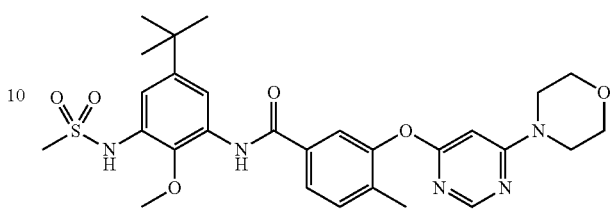

(reaction takes place in tetrahydrofuran at ambient temperature)
$R_f$ value: 0.5 (silica gel, dichloromethane/methanol/conc. ammonia=90:10:1)
Mass spectrum (ESI$^+$): m/z=570 [M+H]$^+$ (6)  (R)—N-(5-tert-butyl-3-methanesulphonylamino-2-methoxy-phenyl)-3-[2-(3-dimethylamino-pyrrolidin-1-yl)-pyrimidin-4-yloxy]-4-methyl-benzamide

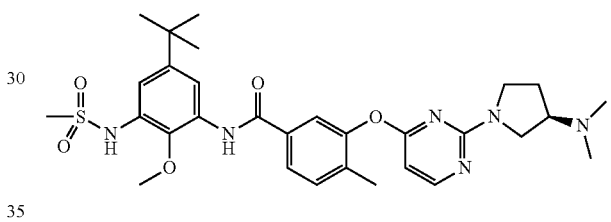

(reaction takes place in N,N-dimethylformamide in the presence of diisopropylethylamine at 50° C.)
$R_f$ value: 0.3 (silica gel, dichloromethane/methanol/conc. ammonia=90:10:1)
Mass spectrum (ESI$^+$): m/z=597 [M+H]$^+$ (7) (S)—N-(5-tert-butyl-3-methanesulphonylamino-2-methoxy-phenyl)-3-[2-(3-dimethylamino-pyrrolidin-1-yl)-pyrimidin-4-yloxy]-4-methyl-benzamide

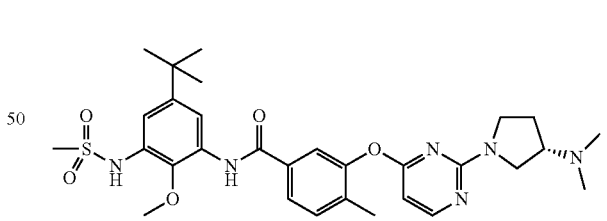

(reaction takes place in N,N-dimethylformamide in the presence of diisopropylethylamine at 50° C.)
$R_f$ value: 0.3 (silica gel, dichloromethane/methanol/conc. ammonia=90:10:1)
Mass spectrum (ESI$^+$): m/z=597 [M+H]$^+$ (8)  N-(5-tert-butyl-3-methanesulphonylamino-2-methoxy-phenyl)-3-[2-(4-dimethylamino-piperidin-1-yl)-pyrimidin-4-yloxy]-4-methyl-benzamide

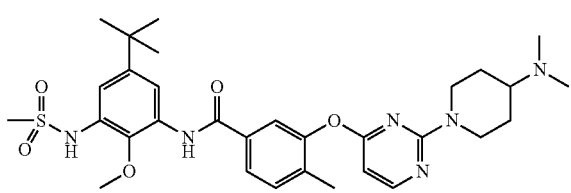

(reaction takes place in N,N-dimethylformamide in the presence of diisopropylethylamine at 50° C.)

Mass spectrum (ESI+): m/z=611 [M+H]+

(9) N-(5-tert-butyl-3-methanesulphonylamino-2-methoxy-phenyl)-4-methyl-3-[2-(1-methyl-piperidin-4-ylamino)-pyrimidin-4-yloxy]-benzamide

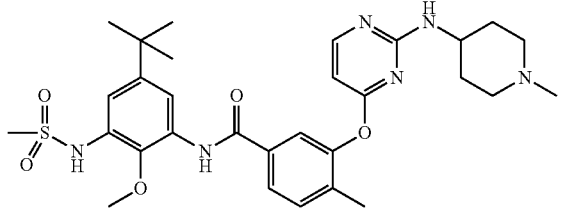

(reaction takes place in dimethylformamide at 50° C.)

Mass spectrum (ESI+): m/z=597 [M+H]+

(10) N-(5-tert-butyl-3-methanesulphonylamino-2-methoxy-phenyl)-4-methyl-3-[6-(1-methyl-piperidin-4-ylamino)-pyrimidin-4-yloxy]-benzamide

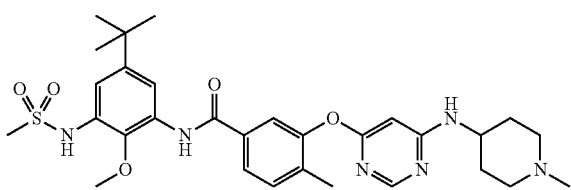

(reaction takes place in tetrahydrofuran at ambient temperature)

HPLC (method 1): retention time=2.70 min

Mass spectrum (ESI+): m/z=597 [M+H]+

(11) N-(5-tert-butyl-3-methanesulphonylamino-2-methoxy-phenyl)-3-[6-(4-dimethylamino-piperidin-1-yl)-pyrimidin-4-yloxy]-4-methyl-benzamide

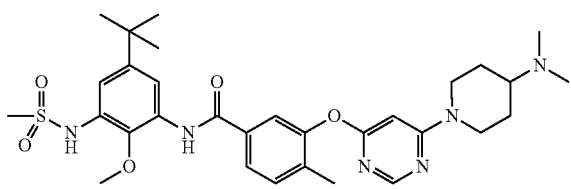

(reaction takes place in N,N-dimethylformamide in the presence of diisopropylethylamine at ambient temperature)

HPLC (method 1): retention time=2.81 min

Mass spectrum (ESI+): m/z=611 [M+H]+

(12) N-(5-tert-butyl-3-methanesulphonylamino-2-methoxy-phenyl)-3-[6-((R)-3-dimethylamino-pyrrolidin-1-yl)-pyrimidin-4-yloxy]-4-methyl-benzamide

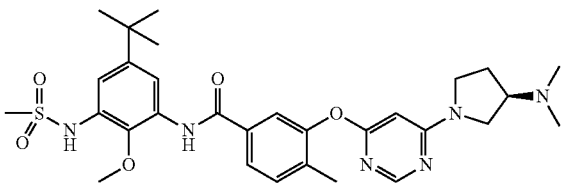

(reaction takes place in a mixture of acetonitrile and N-methylpyrrolidinone in the presence of diisopropylethylamine at ambient temperature)

$R_f$ value: 0.4 (silica gel, dichloromethane/methanol/conc. ammonia=90:10:0.1)

Mass spectrum (ESI+): m/z=597 [M+H]+

(13) N-(5-tert-butyl-3-methanesulphonylamino-2-methoxy-phenyl)-3-[6-((S)-3-dimethylamino-pyrrolidin-1-yl)-pyrimidin-4-yloxy]-4-methyl-benzamide

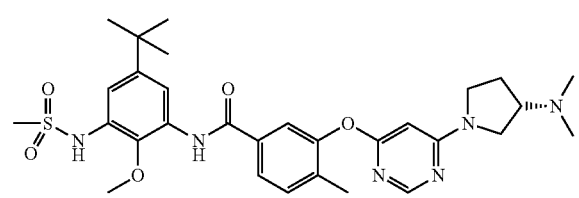

(reaction takes place in a mixture of acetonitrile and N-methylpyrrolidinone in the presence of diisopropylethylamine at ambient temperature)

$R_f$ value: 0.4 (silica gel, dichloromethane/methanol/conc. ammonia=90:10:0.1)

Mass spectrum (ESI+): m/z=597 [M+H]+

(14) N-(5-tert-butyl-3-methanesulphonylamino-2-methoxy-phenyl)-4-chloro-3-[6-(1-methyl-piperidin-4-ylamino)-pyrimidin-4-yloxy]-benzamide

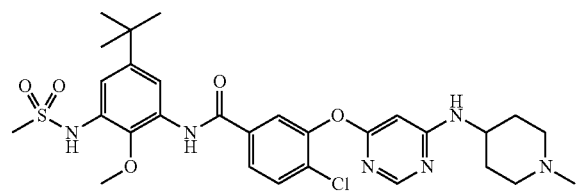

(reaction takes place without additional base with 2.5 equivalents of 1-methyl-piperidin-4-ylamine in acetonitrile at 60° C.)

$R_f$ value: 0.3 (silica gel, dichloromethane/methanol/methanolic ammonia=95:5:0.1)

Mass spectrum (ESI+): m/z=617/619 (Cl) [M+H]+

(15) N-(5-tert-butyl-3-methanesulphonylamino-2-methoxy-phenyl)-4-chloro-3-[2-(1-methyl-piperidin-4-ylamino)-pyrimidin-4-yloxy]-benzamide

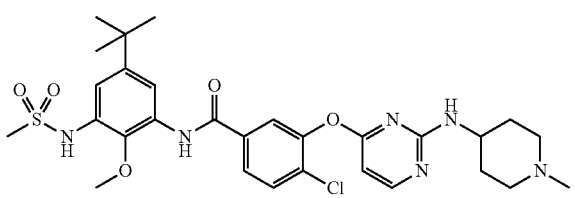

(reaction takes place without additional base with 2.5 equivalents of 1-methyl-piperidin-4-ylamine in acetonitrile at 90° C.)

$R_f$ value: 0.4 (silica gel, dichloromethane/methanol/methanolic ammonia=95:5:0.1)

Mass spectrum (ESI⁺): m/z=617/619 (Cl) [M+H]⁺

(16) N-(5-tert-butyl-3-methanesulphonylamino-2-methoxyphenyl)-4-methyl-3-{2-[methyl-(1-methyl-piperidin-4-yl)-amino]-pyrimidin-4-yloxy}-benzamide

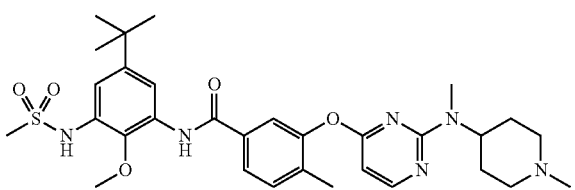

(reaction takes place in N,N-dimethylformamide with diisopropylethylamine at ambient temperature)

$R_f$ value: 0.3 (silica gel, dichloromethane/methanol/conc. ammonia=90:10:0.1)

Mass spectrum (ESI⁺): m/z=611 [M+H]⁺

(17) N-(5-tert-butyl-3-methanesulphonylamino-2-methoxyphenyl)-4-methyl-3-{6-[methyl-(1-methyl-piperidin-4-yl)-amino]-pyrimidin-4-yloxy}-benzamide

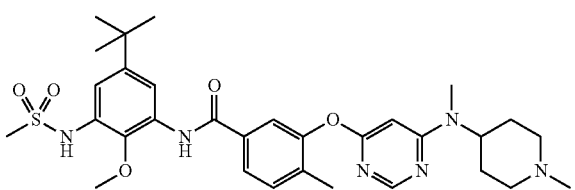

(reaction takes place in N,N-dimethylformamide with diisopropylethylamine at ambient temperature)

$R_f$ value: 0.3 (silica gel, dichloromethane/methanol/conc. ammonia=90:10:0.1)

Mass spectrum (ESI⁺): m/z=611 [M+H]⁺

(18) N-(5-tert-butyl-3-methanesulphonylamino-2-methoxyphenyl)-3-[2-(trans-4-dimethylamino-cyclohexylamino)-pyrimidin-4-yloxy]-4-methyl-benzamide

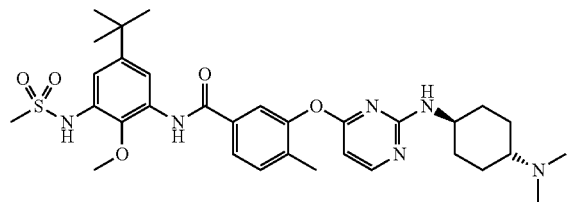

(reaction takes place in N,N-dimethylformamide with diisopropylethylamine at 40° C.)

Mass spectrum (ESI⁺): m/z=625 [M+H]⁺

(19) N-(5-tert-butyl-3-methanesulphonylamino-2-methoxyphenyl)-4-methyl-3-{2-[methyl-(1-methyl-pyrrolidin-3-yl)-amino]-pyrimidin-4-yloxy}-benzamide

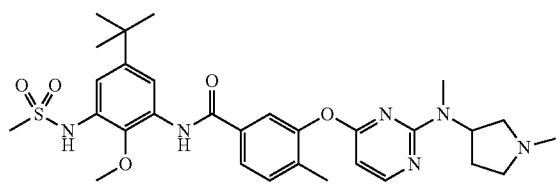

(reaction takes place in N,N-dimethylformamide with diisopropylethylamine at 40° C.)

$R_f$ value: 0.3 (silica gel, dichloromethane/methanol/conc. ammonia=90:10:0.1)

Mass spectrum (ESI⁺): m/z=597 [M+H]⁺

(20) N-(5-tert-butyl-3-methanesulphonylamino-2-methoxyphenyl)-4-methyl-3-{6-[methyl-(1-methyl-pyrrolidin-3-yl)-amino]-pyrimidin-4-yloxy}-benzamide

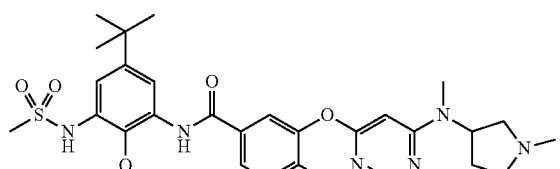

(reaction takes place in N,N-dimethylformamide with diisopropylethylamine at 40° C.)

$R_f$ value: 0.3 (silica gel, dichloromethane/methanol/conc. ammonia=90:10:0.1)

Mass spectrum (ESI⁺): m/z=597 [M+H]⁺

Example 5

N-(5-tert-butyl-3-methanesulphonylamino-2-methoxy-phenyl)-4-methyl-3-(2-piperazin-1-yl-pyrimidin-4-yloxy)-benzamide x trifluoroacetic acid

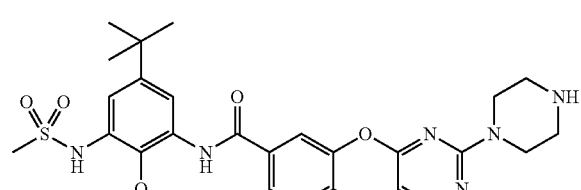

1.5 ml trifluoroacetic acid are added to 433 mg tert-butyl 4-{4-[5-(5-tert-butyl-3-methanesulphonylamino-2-methoxy-phenylcarbamoyl)-2-methyl-phenoxy]-pyrimidin-2-yl}-piperazine-1-carboxylate in 5 ml dichloromethane, and the reaction mixture is stirred for 3 h at ambient temperature. Then the colourless solution is evaporated down, combined with diethyl ether and stirred overnight to at ambient temperature. The precipitate formed is suction filtered and dried in the desiccator.

Yield: 299 mg (68% of theory)

Mass spectrum (ESI⁺): m/z=569 [M+H]⁺

The following compounds are obtained analogously to Example 5; in a departure from the method described, some of the following compounds were isolated as bases after aqueous working up and chromatography on silica gel:

(1) N-(5-tert-butyl-3-methanesulphonylamino-2-methoxy-phenyl)-4-methyl-3-(6-piperazin-1-yl-pyrimidin-4-yloxy)-benzamide

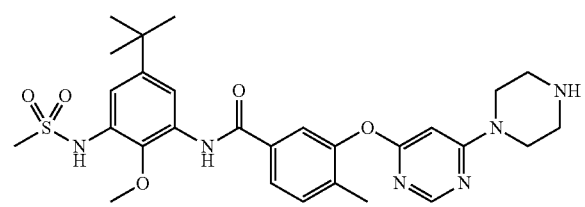 [SMILES: COc1c(NC(=O)c2ccc(C)c(Oc3cc(N4CCNCC4)ncn3)c2)cc(C(C)(C)C)cc1NS(C)(=O)=O]

R$_f$ value: 0.2 (silica gel, dichloromethane/methanol/conc. ammonia=90:10:1)

Mass spectrum (ESI⁺): m/z=569 [M+H]⁺

(2) N-(5-tert-butyl-3-methanesulphonylamino-2-methoxy-phenyl)-4-methyl-3-[6-(piperazine-1-carbonyl)-pyrimidin-4-yloxy]-benzamide x trifluoroacetic acid

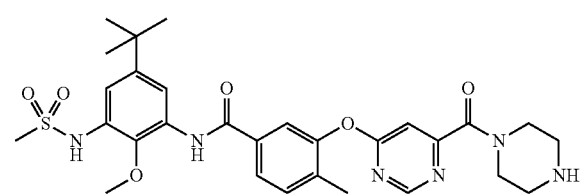 [SMILES: COc1c(NC(=O)c2ccc(C)c(Oc3cc(C(=O)N4CCNCC4)ncn3)c2)cc(C(C)(C)C)cc1NS(C)(=O)=O]

R$_f$ value: 0.2 (silica gel, dichloromethane/methanol/conc. ammonia=90:10:1)

Mass spectrum (ESI⁺): m/z=597 [M+H]⁺

(3) N-(5-tert-butyl-3-methanesulphonylamino-2-methoxy-phenyl)-4-chloro-3-[6-(piperazine-1-carbonyl)-pyrimidin-4-yloxy]-benzamide

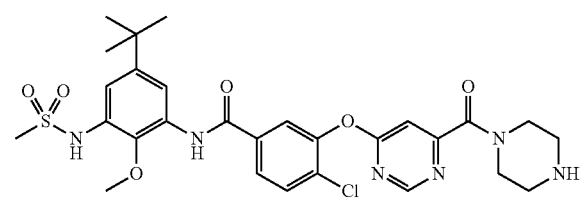 [SMILES: COc1c(NC(=O)c2ccc(Cl)c(Oc3cc(C(=O)N4CCNCC4)ncn3)c2)cc(C(C)(C)C)cc1NS(C)(=O)=O]

R$_f$ value: 0.2 (silica gel, dichloromethane/methanol/conc. ammonia=90:10:1)

Mass spectrum (ESI⁺): m/z=617/619 (Cl) [M+H]⁺

(4) N-(5-tert-butyl-3-methanesulphonylamino-2-methoxy-phenyl)-3-(2-piperazin-1-yl-pyrimidin-4-yloxy)-4-trifluoromethyl-benzamide x trifluoroacetic acid

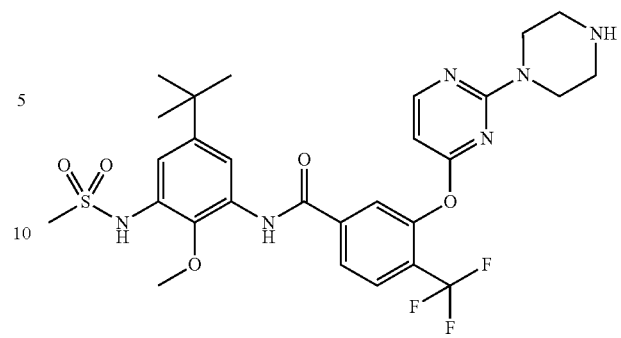

R$_f$ value: 0.5 (silica gel, dichloromethane/methanol/conc. ammonia=90:10:1)

Mass spectrum (ESI⁺): m/z=623 [M+H]⁺

(5) N-(5-tert-butyl-3-methanesulphonylamino-2-methoxy-phenyl)-4-chloro-3-(2-piperazin-1-yl-pyrimidin-4-yloxy)-benzamide

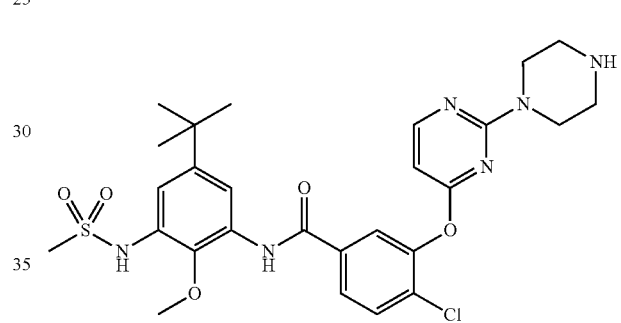

R$_f$ value: 0.3 (silica gel, dichloromethane/methanol/conc. ammonia=90:10:1)

Mass spectrum (ESI⁺): m/z=589/591 (Cl) [M+H]⁺

(6) N-(5-tert-butyl-3-methanesulphonylamino-2-methoxy-phenyl)-4-methyl-3-(2-piperazin-1-ylmethyl-pyrimidin-4-yloxy)-benzamide

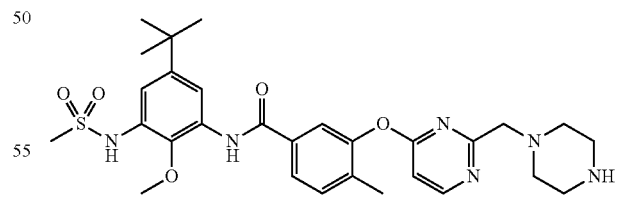

R$_f$ value: 0.2 (silica gel, dichloromethane/methanol/conc. ammonia=90:10:0.1)

Mass spectrum (ESI⁺): m/z=583 [M+H]⁺

(7) N-(5-tert-butyl-3-methanesulphonylamino-2-methoxy-phenyl)-4-methyl-3-(6-piperazin-1-ylmethyl-pyrimidin-4-yloxy)-benzamide

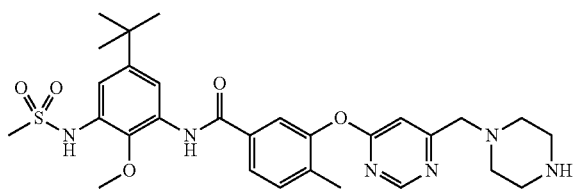 [SMILES: COc1c(NC(=O)c2ccc(C)c(Oc3cc(CN4CCNCC4)ncn3)c2)cc(C(C)(C)C)cc1NS(C)(=O)=O]

R_f value: 0.3 (silica gel, dichloromethane/methanol/conc. ammonia=90:10:1)

Mass spectrum (ESI⁺): m/z=583 [M+H]⁺

(8) N-(5-tert-butyl-3-methanesulphonylamino-2-methoxyphenyl)-4-methoxy-3-(2-piperazin-1-yl-pyrimidin-4-yloxy)-benzamide

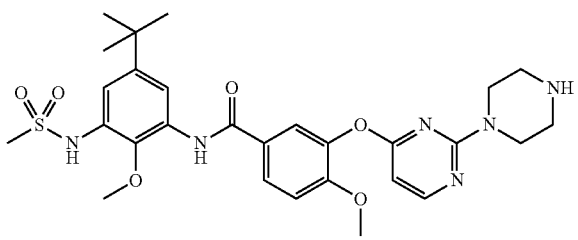 [SMILES: COc1ccc(C(=O)Nc2cc(C(C)(C)C)cc(NS(C)(=O)=O)c2OC)cc1Oc1ccnc(N2CCNCC2)n1]

R_f value: 0.6 (silica gel, dichloromethane/methanol/conc. ammonia=90:10:0.1)

Mass spectrum (ESI⁺): m/z=585 [M+H]⁺

(9) N-(5-tert-butyl-3-methanesulphonylamino-2-methoxyphenyl)-4-methyl-3-(2-piperazin-1-ylmethyl-pyridin-4-yloxy)-benzamide x trifluoroacetic acid

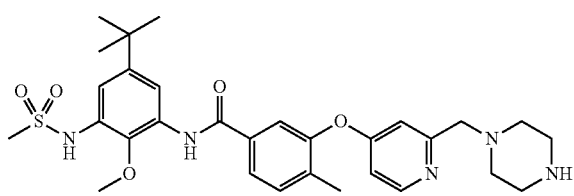 [SMILES: COc1c(NC(=O)c2ccc(C)c(Oc3ccnc(CN4CCNCC4)c3)c2)cc(C(C)(C)C)cc1NS(C)(=O)=O]

Mass spectrum (ESI⁺): m/z=582 [M+H]⁺

(10) N-(5-tert-butyl-3-methanesulphonylamino-2-methoxyphenyl)-4-fluoro-3-(2-piperazin-1-yl-pyrimidin-4-yloxy)-benzamide x trifluoroacetic acid

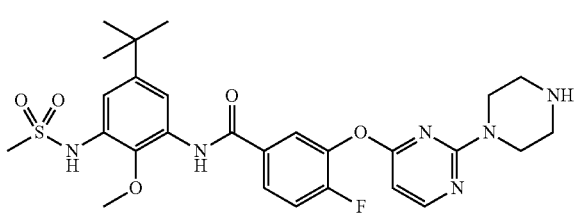 [SMILES: COc1c(NC(=O)c2ccc(F)c(Oc3ccnc(N4CCNCC4)n3)c2)cc(C(C)(C)C)cc1NS(C)(=O)=O]

R_f value: 0.1 (silica gel, dichloromethane/methanol/conc. ammonia=95:5:0.1)

Mass spectrum (ESI⁺): m/z=573 [M+H]⁺

(11) N-(5-tert-butyl-3-methanesulphonylamino-2-methoxyphenyl)-4-bromo-3-(2-piperazin-1-yl-pyrimidin-4-yloxy)-benzamide

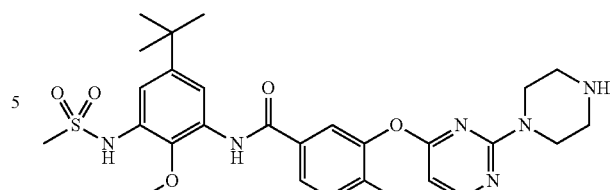

R_f value: 0.35 (silica gel, dichloromethane/methanol/conc. ammonia=95:5:0.1)

Mass spectrum (ESI⁺): m/z=633/635 (Br) [M+H]⁺

(12) N-(5-tert-butyl-3-methanesulphonylamino-2-methoxyphenyl)-3-chloro-4-methyl-5-(2-piperazin-1-yl-pyrimidin-4-yloxy)-benzamide

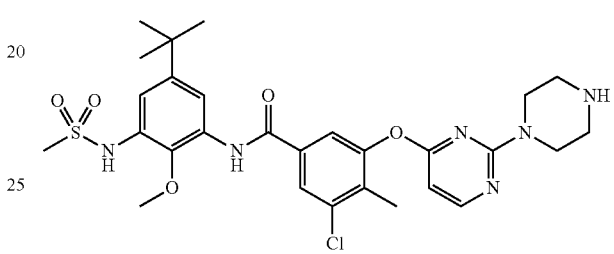

R_f value: 0.3 (silica gel, dichloromethane/methanol/conc. ammonia=95:5:0.1)

Mass spectrum (ESI⁺): m/z=603/605 (Cl) [M+H]⁺

(13) N-(5-tert-butyl-3-methanesulphonylamino-2-methoxyphenyl)-3-fluoro-4-methyl-5-(2-piperazin-1-yl-pyrimidin-4-yloxy)-benzamide

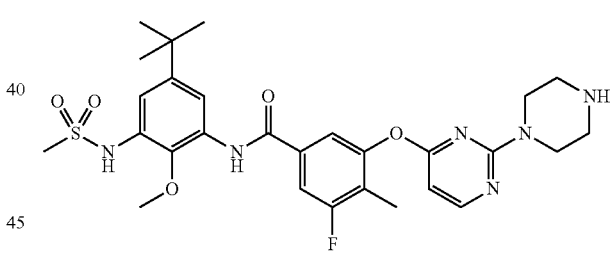

R_f value: 0.3 (silica gel, dichloromethane/methanol/conc. ammonia=95:5:0.1)

Mass spectrum (ESI⁺): m/z=587 [M+H]⁺

(14) N-(5-tert-butyl-3-methanesulphonylamino-2-methoxyphenyl)-4-methyl-3-[2-(N-methyl-N-piperidin-4-ylamino)-pyrimidin-4-yloxy]-benzamide

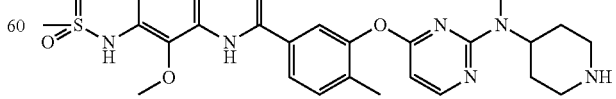

R_f value: 0.1 (silica gel, dichloromethane/methanol/conc. ammonia=90:10:0.1)

Mass spectrum (ESI⁺): m/z=597 [M+H]⁺

(15) N-(5-tert-butyl-3-methanesulphonylamino-2-methoxyphenyl)-4-ethyl-5-(2-piperazin-1-yl-pyrimidin-4-yloxy)-benzamide

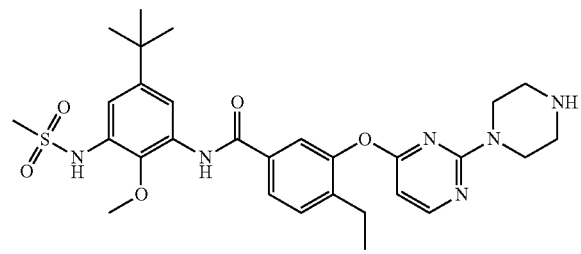 [SMILES: CCc1ccc(C(=O)Nc2cc(C(C)(C)C)cc(NS(C)(=O)=O)c2OC)cc1Oc1ccnc(N2CCNCC2)n1]

$R_f$ value: 0.4 (silica gel, dichloromethane/methanol/conc. ammonia=95:5:0.1)
Mass spectrum (ESI⁺): m/z=583 [M+H]⁺

(16) N-(5-tert-butyl-3-methanesulphonylamino-2-methoxyphenyl)-4-methyl-3-[2-(piperidin-4-ylamino)-pyrimidin-4-yloxy]-benzamide

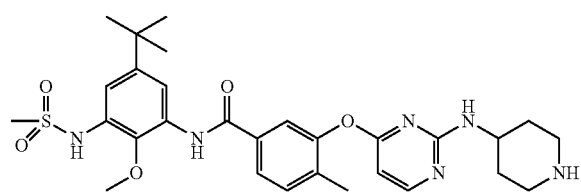 [SMILES: COc1c(NC(=O)c2ccc(C)c(Oc3ccnc(NC4CCNCC4)n3)c2)cc(C(C)(C)C)cc1NS(C)(=O)=O]

Mass spectrum (ESI⁺): m/z=583 [M+H]⁺

(17) N-(5-tert-butyl-3-methanesulphonylamino-2-methoxyphenyl)-4-methyl-3-[6-(piperidin-4-ylamino)-pyrimidin-4-yloxy]-benzamide x trifluoroacetic acid

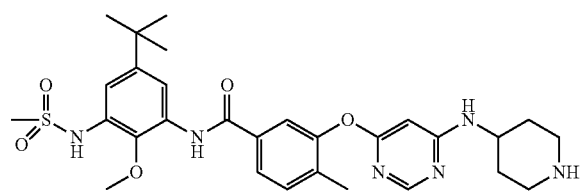 [SMILES: COc1c(NC(=O)c2ccc(C)c(Oc3cc(NC4CCNCC4)ncn3)c2)cc(C(C)(C)C)cc1NS(C)(=O)=O]

Mass spectrum (ESI⁺): m/z=583 [M+H]⁺

(18) N-(5-tert-butyl-3-methanesulphonylamino-2-methoxyphenyl)-4-methyl-3-(6-piperidin-4-ylmethyl-pyrimidin-4-yloxy)-benzamide

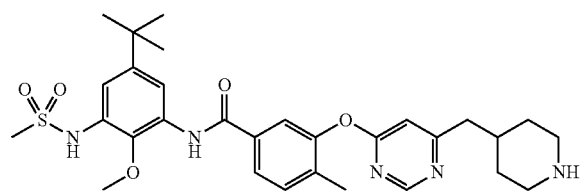 [SMILES: COc1c(NC(=O)c2ccc(C)c(Oc3cc(CC4CCNCC4)ncn3)c2)cc(C(C)(C)C)cc1NS(C)(=O)=O]

Mass spectrum (ESI⁺): m/z=582 [M+H]⁺

(19) N-(5-tert-butyl-3-methanesulphonylamino-2-methoxyphenyl)-4-methyl-3-(2-piperidin-4-ylmethyl-pyrimidin-4-yloxy)-benzamide

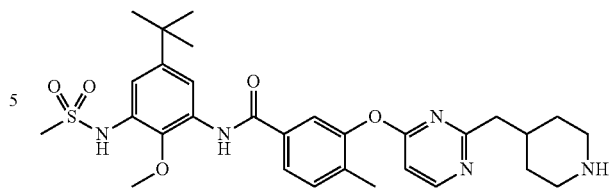

HPLC (method 1): retention time=2.72 min
Mass spectrum (ESI⁺): m/z=582 [M+H]⁺

(20) N-(5-tert-butyl-3-methanesulphonylamino-2-methoxyphenyl)-4-methyl-3-(2-piperidin-4-ylmethyl-pyridin-4-yloxy)-benzamide

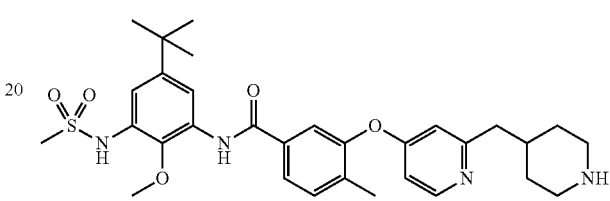

HPLC (method 1): retention time=2.31 min
Mass spectrum (ESI⁺): m/z=581 [M+H]⁺

(21) N-(5-tert-butyl-3-methanesulphonylamino-2-methoxyphenyl)-3-methyl-5-[2-(piperazine-1-carbonyl)-pyrimidin-4-yloxy]-benzamide x trifluoroacetic acid

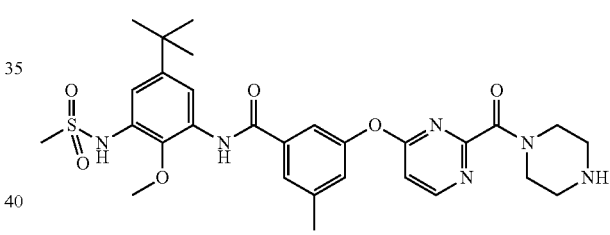

$R_f$ value: 0.45 (Reversed phase ready-made TLC plate (E. Merck), acetonitrile/water/trifluoroacetic acid=50:50:1)
Mass spectrum (ESI⁺): m/z=597 [M+H]⁺

(22) N-(5-tert-butyl-3-methanesulphonylamino-2-methoxyphenyl)-3-methyl-5-(2-piperazin-1-ylmethyl-pyrimidin-4-yloxy)-benzamide

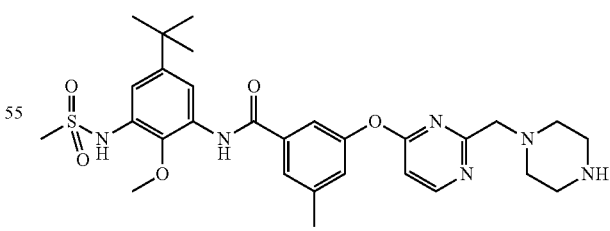

$R_f$ value: 0.5 (Reversed phase ready-made TLC plate (E. Merck), acetonitrile/water/trifluoroacetic acid=50:50:1)
Mass spectrum (ESI⁺): m/z=583 [M+H]⁺

(23) N-(5-tert-butyl-3-methanesulphonylamino-2-methoxyphenyl)-4-methyl-3-[2-(pyrrolidin-3-ylamino)-pyrimidin-4-yloxy]-benzamide

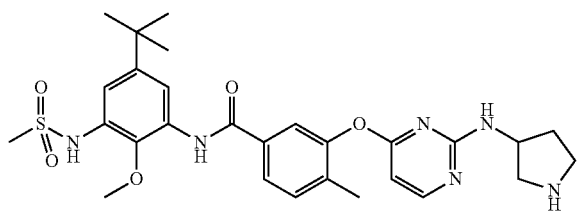 [SMILES: COc1c(NC(=O)c2ccc(C)c(Oc3ccnc(NC4CCNC4)n3)c2)cc(C(C)(C)C)cc1NS(C)(=O)=O]

HPLC (method 1): retention time=2.73 min
Mass spectrum (ESI⁺): m/z=569 [M+H]⁺
(24) N-(5-tert-butyl-3-methanesulphonylamino-2-methoxyphenyl)-4-methyl-3-[2-(methyl-pyrrolidin-3-yl-amino)-pyrimidin-4-yloxy]-benzamide

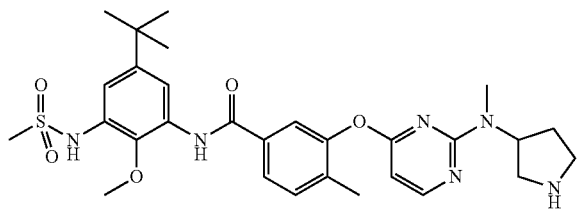 [SMILES: COc1c(NC(=O)c2ccc(C)c(Oc3ccnc(N(C)C4CCNC4)n3)c2)cc(C(C)(C)C)cc1NS(C)(=O)=O]

$R_f$ value: 0.3 (silica gel, dichloromethane/methanol/conc. ammonia=90:10:0.1)
Mass spectrum (ESI⁺): m/z=583 [M+H]⁺
(25) N-(5-tert-butyl-3-methanesulphonylamino-2-methoxyphenyl)-4-methyl-3-[2-(methyl-piperidin-4-yl-amino)-pyrimidin-4-yloxy]-benzamide

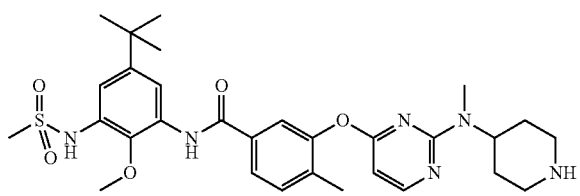 [SMILES: COc1c(NC(=O)c2ccc(C)c(Oc3ccnc(N(C)C4CCNCC4)n3)c2)cc(C(C)(C)C)cc1NS(C)(=O)=O]

$R_f$ value: 0.2 (silica gel, dichloromethane/methanol/conc. ammonia=90:10:0.1)
Mass spectrum (ESI⁺): m/z=597 [M+H]⁺
(26) N-(5-tert-butyl-3-methanesulphonylamino-2-methoxyphenyl)-4-methyl-3-[6-(pyrrolidin-3-ylamino)-pyrimidin-4-yloxy]-benzamide

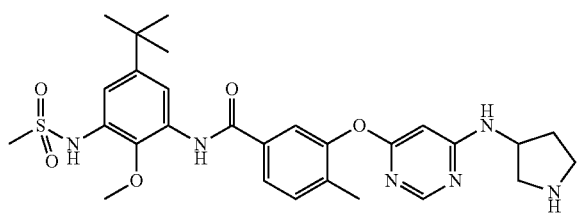 [SMILES: COc1c(NC(=O)c2ccc(C)c(Oc3cc(NC4CCNC4)ncn3)c2)cc(C(C)(C)C)cc1NS(C)(=O)=O]

$R_f$ value: 0.2 (silica gel, dichloromethane/methanol/conc. ammonia=90:10:0.1)
Mass spectrum (ESI⁺): m/z=569 [M+H]⁺
(27) N-(5-tert-butyl-3-methanesulphonylamino-2-methoxyphenyl)-4-chloro-3-[6-(piperidin-4-ylamino)-pyrimidin-4-yloxy]-benzamide

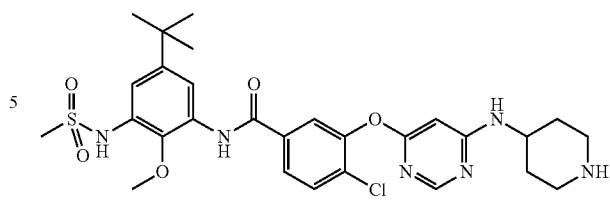

$R_f$ value: 0.1 (silica gel, dichloromethane/methanol/methanolic ammonia=95:5:0.1)
Mass spectrum (ESI⁺): m/z=603/605 (Cl) [M+H]⁺
(28) N-(5-tert-butyl-3-methanesulphonylamino-2-methoxyphenyl)-4-chloro-3-[2-(piperidin-4-ylamino)-pyrimidin-4-yloxy]-benzamide

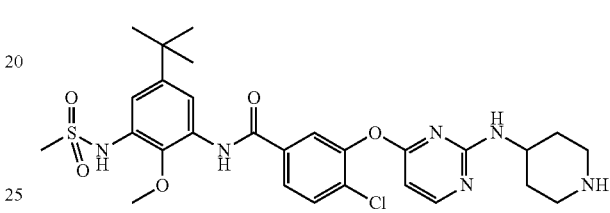

$R_f$ value: 0.2 (silica gel, dichloromethane/methanol/methanolic ammonia=90:10:0.1)
Mass spectrum (ESI⁺): m/z=603/605 (Cl) [M+H]⁺
(29) N-(5-tert-butyl-3-methanesulphonylamino-2-methoxyphenyl)-4-chloro-3-(2-piperidin-4-ylmethyl-pyridin-4-yloxy)-benzamide

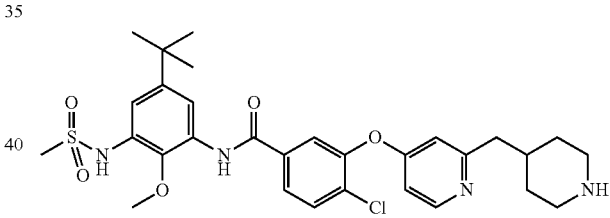

$R_f$ value: 0.05 (silica gel, dichloromethane/methanol/methanolic ammonia=95:5:0.1)
Mass spectrum (ESI⁺): m/z=601/603 (Cl) [M+H]⁺
(30) N-(5-tert-butyl-3-methanesulphonylamino-2-methoxyphenyl)-4-chloro-3-(2-piperidin-4-ylmethyl-pyrimidin-4-yloxy)-benzamide

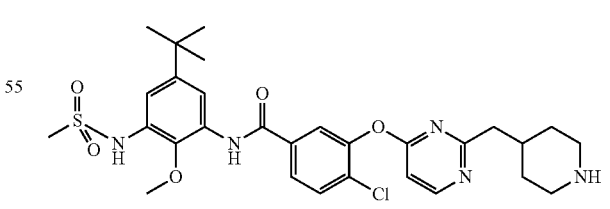

$R_f$ value: 0.05 (silica gel, dichloromethane/methanol/methanolic ammonia=95:5:0.1)
Mass spectrum (ESI⁺): m/z=602/604 (Cl) [M+H]⁺
(31) N-(5-tert-butyl-3-methanesulphonylamino-2-methoxyphenyl)-4-chloro-3-[2-(piperidin-4-ylamino)-pyridin-4-yloxy]-benzamide

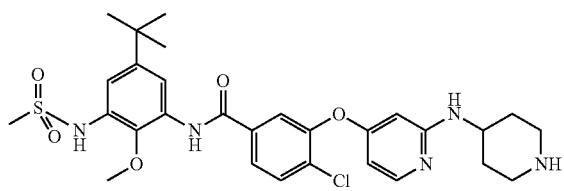 [SMILES: COc1c(NC(=O)c2ccc(Cl)c(Oc3ccnc(NC4CCNCC4)c3)c2)cc(C(C)(C)C)cc1NS(C)(=O)=O]

$R_f$ value: 0.1 (silica gel, dichloromethane/methanol/methanolic ammonia=90:10:0.1)

Mass spectrum (ESI⁺): m/z=602/604 (Cl) [M+H]⁺

(32) N-(5-tert-butyl-3-methanesulphonylamino-2-methoxyphenyl)-4-chloro-3-(6-piperazin-1-ylmethyl-pyrimidin-4-yloxy)-benzamide

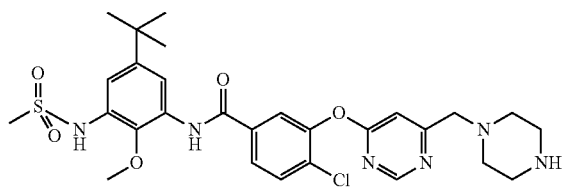 [SMILES: COc1c(NC(=O)c2ccc(Cl)c(Oc3cc(CN4CCNCC4)ncn3)c2)cc(C(C)(C)C)cc1NS(C)(=O)=O]

$R_f$ value: 0.1 (silica gel, dichloromethane/methanol/methanolic ammonia=95:5:0.1)

Mass spectrum (ESI⁺): m/z=603/605 (Cl) [M+H]⁺

(33) N-(5-tert-butyl-3-methanesulphonylamino-2-methoxyphenyl)-4-chloro-3-(6-piperidin-4-ylmethyl-pyrimidin-4-yloxy)-benzamide

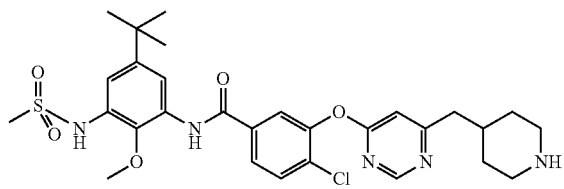 [SMILES: COc1c(NC(=O)c2ccc(Cl)c(Oc3cc(CC4CCNCC4)ncn3)c2)cc(C(C)(C)C)cc1NS(C)(=O)=O]

$R_f$ value: 0.1 (silica gel, dichloromethane/methanol/methanolic ammonia=95:5:0.1

Mass spectrum (ESI⁺): m/z=602/604 (Cl) [M+H]⁺

(34) N-(5-tert-butyl-3-methanesulphonylamino-2-methoxyphenyl)-4-chloro-3-(2-piperazin-1-ylmethyl-pyridin-4-yloxy)-benzamide

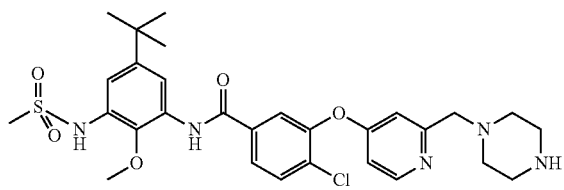 [SMILES: COc1c(NC(=O)c2ccc(Cl)c(Oc3ccnc(CN4CCNCC4)c3)c2)cc(C(C)(C)C)cc1NS(C)(=O)=O]

$R_f$ value: 0.15 (silica gel, dichloromethane/methanol/methanolic ammonia=95:5:0.1)

Mass spectrum (ESI⁺): m/z=602/604 (Cl) [M+H]⁺

(35) N-(5-tert-butyl-3-methanesulphonylamino-2-methoxyphenyl)-4-chloro-3-(2-piperazin-1-ylmethyl-pyrimidin-4-yloxy)-benzamide

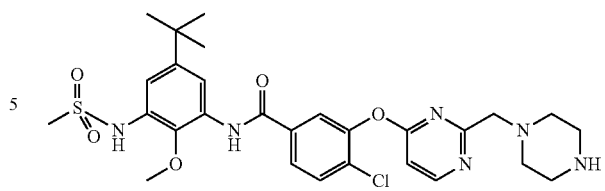

$R_f$ value: 0.1 (silica gel, dichloromethane/methanolic ammonia=95:5:0.1)

Mass spectrum (ESI⁺): m/z=603/605 (Cl) [M+H]⁺

(36) N-(5-tert-butyl-3-methanesulphonylamino-2-methoxyphenyl)-4-chloro-3-(6-[1,4]diazepan-1-ylmethyl-pyrimidin-4-yloxy)-benzamide

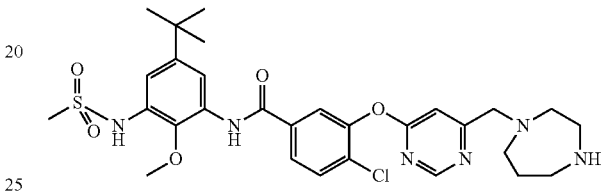

$R_f$ value: 0.1 (silica gel, dichloromethane/methanol/methanolic ammonia=95:5:0.1

Mass spectrum (ESI⁺): m/z=617/619 (Cl) [M+H]⁺

(37) N-(5-tert-butyl-3-methanesulphonylamino-2-methoxyphenyl)-4-chloro-3-(2-[1,4]diazepan-1-ylmethyl-pyridin-4-yloxy)-benzamide

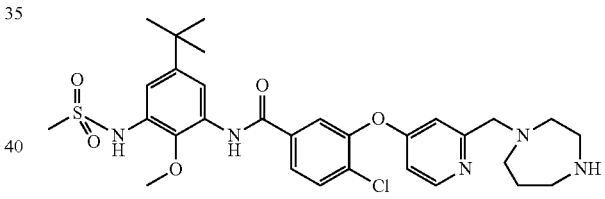

$R_f$ value: 0.05 (silica gel, dichloromethane/methanol/methanolic ammonia=95:5:0.1)

Mass spectrum (ESI⁺): m/z=616/618 (Cl) [M+H]⁺

(38) N-(5-tert-butyl-3-methanesulphonyl-2-methoxy-phenyl)-4-methyl-3-(2-piperidin-4-ylmethyl-pyrimidin-4-yloxy)-benzamide

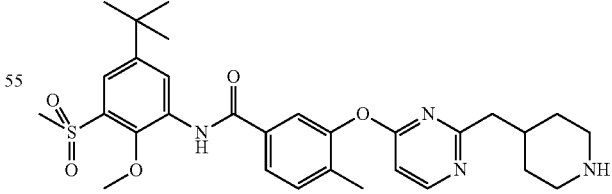

$R_f$ value: 0.05 (silica gel, dichloromethane/methanol/methanolic ammonia=95:5:0.1)

Mass spectrum (ESI⁺): m/z=567 [M+H]⁺

(39) N-(5-tert-butyl-3-methanesulphonyl-2-methoxy-phenyl)-3-(2-[1,4]diazepan-1-ylmethyl-pyridin-4-yloxy)-4-methyl-benzamide

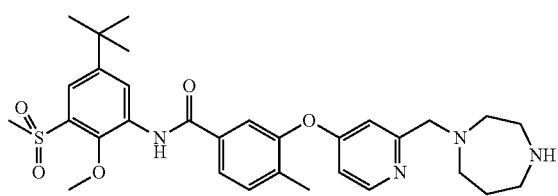 [SMILES: COc1c(NC(=O)c2ccc(C)c(Oc3ccnc(CN4CCCNCC4)c3)c2)cc(C(C)(C)C)cc1S(C)(=O)=O]

$R_f$ value: 0.4 (Reversed phase ready-made TLC plate (E. Merck), acetonitrile/water/trifluoroacetic acid=50:50:1)

Mass spectrum (ESI⁺): m/z=596 [M+H]⁺

(40) N-(5-tert-butyl-2-methoxy-3-methylsulphanylmethyl-phenyl)-4-methyl-3-(2-piperidin-4-ylmethyl-pyridin-4-yloxy)-benzamide

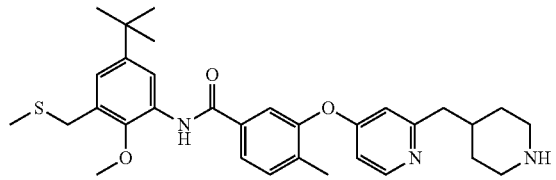 [SMILES: COc1c(CSC)cc(C(C)(C)C)cc1NC(=O)c1ccc(C)c(Oc2ccnc(CC3CCNCC3)c2)c1]

HPLC (method 1): retention time=2.81 min

Mass spectrum (ESI⁺): m/z=548 [M+H]⁺

(41) N-(5-tert-butyl-3-methanesulphonylmethyl-2-methoxy-phenyl)-4-methyl-3-(2-piperidin-4-ylmethyl-pyridin-4-yloxy)-benzamide

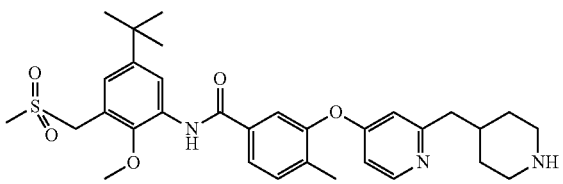 [SMILES: COc1c(CS(C)(=O)=O)cc(C(C)(C)C)cc1NC(=O)c1ccc(C)c(Oc2ccnc(CC3CCNCC3)c2)c1]

Mass spectrum (ESI⁺): m/z=580 [M+H]⁺

(42) N-(5-tert-butyl-2-methoxy-3-methylsulphinylmethyl-phenyl)-4-methyl-3-(2-piperidin-4-ylmethyl-pyridin-4-yloxy)-benzamide

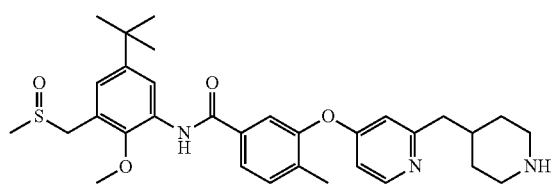 [SMILES: COc1c(CS(C)=O)cc(C(C)(C)C)cc1NC(=O)c1ccc(C)c(Oc2ccnc(CC3CCNCC3)c2)c1]

Mass spectrum (ESI⁺): m/z=564 [M+H]⁺

(43) N-[5-tert-butyl-3-(cyclopropanecarbonyl-amino)-2-methoxy-phenyl]-4-methyl-3-(2-piperidin-4-ylmethyl-pyridin-4-yloxy)-benzamide

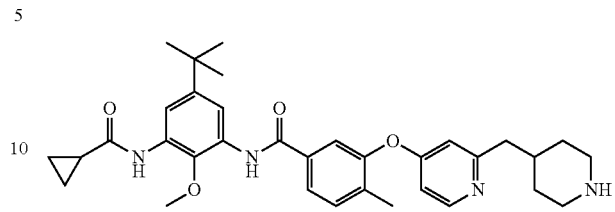

HPLC (method 1): retention time=2.46 min

Mass spectrum (ESI⁺): m/z=571 [M+H]⁺

(44) N-(5-tert-butyl-2-isopropoxy-3-methanesulphonylamino-phenyl)-4-methyl-3-(2-piperidin-4-ylmethyl-pyridin-4-yloxy)-benzamide

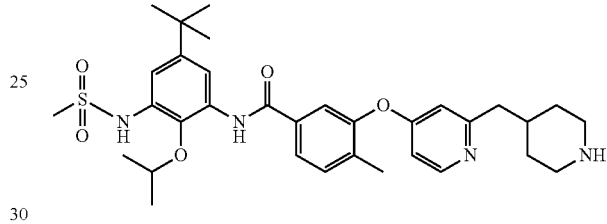

HPLC (method 1): retention time=2.55 min

Mass spectrum (ESI⁺): m/z=609 [M+H]⁺

(45) N-(5-tert-butyl-2-ethoxy-3-methanesulphonylamino-phenyl)-4-methyl-3-(2-piperidin-4-ylmethyl-pyridin-4-yloxy)-benzamide

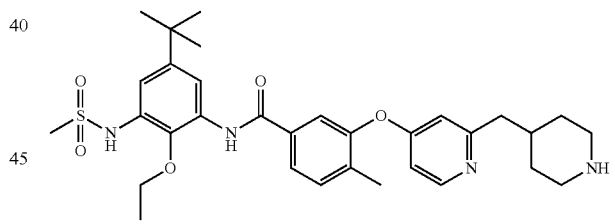

HPLC (method 1): retention time=2.45 min

Mass spectrum (ESI⁺): m/z=595 [M+H]⁺

(46) N-[5-tert-butyl-2-methoxy-3-(2-methyl-propane-1-sulphonylamino)-phenyl]-4-methyl-3-(2-piperidin-4-ylmethyl-pyridin-4-yloxy)-benzamide

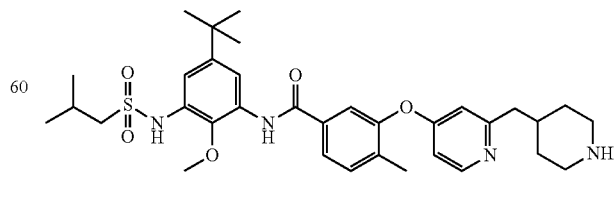

HPLC (method 1): retention time=2.78 min

Mass spectrum (ESI⁺): m/z=623 [M+H]⁺

(47) N-(5-tert-butyl-3-isobutyrylamino-2-methoxy-phenyl)-4-methyl-3-(2-piperidin-4-ylmethyl-pyridin-4-yloxy)-benzamide

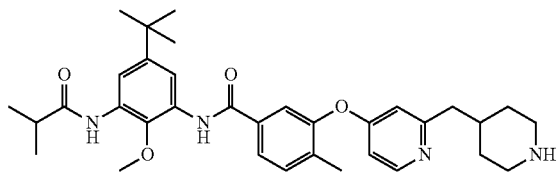 [SMILES: COc1c(NC(=O)c2ccc(C)c(Oc3ccnc(CC4CCNCC4)c3)c2)cc(C(C)(C)C)cc1NC(=O)C(C)C]

Mass spectrum (ESI⁺): m/z=573 [M+H]⁺

(48) N-(5-tert-butyl-3-methanesulphinyl-2-methoxy-phenyl)-4-methyl-3-(2-piperidin-4-ylmethyl-pyridin-4-yloxy)-benzamide

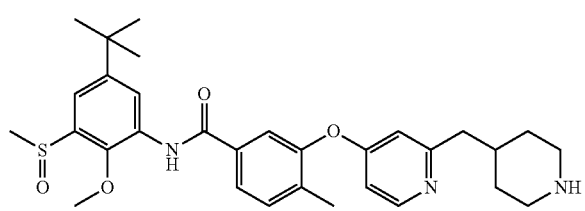 [SMILES: COc1c(NC(=O)c2ccc(C)c(Oc3ccnc(CC4CCNCC4)c3)c2)cc(C(C)(C)C)cc1S(C)=O]

HPLC (method 1): retention time=2.18 min

Mass spectrum (ESI⁺): m/z=550 [M+H]⁺

(49) N-(3-methanesulphonylamino-2-methoxy-5-trifluoromethyl-phenyl)-4-methyl-3-(2-piperidin-4-ylmethyl-pyridin-4-yloxy)-benzamide

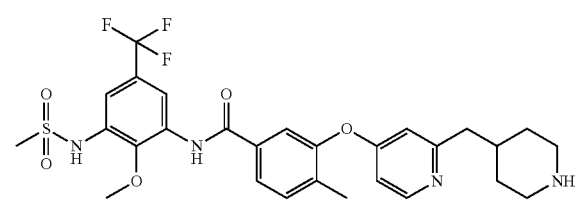 [SMILES: COc1c(NC(=O)c2ccc(C)c(Oc3ccnc(CC4CCNCC4)c3)c2)cc(C(F)(F)F)cc1NS(C)(=O)=O]

HPLC (method 1): retention time=2.27 min

Mass spectrum (ESI⁺): m/z=593 [M+H]⁺

(50) N-[5-tert-butyl-2-methoxy-3-(propane-2-sulphonylamino)-phenyl]-4-methyl-3-(2-piperidin-4-ylmethyl-pyridin-4-yloxy)-benzamide

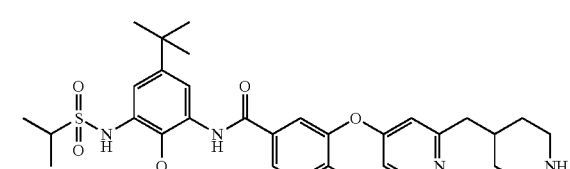

HPLC (method 1): retention time=2.56 min

Mass spectrum (ESI⁺): m/z=609 [M+H]⁺

(51) N-(5-tert-butyl-3-cyclopropanesulphonylamino-2-methoxy-phenyl)-4-methyl-3-(2-piperidin-4-ylmethyl-pyridin-4-yloxy)-benzamide

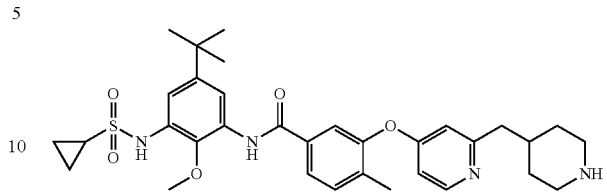

HPLC (method 1): retention time=2.51 min

Mass spectrum (ESI⁺): m/z=607 [M+H]⁺

(52) 3-(2-azepan-4-ylmethyl-pyridin-4-yloxy)-N-(5-tert-butyl-3-methanesulphonylamino-2-methoxy-phenyl)-4-methyl-benzamide

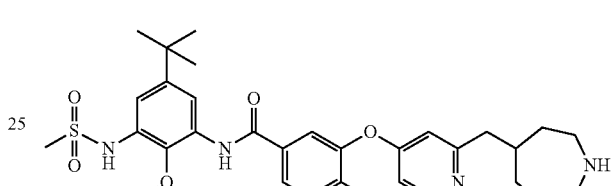

R$_f$ value: 0.05 (silica gel, dichloromethane/methanol/methanolic ammonia=90:10:0.1)

Mass spectrum (ESI⁺): m/z=595 [M+H]⁺

(53) 3-(2-azepan-4-ylmethyl-pyrimidin-4-yloxy)-N-(5-tert-butyl-3-methanesulphonylamino-2-methoxy-phenyl)-4-methyl-benzamide

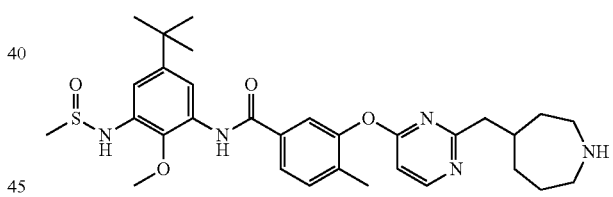

R$_f$ value: 0.1 (silica gel, dichloromethane/methanol/methanolic ammonia=90:10:0.1)

Mass spectrum (ESI⁺): m/z=596 [M+H]⁺

(54) 3-(6-azepan-4-ylmethyl-pyrimidin-4-yloxy)-N-(5-tert-butyl-3-methanesulphonylamino-2-methoxy-phenyl)-4-methyl-benzamide

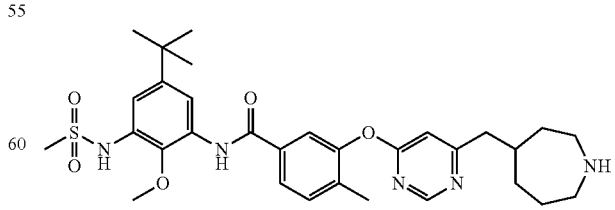

R$_f$ value: 0.1 (silica gel, dichloromethane/methanol/methanolic ammonia=90:10:0.1)

Mass spectrum (ESI⁺): m/z=596 [M+H]⁺

(55) N-(3-methanesulphonylamino-2-methoxy-5-pentafluoroethyl-phenyl)-4-methyl-3-(2-piperidin-4-ylmethyl-pyridin-4-yloxy)-benzamide

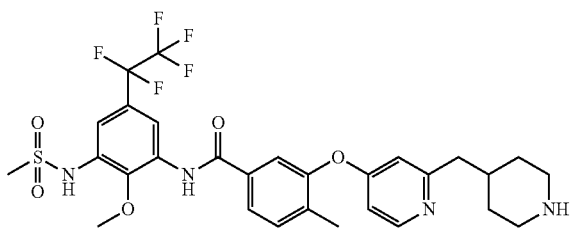 [SMILES: COc1c(NC(=O)c2ccc(C)c(Oc3ccnc(CC4CCNCC4)c3)c2)cc(C(F)(F)C(F)(F)F)cc1NS(C)(=O)=O]

Mass spectrum (ESI$^+$): m/z=643 [M+H]$^+$

Example 6

N-(5-tert-butyl-3-methanesulphonylamino-2-methoxy-phenyl)-3-methyl-5-(pyridin-4-yloxy)-benzamide

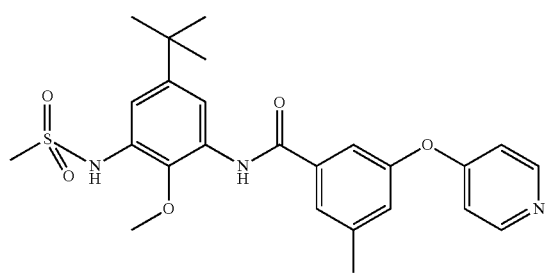 [SMILES: COc1c(NC(=O)c2cc(C)cc(Oc3ccncc3)c2)cc(C(C)(C)C)cc1NS(C)(=O)=O]

200 mg 4-iodopyridine, 20 μl 2,2,6,6-tetramethylheptan-3,5-dione and 35 mg copper(I)chloride are added under argon to 200 mg N-(5-tert-butyl-3-methanesulphonylamino-2-methoxy-phenyl)-3-hydroxy-5-methyl-benzamide and 325 mg caesium carbonate in 4 ml N,N-dimethylformamide. The reaction mixture is heated to 160° C. and stirred for 1 h at this temperature. After cooling to ambient temperature the dark reaction mixture is mixed with water and extracted with ethyl acetate. The combined ethyl acetate extracts are washed with saturated aqueous sodium chloride solution, dried on magnesium sulphate and evaporated down. The flask residue is chromatographed through a silica gel column with dichloromethane/methanol (99:1→90:10).

Yield: 112 mg (47% of theory)

R$_f$ value: 0.75 (silica gel, dichloromethane/methanol=90:10)

Mass spectrum (ESI$^+$): m/z=484 [M+H]$^+$

Example 7

6-[5-(5-tert-butyl-3-methanesulphonylamino-2-methoxy-phenylaminocarbonyl)-2-methyl-phenoxy]-pyrimidin-4-carboxylic acid-methylamide

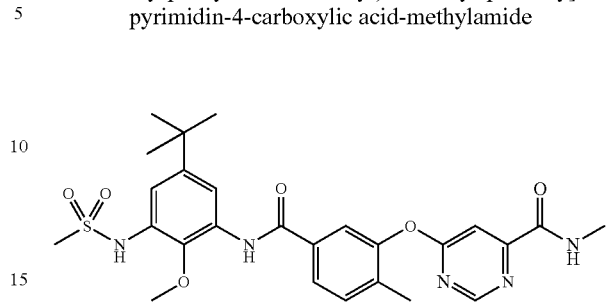

65 mg 6-chloro-pyrimidin-4-carboxylic acid-methylamide are added under argon to 140 mg N-(5-tert-butyl-3-methanesulphonylamino-2-methoxy-phenyl)-3-hydroxy-4-methyl-benzamide and 46 mg potassium-tert-butoxide in 2 ml N,N-dimethylformamide, and the reaction mixture is stirred for 20 h at ambient temperature. Then it is mixed with water and extracted with ethyl acetate. The combined ethyl acetate extracts are washed with saturated aqueous sodium chloride solution, dried on magnesium sulphate and evaporated down. The flask residue is chromatographed on a silica gel column with cyclohexane/ethyl acetate (40:60→20:80) as eluant. The chromatography product is stirred with tert-butylmethyl-ether, suction filtered and dried.

Yield: 104 mg (56% of theory)

R$_f$ value: 0.22 (silica gel, petroleum ether/ethyl acetate=1:2)

Mass spectrum (ESI$^+$): m/z=542 [M+H]$^+$

The following compounds are obtained analogously to Example 7:

(1) N-(5-tert-butyl-3-methanesulphonylamino-2-methoxy-phenyl)-4-methyl-3-[6-(morpholine-4-carbonyl)-pyrimidin-4-yloxy]-benzamide

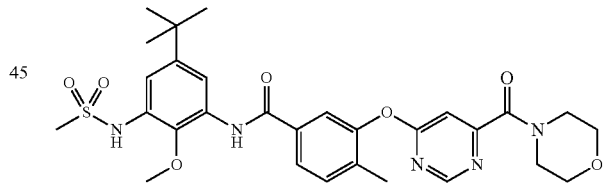

R$_f$ value: 0.55 (silica gel, dichloromethane/methanol=95:5)

Mass spectrum (ESI$^+$): m/z=598 [M+H]$^+$ (2) N-(5-tert-butyl-3-methanesulphonylamino-2-methoxy-phenyl)-4-methyl-3-[6-(4-methyl-piperazine-1-carbonyl)-pyrimidin-4-yloxy]-benzamide

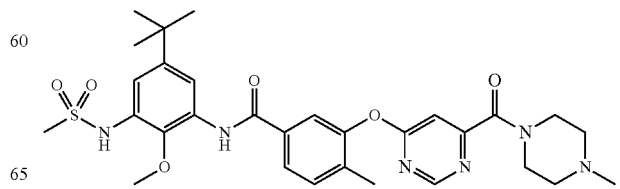

$R_f$ value: 0.45 (silica gel, dichloromethane/methanol=90:10)

Mass spectrum (ESI⁺): m/z=611 [M+H]⁺

(3) N-(5-tert-butyl-3-methanesulphonylamino-2-methoxyphenyl)-3-fluoro-4-methyl-5-[2-(4-methyl-piperazin-1-ylmethyl)-pyrimidin-4-yloxy]-benzamide

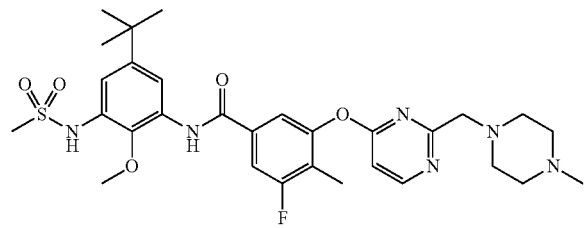

(reaction takes place in dimethylsulphoxide at ambient temperature)

$R_f$ value: 0.4 (silica gel, dichloromethane/methanol/conc. ammonia=95:5:0.1)

Mass spectrum (ESI⁺): m/z=615 [M+H]⁺

(4) N-(5-tert-butyl-3-methanesulphonylamino-2-methoxyphenyl)-4-chloro-3-[2-(4-methyl-piperazin-1-ylmethyl)-pyrimidin-4-yloxy]-benzamide

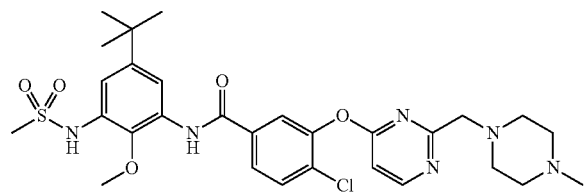

(reaction takes place in dimethylsulphoxide at ambient temperature)

$R_f$ value: 0.4 (silica gel, dichloromethane/methanol/conc. ammonia=95:5:0.1)

Mass spectrum (ESI⁺): m/z=617/619 (Cl) [M+H]⁺

(5) N-(5-tert-butyl-3-methanesulphonylamino-2-methoxyphenyl)-3-chloro-4-methyl-5-[2-(4-methyl-piperazin-1-ylmethyl)-pyrimidin-4-yloxy]-benzamide

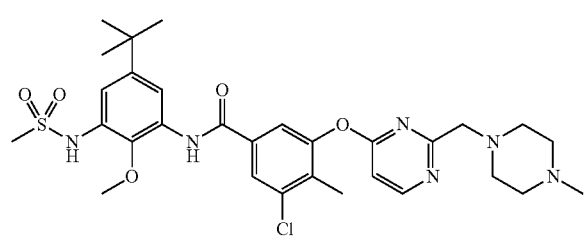

(reaction takes place in dimethylsulphoxide at ambient temperature)

$R_f$ value: 0.3 (silica gel, dichloromethane/methanol/conc. ammonia=95:5:0.1)

Mass spectrum (ESI⁺): m/z=631/633 (Cl) [M+H]⁺

Example 8

N-(5-tert-butyl-3-methanesulphonylamino-2-methoxy-phenyl)-4-methyl-3-(6-morpholin-4-ylmethyl-pyrimidin-4-yloxy)-benzamide

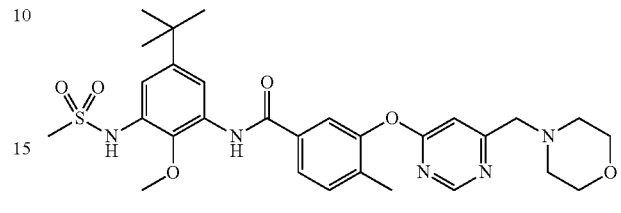

114 μl glacial acetic acid and 171 μl morpholine are added to 200 mg N-(5-tert-butyl-3-methanesulphonylamino-2-methoxy-phenyl)-3-(6-formyl-pyrimidin-4-yloxy)-4-methyl-benzamide in 4 ml 1,2-dichloroethane, and the reaction mixture is stirred for 20 minutes at ambient temperature. Then 107 mg sodium triacetoxyborohydride are added, and the mixture is stirred overnight at ambient temperature. Then the reaction mixture is combined with saturated aqueous sodium hydrogen carbonate solution, stirred for five minutes and then extracted with dichloromethane. The combined organic phases are evaporated down and the flask residue is chromatographed through a silica gel column with cyclohexane/ethyl acetate (50:50→5:95) followed by ethyl acetate/methanol (95:5→80:20) as eluant.

Yield: 20 mg (11% of theory)

$R_f$ value: 0.8 (silica gel, dichloromethane/methanol/conc. ammonia=90:10:1)

Mass spectrum (ESI⁺): m/z=584 [M+H]⁺

The following compounds are obtained analogously to Example 8:

(1) N-(5-tert-butyl-3-methanesulphonylamino-2-methoxyphenyl)-4-methyl-3-(6-methylaminomethyl-pyrimidin-4-yloxy)-benzamide

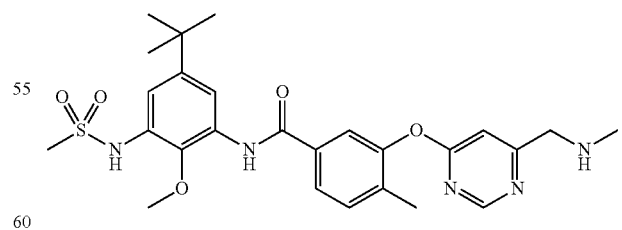

$R_f$ value: 0.5 (silica gel, dichloromethane/methanol/conc. ammonia=90:10:1)

Mass spectrum (ESI⁺): m/z=528 [M+H]⁺

(2) N-(5-tert-butyl-3-methanesulphonylamino-2-methoxy-phenyl)-4-methyl-3-[6-(4-methyl-piperazin-1-ylmethyl)-pyrimidin-4-yloxy]-benzamide

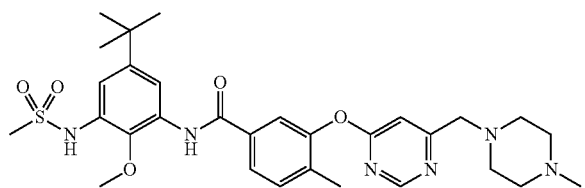

$R_f$ value: 0.5 (silica gel, dichloromethane/methanol/conc. ammonia=90:10:1)
Mass spectrum (ESI$^+$): m/z=597 [M+H]$^+$ (3) N-(5-tert-butyl-3-methanesulphonylamino-2-methoxy-phenyl)-4-methyl-3-(2-morpholin-4-ylmethyl-pyrimidin-4-yloxy)-benzamide

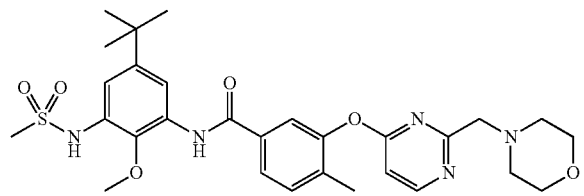

$R_f$ value: 0.4 (silica gel, dichloromethane/methanol=95:5)
Mass spectrum (ESI$^+$): m/z=584 [M+H]$^+$ (4) N-(5-tert-butyl-3-methanesulphonylamino-2-methoxy-phenyl)-4-methyl-3-(2-methylaminomethyl-pyrimidin-4-yloxy)-benzamide

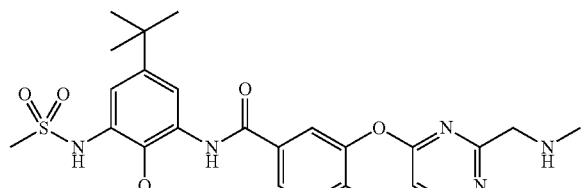

$R_f$ value: 0.25 (silica gel, dichloromethane/methanol/conc. ammonia=95:5:0.1)
Mass spectrum (ESI$^+$): m/z=528 [M+H]$^+$ (5) N-(5-tert-butyl-3-methanesulphonylamino-2-methoxy-phenyl)-4-methyl-3-[2-(3-oxo-piperazin-1-ylmethyl)-pyrimidin-4-yloxy]-benzamide

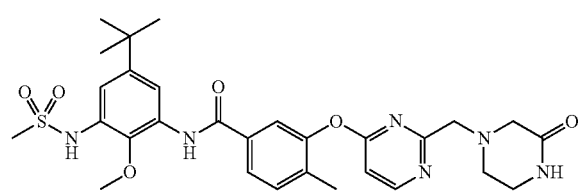 [SMILES: COc1c(NC(=O)c2ccc(C)c(Oc3ccnc(CN4CCNC(=O)C4)n3)c2)cc(C(C)(C)C)cc1NS(C)(=O)=O]

$R_f$ value: 0.10 (silica gel, dichloromethane/methanol=95:5)
Mass spectrum (ESI$^+$): m/z=597 [M+H]$^+$ (6) N-(5-tert-butyl-3-methanesulphonylamino-2-methoxy-phenyl)-4-methyl-3-[2-(4-methyl-piperazin-1-ylmethyl)-pyrimidin-4-yloxy]-benzamide

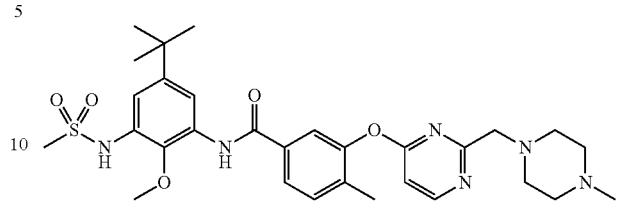

$R_f$ value: 0.25 (silica gel, dichloromethane/methanol/conc. ammonia=95:5:0.1)
Mass spectrum (ESI$^-$): m/z=595 [M−H]$^-$ (7) N-(5-tert-butyl-3-methanesulphonylamino-2-methoxy-phenyl)-4-methyl-3-[6-(3-oxo-piperazin-1-ylmethyl)-pyrimidin-4-yloxy]-benzamide

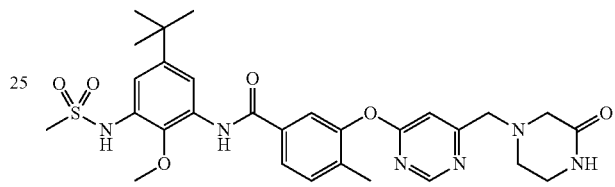

$R_f$ value: 0.5 (silica gel, dichloromethane/methanol/conc. ammonia=90:10:1)
Mass spectrum (ESI$^+$): m/z=597 [M+H]$^+$ (9) N-(5-tert-butyl-3-methanesulphonylamino-2-methoxy-phenyl)-4-methyl-3-(2-morpholin-4-ylmethyl-pyridin-4-yloxy)-benzamide

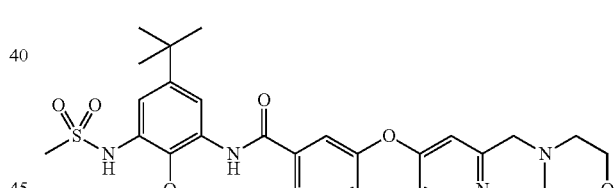

$R_f$ value: 0.5 (silica gel, dichloromethane/methanol/conc. ammonia=90:10:1)
Mass spectrum (ESI$^+$): m/z=583 [M+H]$^+$

(10) N-(5-tert-butyl-3-methanesulphonylamino-2-methoxy-phenyl)-4-methyl-3-[2-(4-methyl-piperazin-1-ylmethyl)-pyridin-4-yloxy]-benzamide

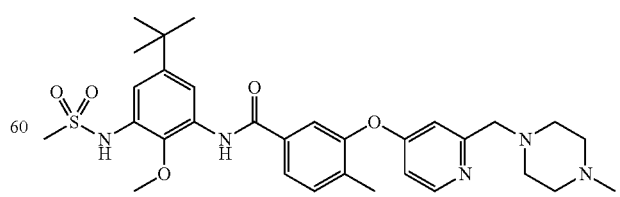

$R_f$ value: 0.3 (silica gel, dichloromethane/methanol/conc. ammonia=90:10:1)
Mass spectrum (ESI$^+$): m/z=596 [M+H]$^+$

(11) (S)—N-(5-tert-butyl-3-methanesulphonylamino-2-methoxy-phenyl)-4-methyl-3-{2-[(tetrahydro-furan-3-ylamino)-methyl]-pyridin-4-yloxy}-benzamide

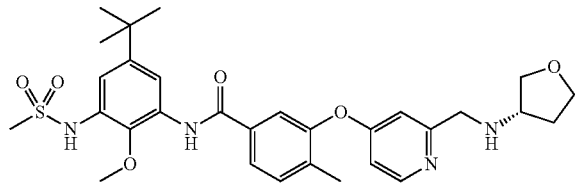 [SMILES: COc1c(NC(=O)c2ccc(C)c(Oc3ccnc(CN[C@H]4CCOC4)c3)c2)cc(C(C)(C)C)cc1NS(C)(=O)=O]

R$_f$ value: 0.4 (silica gel, dichloromethane/methanol/conc. ammonia=90:10:1)
Mass spectrum (ESI$^+$): m/z=583 [M+H]$^+$

(12) (R)—N-(5-tert-butyl-3-methanesulphonylamino-2-methoxy-phenyl)-3-[2-(3-hydroxy-pyrrolidin-1-ylmethyl)-pyridin-4-yloxy]-4-methyl-benzamide

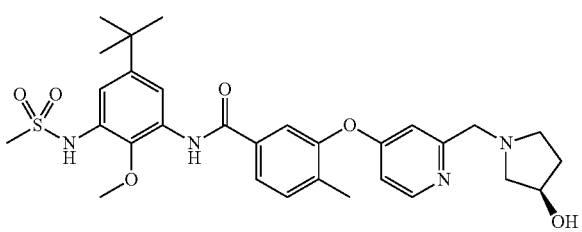

R$_f$ value: 0.4 (silica gel, dichloromethane/methanol/conc. ammonia=90:10:1)
Mass spectrum (ESI$^+$): m/z=583 [M+H]$^+$

(13) (S)—N-(5-tert-butyl-3-methanesulphonylamino-2-methoxy-phenyl)-3-[2-(3-hydroxy-pyrrolidin-1-ylmethyl)-pyridin-4-yloxy]-4-methyl-benzamide

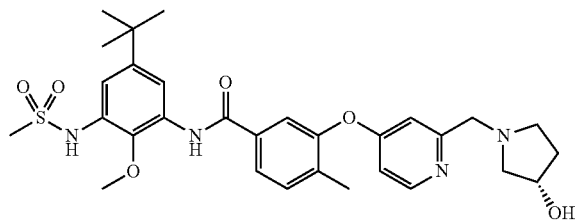 [SMILES: COc1c(NC(=O)c2ccc(C)c(Oc3ccnc(CN4CC[C@H](O)C4)c3)c2)cc(C(C)(C)C)cc1NS(C)(=O)=O]

R$_f$ value: 0.4 (silica gel, dichloromethane/methanol/conc. ammonia=90:10:1)
Mass spectrum (ESI$^+$): m/z=583 [M+H]$^+$

(14) N-(5-tert-butyl-3-methanesulphonylamino-2-methoxy-phenyl)-4-methyl-3-(2-methylaminomethyl-pyridin-4-yloxy)-benzamide

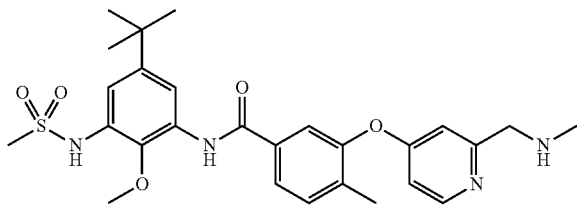

R$_f$ value: 0.2 (silica gel, dichloromethane/methanol/conc. ammonia=90:10:1)
Mass spectrum (ESI$^+$): m/z=527 [M+H]$^+$

(15) (R)—N-(5-tert-butyl-3-methanesulphonylamino-2-methoxy-phenyl)-4-methyl-3-{2-[(tetrahydro-furan-3-ylamino)-methyl]-pyridin-4-yloxy}-benzamide

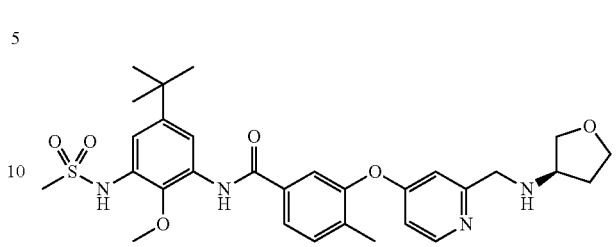

Mass spectrum (ESI$^+$): m/z=583 [M+H]$^+$

(16) N-(5-tert-butyl-3-methanesulphonylamino-2-methoxy-phenyl)-4-methyl-3-[2-(4-methyl-homopiperazin-1-ylmethyl)-pyrimidin-4-yloxy]-benzamide

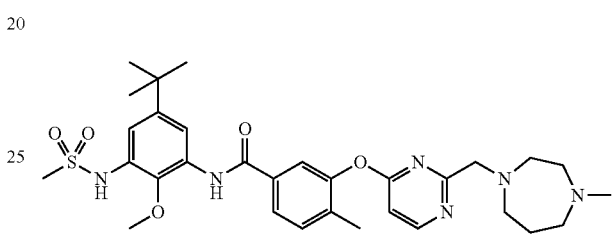

R$_f$ value: 0.2 (silica gel, dichloromethane/methanol/conc. ammonia=95:5:0.1)
Mass spectrum (ESI$^+$): m/z=611 [M+H]$^+$

(17) N-(5-tert-butyl-3-methanesulphonylamino-2-methoxy-phenyl)-4-methyl-3-{2-[(1-methyl-piperidin-4-ylamino)-methyl]-pyrimidin-4-yloxy}-benzamide

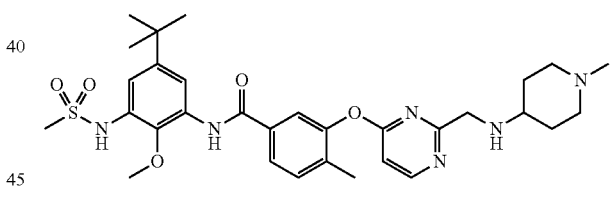

R$_f$ value: 0.2 (silica gel, dichloromethane/methanol/conc. ammonia=95:5:0.1)
Mass spectrum (ESI$^+$): m/z=611 [M+H]$^+$

(18) N-(5-tert-butyl-3-methanesulphonylamino-2-methoxy-phenyl)-4-methyl-3-{2-[(1-methyl-piperidin-3-ylamino)-methyl]-pyrimidin-4-yloxy}-benzamide

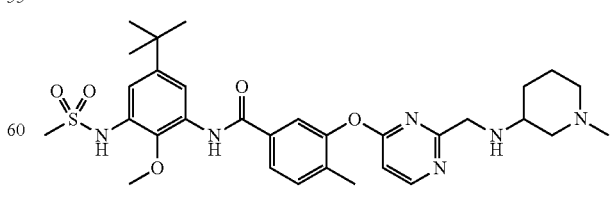

R$_f$ value: 0.45 (silica gel, dichloromethane/methanol/conc. ammonia=95:5:0.1)
Mass spectrum (ESI$^+$): m/z=611 [M+H]$^+$

(19) N-(5-tert-butyl-3-methanesulphonylamino-2-methoxy-phenyl)-4-methyl-3-(2-{[methyl-(1-methyl-pyrrolidin-3-yl)-amino]-methyl}-pyrimidin-4-yloxy)-benzamide

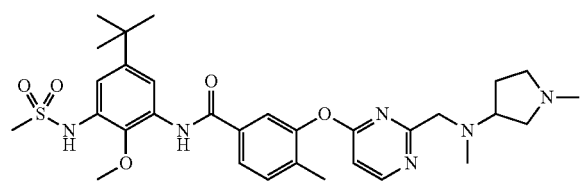

R$_f$ value: 0.3 (silica gel, dichloromethane/methanol/conc. ammonia=95:5:0.1)

Mass spectrum (ESI$^+$): m/z=611 [M+H]$^+$

(20) N-(5-tert-butyl-3-methanesulphonylamino-2-methoxy-phenyl)-4-methyl-3-[2-(4-methyl-homopiperazin-1-ylmethyl)-pyridin-4-yloxy]-benzamide

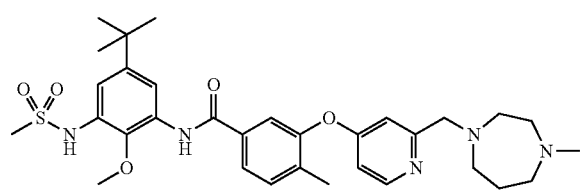

R$_f$ value: 0.4 (silica gel, dichloromethane/methanol/conc. ammonia=90:10:1)

Mass spectrum (ESI$^+$): m/z=610 [M+H]$^+$

(21) (S)—N-(5-tert-butyl-3-methanesulphonylamino-2-methoxy-phenyl)-3-[2-(3-dimethylamino-pyrrolidin-1-ylmethyl)-pyrimidin-4-yloxy]-4-methyl-benzamide

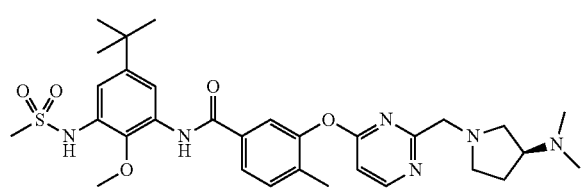

Mass spectrum (ESI$^+$): m/z=611 [M+H]$^+$

(22) (R)—N-(5-tert-butyl-3-methanesulphonylamino-2-methoxy-phenyl)-3-[2-(3-dimethylamino-pyrrolidin-1-ylmethyl)-pyrimidin-4-yloxy]-4-methyl-benzamide

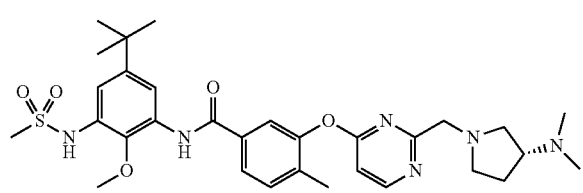

Mass spectrum (ESI$^+$): m/z=611 [M+H]$^+$

(23) N-(5-tert-butyl-3-methanesulphonylamino-2-methoxy-phenyl)-4-methyl-3-{2-[(1-methyl-pyrrolidin-3-ylamino)-methyl]-pyrimidin-4-yloxy}-benzamide

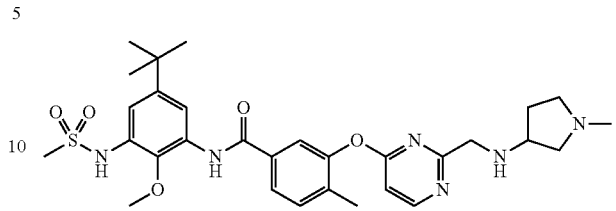

R$_f$ value: 0.25 (silica gel, dichloromethane/methanol/conc. ammonia=90:10:0.1)

Mass spectrum (ESI$^+$): m/z=597 [M+H]$^+$

(24) N-(5-tert-butyl-3-methanesulphonylamino-2-methoxy-phenyl)-3-(2-{[N-(2-dimethylamino-ethyl)-N-methyl-amino]-methyl}-pyrimidin-4-yloxy)-4-methyl-benzamide

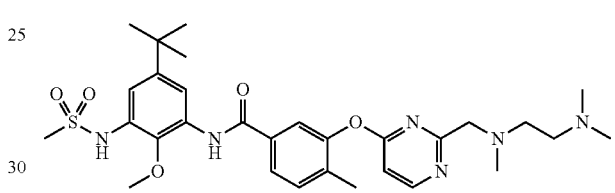

HPLC (method 1): retention time=2.63 min

Mass spectrum (ESI$^+$): m/z=599 [M+H]$^+$

(25) N-(5-tert-butyl-3-methanesulphonylamino-2-methoxy-phenyl)-3-{2-[(2-dimethylamino-ethylamino)-methyl]-pyrimidin-4-yloxy}-4-methyl-benzamide

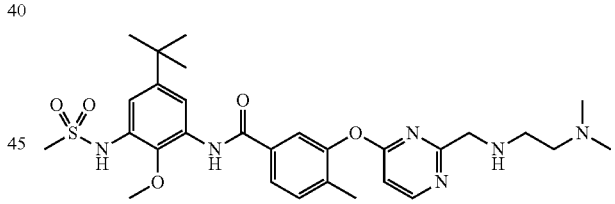

HPLC (method 1): retention time=2.32 min

Mass spectrum (ESI$^+$): m/z=585 [M+H]$^+$

(26) N-(5-tert-butyl-3-methanesulphonylamino-2-methoxy-phenyl)-3-(2-{[(2-dimethylamino-ethyl)-methyl-amino]-methyl}-pyridin-4-yloxy)-4-methyl-benzamide

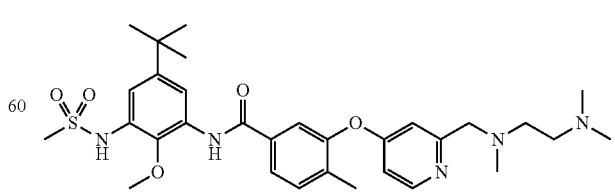

HPLC (method 1): retention time=2.41 min

Mass spectrum (ESI$^+$): m/z=598 [M+H]$^+$

(27) N-(5-tert-butyl-3-methanesulphonylamino-2-methoxyphenyl)-3-{2-[(2-dimethylamino-ethylamino)-methyl]-pyridin-4-yloxy}-4-methyl-benzamide

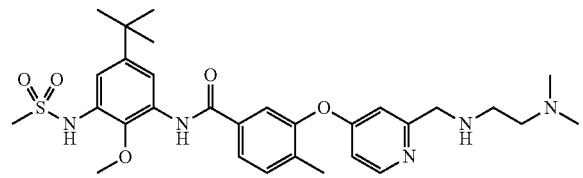

HPLC (method 1): retention time=2.39 min

Mass spectrum (ESI$^+$): m/z=584 [M+H]$^+$

(28) N-(5-tert-butyl-3-methanesulphonylamino-2-methoxyphenyl)-3-methyl-5-[2-(4-methyl-piperazin-1-ylmethyl)-pyrimidin-4-yloxy]-benzamide

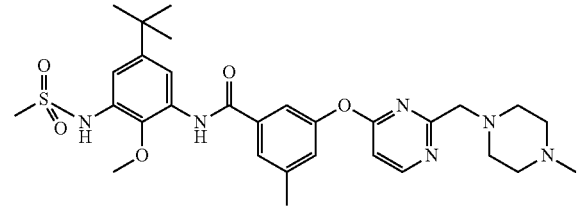

R$_f$ value: 0.55 (silica gel, dichloromethane/methanol=90:10)

Mass spectrum (ESI$^+$): m/z=597 [M+H]$^+$

(29) N-(5-tert-butyl-3-methanesulphonylamino-2-methoxyphenyl)-3-{6-[(2-dimethylamino-ethylamino)-methyl]-pyrimidin-4-yloxy}-4-methyl-benzamide

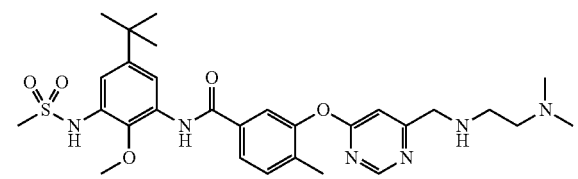

HPLC (method 1): retention time=2.38 min

Mass spectrum (ESI$^+$): m/z=585 [M+H]$^+$

(30) N-(5-tert-butyl-3-methanesulphonylamino-2-methoxyphenyl)-3-(6-{[(2-dimethylamino-ethyl)-methyl-amino]-methyl}-pyrimidin-4-yloxy)-4-methyl-benzamide

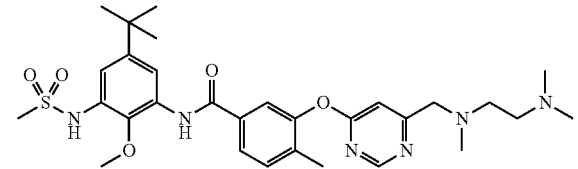

HPLC (method 1): retention time=2.73 min

Mass spectrum (ESI$^+$): m/z=599 [M+H]$^+$

(31) N-(5-tert-butyl-3-methanesulphonylamino-2-methoxyphenyl)-4-chloro-3-{6-[(2-dimethylamino-ethylamino)-methyl]-pyrimidin-4-yloxy}-benzamide

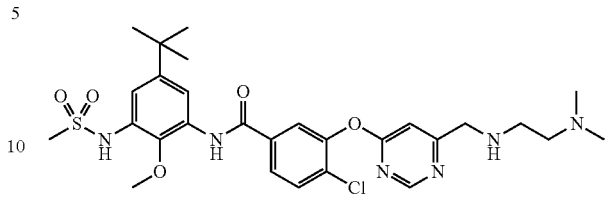

R$_f$ value: 0.4 (silica gel, dichloromethane/methanol/methanolic ammonia=95:5:0.1

Mass spectrum (ESI$^+$): m/z=605/607 (Cl) [M+H]$^+$

(32) N-(5-tert-butyl-3-methanesulphonylamino-2-methoxyphenyl)-4-chloro-3-(6-{[(2-dimethylamino-ethyl)-methyl-amino]-methyl}-pyrimidin-4-yloxy)-benzamide

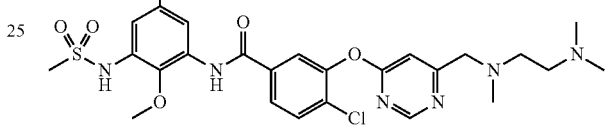

R$_f$ value: 0.4 (silica gel, dichloromethane/methanol/methanolic ammonia=95:5:0.1)

Mass spectrum (ESI$^+$): m/z=619/621 (Cl) [M+H]$^+$

(33) N-(5-tert-butyl-3-methanesulphonylamino-2-methoxyphenyl)-4-chloro-3-(2-{[(2-dimethylamino-ethyl)-methyl-amino]-methyl}-pyridin-4-yloxy)-benzamide

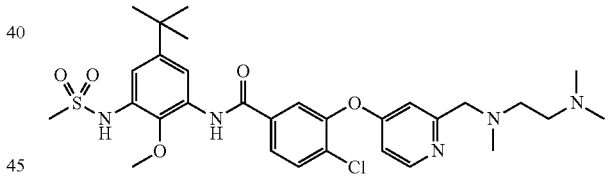

R$_f$ value: 0.35 (silica gel, dichloromethane/methanol/methanolic ammonia=95:5:0.1)

Mass spectrum (ESI$^+$): m/z=618/620 (Cl) [M+H]$^+$

(34) N-(5-tert-butyl-3-methanesulphonylamino-2-methoxyphenyl)-4-chloro-3-{2-[(2-dimethylamino-ethylamino)-methyl]-pyridin-4-yloxy}-benzamide

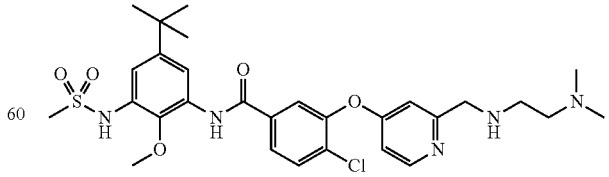

R$_f$ value: 0.3 (silica gel, dichloromethane/methanol/methanolic ammonia=95:5:0.1)

Mass spectrum (ESI$^+$): m/z=604/606 (Cl) [M+H]$^+$

(35) N-(5-tert-butyl-3-methanesulphonylamino-2-methoxy-phenyl)-4-chloro-3-[2-(4-methyl-[1,4]diazepan-1-ylmethyl)-pyrimidin-4-yloxy]-benzamide

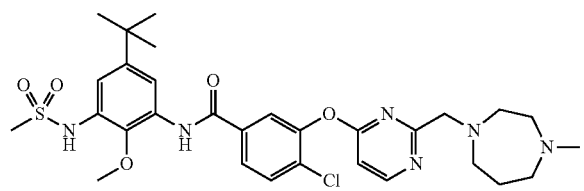

$R_f$ value: 0.2 (silica gel, dichloromethane/methanol/methanolic ammonia=95:5:0.1)
Mass spectrum (ESI$^+$): m/z=631/633 (Cl) [M+H]$^+$

(36) N-(5-tert-butyl-3-methanesulphonylamino-2-methoxy-phenyl)-4-chloro-3-(2-{[(2-dimethylamino-ethyl)-methyl-amino]-methyl}-pyrimidin-4-yloxy)-benzamide

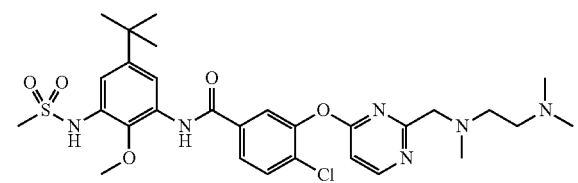

$R_f$ value: 0.25 (silica gel, dichloromethane/methanol/methanolic ammonia=95:5:0.1)
Mass spectrum (ESI$^+$): m/z=619/621 (Cl) [M+H]$^+$

(37) N-(5-tert-butyl-3-methanesulphonylamino-2-methoxy-phenyl)-4-chloro-3-{2-[(2-dimethylamino-ethylamino)-methyl]-pyrimidin-4-yloxy}-benzamide

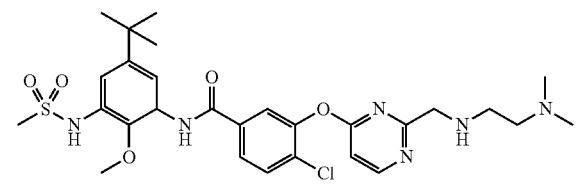

$R_f$ value: 0.2 (silica gel, dichloromethane/methanol/methanolic ammonia=95:5:0.1)
Mass spectrum (ESI$^+$): m/z=605/607 (Cl) [M+H]$^+$

(38) N-(5-tert-butyl-3-methanesulphonylamino-2-methoxy-phenyl)-4-chloro-3-[6-(4-methyl-[1,4]diazepan-1-ylmethyl)-pyrimidin-4-yloxy]-benzamide

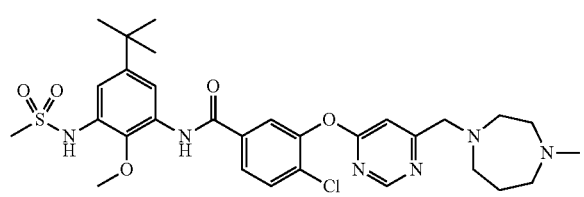

$R_f$ value: 0.3 (silica gel, dichloromethane/methanol/methanolic ammonia=95:5:0.1)
Mass spectrum (ESI$^+$): m/z=631/633 (Cl) [M+H]$^+$

(39) N-(5-tert-butyl-3-methanesulphonylamino-2-methoxy-phenyl)-4-chloro-3-[2-(4-methyl-[1,4]diazepan-1-ylmethyl)-pyridin-4-yloxy]-benzamide

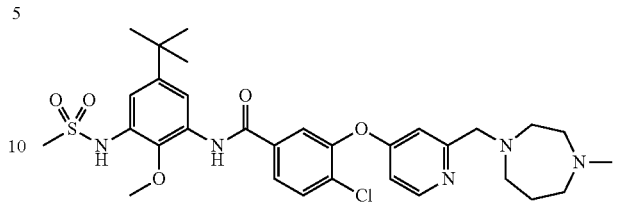

$R_f$ value: 0.1 (silica gel, dichloromethane/methanol/methanolic ammonia=95:5:0.1)
Mass spectrum (ESI$^+$): m/z=630/632 (Cl) [M+H]$^+$ Example 9

N-(5-tert-butyl-3-methanesulphonylamino-2-methoxy-phenyl)-4-methyl-3-[6-(1-methyl-piperidin-4-ylmethyl)-pyrimidin-4-yloxy]-benzamide

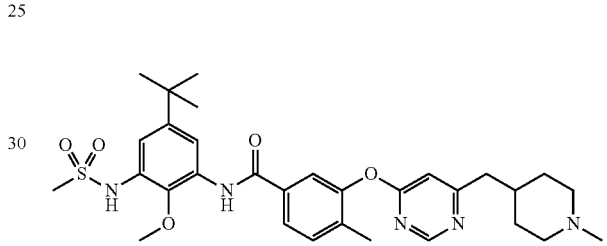

40 µl Paraformaldehyde (37% in water) and 30 mg palladium on activated charcoal (10%) are added to 260 mg N-(5-tert-butyl-3-methanesulphonylamino-2-methoxy-phenyl)-4-methyl-3-(6-piperidin-4-ylmethyl-pyrimidin-4-yloxy)-benzamide in 10 ml of methanol and the reaction mixture is hydrogenated at ambient temperature and a partial hydrogen pressure of 4 bar. After the uptake of hydrogen has ended the catalyst is suction filtered and the filtrate is evaporated down. The flask residue is chromatographed on aluminium oxide with dichloromethane/methanol (99:1→95:5) as eluant.

Yield: 172 mg (65% of theory)
HPLC (method 1): retention time=2.69 min
Mass spectrum (ESI$^+$): m/z=596 [M+H]$^+$ The following compounds are obtained analogously to Example 9:

(1) N-(5-tert-butyl-3-methanesulphonylamino-2-methoxy-phenyl)-4-methyl-3-[2-(1-methyl-piperidin-4-ylmethyl)-pyrimidin-4-yloxy]-benzamide

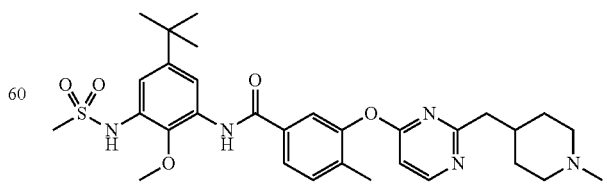

HPLC (method 1): retention time=2.78 min
Mass spectrum (ESI$^+$): m/z=596 [M+H]$^+$ (2) N-(5-tert-butyl-3-methanesulphonylamino-2-methoxy-phenyl)-4-methyl-3-[2-(1-methyl-piperidin-4-ylmethyl)-pyridin-4-yloxy]-benzamide

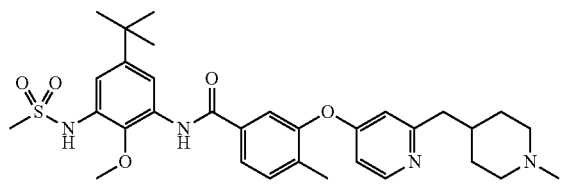

HPLC (method 1): retention time=2.27 min
Mass spectrum (ESI$^+$): m/z=595 [M+H]$^+$ (3) N-(5-tert-butyl-3-hydroxymethyl-2-methoxy-phenyl)-4-methyl-3-[2-(4-methyl-piperazin-1-ylmethyl)-pyridin-4-yloxy]-benzamide

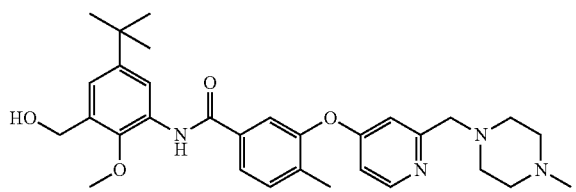

Mass spectrum (ESI$^+$): m/z=533 [M+H]$^+$ (4) N-(5-tert-butyl-3-hydroxymethyl-2-methoxy-phenyl)-4-methyl-3-[2-(4-methyl-[1,4]diazepan-1-ylmethyl)-pyridin-4-yloxy]-benzamide

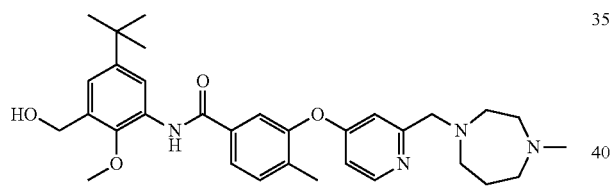

Mass spectrum (ESI$^+$): m/z=547 [M+H]$^+$

Example 10

N-(5-tert-butyl-3-methanesulphonylamino-2-methoxy-phenyl)-4-chloro-3-[2-(1-methyl-piperidin-4-ylamino)-pyridin-4-yloxy]-benzamide

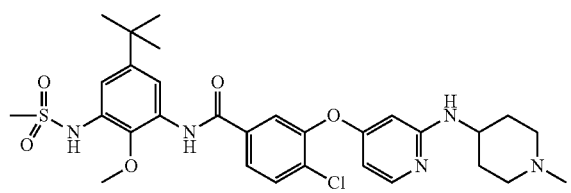

48 µl 2,8,9-triisobutyl-2,5,8,9-tetraaza-1-phosphabicyclo[3.3.3]undecane and 31 mg Pd$_2$(dibenzylideneacetone)$_3$ are added to a mixture of 300 mg N-(5-tert-butyl-3-methanesulphonylamino-2-methoxy-phenyl)-4-chloro-3-(2-chloro-pyridin-4-yloxy)-benzamide, 110 mg 1-methyl-piperidin-4-ylamine and 250 mg KO$^t$Bu in 5 ml of toluene kept under an argon atmosphere. The mixture is heated to 105° C. and stirred overnight at this temperature. Then it is cooled to ambient temperature and ethyl acetate is added. The mixture is then washed with a little water and then extracted twice with 1 M aqueous hydrochloric acid. The combined aqueous, acidic extracts are made alkaline with aqueous K$_2$CO$_3$ solution and then extracted with ethyl acetate. The combined organic extracts are washed with saturated saline solution, dried (Na$_2$SO$_4$) and then freed from the solvent. The flask residue is chromatographed on silica gel with dichloromethane/methanol/methanolic ammonia (97:2:1→96:3:1) as eluant.

Yield: 18 mg (5% of theory)
R$_f$ value: 0.3 (silica gel, dichloromethane/methanol/conc. ammonia=95:5:0.1)
Mass spectrum (ESI$^+$): m/z=616/618 (Cl) [M+H]$^+$ Example 11

N-(5-tert-butyl-3-methanesulphonylamino-2-methoxy-phenyl)-4-chloro-3-[6-(piperidin-4-ylamino)-pyrimidin-4-yloxy]-benzamide

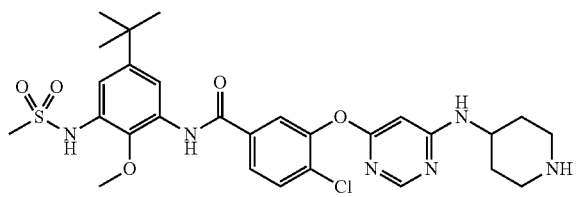 [SMILES: COc1c(NC(=O)c2ccc(Cl)c(Oc3cc(NC4CCNCC4)ncn3)c2)cc(C(C)(C)C)cc1NS(C)(=O)=O]

1 mL 5-6 M isopropanolic hydrochloric acid is added at ambient temperature to a solution of 138 mg tert-butyl 4-{6-[5-(5-tert-butyl-3-methanesulphonylamino-2-methoxy-phenyl-carbamoyl)-2-chloro-phenoxy]-pyrimidin-4-ylamino}piperidine-1-carboxylate in 2 ml dichloromethane. The solution is stirred overnight at ambient temperature and then evaporated down. The residue is taken up in water and the solution is made alkaline with aqueous K$_2$CO$_3$ solution. The alkaline solution is extracted with an approx. 20:1 mixture of dichloromethane and methanol, and the combined extracts are dried (MgSO$_4$) and evaporated down. The residue is stirred with diethyl ether and then dried.

Yield: 105 mg (89% of theory)
R$_f$ value: 0.1 (silica gel, dichloromethane/methanol/methanolic ammonia=95:5:0.1)
Mass spectrum (ESI$^+$): m/z=603/605 (Cl) [M+H]$^+$ The following compounds are obtained analogously to Example 11:

(1) N-[3-(butan-1-sulphonylamino)-5-tert-butyl-2-methoxy-phenyl]-4-methyl-3-(2-piperidin-4-ylmethyl-pyridin-4-yloxy)-benzamide

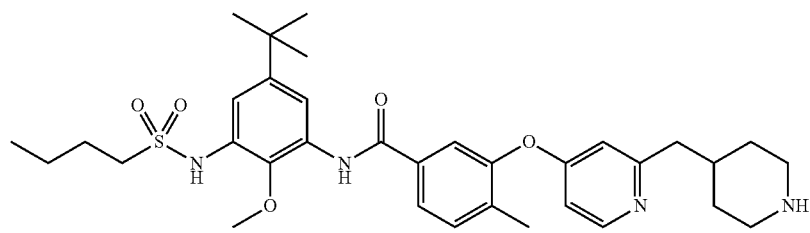 [SMILES: CCCCS(=O)(=O)Nc1cc(C(C)(C)C)cc(NC(=O)c2ccc(C)c(Oc3ccnc(CC4CCNCC4)c3)c2)c1OC]

HPLC (method 1): retention time=2.81 min
Mass spectrum (ESI⁺): m/z=623 [M+H]⁺

(2) N-(5-tert-butyl-2-methoxy-3-pentanoylamino-phenyl)-4-methyl-3-(2-piperidin-4-ylmethyl-pyridin-4-yloxy)-benzamide

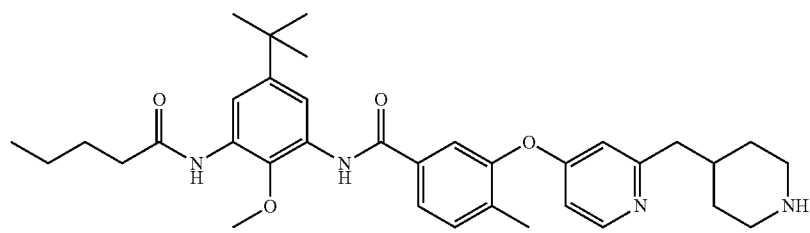 [SMILES: CCCCC(=O)Nc1cc(C(C)(C)C)cc(NC(=O)c2ccc(C)c(Oc3ccnc(CC4CCNCC4)c3)c2)c1OC]

HPLC (method 1): retention time=2.69 min
Mass spectrum (ESI⁺): m/z=587 [M+H]⁺

(3) N-(5-tert-butyl-3-methanesulphonyl-2-methoxy-phenyl)-4-methyl-3-(2-piperidin-4-ylmethyl-pyridin-4-yloxy)-benzamide

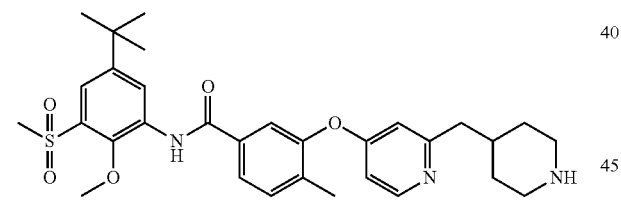

HPLC (method 1): retention time=2.46 min
Mass spectrum (ESI⁺): m/z=566 [M+H]⁺

(4) N-[5-tert-butyl-2-methoxy-3-(3-methyl-butyrylamino)-phenyl]-4-methyl-3-(2-piperidin-4-ylmethyl-pyridin-4-yloxy)-benzamide

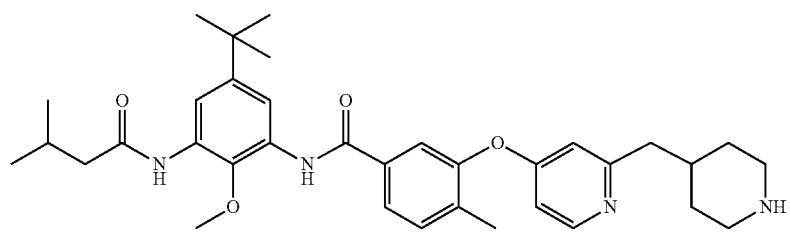 [SMILES: COc1c(NC(=O)CC(C)C)cc(C(C)(C)C)cc1NC(=O)c1ccc(C)c(Oc2ccnc(CC3CCNCC3)c2)c1]

HPLC (method 1): retention time=2.65 min
Mass spectrum (ESI⁺): m/z=587 [M+H]⁺

(5) N-(5-tert-butyl-3-dimethylaminomethyl-2-methoxy-phenyl)-4-methyl-3-(2-piperidin-4-ylmethyl-pyridin-4-yloxy)-benzamide

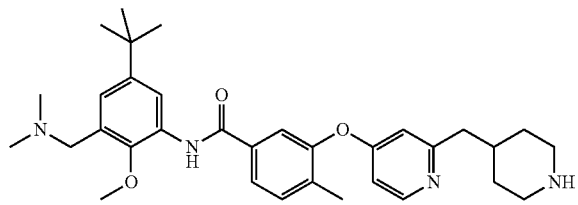 [SMILES: COc1c(CN(C)C)cc(C(C)(C)C)cc1NC(=O)c1ccc(C)c(Oc2ccnc(CC3CCNCC3)c2)c1]

HPLC (method 3): retention time=4.40 min
Mass spectrum (ESI$^+$): m/z=545 [M+H]$^+$ (6) N-(5-tert-butyl-2-methoxy-3-pyrrolidin-1-ylmethyl-phenyl)-4-methyl-3-(2-piperidin-4-ylmethyl-pyridin-4-yloxy)-benzamide

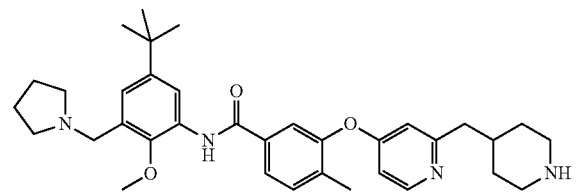 [SMILES: COc1c(CN2CCCC2)cc(C(C)(C)C)cc1NC(=O)c1ccc(C)c(Oc2ccnc(CC3CCNCC3)c2)c1]

HPLC (method 1): retention time=1.94 min
Mass spectrum (ESI$^+$): m/z=571 [M+H]$^+$ (7) N-(5-tert-butyl-3-cyclopropylaminomethyl-2-methoxy-phenyl)-4-methyl-3-(2-piperidin-4-ylmethyl-pyridin-4-yloxy)-benzamide

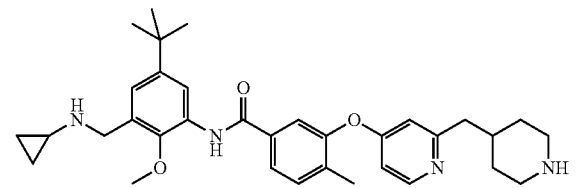 [SMILES: COc1c(CNC2CC2)cc(C(C)(C)C)cc1NC(=O)c1ccc(C)c(Oc2ccnc(CC3CCNCC3)c2)c1]

Mass spectrum (ESI$^+$): m/z=557 [M+H]$^+$

Example 12

N-(5-tert-butyl-3-methanesulphonylamino-2-methoxy-phenyl)-4-methyl-3-[2-(1-methyl-azepan-4-ylmethyl)-pyridin-4-yloxy]-benzamide

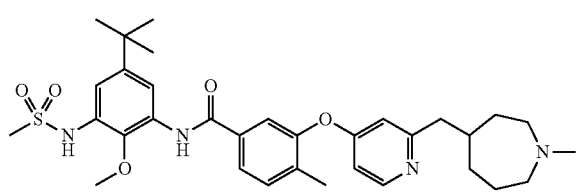

At ambient temperature 141 mg sodium-triacetoxyborohydride are added to a solution of 330 mg 3-(2-azepan-4-ylmethyl-pyridin-4-yloxy)-N-(5-tert-butyl-3-methanesulphonyl-amino-2-methoxy-phenyl)-4-methyl-benzamide and 50 µl of a 37% aqueous formaldehyde solution in 5 ml of methanol. Then the solution is evaporated down and the residue is taken up in ethyl acetate. The organic phase is washed with aqueous sodium carbonate solution and saturated aqueous saline solution and then dried (Na$_2$SO$_4$). The solvent is removed and the flask residue is chromatographed on silica gel with dichloromethane/methanol/methanolic ammonia solution (94:5:1→90:9:1) as eluant.

Yield: 226 mg (67% of theory)
R$_f$ value: 0.25 (silica gel, dichloromethane/methanol/methanolic ammonia=90:10:0.1)
Mass spectrum (ESI$^+$): m/z=609 [M+H]$^+$ The following compounds are obtained analogously to Example 12:

(1) N-(5-tert-butyl-3-methanesulphonylamino-2-methoxy-phenyl)-4-chloro-3-[6-(4-methyl-piperazin-1-ylmethyl)-pyrimidin-4-yloxy]-benzamide

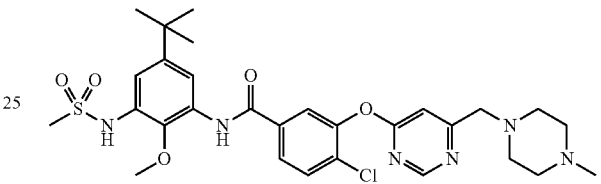

R$_f$ value: 0.4 (silica gel, dichloromethane/methanol/methanolic ammonia=95:5:0.1)
Mass spectrum (ESI$^+$): m/z=617/619 (Cl) [M+H]$^+$ (2) N-(5-tert-butyl-3-methanesulphonylamino-2-methoxy-phenyl)-4-chloro-3-[6-(1-methyl-piperidin-4-ylmethyl)-pyrimidin-4-yloxy]-benzamide

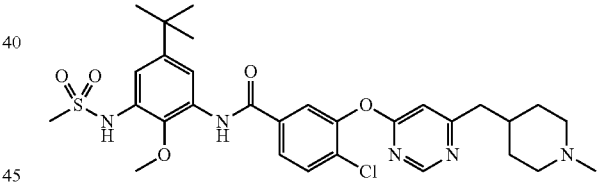

R$_f$ value: 0.35 (silica gel, dichloromethane/methanol/methanolic ammonia=95:5:0.1)
Mass spectrum (ESI$^+$): m/z=616/618 (Cl) [M+H]$^+$ (3) N-(5-tert-butyl-3-methanesulphonylamino-2-methoxy-phenyl)-4-chloro-3-[2-(1-methyl-piperidin-4-ylmethyl)-pyrimidin-4-yloxy]-benzamide

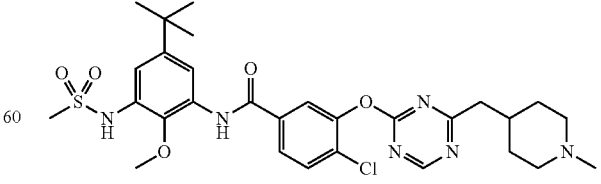

R$_f$ value: 0.3 (silica gel, dichloromethane/methanol/methanolic ammonia=95:5:0.1)
Mass spectrum (ESI$^+$): m/z=616/618 (Cl) [M+H]$^+$ (4) N-(5-tert-butyl-3-methanesulphonylamino-2-methoxy-phenyl)-4-chloro-3-[2-(4-methyl-piperazin-1-ylmethyl)-pyridin-4-yloxy]-benzamide

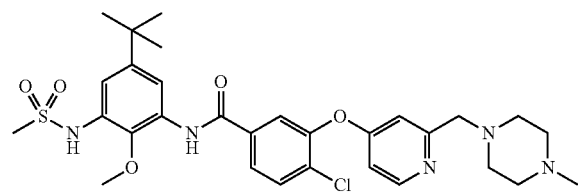

R$_f$ value: 0.4 (silica gel, dichloromethane/methanol/methanolic ammonia=95:5:0.1)
Mass spectrum (ESI$^+$): m/z=616/618 (Cl) [M+H]$^+$ (5) N-(5-tert-butyl-3-methanesulphonylamino-2-methoxy-phenyl)-4-chloro-3-[2-(1-methyl-piperidin-4-ylmethyl)-pyridin-4-yloxy]-benzamide

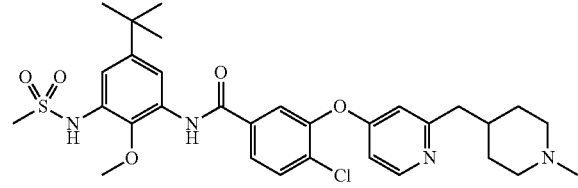

R$_f$ value: 0.15 (silica gel, dichloromethane/methanol/methanolic ammonia=95:5:0.1)
Mass spectrum (ESI$^+$): m/z=615/617 (Cl) [M+H]$^+$ (6) N-(5-tert-butyl-3-methanesulphonylamino-2-methoxy-phenyl)-4-methyl-3-[2-(1-methyl-azepan-4-ylmethyl)-pyrimidin-4-yloxy]-benzamide

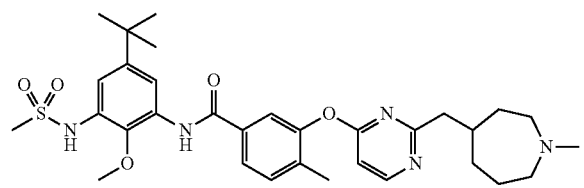

R$_f$ value: 0.2 (silica gel, dichloromethane/methanol/methanolic ammonia=90:10:0.1)
Mass spectrum (ESI$^+$): m/z=610 [M+H]$^+$ (7) N-(5-tert-butyl-3-methanesulphonylamino-2-methoxy-phenyl)-4-methyl-3-[6-(1-methyl-azepan-4-ylmethyl)-pyrimidin-4-yloxy]-benzamide

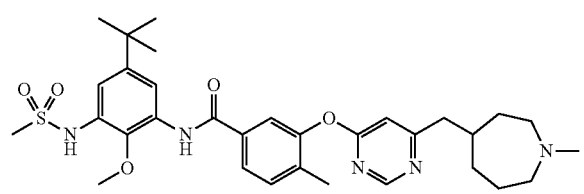

R$_f$ value: 0.4 (silica gel, dichloromethane/methanol/methanolic ammonia=90:10:0.1)
Mass spectrum (ESI$^+$): m/z=610 [M+H]$^+$ Example 13

N-(5-tert-butyl-3-hydroxymethyl-2-methoxy-phenyl)-4-methyl-3-[2-(4-methyl-piperazin-1-ylmethyl)-pyrimidin-4-yloxy]-benzamide

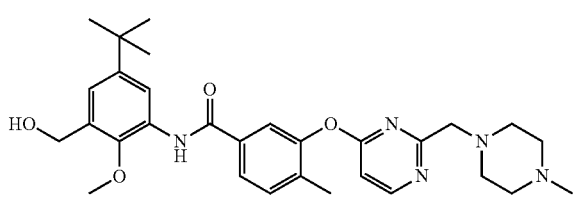 [SMILES: COc1c(CO)cc(C(C)(C)C)cc1NC(=O)c1ccc(C)c(Oc2ccnc(CN3CCN(C)CC3)n2)c1]

144 mg of O-(7-azabenzotriazol-1-yl)-N,N,N',N'-tetramethyl-uronium-hexafluorophosphate, 110 µl diisopropylethylamine and 14 mg 1-hydroxy-7-azabenzotriazole are added under an argon atmosphere to 120 mg 4-methyl-3-[2-(4-methyl-piperazin-1-ylmethyl)-pyrimidin-4-yloxy]-benzoic acid in 2 ml of N,N-dimethylformamide. The mixture is stirred for 15 minutes at ambient temperature, before 66 mg of (3-amino-5-tert-butyl-2-methoxy-phenyl)-methanol are added. The reaction mixture is stirred for 3 h at ambient temperature and then diluted with water and aqueous NaHCO$_3$ solution. The resulting mixture is extracted with ethyl acetate, and the combined extracts are washed with saturated aqueous sodium chloride solution, dried on magnesium sulphate and evaporated down. The flask residue is chromatographed on silica gel with dichloromethane/methanol/methanolic ammonia solution (97:3:0→96:3:1) as eluant.

Yield: 20 mg (18% of theory)
R$_f$ value: 0.3 (silica gel, dichloromethane/methanol/methanolic ammonia=95:5:0.1)
Mass spectrum (ESI$^+$): m/z=534 [M+H]$^+$ The following compound is obtained analogously to Example 13:

(1) N-(5-tert-butyl-3-methanesulphinyl-2-methoxy-phenyl)-4-methyl-3-[2-(4-methyl-piperazin-1-ylmethyl)-pyrimidin-4-yloxy]-benzamide

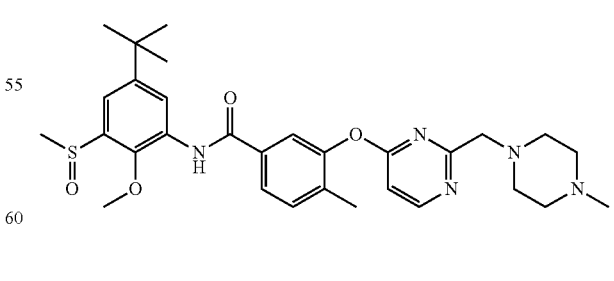

R$_f$ value: 0.5 (silica gel, dichloromethane/methanol/methanolic ammonia=95:5:0.1
Mass spectrum (ESI$^+$): m/z=566 [M+H]$^+$

Example 14

N-(5-tert-butyl-3-methanesulphonylamino-2-methoxy-phenyl)-4-methyl-3-{2-[4-(2,2,2-trifluoroethyl)-piperazin-1-ylmethyl]-pyridin-4-yloxy}-benzamide

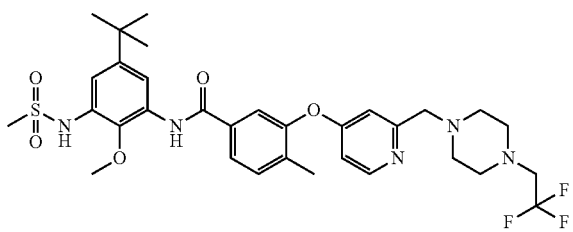 [SMILES: COc1c(NC(=O)c2ccc(C)c(Oc3ccnc(CN4CCN(CC(F)(F)F)CC4)c3)c2)cc(C(C)(C)C)cc1NS(C)(=O)=O]

At ambient temperature 40 μl 2,2,2-trifluoroethyl trifluoromethanesulphonate are added to a solution of 149 mg N-(5-tert-butyl-3-methanesulphonylamino-2-methoxy-phenyl)-4-methyl-3-(2-piperazin-1-ylmethyl-pyridin-4-yloxy)-benzamide and 100 μl ethyldiisopropylamine in 2 ml of tetrahydrofuran. The solution is stirred overnight at ambient temperature, before 100 μl 2,2,2-trifluoro-ethyl trifluoromethanesulphonate are added. After another 24 h stirring at ambient temperature the solution is diluted with ethyl acetate and washed with water and saturated aqueous saline solution. The organic phase is dried on magnesium sulphate and evaporated down. The flask residue is chromatographed on silica gel with dichloromethane/methanol (99:1→80:20) as eluant.

Yield: 89 mg (52% of theory)

$R_f$ value: 0.49 (silica gel, dichloromethane/methanol=90:10)

Mass spectrum (ESI$^+$): m/z=664 [M+H]$^+$

Example 15

N-(5-tert-butyl-3-methanesulphonylamino-2-methoxy-phenyl)-3-[2-(4-cyanomethyl-piperazin-1-ylmethyl)-pyridin-4-yloxy]-4-methyl-benzamide

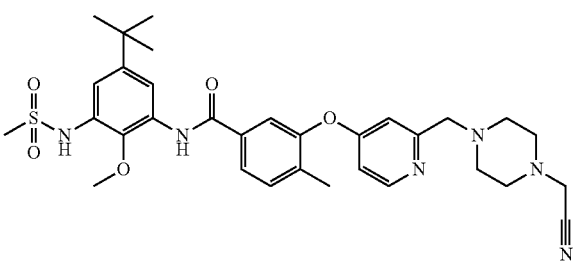 [SMILES: COc1c(NC(=O)c2ccc(C)c(Oc3ccnc(CN4CCN(CC#N)CC4)c3)c2)cc(C(C)(C)C)cc1NS(C)(=O)=O]

At ambient temperature 18 μl bromoacetonitrile are added to a mixture of 149 mg N-(5-tert-butyl-3-methanesulphonylamino-2-methoxy-phenyl)-4-methyl-3-(2-piperazin-1-ylmethyl-pyridin-4-yloxy)-benzamide, 71 mg potassium carbonate and 2 ml acetonitrile. The mixture is stirred overnight at ambient temperature and then diluted with ethyl acetate. The resulting mixture is washed with water and saturated aqueous saline solution, dried (magnesium sulphate) and evaporated down. The flask residue is chromatographed by HPLC (reversed phase, XBridge C18) with water/methanol (90:100:100) as eluant.

Yield: 48 mg (30% of theory)

$R_f$ value: 0.82 (silica gel, dichloromethane/methanol=80:20)

Mass spectrum (ESI$^+$): m/z=621 [M+H]$^+$

Example 16

N-(5-tert-butyl-3-hydroxymethyl-2-methoxy-phenyl)-4-methyl-3-(2-piperazin-1-ylmethyl-pyridin-4-yloxy)-benzamide

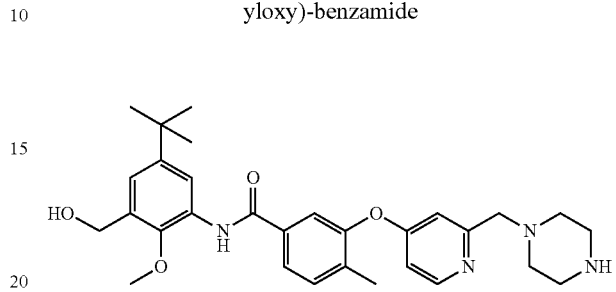

0.78 ml of a 1 M solution of LiAlH$_4$ in tetrahydrofuran are added to a solution of 210 mg methyl 5-tert-butyl-2-methoxy-3-[4-methyl-3-(2-piperazin-1-ylmethyl-pyridin-4-yloxy)-benzoylamino]-benzoate in 4 ml tetrahydro-furan which has been cooled to 0° C. The solution is stirred for 2 h at 0° C. and then combined with 0.80 ml of an aqueous 2 N NaOH solution. The mixture is diluted with ethyl acetate and filtered through Celite. The filtrate is dried on MgSO$_4$ and evaporated to dryness.

Yield: 195 mg (98% of theory)

Mass spectrum (ESI$^+$): m/z=519 [M+H]$^+$

The following compound is obtained analogously to Example 16:

(1) N-(5-tert-butyl-3-hydroxymethyl-2-methoxy-phenyl)-3-(2-[1,4]diazepan-1-ylmethyl-pyridin-4-yloxy)-4-methyl-benzamide

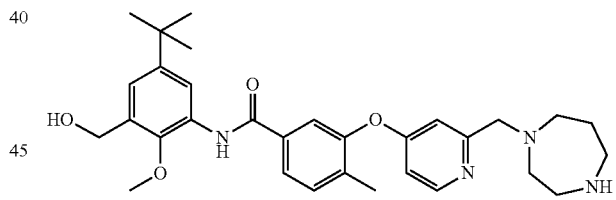

Mass spectrum (ESI$^+$): m/z=533 [M+H]$^+$

The following are examples of formulations, in which the term "active substance" denotes one or more compounds according to the invention, including the salts thereof. In the case of one of the combinations described hereinbefore having one or more additional active substances, the term "active substance" also includes the additional active substances.

Example A

Coated tablets containing 75 mg active substance

Composition:

1 tablet core contains:

| | |
|---|---|
| active substance | 75.0 mg |
| calcium phosphate | 93.0 mg |
| corn starch | 35.5 mg |

-continued

| | |
|---|---|
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

Example B

Tablets containing 100 mg of active substance
Composition
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

Example C

Tablets containing 150 mg of active substance
Composition
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

Example D

Hard gelatine capsules containing 150 mg of active substance
Composition
1 capsule contains:

| | |
|---|---|
| active substance | 150.0 mg |
| corn starch (dried | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Example E

Suppositories containing 150 mg of active substance
Composition
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example F

Suspension containing 50 mg of active substance
Composition
100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example G

Ampoules containing 10 mg active substance
Composition

| active substance | 10.0 mg |
|---|---|
| 0.01N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Example H

Ampoules containing 50 mg of active substance
Composition

| active substance | 50.0 mg |
|---|---|
| 0.01N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

Example I

Capsules for powder inhalation containing 5 mg of active substance
1 capsule contains:

| active substance | 5.0 mg |
|---|---|
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

weight of capsule: 70.0 mg
size of capsule: 3

Example J

Solution for Inhalation for Hand-Held Nebulisers Containing 2.5 mg Active Substance 1 spray contains:

| active substance | 2.500 mg |
|---|---|
| benzalkonium chloride | 0.001 mg |
| 1N hydrochloric acid | q.s. |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

The invention claimed is:

1. A compound of the formula I

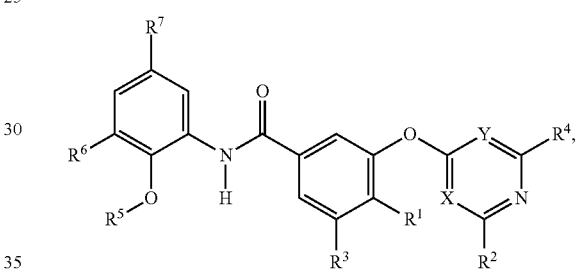

wherein
$R^1$ is $L_1$-$R_8$,
where $L_1$ is selected from a bond, O, CO, NH, CONH, NHCO, SO, $SO_2$, $SO_2NH$, $NHSO_2$ and $C_1$-$C_4$-alkylene,
where $R_8$ is selected from hydrogen, halogen, $C_{1-6}$-alkyl, $C_{2-6}$-alkynyl, $C_{2-6}$-alkenyl, $C_{3-8}$-cycloalkyl, $C_{3-8}$-heterocycloalkyl, $C_{6-10}$-aryl, $C_{5-10}$-heteroaryl, cyano, carboxy, $C_{1-4}$-alkyloxycarbonyl, nitro, amino, di-($C_{1-4}$-alkyl)-amino, hydroxy, $C_{1-6}$-alkylsulphanyl,
$R_8$ may be partly or completely fluorinated and/or may be substituted by one or more substituents L, and
wherein in heterocycloalkyl groups a methylene group may be substituted by CO, SO or $SO_2$, and
wherein $R^1$ is not hydrogen if $R^3$ denotes hydrogen, and
$R^2$ is $L_2$-$R_9$,
wherein $L_2$ is selected from a bond, O, CO, NH, CONH, NHCO, SO, $SO_2$, $SO_2NH$, $NHSO_2$ and $C_1$-$C_4$-alkylene
wherein $R_9$ is selected from hydrogen, halogen, $C_{1-6}$-alkyl, $C_{2-6}$-alkynyl, $C_{2-5}$-alkenyl, $C_{3-8}$-cycloalkyl, $C_{4-8}$-cycloalkenyl, $C_{3-8}$-heterocycloalkyl, $C_{6-10}$-aryl, $C_{5-10}$-heteroaryl, cyano, carboxy, $C_{1-4}$-alkyloxycarbonyl, nitro, amino, di-($C_{1-4}$-alkyl)-amino, hydroxy, $C_{1-6}$-alkylsulphanyl,
wherein $R_9$ may be partly or completely fluorinated and/or may be substituted by one or more substituents L, and
wherein in the alkyl groups mentioned optionally one or two $CH_2$ groups may be exchanged for O and/or $NR^N$,
wherein in the cycloalkyl groups mentioned one or two $CH_2$ groups may be replaced independently of one another by $NR^N$, O, S, CO, SO or $SO_2$ and one or two CH groups may be replaced by N, and $R^3$ is $L_3$-$R_{10}$ wherein $L_3$ is selected from a bond, O, CO, NH, CONH, NHCO, SO, $SO_2$, $SO_2$NH, $NHSO_2$ and $C_1$-$C_4$-alkylene wherein $R_{10}$ is selected from hydrogen, halogen, $C_{1-6}$-alkyl, $C_{2-6}$-alkynyl, $C_{2-6}$-alkenyl, $C_{3-8}$-cycloalkyl, $C_{4-8}$-cycloalkenyl, $C_{3-8}$-heterocycloalkyl, $C_{5-10}$-aryl, $C_{5-10}$-heteroaryl, cyano, carboxy, $C_{1-4}$-alkyloxycarbonyl, nitro, amino, di-($C_{1-4}$-alkyl)-amino, hydroxy, $C_{1-6}$-alkylsulphanyl wherein $R_{10}$ may be partly or completely fluorinated and/or may be substituted by one or more substituents L, and wherein $R^3$ is not hydrogen if $R^1$ denotes hydrogen, $R^4$ is $L_4$-$R_{11}$ wherein $L_4$ is selected from a bond, O, CO, NH, CONH, NHCO, wherein $R_{11}$ is selected from hydrogen, halogen, amino, $C_{1-6}$-alkyl, $C_{3-8}$-cycloalkyl, $C_{3-8}$-heterocycloalkyl, trifluoromethyl, difluoromethyl, cyano, carboxy, $C_{1-4}$-alkyloxycarbonyl, di-($C_{1-4}$-alkyl)-amino, $C_{1-4}$-alkylsulphanyl, $R^5$ is $C_{1-6}$-alkyl, $R^6$ is dimethylamino-$C_{1-3}$-alkyl, cyclopropylamino-$C_{1-3}$-alkyl, pyrrolidinyl-$C_{1-3}$-alkyl, hydroxy-$C_{1-3}$-alkyl, methylsulphanyl-$C_{1-3}$-alkyl, methylsulphinyl-$C_{1-3}$-alkyl, methylsulphonyl-$C_{1-3}$-alkyl, $C_{1-4}$-alkylcarbonylamino, $C_{3-5}$-cycloalkyl-carbonylamino, $C_{1-4}$-alkylsulphonylamino, $C_{3-5}$-cycloalkylsulphonylamino, $C_{1-3}$-alkylsulphinyl and $C_{1-3}$-alkylsulphonyl $R^7$ is $C_{1-6}$-alkyl, trifluoromethyl, pentafluoroethyl, X,Y independently of one another denote N or C—$R_{13}$, wherein one of X and Y is N and the other is C—$R_{13}$ and $R_{13}$ is selected from hydrogen, fluorine, chlorine, $C_{1-4}$-alkyl, trifluoromethyl, OH, $C_{1-4}$-alkyloxy, trifluoromethoxy, difluoromethoxy and cyano, $R^N$ is selected from H, $C_{1-4}$-alkyl, 1,1,1-trifluoroethyl, cyanmethyl, acetyl, methylsulphonyl, $C_{6-10}$-arylmethyl, L is selected from among halogen, cyano, $C_{1-6}$-alkyl, $C_{1-6}$-alkyloxy, amino, $C_{1-3}$-alkylamino, di-($C_{1-3}$-alkyl)-amino, $C_{1-4}$-alkylcarbonylamino, difluoromethyl, $C_{1-4}$-alkylsulphonylamino trifluoromethyl, hydroxy, $C_{1-3}$-alkoxy, difluoromethoxy, trifluoromethoxy, acetylamino, $C_{6-10}$-aryl and $C_{5-10}$-heteroaryl.

2. The compound according to claim 1 wherein $R^1$ is selected from hydrogen, halogen, $C_{1-6}$-alkyl, $C_{2-6}$-alkynyl, $C_{2-5}$-alkenyl, $C_{3-7}$-cycloalkyl, $C_{3-7}$-cycloalkyl-$C_{1-3}$-alkyl, $C_{6-10}$-aryl, $C_{5-10}$-heteroaryl, $C_{6-10}$-aryl-$C_{1-3}$-alkyl, $C_{5-10}$-heteroaryl-$C_{1-3}$-alkyl, $C_{1-4}$-alkylcarbonyl, cyano, aminocarbonyl, $C_{1-4}$-alkyl-aminocarbonyl, di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)-piperazin-1-ylcarbonyl, carboxy, $C_{1-4}$-alkyloxycarbonyl, nitro, amino, $C_{1-4}$-alkylamino, di-($C_{1-3}$-alkyl)-amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-4}$-alkylsulphonylamino, hydroxy, $C_{1-6}$-alkyloxy, $C_{3-7}$-cycloalkyloxy, $C_{6-10}$-aryloxy, $C_{1-4}$-alkylsulphanyl, $C_{1-4}$-alkylsulphinyl and $C_{1-4}$-alkylsulphonyl, wherein alkyl, alkenyl, alkynyl, cycloalkyl and heterocycloalkyl groups may be partly or completely fluorinated and/or mono- or disubstituted by identical or different substituents selected from cyano, hydroxy, $C_{1-3}$-alkyloxy, acetylamino, methylsulphonylamino and $C_{1-3}$-alkyl, and wherein in cycloalkyl groups one or two methylene groups may be substituted independently of one another by O, S, CO, SO or $SO_2$, and wherein in N-heterocycloalkyl groups a methylene group may be substituted by CO or $SO_2$, wherein $R^1$ is not hydrogen if $R^3$ denotes hydrogen, and $R^2$ is selected from hydrogen, $C_{1-8}$-alkyl, $C_{2-6}$-alkenyl, $C_{2-6}$-alkynyl, $C_{3-7}$-cycloalkyl-$C_{1-4}$-alkyl, $C_{1-6}$-alkylcarbonyl-$C_{1-3}$-alkyl, $C_{6-10}$-aryl-$C_{1-4}$-alkyl, $C_{5-10}$-heteroaryl-$C_{1-4}$-alkyl, $C_{3-7}$-cycloalkyl, $C_{1-6}$-alkylcarbonyl, $C_{3-7}$-cycloalkyl-carbonyl, cyano, aminocarbonyl, carboxy, amino, $C_{1-4}$-alkylcarbonylamino, $C_{1-4}$-alkylsulphonylamino, $C_{1-4}$-alkyloxy, $C_{6-10}$-aryl, $C_{5-10}$-heteroaryl, hydroxy, wherein all the above-mentioned alkyl, alkenyl, alkynyl and cycloalkyl groups may be partly or completely fluorinated and/or mono-, di- or trisubstituted by identical or different substituents selected from $C_{1-3}$-alkyl, cyano, hydroxy, $C_{1-3}$-alkyloxy, amino, $C_{1-3}$-alkylamino, di-($C_{1-3}$-alkyl)amino, acetylamino, methylsulphonylamino, $C_{6-10}$-aryl and $C_{5-10}$-heteroaryl, wherein in the alkyl groups mentioned one or two $CH_2$ groups may optionally be exchanged for O and/or $NR^N$, wherein in the cycloalkyl groups mentioned one or two $CH_2$ groups may be replaced independently of one another by $NR^N$, O, S, CO, SO or $SO_2$ and one or two CH groups may be replaced by N, and $R^3$ is selected from hydrogen, halogen, $C_{1-4}$-alkyl, $C_{2-6}$-alkynyl, $C_{2-6}$-alkenyl, $C_{3-7}$-cycloalkyl-$C_{1-3}$-alkyl, $C_{3-6}$-cycloalkyl, trifluoromethyl, difluoromethyl, hydroxy, $C_{1-4}$-alkyloxy, trifluoromethoxy, difluoromethoxy, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, $C_{1-4}$-alkylcarbonylamino, $C_{1-4}$-alkylsulphonylamino, wherein $R^3$ is not hydrogen if $R^1$ denotes hydrogen, $R^4$ is selected from hydrogen, $C_{1-4}$-alkyl, $C_{3-6}$-cycloalkyl, trifluoromethyl, difluoromethyl, cyano, carboxy, aminocarbonyl, $C_{1-3}$-alkylaminocarbonyl, di-($C_{1-3}$-alkyl) aminocarbonyl, $C_{1-4}$-alkyloxycarbonyl, amino, $C_{1-3}$-alkylamino, di-($C_{1-3}$-alkyl)amino, hydroxy, $C_{1-4}$-alkyloxy, $C_{1-4}$-alkylsulphanyl, $R^5$ is $C_{1-4}$-alkyl, $R^6$ is selected from dimethylaminomethyl, cyclopropylaminomethyl, pyrrolidin-1-ylamino, hydroxymethyl, methylsulphanylmethyl, methylsulphinylmethyl, methylsulphonylmethyl, n-butylcarbonyl-amino, isopropylcarbonyl-amino, isobutylcarbonylamino, cyclopropylcarbonylamino, methylsulphonylamino, isopropylsulphonylamino, n-butylsulphonylamino, isobutylsulphonyl-amino, cyclopropyl-sulphonylamino, methylsulphinyl and methylsulphonyl, $R^7$ is selected from $C_4$-alkyl, trifluoromethyl, pentafluoroethyl, $R_{13}$ is selected from hydrogen, fluorine, chlorine, $C_{1-4}$-alkyl, trifluoromethyl, hydroxy, $C_{1-4}$-alkyloxy, trifluoromethoxy, difluoromethoxy, cyano, $R^N$ is selected from H, $C_{1-4}$-alkyl, 1,1,1-trifluoroethyl, cyanomethyl, acetyl, methylsulphonyl, $C_{6-10}$-arylmethyl, L selected from among fluorine, chlorine, bromine, $C_{1-3}$-alkyl, difluoromethyl, trifluoromethyl, hydroxy, $C_{1-3}$-alkoxy, difluoromethoxy, trifluoromethoxy, acetylamino, methylsulphonylamino and cyano, wherein by the $C_{5-10}$-aryl groups mentioned in the definition of the above groups are meant phenyl or naphthyl groups, which may be mono- or disubstituted independently of one another by identical or different groups L; and
by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group,
or a pyrrolyl, furanyl, thienyl or pyridyl group is meant, wherein one or two methyne groups are replaced by nitrogen atoms,
or an indolyl, benzofuranyl, benzothiophenyl, quinolinyl or isoquinolinyl group is meant, wherein one to three methyne groups are replaced by nitrogen atoms,
wherein the above-mentioned heteroaryl groups may be mono- or disubstituted independently of one another by identical or different groups L;
wherein, unless stated otherwise, the above-mentioned alkyl groups may be straight-chain or branched,
the tautomers, the stereoisomers, the mixtures and the physiologically acceptable salts thereof.

3. The compound according to claim 2 wherein
$R^1$ is selected from hydrogen, fluorine, chlorine, bromine, $C_{1-4}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, pyrrolidin-1-yl, piperidin-1-yl, morpholin-4-yl, acetylamino, methylsulphonylamino, hydroxy, $C_{1-4}$-alkyloxy, trifluoromethoxy, difluoromethoxy and $C_{1-4}$-alkylsulphonyl,
wherein the above-mentioned alkyl, cycloalkyl and N-heterocycloalkyl groups may be mono- or disubstituted by identical or different substituents selected from cyano, hydroxy, $C_{1-3}$-alkyloxy, acetylamino, methylsulphonylamino and $C_{1-3}$-alkyl, and wherein in the cycloalkyl groups mentioned one or two methylene groups may be substituted independently of one another by 0, CO or $SO_2$ and in the above-mentioned N-heterocycloalkyl groups a methylene group may be substituted by CO or $SO_2$, and
wherein $R^1$ is not hydrogen if $R^3$ denotes hydrogen.

4. The compound according to claim 3 wherein
$R^1$ is selected from hydrogen, fluorine, chlorine, bromine, $C_{1-4}$-alkyl, trifluoromethyl, $C_{3-6}$-cycloalkyl, cyano, aminocarbonyl, $C_{1-4}$-alkyl-aminocarbonyl, di-($C_{1-3}$-alkyl)-aminocarbonyl, carboxy, $C_{1-4}$-alkyloxycarbonyl, amino, $C_{1-4}$-alkylamino, di-($C_{1-3}$-alkyl)-amino, pyrrolidin-1-yl, piperidin-1-yl, morpholin-4-yl, acetylamino, methylsulphonylamino, hydroxy, $C_{1-4}$-alkyloxy, trifluoromethoxy, difluoromethoxy and $C_{1-4}$-alkylsulphonyl, wherein $R^1$ is not hydrogen if $R^3$ denotes hydrogen.

5. The compound according to claim 4 wherein $R^1$ is selected from hydrogen, fluorine, chlorine, bromine, methyl, ethyl and trifluoromethyl, wherein $R^1$ is not hydrogen if $R^3$ denotes hydrogen.

6. The compound according to claim 5 wherein
$R^2$ is selected from hydrogen, $C_{1-4}$-alkyl, $C_{3-6}$-cycloalkyl-$C_{1-3}$-alkyl, $C_{3-6}$-cycloalkylamino-$C_{1-3}$-alkyl, pyrrolidinyl-$C_{1-3}$-alkyl, piperidin-$C_{1-3}$-alkyl, azepanyl-$C_{1-3}$-alkyl, piperazinyl-$C_{1-3}$-alkyl, morpholinyl-$C_{1-3}$-alkyl, homopiperazinyl-$C_{1-3}$-alkyl, pyrrolidin-3-ylamino-$C_{1-3}$-alkyl, piperidin-3-ylamino-$C_{1-3}$-alkyl, piperidin-4-ylamino-$C_{1-3}$-alkyl, $C_{3-6}$-cycloalkyl, trifluoromethyl, cyano, aminocarbonyl, $C_{1-4}$-alkyl-aminocarbonyl, di-($C_{1-3}$-alkyl)-aminocarbonyl, piperazin-1-ylcarbonyl, morpholin-4-ylcarbonyl, carboxy, $C_{1-4}$-alkyloxycarbonyl, amino, $C_{1-4}$-alkylamino, $C_{3-6}$-cycloalkylamino, $C_{3-6}$-cycloalkyl-$C_{1-3}$-alkylamino, pyrrolidin-1-yl, piperidin-1-yl, piperazin-1-yl, morpholin-4-yl, $C_{1-3}$-alkyl-amino-$C_{2-3}$-alkylamino, pyrrolidin-3-ylamino, piperidin-3-ylamino, pyrrolidinyl-$C_{1-3}$-alkyl-amino, piperidin-$C_{1-3}$-alkyl-amino, piperazinyl-$C_{1-3}$-alkyl-amino, morpholinyl-$C_{1-3}$-alkyl-amino, homopiperazinyl-$C_{1-3}$-alkyl-amino, acetylamino, methylsulphonylamino,
hydroxy, $C_{1-4}$-alkyloxy, trifluoromethoxy, difluoromethoxy, $C_{3-6}$-cycloalkyloxy, $C_{3-6}$-cycloalkyl-$C_{1-3}$-alkyloxy, $C_{1-3}$-alkylamino-$C_{2-3}$-alkyloxy, di-($C_{1-3}$-alkyl)-amino-$C_{2-3}$-alkyloxy, pyrrolidinyl-$C_{2-3}$-alkyloxy, piperidin-$C_{2-3}$-alkyloxy, piperazinyl-$C_{2-3}$-alkyloxy, morpholinyl-$C_{2-3}$-alkyloxy, homopiperazinyl-$C_{2-3}$-alkyloxy,
wherein the above mentioned alkyl, cycloalkyl and N-heterocycloalkyl groups may be mono- or disubstituted by identical or different substituents selected from $C_{1-3}$-alkyl, cyano, amino, $C_{1-3}$-alkylamino, di-($C_{1-3}$-alkyl) amino, acetylamino, methylsulphonylamino, hydroxy and $C_{1-3}$-alkyloxy, and
wherein in the above mentioned cycloalkyl groups one or two methylene groups may be substituted independently of one another by O and/or CO and in the above-mentioned N-heterocycloalkyl groups a methylene group may be substituted by CO or $SO_2$, and wherein optional all the NH groups contained in the above mentioned groups are replaced by N-Me, N-Et, N-acetyl and N—$SO_2$Me.

7. The compound according to claim 5 wherein
$R^2$ is selected from hydrogen, $C_{1-4}$-alkyl, $C_{1-3}$-alkylamino-$C_{1-3}$-alkyl, tetrahydrofuran-3-ylamino-$C_{1-3}$-alkyl, pyrrolidinyl-$C_{1-3}$-alkyl, piperidinyl-$C_{1-3}$-alkyl, azepanyl-$C_{1-3}$-alkyl, piperazinyl-$C_{1-3}$-alkyl, 4-(1,1,1-trifluoroethyl)-piperazin-1-yl-$C_{1-3}$-alkyl, 4-cyanomethyl-piperazin-1-yl-$C_{1-3}$-alkyl, homopiperazinyl-$C_{1-3}$-alkyl, morpholinyl-$C_{1-3}$-alkyl, N-(pyrrolidin-3-yl)-N—($C_{1-3}$-alkyl)-amino-$C_{1-3}$-alkyl, pyrrolidin-3-ylamino-$C_{1-3}$-alkyl, N-[di-($C_{1-3}$-alkyl)amino-$C_{2-3}$-alkyl]-N—($C_{1-3}$-alkyl)-amino-$C_{1-3}$-alkyl, N-[di-($C_{1-3}$-alkyl)amino-$C_{2-3}$-alkyl]-amino-$C_{1-3}$-alkyl, N-(piperidinyl)-N—($C_{1-3}$-alkyl)-amino-$C_{1-3}$-alkyl, piperidinylamino-$C_{1-3}$-alkyl, $C_{1-3}$-alkyl-aminocarbonyl, piperazin-1-ylcarbonyl, morpholin-4-ylcarbonyl, amino, $C_{1-3}$-alkylamino, $C_{5-6}$-cycloalkylamino, pyrrolidin-1-yl, piperidin-1-yl, piperazin-1-yl, morpholin-4-yl, pyrrolidin-3-ylamino, N—($C_{1-3}$-alkyl)-N-(pyrrolidin-3-yl)-amino, piperidin-4-ylamino, N—($C_{1-3}$-alkyl)-N-(piperidin-4-yl)-amino, di-($C_{1-3}$-alkyl)-amino-$C_{2-3}$-alkylamino, N-[di-($C_{1-3}$-alkyl)-amino-$C_{2-3}$-alkyl]-N—($C_{1-3}$-alkyl)-amino, pyrrolidin-1-yl-$C_{2-3}$-alkyl-amino, hydroxy-$C_{2-3}$-alkyl-amino, hydroxy,
wherein in the above-mentioned N- and O-heterocycloalkyl groups a $CH_2$ group is optionally replaced by C═O and each of these cyclic groups is optionally substituted by a group selected from $C_{1-3}$-alkyl, amino, $C_{1-3}$-alkyl-amino, di-($C_{1-3}$-alkyl)-amino and hydroxy.

8. The compound according to claim 5 wherein
$R^2$ is selected from hydrogen, methyl, methylaminomethyl, 3-hydroxypyrrolidin-1-ylmethyl, 3-dimethylaminopyrrolidin-1-ylmethyl, N-(1-methylpyrrolidin-3-yl)-N-methyl-aminomethyl, piperidin-4-ylmethyl, N-methyl-piperidin-4-ylmethyl, azepan-4-ylmethyl, 1-methyl-azepan-4-ylmethyl, N-(2-dimethylaminoethyl)-N-methyl-aminomethyl, N-(2-dimethyl-aminoethyl)-aminomethyl, N-(1-methylpyrrolidin-3-yl)-aminomethyl, 1-methylpiperidin-4-ylaminomethyl, 1-methylpiperidin-3-yl-aminomethyl, piperazin-1-ylmethyl, 4-methyl-piperazin-1-ylmethyl, 4-(1,1,1-trifluoroethyl)-piperazin-1-ylmethyl, 4-cyanomethyl-piperazin-1-ylmethyl, piperazin-2-one-4-ylmethyl, morpholin-4-ylmethyl, tetrahydrofuran-3-ylaminomethyl, homo-piperazin-1-ylmethyl, 4-methylhomopiperazin-1-ylmethyl, methylaminocarbonyl, piperazin-1-ylcarbonyl, 4-methylpiperazin-1-ylcarbonyl, morpholin-4-ylcarbonyl, methylamino, 4-dimethylaminocyclohexyl-amino, 3-dimethyl-amino-pyrrolidin-1-yl, pyrrolidin-3-ylamino, N-methyl-N-pyrrolidin-3-yl-amino, N-methyl-N-(1-methylpyrrolidin-3-yl)-amino, piperidin-4-ylamino, 1-methyl-piperidin-4-ylamino, N-methyl-N-piperidin-4-yl-amino, 4-dimethylamino-piperidin-1-yl, piperazin-1-yl, piperazin-2-one-4-yl, morpholin-4-yl, 2-(dimethylamino)ethyl-amino, 2-(pyrrolidin-1-yl)ethylamino, 2-hydroxy-ethylamino, N-(2-dimethylaminoethyl)-N-methyl-amino, hydroxy.

9. The compound according to claim 8 wherein $R^3$ is selected from hydrogen, $C_{1-3}$-alkyl, $C_{3-6}$-cycloalkyl, fluorine, chlorine, bromine, trifluoromethyl, difluoromethyl, hydroxy, $C_{1-3}$-alkyloxy, trifluoromethoxy, difluoromethoxy and cyano, wherein $R^3$ is not hydrogen if $R^1$ denotes hydrogen.

10. The compound according to claim 8 wherein $R^3$ is selected from hydrogen, $C_{1-3}$-alkyl, fluorine, chlorine, trifluoromethyl, $C_{1-3}$-alkyloxy and cyano, wherein $R^3$ is not hydrogen if $R^1$ denotes hydrogen.

11. The compound according to claim 8 wherein $R^3$ is selected from hydrogen, methyl, fluorine and chlorine, wherein $R^3$ is not hydrogen if $R^1$ denotes hydrogen.

12. The compound according to claim 11 wherein $R^4$ is selected from hydrogen, $C_{1-3}$-alkyl, trifluoromethyl, carboxy, aminocarbonyl, methylaminocarbonyl, dimethylamino-carbonyl, amino, $C_{1-3}$-alkylamino, di-($C_{1-3}$-alkyl)-amino, hydroxy and $C_{1-3}$-alkyloxy.

13. The compound according to claim 11 wherein $R^4$ is selected from hydrogen, methyl, dimethylamino, hydroxy and methoxy.

14. The compound according to claim 11 wherein $R^4$ is hydrogen.

15. The compound according to claim 13 wherein $R^5$ is selected from methyl, ethyl, n-propyl and isopropyl.

16. The compound according to claim 14 wherein $R^5$ is selected from methyl, ethyl and isopropyl.

17. The compound according to claim 14 wherein $R^5$ is methyl.

18. The compound according to claim 17 wherein $R^6$ is methylsulphonylamino.

19. The compound according to claim 18 wherein $R^7$ is selected from isobutyl, tert-butyl, trifluoromethyl and pentafluoroethyl.

20. The compound according to claim 18 wherein $R^7$ is selected from tert-butyl, trifluoromethyl and pentafluoroethyl.

21. The compound according to claim 18 wherein $R^7$ is tert-butyl.

22. The compound according to claim 21 wherein X and Y are selected independently of one another from N, C—H, C—F, C—Cl, C—$C_{1-3}$-alkyl and $C_{1-3}$-alkyloxy.

23. The compound according to claim 21 X and Y are selected independently of one another from N, C—H, C—F and C-Me.

24. The compound according to claim 21 X and Y are N and CH or CH and N.

25. A compound chosen from
N-(5-tert-butyl-3-methanesulphonylamino-2-methoxy-phenyl)-4-methyl-3-(2-methylamino-pyrimidin-4-yloxy)-benzamide;
N-(5-tert-butyl-3-methanesulphonylamino-2-methoxy-phenyl)-4-methyl-3-(6-methylamino-pyrimidin-4-yloxy)-benzamide;
N-(5-tert-butyl-3-methanesulphonylamino-2-methoxy-phenyl)-4-methyl-3-[2-(2-pyrrolidin-1-yl-ethylamino)-pyrimidin-4-yloxy]-benzamide;
N-(5-tert-butyl-3-methanesulphonylamino-2-methoxy-phenyl)-3-[6-(2-hydroxy-ethylamino)-pyrimidin-4-yloxy]-4-methyl-benzamide;
N-(5-tert-butyl-3-methanesulphonylamino-2-methoxy-phenyl)-3-[6-(2-dimethylamino-ethylamino)-pyrimidin-4-yloxy]-4-methyl-benzamide;
N-(5-tert-butyl-3-methanesulphonylamino-2-methoxy-phenyl)-4-methyl-3-[6-(3-oxo-piperazin-1-yl)-pyrimidin-4-yloxy]-benzamide;
N-(5-tert-butyl-3-methanesulphonylamino-2-methoxy-phenyl)-4-methyl-3-(6-pyrrolidin-1-yl-pyrimidin-4-yloxy)-benzamide;
N-(5-tert-butyl-3-methanesulphonylamino-2-methoxy-phenyl)-4-methyl-3-(6-morpholin-4-yl-pyrimidin-4-yloxy)-benzamide;
(R)—N-(5-tert-butyl-3-methanesulphonylamino-2-methoxy-phenyl)-3-[2-(3-dimethylamino-pyrrolidin-1-yl)-pyrimidin-4-yloxy]-4-methyl-benzamide;
(S)—N-(5-tert-butyl-3-methanesulphonylamino-2-methoxy-phenyl)-3-[2-(3-dimethylamino-pyrrolidin-1-yl)-pyrimidin-4-yloxy]-4-methyl-benzamide;
N-(5-tert-butyl-3-methanesulphonylamino-2-methoxy-phenyl)-3-[2-(4-dimethylamino-piperidin-1-yl)-pyrimidin-4-yloxy]-4-methyl-benzamide;
N-(5-tert-butyl-3-methanesulphonylamino-2-methoxy-phenyl)-4-methyl-3-[2-(1-methyl-piperidin-4-ylamino)-pyrimidin-4-yloxy]-benzamide;
N-(5-tert-butyl-3-methanesulphonylamino-2-methoxy-phenyl)-4-methyl-3-(2-piperazin-1-yl-pyrimidin-4-yloxy)-benzamide;
N-(5-tert-butyl-3-methanesulphonylamino-2-methoxy-phenyl)-4-methyl-3-(6-piperazin-1-yl-pyrimidin-4-yloxy)-benzamide;
N-(5-tert-butyl-3-methanesulphonylamino-2-methoxy-phenyl)-4-methyl-3-[6-(piperazine-1-carbonyl)-pyrimidin-4-yloxy]-benzamide;
N-(5-tert-butyl-3-methanesulphonylamino-2-methoxy-phenyl)-4-chloro-3-[6-(piperazine-1-carbonyl)-pyrimidin-4-yloxy]-benzamide;
N-(5-tert-butyl-3-methanesulphonylamino-2-methoxy-phenyl)-3-(2-piperazin-1-yl-pyrimidin-4-yloxy)-4-trifluoromethyl-benzamide;
N-(5-tert-butyl-3-methanesulphonylamino-2-methoxy-phenyl)-4-chloro-3-(2-piperazin-1-yl-pyrimidin-4-yloxy)-benzamide;
N-(5-tert-butyl-3-methanesulphonylamino-2-methoxy-Phenyl)-4-methyl-3-(2-piperazin-1-ylmethyl-pyrimidin-4-yloxy)-benzamide;
N-(5-tert-butyl-3-methanesulphonylamino-2-methoxy-phenyl)-4-methyl-3-(6-piperazin-1-ylmethyl-pyrimidin-4-yloxy)-benzamide;
N-(5-tert-butyl-3-methanesulphonylamino-2-methoxy-phenyl)-4-methoxy-3-(2-piperazin-1-yl-pyrimidin-4-yloxy)-benzamide;
N-(5-tert-butyl-3-methanesulphonylamino-2-methoxy-phenyl)-4-fluoro-3-(2-piperazin-1-yl-pyrimidin-4-yloxy)-benzamide;

N-(5-tert-butyl-3-methanesulphonylamino-2-methoxy-phenyl)-4-bromo-3-(2-piperazin-1-yl-pyrimidin-4-yloxy)-benzamide;
N-(5-tert-butyl-3-methanesulphonylamino-2-methoxy-phenyl)-3-chloro-4-methyl-5-(2-piperazin-1-yl-pyrimidin-4-yloxy)-benzamide;
N-(5-tert-butyl-3-methanesulphonylamino-2-methoxy-phenyl)-3-fluoro-4-methyl-5-(2-piperazin-1-yl-pyrimidin-4-yloxy)-benzamide;
N-(5-tert-butyl-3-methanesulphonylamino-2-methoxy-phenyl)-4-methyl-3-[2-(N-methyl-N-piperidin-4-yl-amino)-pyrimidin-4-yloxy]-benzamide;
N-(5-tert-butyl-3-methanesulphonylamino-2-methoxy-phenyl)-4-ethyl-5-(2-piperazin-1-yl-pyrimidin-4-yloxy)-benzamide;
N-(5-tert-butyl-3-methanesulphonylamino-2-methoxy-phenyl)-4-methyl-3-[2-(piperidin-4-ylamino)-pyrimidin-4-yloxy]-benzamide;
N-(5-tert-butyl-3-methanesulphonylamino-2-methoxy-phenyl)-4-methyl-3-[6-(piperidin-4-ylamino)-pyrimidin-4-yloxy]-benzamide;
N-(5-tert-butyl-3-methanesulphonylamino-2-methoxy-phenyl)-4-methyl-3-(6-piperidin-4-ylmethyl-pyrimidin-4-yloxy)-benzamide;
N-(5-tert-butyl-3-methanesulphonylamino-2-methoxy-phenyl)-4-methyl-3-(2-piperidin-4-ylmethyl-pyrimidin-4-yloxy)-benzamide;
N-(5-tert-butyl-3-methanesulphonylamino-2-methoxy-phenyl)-3-methyl-5-[2-(piperazine-1-carbonyl)-pyrimidin-4-yloxy]-benzamide;
N-(5-tert-butyl-3-methanesulphonylamino-2-methoxy-phenyl)-3-methyl-5-(2-piperazin-1-ylmethyl-pyrimidin-4-yloxy)-benzamide;
6-[5-(5-tert-butyl-3-methanesulphonylamino-2-methoxy-phenylaminocarbonyl)-2-methyl-phenoxy]-pyrimidin-4-carboxylic acid-methylamide;
N-(5-tert-butyl-3-methanesulphonylamino-2-methoxy-phenyl)-4-methyl-3-[6-(morpholine-4-carbonyl)-pyrimidin-4-yloxy]-benzamide;
N-(5-tert-butyl-3-methanesulphonylamino-2-methoxy-phenyl)-4-methyl-3-[6-(4-methyl-piperazine-1-carbonyl)-pyrimidin-4-yloxy]-benzamide;
N-(5-tert-butyl-3-methanesulphonylamino-2-methoxy-phenyl)-4-methyl-3-(6-morpholin-4-ylmethyl-pyrimidin-4-yloxy)-benzamide;
N-(5-tert-butyl-3-methanesulphonylamino-2-methoxy-phenyl)-4-methyl-3-(6-methylaminomethyl-pyrimidin-4-yloxy)-benzamide;
N-(5-tert-butyl-3-methanesulphonylamino-2-methoxy-phenyl)-4-methyl-3-[6-(4-methyl-piperazin-1-ylmethyl)-pyrimidin-4-yloxy]-benzamide;
N-(5-tert-butyl-3-methanesulphonylamino-2-methoxy-phenyl)-4-methyl-3-(2-morpholin-4-ylmethyl-pyrimidin-4-yloxy)-benzamide;
N-(5-tert-butyl-3-methanesulphonylamino-2-methoxy-phenyl)-4-methyl-3-(2-methylaminomethyl-pyrimidin-4-yloxy)-benzamide;
N-(5-tert-butyl-3-methanesulphonylamino-2-methoxy-phenyl)-4-methyl-3-[2-(3-oxo-piperazin-1-ylmethyl)-pyrimidin-4-yloxy]-benzamide;
N-(5-tert-butyl-3-methanesulphonylamino-2-methoxy-phenyl)-4-methyl-3-[2-(4-methyl-piperazin-1-ylmethyl)-pyrimidin-4-yloxy]-benzamide;
N-(5-tert-butyl-3-methanesulphonylamino-2-methoxy-phenyl)-4-methyl-3-[6-(3-oxo-piperazin-1-ylmethyl)-pyrimidin-4-yloxy]-benzamide;
N-(5-tert-butyl-3-methanesulphonylamino-2-methoxy-phenyl)-4-methyl-3-(6-piperazin-1-ylmethyl-pyrimidin-4-yloxy)-benzamide;
N-(5-tert-butyl-3-methanesulphonylamino-2-methoxy-phenyl)-4-methyl-3-[2-(4-methyl-homopiperazin-1-yl-methyl)-pyrimidin-4-yloxy]-benzamide;
N-(5-tert-butyl-3-methanesulphonylamino-2-methoxy-phenyl)-4-methyl-3-{2-[(1-methyl-piperidin-4-ylamino)-methyl]-pyrimidin-4-yloxy}-benzamide;
N-(5-tert-butyl-3-methanesulphonylamino-2-methoxy-phenyl)-4-methyl-3-{2-[(1-methyl-piperidin-3-ylamino)-methyl]pyrimidin-4-yloxy}-benzamide;
N-(5-tert-butyl-3-methanesulphonylamino-2-methoxy-phenyl)-4-methyl-3-(2-{[methyl-(1-methyl-pyrrolidin-3-yl)-amino]-methyl}-pyrimidin-4-yloxy)-benzamide;
(S)—N-(5-tert-butyl-3-methanesulphonylamino-2-methoxy-phenyl)-3-[2-(3-dimethylamino-pyrrolidin-1-ylmethyl)-pyrimidin-4-yloxy]-4-methyl-benzamide;
(R)—N-(5-tert-butyl-3-methanesulphonylamino-2-methoxy-phenyl)-3-[2-(3-dimethylamino-pyrrolidin-1-ylmethyl)-pyrimidin-4-yloxy]-4-methyl-benzamide;
N-(5-tert-butyl-3-methanesulphonylamino-2-methoxy-phenyl)-4-methyl-3-{2-[(1-methyl-pyrrolidin-3-ylamino)-methyl]-pyrimidin-4-yloxy}-benzamide;
N-(5-tert-butyl-3-methanesulphonylamino-2-methoxy-phenyl)-3-(2-{[N-(2-dimethylamino-ethyl)-N-methyl-amino]-methyl}-pyrimidin-4-yloxy)-4-methyl-benzamide;
N-(5-tert-butyl-3-methanesulphonylamino-2-methoxy-phenyl)-3-{2-[(2-dimethylamino-ethylamino)-methyl]-pyrimidin-4-yloxy}-4-methyl-benzamide;
N-(5-tert-butyl-3-methanesulphonylamino-2-methoxy-phenyl)-3-methyl-5-[2-(4-methyl-piperazin-1-ylmethyl)-pyrimidin-4-yloxy]-benzamide;
N-(5-tert-butyl-3-methanesulphonylamino-2-methoxy-phenyl)-3-{6-[(2-dimethylamino-ethylamino)-methyl]-pyrimidin-4-yloxy}-4-methyl-benzamide;
N-(5-tert-butyl-3-methanesulphonylamino-2-methoxy-phenyl)-3-(6-{[(2-dimethylamino-ethyl)-methyl-amino]-methyl}-pyrimidin-4-yloxy)-4-methyl-benzamide;
N-(5-tert-butyl-3-methanesulphonylamino-2-methoxy-phenyl)-4-methyl-3-[6-(1-methyl-piperidin-4-ylmethyl)-pyrimidin-4-yloxy]-benzamide;
N-(5-tert-butyl-3-methanesulphonylamino-2-methoxy-phenyl)-4-methyl-3-[2-(1-methyl-pipendin-4-ylmethyl)-pyrimidin-4-yloxy]-benzamide;
N-(5-tert-butyl-3-methanesulphonylamino-2-methoxy-phenyl)-4-methyl-3-[2-(pyrrolidin-3-ylamino)-pyrimidin-4-yloxy]-benzamide;
N-(5-tert-butyl-3-methanesulphonylamino-2-methoxy-phenyl)-4-chloro-3-[2-(4-methyl-piperazin-1-ylmethyl)-pyrimidin-4-yloxy]-benzamide;
N-(5-tert-butyl-3-methanesulphonylamino-2-methoxy-phenyl)-3-chloro-4-methyl-5-[2-(4-methyl-piperazin-1-ylmethyl)-pyrimidin-4-yloxy]-benzamide;
N-(5-tert-butyl-3-methanesulphonylamino-2-methoxy-phenyl)-4-chloro-3-[6-(1-methyl-piperidin-4-ylamino)-pyrimidin-4-yloxy]-benzamide;
N-(5-tert-butyl-3-methanesulphonylamino-2-methoxy-phenyl)-4-chloro-3-[6-(piperidin-4-ylamino)-pyrimidin-4-yloxy]-benzamide;
N-(5-tert-butyl-3-methanesulphonylamino-2-methoxy-phenyl)-4-chloro-3-[2-(1-methyl-piperidin-4-ylamino)-pyrimidin-4-yloxy]-benzamide;

N-(5-tert-butyl-3-methanesulphonylamino-2-methoxy-phenyl)-4-methyl-3-{2-[methyl-(1-methyl-piperidin-4-yl)-amino]-pyrimidin-4-yloxy}-benzamide;
N-(5-tert-butyl-3-methanesulphonylamino-2-methoxy-phenyl)-4-methyl-3-[6-[methyl-(1-methyl-piperidin-4-yl)-amino]-pyrimidin-4-yloxy]-benzamide;
N-(5-tert-butyl-3-methanesulphonylamino-2-methoxy-phenyl)-4-chloro-3-[2-(piperidin-4-ylamino)-pyrimidin-4-yloxy]-benzamide;
N-(5-tert-butyl-3-methanesulphonylamino-2-methoxy-phenyl)-4-chloro-3-(2-piperidin-4-ylmethyl-pyrimidin-4-yloxy)-benzamide;
N-(5-tert-butyl-3-methanesulphonylamino-2-methoxy-phenyl)-4-chloro-3-{6-[(2-dimethylamino-ethylamino)-methyl]-pyrimidin-4-yloxy}-benzamide;
N-(5-tert-butyl-3-methanesulphonylamino-2-methoxy-phenyl)-4-chloro-3-(6-{[(2-dimethylamino-ethyl)-methyl-amino]-methyl}-pyrimidin-4-yl oxy)-benzamide;
N-(5-tert-butyl-3-methanesulphonylamino-2-methoxy-phenyl)-4-chloro-3-(6-piperazin-1-ylmethyl-pyrimidin-4-yloxy)-benzamide;
N-(5-tert-butyl-3-methanesulphonylamino-2-methoxy-phenyl)-4-chloro-3-(6-piperidin-4-ylmethyl-pyrimidin-4-yloxy)-benzamide;
N-(5-tert-butyl-3-methanesulphonylamino-2-methoxy-phenyl)-4-chloro-3-[6-(4-methyl-piperazin-1-ylmethyl)-pyrimidin-4-yloxy]-benzamide;
N-(5-tert-butyl-3-methanesulphonylamino-2-methoxy-phenyl)-4-chloro-3-[6-(1-methyl-piperidin-4-ylmethyl)-pyrimidin-4-yloxy]-benzamide;
N-(5-tert-butyl-3-methanesulphonylamino-2-methoxy-phenyl)-4-chloro-3-[2-(1-methyl-piperidin-4-ylmethyl)-pyrimidin-4-yloxy]-benzamide;
N-(5-tert-butyl-3-methanesulphonylamino-2-methoxy-phenyl)-3-[2-(trans-4-dimethylamino-cyclohexylamino)-pyrimidin-4-yloxy]-4-methyl-benzamide;
N-(5-tert-butyl-3-methanesulphonylamino-2-methoxy-phenyl)-4-methyl-3-{2-[methyl-(1-methyl-pyrrolidin-3-yl)-amino]-pyrimidin-4-yloxy}-benzamide;
N-(5-tert-butyl-3-methanesulphonylamino-2-methoxy-phenyl)-4-methyl-3-{6-[methyl-(1-methyl-pyrrolidin-3-yl)-amino]-pyrimidin-4-yloxy}-benzamide;
N-(5-tert-butyl-3-methanesulphonylamino-2-methoxy-phenyl)-4-chloro-3-[2-(4-methyl-[1,4]diazepan-1-ylmethyl)-pyrimidin-4-yloxy]-benzamide;
N-(5-tert-butyl-3-methanesulphonylamino-2-methoxy-phenyl)-4-chloro-3-(2-{[(2-dimethylamino-ethyl)-methyl-amino]methyl}-pyrimidin-4-yloxy)-benzamide;
N-(5-tert-butyl-3-methanesulphonylamino-2-methoxy-phenyl)-4-chloro-3-{2-[(2-dimethylamino-ethylamino)-methyl]-pyrimidin-4-yloxy}-benzamide;
N-(5-tert-butyl-3-methanesulphonylamino-2-methoxy-phenyl)-4-chloro-3-[6-(4-methyl-[1,4]diazepan-1-ylmethyl)-pyrimidin-4-yloxy]-benzamide;
N-(5-tert-butyl-3-methanesulphonylamino-2-methoxy-phenyl)-4-chloro-3-(2-piperazin-1-ylmethyl-pyrimidin-4-yloxy)-benzamide;
N-(5-tert-butyl-3-methanesulphonylamino-2-methoxy-phenyl)-4-chloro-3-(6-[1,4]diazepan-1-ylmethyl-pyrimidin-4-yloxy)-benzamide;
N-(5-tert-butyl-3-methanesulphonyl-2-methoxy-phenyl)-4-methyl-3-(2-pipendin-4-ylmethyl-pyrimidin-4-yloxy)-benzamide;
3-(2-azepan-4-ylmethyl-pyrimidin-4-yloxy)-N-(5-tert-butyl-3-methanesulphonylamino-2-methoxy-phenyl)-4-methyl-benzamide;
N-(5-tert-butyl-3-methanesulphonylamino-2-methoxy-phenyl)-4-methyl-3-[2-(1-methyl-azepan-4-ylmethyl)-pyrimidin-4-yloxy]-benzamide;
3-(6-azepan-4-ylmethyl-pyrimidin-4-yloxy)-N-(5-tert-butyl-3-methanesulphonylamino-2-methoxy-phenyl)-4-methyl-benzamide;
N-(5-tert-butyl-3-methanesulphonylamino-2-methoxy-phenyl)-4-methyl-3-[6-(1-methyl-azepan-4-ylmethyl)-pyrimidin-4-yloxy]-benzamide;
N-(5-tert-butyl-3-hydroxymethyl-2-methoxy-phenyl)-4-methyl-3-[2-(4-methyl-piperazin-1-ylmethyl)-pyrimidin-4-yloxy]-benzamide;
N-(5-tert-butyl-3-methanesulphinyl-2-methoxy-phenyl)-4-methyl-3-[2-(4-methyl-piperazin-1-ylmethyl)-pyrimidin-4-yloxy]-benzamide;

or a tautomer, stereoisomer or mixture thereof or a physiologically acceptable salt thereof.

26. A pharmaceutical composition comprising a therapeutically effective amount of a compound according to claim 1 or a physiologically acceptable salt and one or more inert carriers, preservatives and/or diluents.

27. A process for preparing a compound of the formula I according to claim 1 comprising reacting a compound of formula II,

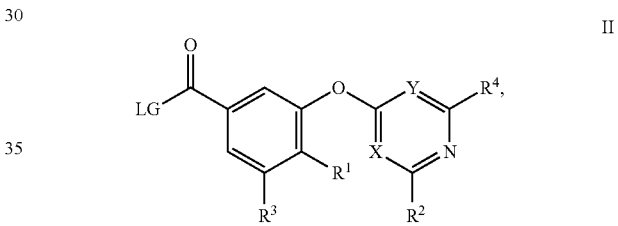

wherein $R^1$ to $R^4$, X and Y have the meanings given in claim 1 and LG denotes fluorine, chlorine, bromine, cyano, $C_{1-10}$-alkoxy, $C_{1-6}$-alkylsulphanyl, $C_{2-4}$-alkenyloxy, $C_{2-4}$-alkynyloxy, benzotriazol-1-yloxy, [1.2.3]triazolo[4,5-b]pyridin-3-yloxy, $C_{5-10}$-heteroaryl (linked to II via N), succinyl-N-oxy, $C_{1-4}$-alkylcarbonyloxy, di-($C_{1-4}$-alkyl)aminocarbonyloxy, pyrrol-1-ylcarbonyloxy, piperidin-1-yl-carbonyloxy, morpholin-4-ylcarbonyloxy, tri-($C_{1-4}$-alkyl)carbamimidoyloxy, N,N,N',N'-tetra-($C_{1-4}$-alkyl)-uronium-O-yl, N,N'-dicyclohexyl-uron-O-yl, N-(3-dimethylaminopropyl)-N'-ethyl-uronyl, di-($C_{1-4}$-alkyloxy)-phosphoryloxy, bis(di-$C_{1-4}$-alkylamino)-phosphoryloxy, dipyrrolidinyl-phosphoryloxy, $C_{6-10}$-arylsulphanyl, $C_{5-10}$-heteroarylsulphanyl, $C_{6-10}$-aryloxy or $C_{5-10}$-heteroaryloxy, wherein all the alkyl, alkenyl and alkynyl groups mentioned in the definition may be mono- or polysubstituted by fluorine, chlorine, $C_{1-3}$-alkyl and/or $C_{1-3}"$ alkoxy, wherein all the aryl groups mentioned in the definition represent phenyl or naphthyl and all the heteroaryl groups represent pyridinyl, pyrimidinyl, triazinyl, imidazolyl, pyrazolyl, triazolyl or tetrazolyl, which, both aryl and heteroaryl groups, are optionally mono- or polysubstituted by identical or different groups selected from among fluorine, chlorine, bromine, $C_{1-3}$-alkyl, $C_{1-3}$-alkyloxy, nitro, cyano and di-($C_{1-3}$-alkyl)amino, with an aniline of formula

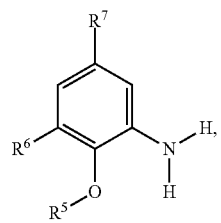

wherein $R^5$, $R^6$ and $R^7$ have the meanings given in claim 1,
optionally in the presence of Triethylamine, pyridine, ethyldiisopropylamine, 4-dimethylaminopyridine, potassium carbonate or 1-hydroxybenzotriazole; and
optionally any protecting group used in the reactions described hereinbefore under a) and b) is cleaved again, and/or
optionally a compound of general formula I thus obtained is resolved into its stereoisomers and/or
optionally a compound of general formula I thus obtained is converted into the salts thereof.

28. A process for preparing a compound of the formula I according to claim 1 comprising reacting a compound of general formula III

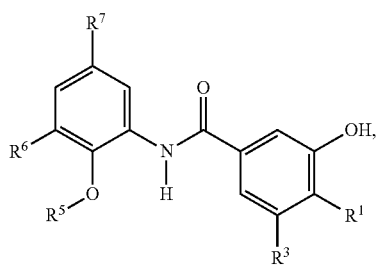

wherein $R^1$, $R^3$, $R^5$, $R^6$ and $R^7$ have the meanings given in claim 1, with a compound of formula IV

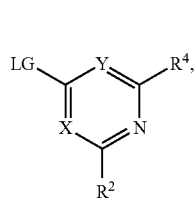

wherein $R^2$ and $R^4$ have the meanings given in claim 1 and
LG denotes a leaving group, in particular LG denotes F, Cl, Br, I, O—$C_{1-6}$-alkyl, O—$C_{6-10}$-aryl, $S(O)_n$—, —$C_{1-4}$-alkyl, $S(O)_m$—$C_{5-10}$-aryl, $OSO_2$—$C_{1-4}$-alkyl, $OSO_2$—$C_{6-10}$-aryl, $NO_2$,
wherein all the above-mentioned alkyl groups are optionally mono- or polysubstituted by fluorine, $C_{1-3}$-alkyl and/or $C_{1-3}$-alkoxy, and
wherein all the above-mentioned aryl groups represent phenyl or naphthyl, which may optionally be mono- or polysubstituted by identical or different groups selected from fluorine, chlorine, $C_{1-3}$-alkyl, $C_{1-3}$-alkyloxy, nitro and cyano,
wherein n and m independently of one another may be 0, 1 or 2,
in the presence of a base NaH, KH, KOtBu, NaOtBu, NaOMe, NaOEt, NaOiPr, KF, $K_2CO_3$, $Cs_2CO_3$, pyridine, 4-dimethylaminopyridine, $NEt_3$ or $EtNiPr_2$,
optionally in the presence of a catalyst A Cu or Pd complex; and
optionally any protecting group used in the reactions described hereinbefore under a) and b) is cleaved again, and/or
optionally a compound of general formula I thus obtained is resolved into its stereoisomers and/or
optionally a compound of general formula I thus obtained is converted into the salts thereof.

29. A method of treating COPD or asthma comprising administering to a patient a therapeutically effective amount of a compound according to claim 1 or a physiologically acceptable salt thereof.

* * * * *